(12) United States Patent
Shiraishi et al.

(10) Patent No.: US 6,627,651 B1
(45) Date of Patent: Sep. 30, 2003

(54) CYCLIC COMPOUNDS AND USES THEREOF

(75) Inventors: Mitsuru Shiraishi, Amagasaki (JP); Masanori Baba, Kagoshima (JP); Masaki Seto, Ibaraki (JP); Naoyuki Kanzaki, Ibaraki (JP); Osamu Nishimura, Kawanishi (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/980,773

(22) PCT Filed: Apr. 28, 2000

(86) PCT No.: PCT/JP00/02825

§ 371 (c)(1),
(2), (4) Date: Nov. 2, 2001

(87) PCT Pub. No.: WO00/68203

PCT Pub. Date: Nov. 16, 2000

(30) Foreign Application Priority Data

May 7, 1999   (JP) ............................................ 11-127724

(51) Int. Cl.[7] ........................ A61K 31/38; C07D 337/00
(52) U.S. Cl. ........................................... 514/431; 549/9
(58) Field of Search .............................. 514/431; 549/9

(56) References Cited

U.S. PATENT DOCUMENTS

| | | | |
|---|---|---|---|
| 6,235,771 B1 * | 5/2001 | Shiraishi et al. ............. | 514/431 |
| 6,346,527 B1 * | 2/2002 | Takenaka et al. ............ | 514/431 |
| 6,441,022 B1 * | 8/2002 | Frick et al. ................. | 514/431 |
| 6,458,851 B1 * | 10/2002 | Keller et al. ................ | 514/655 |
| 6,479,670 B1 * | 11/2002 | Belloni et al. ............... | 549/9 |

FOREIGN PATENT DOCUMENTS

| | | |
|---|---|---|
| EP | 0 460 488 A1 | 12/1991 |
| WO | WO 96/01267 | 1/1997 |
| WO | WO 97/24325 | 7/1997 |
| WO | WO 96/55475 | 12/1998 |
| WO | WO 99/32100 | 7/1999 |
| WO | WO 99/32468 | 7/1999 |
| WO | WO 00/10965 | 3/2000 |
| WO | WO 00/37455 | 6/2000 |

OTHER PUBLICATIONS

Baba, M. et al. "A small–molecule, nonpeptide CCR5 antagonist with highly potent and selective anti–HIV–1 activity" Proc. Natl. Acad. Sci (USA) vol. 96, pp. 5698–5703, May 1999.

Nagamatsu, et al. "Polycyclic N–Hetero Compounds. XXXVII. A Convenient Synthesis and Evaluation of Anti–platelet Aggregation Activity of 1,2,4,5–Tetrahydro[1]–benzothiepino[4,5–e]imidazo[1,2,c]pyrimidine and Its Related Compounds" J. Heterocyclic Chem. 28: 513 (1991).

* cited by examiner

*Primary Examiner*—Deborah C. Lambkin
(74) *Attorney, Agent, or Firm*—Mark Chao; Elaine M. Ramesh

(57) ABSTRACT

Compounds of general formula (1)

$$R^1-X^1-W-X^2-Z^1-Z^2-R^2$$

or salts thereof, exhibiting preventive and therapeutic effects against HIV infectious diseases wherein $R^1$ is an optionally substituted five- or six-membered ring group; $X^1$ is a free valency or the like; W is a divalent group represented by, e.g., general formula (2)

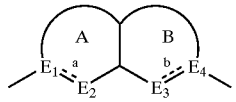

(wherein A and B are each an optionally substituted five- to seven-membered ring; $E_1$ and $E_4$ are each optionally substituted carbon or the like; $E_2$ and $E_3$ are each oxygen or the like; and a and b are each a single bond or a double bond); $X^2$ is a divalent group constituting a straight chain moiety; $Z^1$ is a divalent cyclic group or the like; $Z^2$ is a free valency or the like; and $R^2$ is optionally substituted amino or the like.

35 Claims, No Drawings

CYCLIC COMPOUNDS AND USES THEREOF

This application is 371 of PCT/JP00/02825 Apr. 28, 2000.

1. Technical Field

The present invention relates to novel cyclic ring compounds, which possess CCR antagonistic actions, particularly a CCR5 antagonistic action, and uses thereof.

2. Background Art

In recent years, inhibitors of HIV (human immunodeficiency virus) protease have been developed as therapeutic agents against AIDS (acquired immunodeficiency syndrome), and the use of these drugs in combination with the two HIV reverse transcriptase inhibitors, which have been heretofore employed, have brought a remarkable progress in the treatment of AIDS, whereas this progress is not yet sufficient for eradicating AIDS, whereby the development of new anti-AIDS drugs, which act by still another mechanism, has been desired.

CD4 has been known for some time as a receptor through which HIV enters the target cells, while G-protein-coupled, seven trans-membrane chemokine receptors called CCR5 and CXCR4 have recently been found out as the second group of receptors for macrophage-trophic HIV and T-cell-trophic HIV, respectively, and it is speculated that these chemokine receptors play essential roles in the establishment of infection and transmission of HIV. In fact, there is a report that people who remained resistant to HIV infection in spite of repeated exposures were found to have homozygous deletion in CCR5 gene. Therefore, CCR5 antagonists are expected to be new anti-HIV drugs, and examples of synthesizing new anilide derivatives possessing the CCR5-antagonistic activity are described in patent applications such as PCT/JP98/05708 (WO99/32100), Japanese Patent Application No. 1998-234388 (WO00/10965) and Japanese Patent Application No. 1998-363404 (PCT/JP99/07148), whereas there have so far been no report on commercialization of CCR5 antagonists as the therapeutic agents against AIDS.

DISCLOSURE OF THE INVENTION

The present invention is to provide novel bicyclic ring compounds, which are useful as the prophylactic and therapeutic agents against HIV infectious diseases, particularly AIDS, on the basis of CCR antagonistic actions, particularly a CCR5 antagonistic action.

As a result of intensive investigations on compounds possessing a CCR5 antagonistic action, the present inventors have found that compounds represented by the following formula (I) or salts thereof (hereinafter, may be designated as compounds (I)) possess clinically desirable, medicinal effects such as exhibition of CCR antagonistic actions, particularly an excellent CCR5 antagonistic action, and the like, completing the present invention on the basis of this finding.

In other words, the present invention relates to:

(1) A compound represented by formula (I)

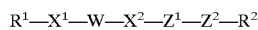

[wherein $R^1$ indicates a 5- to 6-membered cyclic ring group that may be substituted, $X^1$ indicates a bond or a bivalent group, in which the number of atoms constituting the straight-chain portion is 1 to 4, W indicates a bivalent group that is represented by formula

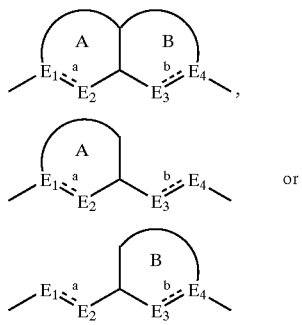

(wherein each of ring A and ring B indicates a 5- to 7-membered cyclic ring group that may be substituted, each of $E_1$ and $E_4$ indicates the carbon atom that may be substituted or the nitrogen atom that may be substituted, each of $E_2$ and $E_3$ indicates the carbon atom that may be substituted or the nitrogen atom that may be substituted, the sulfur atom that may be oxidized or the oxygen atom and each of a and b indicates to be a single bond or a double bond), $X^2$ indicates a bivalent group, in which the number of atoms constituting the straight-chain portion is 1 to 4, $Z^1$ indicates a bond or a bivalent cyclic ring group, $Z^2$ indicates a bond or a bivalent cyclic ring group, in which the number of atoms constituting the straight-chain portion is 1 to 4, and $R^2$ indicates (1) an amino group that may be substituted, where the nitrogen atom may be converted into a quaternary ammonium or the N-oxide, (2) a nitrogen-containing, heterocyclic ring group that may be substituted and may contain the sulfur atom or the oxygen atom as a ring-constituting atom, where the nitrogen atom may be converted into a quaternary ammonium or the N-oxide, (3) a group that is bonded via the sulfur atom, (4) a group represented by formula

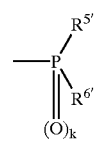

(wherein k indicates 0 or 1, the phosphorus atom may form a phosphonium salt when k is 0, and each of $R^{5'}$ and $R^{6'}$ indicates the hydrocarbon atom that may be substituted, the hydroxyl group that may be substituted or an amino group that may be substituted (preferably, the hydrocarbon atom that may be substituted or an amino group that may be substituted; more preferably the hydrocarbon atom that may be substituted) and $R^{5'}$ and $R^{6'}$ may bind each other to form a cyclic ring group together with the adjacent phosphorus atom), (5) an amidino group that may be substituted or (6) a guanidino group that may be substituted] [provided that, when a group represented by formula $R^1$—$X^1$—W—$X^2$—$Z^1$—$Z^2$— indicates a group represented by formula

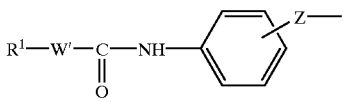

(wherein $R^1$ indicates the same meaning as described above, W' indicates a bivalent group represented by formula

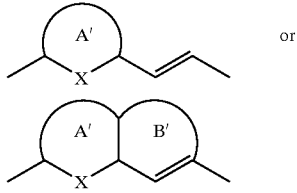

(wherein ring A' indicates a 5- to 6-membered aromatic ring that may be substituted, X indicates the carbon atom that may be substituted, the nitrogen atom that may be substituted, the sulfur atom or the oxygen atom and ring B' indicates a 5- to 7-membered ring that may be substituted) and Z indicates a bivalent group, in which the number of atoms constituting the straight-chain portion is 1 to 4, $R^2$ indicates an amidino group that may be substituted or a guanidino group that may be substituted; when a group represented by formula $R^1-X^1-W-X^2-Z^1-Z^2-$ indicates a group represented by formula

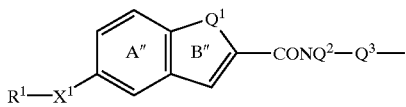

(wherein $R^1$ and $X^1$ indicate the same meanings as described above, ring A" indicates a benzene ring that may be substituted, $Q^1$ indicates a bivalent group, in which ring B" forms a 5- to 7-membered ring, $Q^2$ indicates the hydrogen atom, a hydrocarbon group that may be substituted, a heterocyclic ring group that may be substituted and $Q^3$ indicates a bond or a bivalent group), $R^2$ does not indicate a group represented by formula

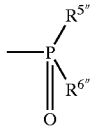

(wherein each of $R^{5''}$ and $R^{6''}$ indicates the hydroxyl group that may be substituted and $R^{5''}$ and $R^{6''}$ may bind each other to form a cyclic ring group together with the adjacent phosphorus atom)], or salts thereof;

(2) A prodrug of the compound or the salt thereof as described in the above-mentioned item (1);

(3) The compound as described in the above-mentioned item (1), wherein $R^1$ is a group that is formed by removing one hydrogen atom from benzene, furan, thiophene, pyridine, cyclopentane, cyclohexane, pyrrolidine, piperidine, piperazine, morpholine, thiomorpholine or tetrahydrofuran, each of which may be substituted;

(4) The compound as described in the above-mentioned item (1), wherein $X^1$ is a phenyl that may be substituted;

(5) The compound as described in the above-mentioned item (1), wherein $R^1$ is a bond, $-(CH_2)_{a'}-$ [a' indicates an integer of 1 to 4], $-(CH_2)_{b'}-X^3-$ [b' indicates an integer of 0 to 3 and $X^3$ indicates an imino group that may be substituted, the carbonyl group, the oxygen atom or the sulfur atom that may be oxidized], $-CH=CH-$, $-C\equiv C-$, $-CO-NH-$ or $-SO_2-NH-$;

(6) The compound as described in the above-mentioned item (1), wherein $X^1$ is a bond;

(7) The compound as described in the above-mentioned item (1), wherein $X^1$ is $-(CH_2)_{b'}-X^3-$ [b' indicates an integer of 0 to 3, and $X^3$ indicates an imino group that may be substituted, the carbonyl group, the oxygen atom or the sulfur atom that may be oxidized];

(8) The compound as described in the above-mentioned item (1), wherein ring A is furan, thiophene, pyrrole, pyridine, pyran or benzene, each of which may be substituted;

(9) The compound as described in the above-mentioned item (1), wherein ring A is a benzene that may be substituted;

(10) The compound as described in the above-mentioned item (1), wherein ring B is a 5- to 7-membered ring that may be substituted at a substitutable optional position, which is represented by formula

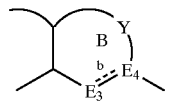

[wherein $E_3$ indicates the carbon atom that may be substituted or the nitrogen atom that may be substituted, $E_4$ indicates the carbon atom that may be substituted or the nitrogen atom, b indicates a single bond or a double bond and Y indicates $-Y'-(CH_2)_{m'}-$ (Y' indicates $-S(O)_m-$ (m indicates an integer of 0 to 2), $-O-$, $-NH-$ or $-CH_2-$, and m' indicates an integer of 0 to 2), $-CH=$, $-CH=CH-$ or $-N=CH-$];

(11) The compound as described in the above-mentioned item (10), wherein Y indicates $-Y'-(CH_2)_2-$ [Y' indicates $-S(O)_m-$ (m indicates an integer of 0 to 2), $-O-$, $-NH-$ or $-CH_2-$];

(12) The compound as described in the above-mentioned item (1), wherein $E_3$ indicates the carbon atom that may be substituted, $E_4$ indicates the carbon atom that may be substituted and b indicates a double bond;

(13) The compound as described in the above-mentioned item (1), wherein $X^2$ is $-(CH_2)_{a'}-$ [a' indicates an integer of 1 to 4], $-(CH_2)_{b'}-X^3-$ [b' indicates an integer of 0 to 3, and $X^3$ indicates an imino group that may be substituted, the carbonyl group, the oxygen atom or the sulfur atom that may be oxidized], $-CH=CH-$, $-C\equiv C-$, $-CO-NH-$ or $-SO_2-NH-$;

(14) The compound as described in the above-mentioned item (1), wherein $X^2$ is $-CO-NH-$;

(15) The compound as described in the above-mentioned item (1), wherein $Z^1$ is (1) a bond or (2) a bivalent cyclic ring group that is formed by removing two hydrogen atoms from benzene, furan, thiophene, pyridine, cyclopentane, cyclohexane, pyrrolidine, piperidine, piperazine, morpholine, thiomorpholine or tetrahydropyran, each of which may be substituted;

(16) The compound as described in the above-mentioned item (1), wherein $Z^1$ is (1) a bond or (2) a bivalent cyclic ring group that is formed by removing two hydrogen atoms from benzene, cyclohexane or piperidine, each of which may be substituted;

(17) The compound as described in the above-mentioned item (1), wherein $Z^1$ is a phenylene that may be substituted;

(18) The compound as described in the above-mentioned item (1), wherein $Z^2$ is a bond or a $C_{1-3}$ alkylene that may be substituted;

(19) The compound as described in the above-mentioned item (1), wherein $Z^2$ is a bivalent group that has a skeleton represented by —Z'—(CH$_2$)n— [Z' indicates —CH(OH)—, —C(O)— or —CH$_2$—, and n indicates an integer of 0 to 2] and may have a substituent at an optional methylene group;

(20) The compound as described in the above-mentioned item (1), wherein $Z^2$ is a bond or a methylene;

(21) The compound as described in the above-mentioned item (1), wherein $Z^1$ is a 6-membered, bicyclic ring group, and $Z^2$ is substituted at the para position of $X^2$;

(22) The compound as described in the above-mentioned item (1), wherein $R^2$ is (1) an amino group that may be substituted, where the nitrogen atom may be converted into a quaternary ammonium or the N-oxide, (2) a nitrogen-containing, heterocyclic ring group that may be substituted and may contain the sulfur atom or the oxygen atom as a ring-constituting atom, where the nitrogen atom may be converted into a quaternary ammonium or the N-oxide, (3) an amidino group that may be substituted or (4) a guanidino group that may be substituted;

(23) The compound as described in the above-mentioned item (1), wherein $R^2$ is an amino group that may be substituted;

(24) The compound as described in the above-mentioned item (1), wherein $R^2$ is an amidino group that may be substituted or a guanidino group that may be substituted;

(25) N-[4-[N-methyl-N-(tetrahydropyran-4-yl)aminomethyl]phenyl]-7-[2-(4-propoxyphenyl)ethoxy]-1,1-dioxo-2,3-dihydro-1-benzothiepine-4-carboxamide, N-[4-[N-methyl-N-(tetrahydropyran-4-yl)aminomethyl]phenyl]-7-[(3-propoxybenzyl)oxy]-1,1-dioxo-2,3-dihydro-1-benzothiepine-4-carboxamide, N-[4-[N-methyl-N-(tetrahydropyran-4-yl)aminomethyl]phenyl]-7-[(2-propoxybenzyl)oxy]-1,1-dioxo-2,3-dihydro-1-benzothiepine-4-carboxamide, N-[4-[N-methyl-N-(tetrahydropyran-4-yl)aminomethyl]phenyl]-7-[(4-propoxyphenyl)methoxy]-1,1-dioxo-2,3-dihydro-1-benzothiepine-4-carboxamide, N-[4-[N-methyl-N-(tetrahydropyran-4-yl)aminomethyl]phenyl]-7-[(4-propoxyethoxyphenyl)methoxy]-1,1-dioxo-2,3-dihydro-1-benzothiepine-4-carboxamide, N-[4-[N-methyl-N-(tetrahydropyran-4-yl)aminomethyl]phenyl]-7-[3-(4-propoxyphenyl)propoxy]-1,1-dioxo-2,3-dihydro-1-benzothiepine-4-carboxamide, or salts thereof;

(26) A prodrug of the compound or salt thereof as described in the above-mentioned item (25);

(27) A pharmaceutical composition comprising the compounds or salt thereof as described in the above-mentioned item (1);

(28) A pharmaceutical composition for CCR antagonisms (preferably, a CCR5 antagonism) which comprises a compound represented by formula

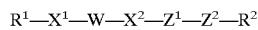

[wherein $R^1$ indicates a 5- to 6-membered cyclic ring group that may be substituted, $X^1$ indicates a bond or a bivalent group, in which the number of atoms constituting the straight-chain portion is 1 to 4, W indicates a bivalent group that is represented by formula

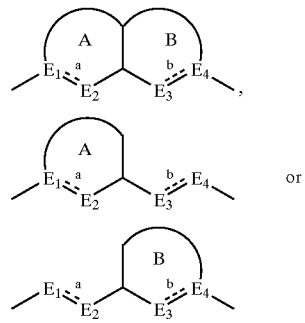

(wherein each of ring A and ring B indicates a 5- to 7-membered cyclic ring group that may be substituted, each of $E_1$ and $E_4$ indicates the carbon atom that may be substituted or the nitrogen atom that may be substituted, each of $E_2$ and $E_3$ indicates the carbon atom that may be substituted or the nitrogen atom that may be substituted, the sulfur atom that may be oxidized or the oxygen atom and each of a and b indicates to be a single bond or a double bond), $X^2$ indicates a bivalent group, in which the number of atoms constituting the straight-chain portion is 1 to 4, $Z^1$ indicates a bond or a bivalent cyclic ring group, $Z^2$ indicates a bond or a bivalent cyclic ring group, in which the number of atoms constituting the straight-chain portion is 1 to 4, and $R^2$ indicates (1) an amino group that may be substituted, where the nitrogen atom may be converted into a quaternary ammonium or the N-oxide, (2) a nitrogen-containing, heterocyclic ring group that may be substituted and may contain the sulfur atom or the oxygen atom as a ring-constituting atom, where the nitrogen atom may be converted into a quaternary ammonium or the N-oxide, (3) a group that bonded via the sulfur atom, (4) a group represented by formula

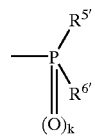

(wherein k indicates 0 or 1, the phosphorus atom may form a phosphonium salt when k is 0, and each of $R^{5'}$ and $R^{6'}$ indicates the hydrocarbon atom that may be substituted, the hydroxyl group that may be substituted or an amino group that may be substituted and $R^{5'}$ and $R^{6'}$ may bind each other to form a cyclic ring group together with the adjacent phosphorus atom), (5) an amidino group that may be substituted or (6) a guanidino group that may be substituted] [provided that, when a group represented by formula $R^1$—$X^1$—W—$X^2$—$Z^1$—$Z^2$— indicates a group represented by formula

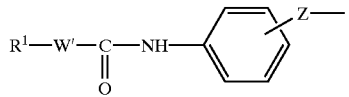

(wherein $R^1$ indicates the same meaning as described above, W' indicates a bivalent group represented by formula

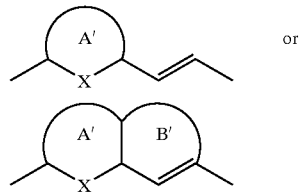

(wherein ring A' indicates a 5- to 6-membered aromatic ring that may be substituted, X indicates the carbon atom that may be substituted, the nitrogen atom that may be substituted, the sulfur atom or the oxygen atom and ring B' indicates a 5- to 7-membered ring that may be substituted) and Z indicates a bivalent group, in which the number of atoms constituting the straight-chain portion is 1 to 4), $R^2$ indicates an amidino group that may be substituted or a guanidino group that may be substituted], or salts thereof;

(29) The composition as described in the above-mentioned item (28) which is a prophylactic/therapeutic agent of HIV infectious diseases;

(30) The composition as described in the above-mentioned item (28) which is a prophylactic/therapeutic agent of AIDS;

(31) The composition as described in the above-mentioned item (28) which is a depressant against the pathologic progress of AIDS;

(32) The composition as described in the above-mentioned item (29) which is in combination with a protease inhibitor and/or a reverse transcriptase inhibitor;

(33) The composition as described in the above-mentioned item (32), wherein the reverse transcriptase inhibitor is zidovudine, didanosine, zalcitabine, lamivudine, stavudine, nevirapine, delavirdine, efavirenz or abacavir;

(34) The composition as described in the above-mentioned item (32), wherein the protease inhibitor is saquinavir, ritonavir, indinavir, amprenavir or nelfinavir;

(35) Use of a compound represented by formula $R^1$—$X^1$—W—$X^2$—$Z^1$—$Z^2$—$R^2$

[wherein $R^1$ indicates a 5- to 6-membered cyclic ring group that may be substituted, $X^1$ indicates a bond or a bivalent group, in which the number of atoms constituting the straight-chain portion is 1 to 4, W indicates a bivalent group that is represented by formula

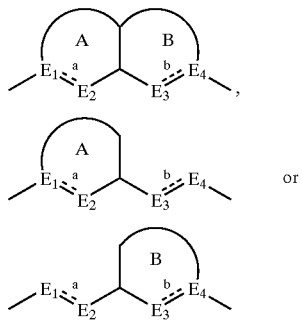

(wherein each of ring A and ring B indicates a 5- to 7-membered cyclic ring group that may be substituted, each of $E_1$ and $E_4$ indicates the carbon atom that may be substituted or the nitrogen atom that may be substituted, each of $E_2$ and $E_3$ indicates the carbon atom that may be substituted or the nitrogen atom that may be substituted, the sulfur atom that may be oxidized or the oxygen atom and each of a and b indicates to be a single bond or a double bond), $X^2$ indicates a bivalent group, in which the number of atoms constituting the straight-chain portion is 1 to 4, $Z^1$ indicates a bond or a bivalent cyclic ring group, $Z^2$ indicates a bond or a bivalent cyclic ring group, in which the number of atoms constituting the straight-chain portion is 1 to 4, and $R^2$ indicates (1) an amino group that may be substituted, where the nitrogen atom may be converted into a quaternary ammonium or the N-oxide, (2) a nitrogen-containing, heterocyclic ring group that may be substituted and may contain the sulfur atom or the oxygen atom as a ring-constituting atom, where the nitrogen atom may be converted into a quaternary ammonium or the N-oxide, (3) a group that bonded via the sulfur atom, (4) a group represented by formula

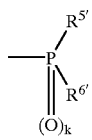

(wherein k indicates 0 or 1, the phosphorus atom may form a phosphonium salt when k is 0, and each of $R^{5'}$ and $R^{6'}$ indicates the hydrocarbon atom that may be substituted, the hydroxyl group that may be substituted or an amino group that may be substituted and $R^{5'}$ and $R^{6'}$ may bind each other to form a cyclic ring group together with the adjacent phosphorus atom), (5) an amidino group that may be substituted or (6) a guanidino group that may be substituted] [provided that, when a group represented by formula $R^1$—$X^1$—W—$X^2$—$Z^1$—$Z^2$— indicates a group represented by formula

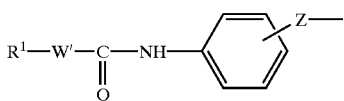

(wherein $R^1$ indicates the same meaning as described above, W' indicates a bivalent group represented by formula

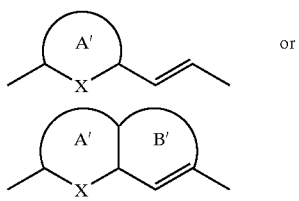

(wherein ring A' indicates a 5- to 6-membered aromatic ring that may be substituted, X indicates the carbon atom that may be substituted, the nitrogen atom that may be substituted, the sulfur atom or the oxygen atom and ring B' indicates a 5- to 7-membered ring that may be substituted) and Z indicates a bivalent group, in which the number of atoms constituting the straight-chain portion is 1 to 4), $R^2$ indicates an amidino group that may be substituted or a guanidino group that may be substituted], or salts thereof, together with a protease inhibitor and/or a reverse transcriptase inhibitor for preventing and/or treating HIV infectious diseases;

(36) A method for antagonizing CCR (preferably, a method for antagonizing CCR5), which comprises administrating an effective dose of the compound or a salt thereof as described in the above-mentioned item (28) to the mammals;

(37) Use of the compound or a salt thereof as described in the above-mentioned item (28) for manufacturing a medicine for the CCR antagonism (preferably, the CCR5 antagonism); and the like.

"A 5- to 6-membered cyclic ring" of "a 5- to 6-membered cyclic ring group that may be substituted", which is indicated by $R^1$ in the above-mentioned formula (I), is exemplified by a group that is formed by removing one hydrogen atom from a 6-membered aromatic hydrocarbon such as benzene or the like, a 5- to 6-membered aliphatic hydrocarbon such as cyclopentane, cyclohexane, cyclopentene, cyclohexene, cyclopentadiene, cyclohexadiene or the like, a 5- to 6-membered, aromatic heterocyclic ring, which contains 1 to 4 heteroatoms of 1 to 2 kinds selected from the nitrogen atom, the sulfur atom and the oxygen atom, such as furan, thiophene, pyrrole, imidazole, pyrazole, thiazole, oxazole, isothiazole, isoxazole, tetrazole, pyridine, pyrazine, pyrimidine, pyridazine, triazole or the like, a 5- to 6-membered, non-aromatic heterocyclic ring, which contains 1 to 4 heteroatoms of 1 to 2 kinds selected from the nitrogen atom, the sulfur atom and the oxygen atom, such as tetrahydrofuran, tetrahydrothiophene, dithiolan, oxathiolan, pyrrolidine, pyrroline, imidazolidine, imidazoline, pyrazolidine, pyrazoline, piperidine, piperazine, oxazine, oxadiazine, thiazine, thiadiazine, morpholine, thiomorpholine, pyran, tetrahydropyran, tetrahydrothiopyran or the like, or the like, where as for "a 5- to 6-membered cyclic ring" is preferably benzene, furan, thiophene, pyridine, cyclopentane, cyclohexane, pyrrolidine, piperidine, piperazine, morpholine, thiomorpholine, tetrahydropyran (preferably, a 6-membered cyclic ring) or the like, particularly benzene.

Examples of "a substituent" that may be possessed by "a 5- to 6-membered cyclic ring" of "a 5- to 6-membered cyclic ring group that may be substituted", which is indicated by $R^1$ in the above-mentioned formula (I), to be used include a halogen atom, nitro, cyano, an alkyl that may be substituted, a cycloalkyl that may be substituted, the hydroxyl group that may be substituted, the thiol group that may be substituted (the sulfur atom may be oxidized to form a sulfinyl group that may be substituted or a sulfonyl group that may be substituted), an amino group that may be substituted, an acyl that may be substituted, the carboxyl group that may be substituted, an aromatic group that may be substituted and the like.

A halogen as a substituent of $R^1$ is exemplified by fluorine, chlorine, bromine, iodine or the like, where fluorine and chlorine are particularly preferable.

An alkyl for an alkyl that may be substituted as a substituent of $R^1$ is exemplified by a straight-chain or branched alkyl having a carbon number of 1 to 10, for example, a $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl or the like, preferably a lower ($C_{1-6}$)alkyl. A substituent in said alkyl that may be substituted is exemplified by a halogen (for example, fluorine, chlorine, bromine, iodine or the like), nitro, cyano, the hydroxyl group, the thiol group that may be substituted (for example, thiol, a $C_{1-4}$ alkylthio or the like), an amino group that may be substituted (for example, amino, a mono-$C_{1-4}$ alkylamino, a di-$C_{1-4}$ alkylamino, a 5- to 6-membered cyclic ring amino such as tetrahydropyrrole, piperazine, piperidine, morpholine, thiomorpholine, pyrrole, imidazole or the like, or the like), the carboxyl group that may be esterified or amidated (for example, carboxyl, a $C_{1-4}$ alkoxycarbonyl, carbamoyl, a mono-$C_{1-4}$ alkylcarbamoyl, a di-$C_{1-4}$ alkylcarbamoyl or the like), a $C_{1-4}$ alkoxyl that may be halogenated (for example, methoxy, ethoxy, propoxy, butoxy, trifluoromethoxy, trifluoroethoxy or the like), a $C_{1-4}$ alkoxy-$C_{1-4}$ alkoxyl that may be halogenated (for example, methoxymethoxy, methoxyethoxy, ethoxyethoxy, trifluoromethoxyethoxy, trifluoroethoxyethoxy or the like), formyl, a $C_{2-4}$ alkanoyl (for example, acetyl, propionyl or the like), a $C_{1-4}$ alkylsulfonyl (for example, methanesulfonyl, ethanesulfonyl or the like) or the like, where the number of the substituents is preferably 1 to 3.

A cycloalkyl for a cycloalkyl that may be substituted as a substituent of $R^1$ is exemplified by, for example, a $C_{3-7}$ cycloalkyl such as cyclopropyl, cyclobutyl, cyclopentyl, cyclohexyl, cycloheptyl or the like. A substituent in said cycloalkyl that may be substituted is exemplified by a halogen (for example, fluorine, chlorine, bromine, iodine or the like), nitro, cyano, the hydroxyl group, the thiol group that may be substituted (for example, thiol, a $C_{1-4}$ alkylthio or the like), an amino group that may be substituted (for example, amino, a mono-$C_{1-4}$ alkylamino, a di-$C_{1-4}$ alkylamino, a 5- to 6-membered cyclic ring amino such as tetrahydropyrrole, piperazine, piperidine, morpholine, thiomorpholine, pyrrole, imidazole or the like, or the like), the carboxyl group that may be esterified or amidated (for example, carboxyl, a $C_{1-4}$ alkoxycarbonyl, carbamoyl, a mono-$C_{1-4}$ alkylcarbamoyl, a di-$C_{1-4}$ alkylcarbamoyl or the like), a $C_{1-4}$ alkoxyl that may be halogenated (for example, methoxy, ethoxy, propoxy, butoxy, trifluoromethoxy, trifluoroethoxy or the like), a $C_{1-4}$ alkoxy-$C_{1-4}$ alkoxyl that may be halogenated (for example, methoxymethoxy, methoxyethoxy, ethoxyethoxy, trifluoromethoxyethoxy, trifluoroethoxyethoxy or the like), formyl, a $C_{2-4}$ alkanoyl (for example, acetyl, propionyl or the like), a $C_{1-4}$ alkylsulfonyl (for example, methanesulfonyl, ethanesulfonyl or the like) or the like, where the number of the substituents is preferably 1 to 3.

A substituent for the hydroxyl group that may be substituted as a substituent of $R^1$ is exemplified by a substituent such as (1) an alkyl that may be substituted (for example, a $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl or the like, preferably a lower ($C_{1-6}$)alkyl, or the like is exemplified);

(2) a cycloalkyl that may be substituted and may contain heteroatoms (for example, a $C_{3-7}$ cycloalkyl such as cyclopropyl, cyclobutyl, cyclopentyl, cyclohexyl, cycloheptyl or the like; a saturated, 5- to 6-membered heterocyclic ring group containing 1 to 2 heteroatoms such as tetrahydrofuranyl, tetrahydrothienyl, pyrrolidinyl, pyrazolidinyl, piperidyl, piperazinyl, morpholinyl, thiomorpholinyl, tetrahydropyranyl, tetrahydrothiopyranyl or the like (preferably, tetrahydropyranyl or the like); or the like is exemplified);

(3) an alkenyl that may be substituted (for example, an alkenyl that has the carbon number of 2 to 10 such as allyl, crotyl, 2-pentenyl, 3-hexenyl or the like, preferably a lower ($C_{2-6}$)alkenyl, or the like is exemplified);

(4) a cycloalkenyl that may be substituted (for example, an cycloalkenyl that has the carbon number of 3 to 7 such as 2-cyclopentenyl, 2-cyclohexenyl 2-cyclopentenylmethyl, 2-cyclohexenylmethyl or the like, or the like is exemplified);

(5) an aralkyl that may be substituted (for example, a phenyl-$C_{1-4}$ alkyl (for example, benzyl, phenethyl or the like) or the like is exemplified);

(6) formyl or an acyl that may be substituted (for example, an alkanoyl that has the carbon number of 2 to 4 (for example, acetyl, propionyl, butyryl, isobutyryl or the like), an alkylsulfonyl that has the carbon number of 1 to 4 (for example, methanesulfonyl, ethanesulfonyl or the like) or the like is exemplified); and (7) an aryl that may be substituted (for example, phenyl, naphthyl or the like is exemplified), where examples of the substituents that may be possessed by (1) an alkyl that may be substituted, (2) a cycloalkyl that may be substituted, (3) an alkenyl that may be substituted, (4) a cycloalkenyl that may be substituted, (5) an aralkyl that may be substituted, (6) an acyl that may be substituted and (7) an aryl that may be substituted, which are described above, include a halogen (for example, fluorine, chlorine, bromine, iodine or the like), nitro, cyano, the hydroxyl group, the thiol group that may be substituted (for example, thiol, a $C_{1-4}$ alkylthio or the like), an amino group that may be substituted (for example, amino, a mono-$C_{1-4}$ alkylamino, a di-$C_{1-4}$ alkylamino, a 5- to 6-membered cyclic ring amino such as tetrahydropyrrole, piperazine, piperidine, morpholine, thiomorpholine, pyrrole, imidazole or the like, or the like), the carboxyl group that may be esterified or amidated (for example, carboxyl, a $C_{1-4}$ alkoxycarbonyl, carbamoyl, a mono-$C_{1-4}$ alkylcarbamoyl, a di-$C_{1-4}$ alkylcarbamoyl or the like), a $C_{1-4}$ alkyl that may be halogenated (for example, trifluoromethyl, methyl, ethyl or the like), a $C_{1-6}$ alkoxyl that may be halogenated (for example, methoxy, ethoxy, propoxy, butoxy, trifluoromethoxy, trifluoroethoxy or the like; preferably, a $C_{1-4}$ alkoxyl that may be halogenated), formyl, a $C_{2-4}$ alkanoyl (for example, acetyl, propionyl or the like), a $C_{1-4}$ alkylsulfonyl (for example, methanesulfonyl, ethanesulfonyl or the like), a 5- to 6-membered, aromatic heterocyclic ring that may be substituted [for example, an aromatic heterocyclic ring, which contains 1 to 4 heteroatoms of 1 to 2 kinds selected from the nitrogen atom, the sulfur atom and the oxygen atom, such as furan, thiophene, pyrrole, imidazole, pyrazole, thiazole, oxazole, isothiazole, isoxazole, tetrazole, pyridine, pyrazine, pyrimidine, pyridazine, triazole or the like; the substituent that may be possessed by said heteroaromatic ring is exemplified by a halogen (for example, fluorine, chlorine, bromine, iodine or the like), nitro, cyano, the hydroxyl group, the thiol group, an amino group, the carboxyl group, a $C_{1-4}$ alkyl that may be halogenated (for example, trifluoromethyl, methyl, ethyl or the like), a $C_{1-6}$ alkoxyl that may be halogenated (for example, methoxy, ethoxy, propoxy, butoxy, trifluoromethoxy, trifluoroethoxy or the like), formyl, a $C_{2-4}$ alkanoyl (for example, acetyl, propionyl or the like), a $C_{1-4}$ alkylsulfonyl (for example, methanesulfonyl, ethanesulfonyl or the like), where the number of the substituents is preferably 1 to 3.], or the like, where the number of the substituents is preferably 1 to 3.

A substituent for the thiol group that may be substituted as a substituent of $R^1$ is exemplified by a substituent similar to "a substituent for the hydroxyl group that may be substituted as a substituent of $R^1$", among which preferable is (1) an alkyl that may be substituted (for example, a $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl or the like, preferably a lower ($C_{1-6}$)alkyl, or the like is exemplified);

(2) a cycloalkyl that may be substituted and may contain heteroatoms (for example, a $C_{3-7}$ cycloalkyl such as cyclopropyl, cyclobutyl, cyclopentyl, cyclohexyl, cycloheptyl or the like is exemplified);

(3) an aralkyl that may be substituted (for example, a phenyl-$C_{1-4}$ alkyl (for example, benzyl, phenethyl or the like) or the like is exemplified); and (4) an aryl that may be substituted (for example, phenyl, naphthyl or the like is exemplified), where examples of the substituents that may be possessed by (1) an alkyl that may be substituted, (2) a cycloalkyl that may be substituted, (3) an aralkyl that may be substituted and (4) an aryl that may be substituted, which are described above, include a halogen (for example, fluorine, chlorine, bromine, iodine or the like), nitro, cyano, the hydroxyl group, the thiol group that may be substituted (for example, thiol, a $C_{1-4}$ alkylthio or the like), an amino group that may be substituted (for example, amino, a mono-$C_{1-4}$ alkylamino, a di-$C_{1-4}$ alkylamino, a 5- to 6-membered cyclic ring amino such as tetrahydropyrrole, piperazine, piperidine, morpholine, thiomorpholine, pyrrole, imidazole or the like, or the like), the carboxyl group that may be esterified or amidated (for example, carboxyl, a $C_{1-4}$ alkoxycarbonyl, carbamoyl, a mono-$C_{1-4}$ alkylcarbamoyl, a di-$C_{1-4}$ alkylcarbamoyl or the like), a $C_{1-4}$ alkoxyl that may be halogenated (for example, methoxy, ethoxy, propoxy, butoxy, trifluoromethoxy, trifluoroethoxy or the like), a $C_{1-4}$ alkoxy-$C_{1-4}$ alkoxyl that may be halogenated (for example, methoxymethoxy, methoxyethoxy, ethoxyethoxy, trifluoromethoxyethoxy, trifluoroethoxyethoxy or the like), formyl, a $C_{2-4}$ alkanoyl (for example, acetyl, propionyl or the like), a $C_{1-4}$ alkylsulfonyl (for example, methanesulfonyl, ethanesulfonyl or the like), where the number of the substituents is preferably 1 to 3.

A substituent for an amino group that may be substituted as a substituent of $R^1$ is exemplified by an amino group that may have 1 to 2 substituents similar to "a substituent for the hydroxyl group that may be substituted as a substituent of $R^1$", among which preferable is (1) an alkyl that may be substituted (for example, a $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl or the like, preferably a lower ($C_{1-6}$)alkyl, or the like is exemplified);

(2) a cycloalkyl that may be substituted and may contain heteroatoms (for example, a $C_{3-7}$ cycloalkyl such as cyclopropyl, cyclobutyl, cyclopentyl, cyclohexyl, cycloheptyl or the like);

(3) an alkenyl that may be substituted (for example, an alkenyl that has the carbon number of 2 to 10 such as allyl, crotyl, 2-pentenyl, 3-hexenyl or the like, preferably a lower ($C_{2-6}$)alkenyl, or the like is exemplified);

(4) a cycloalkenyl that may be substituted (for example, an cycloalkenyl that has the carbon number of 3 to 7 such as 2-cyclopentenyl, 2-cyclohexenyl 2-cyclopentenylmethyl, 2-cyclohexenylmethyl or the like, or the like is exemplified);

(5) formyl, or an acyl that may be substituted (for example, an alkanoyl that has the carbon number of 2 to 4 (for example, acetyl, propionyl, butyryl, isobutyryl or the like), an alkylsulfonyl that has the carbon number of 1 to 4 (for example, methanesulfonyl, ethanesulfonyl or the like) or the like is exemplified); and (6) an aryl that may be substituted (for example, phenyl, naphthyl or the like is exemplified), where examples of the substituents that may be possessed by (1) an alkyl that may be substituted, (2) a cycloalkyl that may be substituted, (3) an alkenyl that may be substituted, (4) a cycloalkenyl that may be substituted, (5) an acyl that may be substituted and (6) an aryl that may be substituted, which are described above, include a halogen (for example, fluorine, chlorine, bromine, iodine or the like), nitro, cyano, the hydroxyl group, the thiol group that may be substituted (for example, thiol, a $C_{1-4}$ alkylthio or the like), an amino group that may be substituted (for example, amino, a mono-$C_{1-4}$ alkylamino, a di-$C_{1-4}$ alkylamino, a 5- to 6-membered cyclic ring amino such as tetrahydropyrrole, piperazine, piperidine, morpholine, thiomorpholine, pyrrole, imidazole or the like, or the like), the carboxyl group that may be esterified or amidated (for example, carboxyl, a $C_{1-4}$ alkoxycarbonyl, carbamoyl, a mono-$C_{1-4}$ alkylcarbamoyl, a di-$C_{1-4}$ alkylcarbamoyl or the like), a $C_{1-6}$ alkoxyl that may be halogenated (for example, methoxy, ethoxy, propoxy, butoxy, trifluoromethoxy, trifluoroethoxy or the like), formyl, a $C_{2-4}$ alkanoyl (for example, acetyl, propionyl or the like), a $C_{1-4}$ alkylsulfonyl (for example, methanesulfonyl, ethanesulfonyl or the like), where the number of the substituents is preferably 1 to 3.

Also, as for the substituents for an amino group that may be substituted as a substituent of $R^1$, the substituents for the amino group may bind together to form a cyclic ring amino group (for example, a cyclic ring amino group that is formed by removing one hydrogen from the nitrogen atom constituting the ring of a 5- to 6-membered cyclic ring such as tetrahydropyrrole, piperazine, piperidine, morpholine, thiomorpholine, pyrrole, imidazole or the like, and has a bond on the nitrogen atom). Said cyclic ring amino group may have substituents, and such substituents are exemplified by a halogen (for example, fluorine, chlorine, bromine, iodine or the like), nitro, cyano, the hydroxyl group, the thiol group that may be substituted (for example, thiol, a $C_{1-4}$ alkylthio or the like), an amino group that may be substituted (for example, amino, a mono-$C_{1-4}$ alkylamino, a di-$C_{1-4}$ alkylamino, a 5- to 6-membered cyclic ring amino such as tetrahydropyrrole, piperazine, piperidine, morpholine, thiomorpholine, pyrrole, imidazole or the like, or the like), the carboxyl group that may be esterified or amidated (for example, carboxyl, a $C_{1-4}$ alkoxycarbonyl, carbamoyl, a mono-$C_{1-4}$ alkylcarbamoyl, a di-$C_{1-4}$ alkylcarbamoyl or the like), a $C_{1-6}$ alkoxyl that may be halogenated (for example, methoxy, ethoxy, propoxy, butoxy, trifluoromethoxy, trifluoroethoxy or the like), a $C_{1-4}$ alkoxy-$C_{1-4}$ alkoxyl that may be halogenated (for example, methoxymethoxy, methoxyethoxy, ethoxyethoxy, trifluoromethoxyethoxy, trifluoroethoxyethoxy or the like), formyl, a $C_{2-4}$ alkanoyl (for example, acetyl, propionyl or the like), a $C_{1-4}$ alkylsulfonyl (for example, methanesulfonyl, ethanesulfonyl or the like), where the number of the substituents is preferably 1 to 3.

An acyl that may be substituted as a substituent of $R^1$ is exemplified by a group, wherein the carbonyl group or the sulfonyl group is bonded with (1) hydrogen, (2) an alkyl that may be substituted (for example, a $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl or the like, preferably a lower ($C_{1-6}$)alkyl, or the like is exemplified);

(3) a cycloalkyl that may be substituted and may contain heteroatoms (for example, a $C_{3-7}$ cycloalkyl such as cyclopropyl, cyclobutyl, cyclopentyl, cyclohexyl, cycloheptyl or the like);

(4) an alkenyl that may be substituted (for example, an alkenyl that has the carbon number of 2 to 10 such as allyl, crotyl, 2-pentenyl, 3-hexenyl or the like, preferably a lower ($C_{2-6}$)alkenyl, or the like is exemplified);

(5) a cycloalkenyl that may be substituted (for example, a cycloalkenyl that has the carbon number of 3 to 7 such as 2-cyclopentenyl, 2-cyclohexenyl, 2-cyclopentenylmethyl, 2-cyclohexenylmethyl or the like, or the like is exemplified); or (6) a 5- to 6-membered, monocyclic ring aromatic group (for example, phenyl, pyridyl or the like is exemplified) that is bonded with the carbonyl group or the sulfonyl group, (for example, acetyl, propionyl, butyryl, isobutyryl, valeryl, isovaleryl, pivaloyl, hexanoyl, heptanoyl, octanoyl, cyclobutanecarbonyl, cyclopentanecarbonyl, cyclohexanecarbonyl, cycloheptanecarbonyl, crotonyl, 2-cyclohexenecarbonyl, benzoyl, nicotinoyl, methanesulfonyl, ethanesulfonyl or the like), where examples of the substituents that may be possessed by (2) an alkyl that may be substituted, (3) a cycloalkyl that may be substituted, (4) an alkenyl that may be substituted, (5) a cycloalkenyl that may be substituted and (6) a 5- to 6-membered, monocyclic ring aromatic group that may be substituted, which are described above, include a halogen (for example, fluorine, chlorine, bromine, iodine or the like), nitro, cyano, the hydroxyl group, the thiol group that may be substituted (for example, thiol, a $C_{1-4}$ alkylthio or the like), an amino group that may be substituted (for example, amino, a mono-$C_{1-4}$ alkylamino, a di-$C_{1-4}$ alkylamino, a 5- to 6-membered cyclic ring amino such as tetrahydropyrrole, piperazine, piperidine, morpholine, thiomorpholine, pyrrole, imidazole or the like, or the like), the carboxyl group that may be esterified or amidated (for example, carboxyl, a $C_{1-4}$ alkoxycarbonyl, carbamoyl, a mono-$C_{1-4}$ alkylcarbamoyl, a di-$C_{1-4}$ alkylcarbamoyl or the like), a $C_{1-6}$ alkoxyl that may be halogenated (for example, methoxy, ethoxy, propoxy, butoxy, trifluoromethoxy, trifluoroethoxy or the like), a $C_{1-4}$ alkoxy-$C_{1-4}$ alkoxyl that may be halogenated (for example, methoxymethoxy, methoxyethoxy, ethoxyethoxy, trifluoromethoxyethoxy, trifluoroethoxyethoxy or the like), formyl, a $C_{2-4}$ alkanoyl (for example, acetyl, propionyl or the like), a $C_{1-4}$ alkylsulfonyl (for example, methanesulfonyl, ethanesulfonyl or t he like), where the number of the substituents is preferably 1 to 3.

The carbonyl group that may be esterified as a substituent of $R^1$ is exemplified by a group, wherein the carbonyloxy group is bonded with (1) hydrogen,
(2) an alkyl that may be substituted (for example, a $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl or the like, preferably a lower ($C_{1-6}$)alkyl, or the like is exemplified);
(3) a cycloalkyl that may be substituted and may contain heteroatoms (for example, a $C_{3-7}$ cycloalkyl such as cyclopropyl, cyclobutyl, cyclopentyl, cyclohexyl, cycloheptyl or the like);
(4) an alkenyl that may be substituted (for example, an alkenyl that has the carbon number of 2 to 10 such as allyl, crotyl, 2-pentenyl, 3-hexenyl or the like, preferably a lower ($C_{2-6}$)alkenyl, or the like is exemplified);
(5) a cycloalkenyl that may be substituted (for example, a cycloalkenyl that has the carbon number of 3 to 7 such as 2-cyclopentenyl, 2-cyclohexenyl, 2-cyclopentenylmethyl, 2-cyclohexenylmethyl or the like, or the like is exemplified); or
(6) an aryl that may be substituted (for example, phenyl, naphthyl or the like is exemplified), preferably carboxyl, a lower ($C_{1-6}$)alkoxycarbonyl and an aryloxycarbonyl (for example, methoxycarbonyl, ethoxycarbonyl, propoxycarbonyl, phenoxycarbonyl, naphthoxycarbonyl or the like), where examples of the substituents that may be possessed by (2) an alkyl that may be substituted, (3) a cycloalkyl that may be substituted, (4) an alkenyl that may be substituted, (5) a cycloalkenyl that may be substituted and (6) an aryl that may be substituted, which are described above, include a halogen (for example, fluorine, chlorine, bromine, iodine or the like), nitro, cyano, the hydroxyl group, the thiol group that may be substituted (for example, thiol, a $C_{1-4}$ alkylthio or the like), an amino group that may be substituted (for example, amino, a mono-$C_{1-4}$ alkylamino, a di-$C_{1-4}$ alkylamino, a 5- to 6-membered cyclic ring amino such as tetrahydropyrrole, piperazine, piperidine, morpholine, thiomorpholine, pyrrole, imidazole or the like, or the like), the carboxyl group that may be esterified or amidated (for example, carboxyl, a $C_{1-4}$ alkoxycarbonyl, carbamoyl, a mono-$C_{1-4}$ alkylcarbamoyl, a di-$C_{1-4}$ alkylcarbamoyl or the like), a $C_{1-6}$ alkoxyl that may be halogenated (for example, methoxy, ethoxy, propoxy, butoxy, trifluoromethoxy, trifluoroethoxy or the like), a $C_{1-4}$ alkoxy-$C_{1-4}$ alkoxyl that may be halogenated (for example, methoxymethoxy, methoxyethoxy, ethoxyethoxy, trifluoromethoxyethoxy, trifluoroethoxyethoxy or the like), formyl, a $C_{2-4}$ alkanoyl (for example, acetyl, propionyl or the like), a $C_{1-4}$ alkylsulfonyl (for example, methanesulfonyl, ethanesulfonyl or the like), where the number of the substituents is preferably 1 to 3.

The aromatic group for an aromatic group that may be substituted as a substituent of $R^1$ is exemplified by a 5- to 6-membered, same element or heterocyclic ring, aromatic group such as phenyl, pyridyl, furyl, thienyl, pyrrolyl, imidazolyl, pyrazolyl, thiazolyl, oxazolyl, isothiazolyl, isooxazolyl, tetrazolyl, pyrazinyl, pyrimidinyl, pyridazinyl, triazinyl or the like, a condensed, heterocyclic ring aromatic group such as benzofuran, indole, benzothiophene, benzoxazole, benzthiazole, indazole, benzimidazole, quinoline, isoquinoline, quinoxaline, phthalazine, quinazoline, cinnoline or the like, or the like. Examples of the substituents for these aromatic groups include a halogen (for example, fluorine, chlorine, bromine, iodine or the like), nitro, cyano, the hydroxyl group, the thiol group that may be substituted (for example, thiol, a $C_{1-4}$ alkylthio or the like), an amino group that may be substituted (for example, amino, a mono-$C_{1-4}$ alkylamino, a di-$C_{1-4}$ alkylamino, a 5- to 6-membered cyclic ring amino such as tetrahydropyrrole, piperazine, piperidine, morpholine, thiomorpholine, pyrrole, imidazole or the like, or the like), the carboxyl group that may be esterified or amidated (for example, carboxyl, a $C_{1-4}$ alkoxycarbonyl, carbamoyl, a mono-$C_{1-4}$ alkylcarbamoyl, a di-$C_{1-4}$ alkylcarbamoyl or the like), a $C_{1-4}$ alkyl that may be halogenated (for example, trifluoromethyl, methyl, ethyl or the like), a $C_{1-6}$ alkoxyl that may be halogenated (for example, methoxy, ethoxy, propoxy, butoxy, trifluoromethoxy, trifluoroethoxy or the like), formyl, a $C_{2-4}$ alkanoyl (for example, acetyl, propionyl or the like), a $C_{1-4}$ alkylsulfonyl (for example, methanesulfonyl, ethanesulfonyl or the like), where the number of the substituents is preferably 1 to 3.

Such a substituent of $R^1$ may be substituted at any position of 1 to 4 (preferably, 1 to 2) of the same or different cyclic rings. Also, in the case where "a 5- to 6-membered cyclic ring" of "a 5- to 6-membered cyclic ring that may be substituted", which is indicated by $R^1$, has 2 or more substituents, 2 substituents of them may be bonded together to form, for example, a lower ($C_{1-6}$)alkylene (for example, trimethylene, tetramethylene or the like), a lower ($C_{1-6}$) alkyleneoxy (for example, $-CH_2-O-CH_2-$, $-O-CH_2-CH_2-$, $-O-CH_2-CH_2-CH_2-$, $-O-CH_2-CH_2-CH_2-CH_2-$, $-O-C(CH_3)(CH_3)-CH_2-CH_2-$ or the like), a lower ($C_{1-6}$)alkylenethio (for example, $-CH_2-S-CH_2-$, $-S-CH_2-CH_2-$, $-S-CH_2-CH_2-CH_2-$, $-S-CH_2-CH_2-CH_2-CH_2-$, $-S-C(CH_3)(CH_3)-CH_2-CH_2-$ or the like), a lower ($C_{1-6}$)alkylenedioxy (for example, $-O-CH_2-O-$, $-O-CH_2-CH_2-O-$, $-O-CH_2-CH_2-CH_2-O-$ or the like), a lower ($C_{1-6}$)alkylenedithio (for example, $-S-CH_2-S-$, $-S-CH_2-CH_2-S-$, $-S-CH_2-CH_2-CH_2-S-$ or the like), an oxy-lower ($C_{1-6}$) alkylenamino (for example, $-O-CH_2-NH-$, $-O-CH_2-CH_2-NH-$ or the like), an oxy-lower ($C_{1-6}$) alkylenethio (for example, $-O-CH_2-S-$, $-O-CH_2-CH_2-S-$ or the like), a lower ($C_{1-6}$)alkylenamino (for example, $-NH-CH_2-CH_2-$, $-NH-CH_2-CH_2-CH_2-$ or the like), a lower ($C_{1-6}$)alkylenediamino (for example, $-NH-CH_2-NH-$, $-NH-CH_2-CH_2-NH-$ or the like), a thia-lower ($C_{1-6}$)alkylenamino (for example, $-S-CH_2-NH-$, $-S-CH_2-CH_2-NH-$ or the like), a lower ($C_{2-6}$)alkenylene (for example, $-CH_2-CH=CH-$, $-CH_2-CH_2-CH=CH-$, $-CH_2-CH=CH-CH_2-CH_2-$ or the like), a lower ($C_{4-6}$) alkadienylene (for example, $-CH=CH-CH=CH-$ or the like) or the like.

Furthermore, the bivalent group that is formed by binding each other 2 substituents of $R^1$ may have 1 to 3 substituents similar to "the substituent" that may be possessed by "a 5- to 6-membered cyclic ring" of "a 5- to 6-membered cyclic ring that may be substituted", which is indicated by $R^1$, (a halogen atom, nitro, cyano, an alkyl that may be substituted, a cycloalkyl that may be substituted, the hydroxyl group that may be substituted, the thiol group that may be substituted (the sulfur atom may be oxidized to form a sulfinyl group that may be substituted or a sulfonyl group that may be substituted), an amino group that may be substituted, an acyl that may be substituted, the carboxyl group that may be esterified or amidated, an aromatic group that may be substituted and the like).

"The substituent" that may be possessed by "a 5- to 6-membered cyclic ring" of "a 5- to 6-membered cyclic ring that may be substituted", which is indicated by $R^1$, is exemplified particularly by a lower ($C_{1-4}$)alkyl that may be halogenated or alkoxylated with a lower ($C_{1-4}$) (for example, methyl, ethyl, t-butyl, trifluoromethyl, methoxymethyl, ethoxymethyl, propoxymethyl, butoxymethyl, methoxyethyl, ethoxyethyl, propoxyethyl, butoxyethyl, or the like), a lower ($C_{1-4}$)alkoxyl that may be halogenated or alkoxylated with a lower ($C_{1-4}$) (for example, methoxy, ethoxy, propoxy, butoxy, t-butoxy, trifluoromethoxy, methoxymethoxy, ethoxymethoxy, propoxymethoxy, butoxymethoxy, methoxyethoxy, ethoxymethoxy, propoxyethoxy, butoxyethoxy, methoxypropoxy, ethoxypropoxy, propoxypropoxy, butoxypropoxy or the like), a halogen (for example, fluorine, chlorine or the like), nitro, cyano, an amino group that may be substituted with 1 to 2 of a lower ($C_{1-4}$)alkyl, formyl or a lower ($C_{1-4}$)alkanoyl (for example, amino, methylamino, dimethylamino, formylamino, acetylamino or the like), a 5- to 6-membered cyclic ring amino group (for example, 1-pyrrolidinyl, 1-piperazinyl, 1-piperidinyl, 4-morpholino, 4-thiomorpholino, 1-imidazolyl, 4-tetrahydropyranyl or the like) or the like.

"A bivalent group, in which the number of atoms constituting the straight-chain portion is 1 to 4", indicated by $X^1$ and $X^2$, is exemplified by, for example, —$(CH_2)_{a'}$— [a' indicates an integer of 1 to 4 (preferably, an integer of 1 to 2)], —$(CH_2)_{b'}$—$X^3$— [b' indicates an integer of 0 to 3 (preferably, an integer of 0 to 1) and $X^3$ indicates an imino group that may be substituted (for example, an imino group that may be substituted with a lower ($C_{1-6}$)lower alkyl, a lower ($C_{3-7}$)cycloalkyl, formyl, a lower ($C_{2-7}$) lower alkanoyl, a lower ($C_{1-6}$)lower alkoxycarbonyl or the like), the carbonyl group, the oxygen atom, the sulfur atom that may be oxidized by the oxygen atom (for example, —$S(O)_m$— (m indicates an integer of 0 to 2) or the like)], —CH=CH—, —C≡C—, —CO—NH—, —$SO_2$—NH— or the like. Although these groups may be bonded with W through either of the left or right bond, it is preferable to be bonded with W through the right hand in the case of $X^1$, whereas it is preferable to be bonded with W through the left hand in the case of $X^2$.

As for $X^1$, a bond, —$(CH_2)_{b'}$—O— [b' indicates an integer of 0, 1 or 2 (preferably, an integer of 0 to 1), —C≡C— or the like is preferable, and a bond is more preferable.

As for $X^2$, —$(CH_2)_{a'}$— [a' indicates an integer of 1 to 2], —$(CH_2)_{b'}$—$X^3$— [b' indicates an integer of 0 to 1 and $X^3$ indicates an imino group that may be substituted, the carbonyl group, the oxygen atom, the sulfur atom that may be oxidized by the oxygen atom], —CH=CH—, —CO—NH—, —$SO_2$—NH— or the like is preferable, and —CO—NH— is more preferable.

In the above-mentioned formula (I), a bivalent group that is represented by formula indicated by W

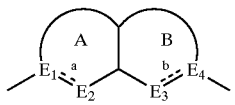

-continued

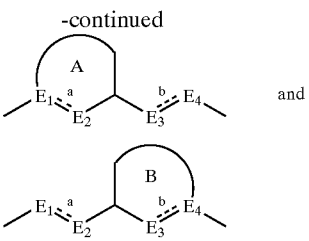

(wherein each of ring A and ring B indicates a 5- to 7-membered cyclic ring group that may be substituted, each of $E_1$ and $E_4$ indicates the carbon atom that may be substituted or the nitrogen atom that may be substituted, each of $E_2$ and $E_3$ indicates the carbon atom that may be substituted or the nitrogen atom that may be substituted, the sulfur atom that may be oxidized (for example, —$S(O)_m$— (m indicates an integer of 0 to 2) or the like) or the oxygen atom and each of a and b indicates to be a single bond or a double bond) indicates that the bonding with adjacent $X^1$ and $X^2$ is made in a mode that is shown respectively by

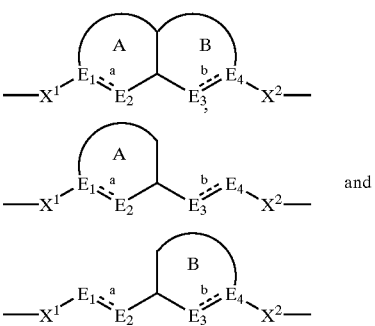

(wherein each of the symbols has the same meaning as that described hereinabove).

In the above-mentioned formula (I), "a 5- to 7-membered cyclic ring" of "a 5- to 7-membered cyclic ring that may be substituted", which is indicated by A, is exemplified by a 5- to 7-membered (preferably, 5- to 6-membered, saturated or unsaturated alicyclic hydrocarbon such as a $C_{5-7}$ cycloalkane (for example, cyclopentane, cyclohexane, cycloheptane or the like), a $C_{5-7}$ cycloalkene (for example, 1-cyclopentene, 2-cyclopentene, 3-cyclopentene, 2-cyclohexene, 3-cyclohexene or the like), a $C_{5-6}$ cycloalkadiene (for example, 2,4-cyclopentadiene, 2,4-cyclohexadiene, 2,5-cyclohexadiene or the like); a 6-membered aromatic hydrocarbon such as benzene; a 5- to 7-membered, aromatic heterocyclic ring, a saturated or unsaturated non-aromatic heterocyclic ring (aliphatic heterocyclic ring) or the like, which contains at least one (preferably, 1 to 4, more preferably 1 to 2) of heteroatoms of 1 to 3 kinds (preferably, 1 to 2 kinds) selected from the oxygen atom, the sulfur atom and the nitrogen atom; or the like.

Herein, "an aromatic heterocyclic ring" is exemplified by a 5- to 7-membered, aromatic monocyclic, heterocyclic ring (for example, furan, thiophene, pyrrole, oxazole, isoxazole, thiazole, isothiazole, imidazole, pyrazole, 1,2,3-oxadiazole, 1,2,4-oxadiazole, 1,3,4-oxadiazole, furazane, 1,2,3-thiadiazole, 1,2,4-thiadiazole, 1,3,4-thiadiazole, 1,2,3-triazole, 1,2,4-triazole, tetrazole, pyridine, pyridazine, pyrimidine, pyrazine, triazine or the like) or the like, and "a non-aromatic heterocyclic ring" is exemplified by, for example, a 5- to 7-membered (preferably, 5- to 6-membered), saturated or unsaturated non-aromatic heterocyclic ring (aliphatic heterocyclic ring) such as pyrrolidine, tetrahydrofuran, thiolane, piperidine, tetrahydropyran, morpholine, thiomorpholine, piperazine, pyran, oxepine, azepine or the like, a 5- to 6-membered, non-aromatic heterocyclic ring, where a part or all of the double bonds in the above-mentioned aromatic monocyclic heterocyclic ring are saturated, or the like.

As for "a 5- to 7-membered cyclic ring" of "a 5- to 7-membered cyclic ring that may be substituted", which is indicated by A, a 5- to 6-membered, aromatic ring is preferable, and further benzene, furan, thiophene, pyrrole, pyridine (preferably, 6-membered) or the like is preferable, where benzene is particularly preferable.

"The substituent" that may be possessed by "a 5- to 7-membered cyclic ring" of "a 5- to 7-membered cyclic ring that may be substituted", which is indicated by A, is exemplified by a group similar to "the substituent" that may be possessed by "a 5- to 6-membered cyclic ring" of "a 5- to 6-membered cyclic ring that may be substituted", which is indicated by $R^1$. Also, such a substituent for A may be substituted at any positions of 1 to 4 (preferably, 1 to 2) of the same or different rings, and the substituent may be possessed at any substitutable position, whether it is any of the positions that are indicated by $E_1$ and $E_2$ or any of other positions.

In the above-mentioned formula (I), "a 5- to 7-membered cyclic ring" of "a 5- to 7-membered cyclic ring that may be substituted", which is indicated by B, is exemplified by a 5- to 7-membered cyclic ring that may have substituents at optional, substitutable positions, which is represented by formula

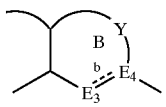

or the like.

In the above-mentioned formula (I), the bivalent group that is indicated by Y indicates a bivalent group, with which ring B forms a 5- to 7-membered cyclic ring that may be substituted, and is exemplified by a bivalent group such as, for example, (1) —$(CH_2)_{a1}$—O—$(CH_2)_{a2}$— (each of a1 and a2 indicates 0, 1 or 2 in the same or different manner. Hereupon, the sum of a1 and a2 is 2 or less), —O—(CH=CH)—, —(CH=CH)—O—, (2) —$(CH_2)_{b1}$—$S(O)_m$—$(CH_2)_{b2}$— (m indicates an integer of 0 to 2, and each of b1 and b2 indicates 0, 1 or 2 in the same or different manner. Hereupon, the sum of b1 and b2 is 2 or less), —$S(O)_m$—(CH=CH)—, —(CH=CH)—$S(O)_m$—, (3) —$(CH_2)_{d1}$— (d1 indicates 0, 1 or 2), —$CH_2$—(CH=CH)—, —(CH=CH)—$CH_2$—, —CH=CH—, —CH=, (4) —$(CH_2)_{e1}$—NH—$(CH_2)_{e2}$— (each of e1 and e2 indicates 0, 1 or 2 in the same or different manner. Hereupon, the sum of e1 and e2 is 2 or less), —NH—(CH=CH)—, —(CH=CH)—NH—, —$(CH_2)_{e6}$—(N=CH)—$(CH_2)_{e7}$—, —$(CH_2)_{e7}$—(CH=N)—$(CH_2)_{e6}$— (either of e6 and e7 indicates 0, and the other indicates 0 or 1), —$(CH_2)_{e8}$—(N=N)—$(CH_2)_{e9}$— (either of e8 and e9 indicates 0, and the other indicates 0 or 1) or the like. Specifically, the bivalent group is exemplified by, for example, a bivalent group such as —O—, —O—$CH_2$—, —O—$CH_2$—$CH_2$—, —O—(CH=CH)—, —$S(O)_m$— (m indicates an integer of 0 to 2), —$S(O)_m$—$CH_2$— (m indicates an integer of 0 to 2), —$S(O)_m$—$CH_2$—$CH_2$— (m indicates an integer of 0 to 2), —$S(O)_m$—(CH=CH)—, (m indicates an integer of 0 to 2), —$CH_2$—, —$(CH_2)_2$—, —$(CH_2)_3$—, —CH=, —CH=CH—, —CH=CH—$CH_2$—, —$CH_2$—CH=CH—, —NH—, —N=CH—, —CH=N—, —N=N— (respectively, the bonding indicated starts from ring A) or the like.

In addition, said bivalent group may have a substituent, and said substituent is exemplified by a group similar to "the substituent" that may be possessed by "a 5- to 6-membered cyclic ring" of "a 5- to 6-membered cyclic ring that may be substituted", which is indicated by $R^1$, oxo and the like, where a lower $(C_{1-3})$alkyl (for example, methyl, ethyl, propyl or the like), phenyl, oxo, the hydroxyl group or the like is particularly preferable. Furthermore, said bivalent group may be —O—C(O)— (the bonding indicated starts from ring A) or the like. The substituent for such a bivalent group may be substituted at any same or different positions of 1 to 4 (preferably, 1 to 2). The substituent position may be any position that is substitutable to said bivalent group.

As for the bivalent group that is indicated by Y, a group such as —Y'—$(CH_2)m'$— (Y' indicates —$S(O)_m$— (m indicates an integer of 0 to 2), —O—, —NH— or —$CH_2$—, and m' indicates an integer of 0 to 2), —CH=, —CH=CH—, —N=CH—, —$(CH_2)m'$—Y'— (Y' indicates —$S(O)_m$— (m indicates an integer of 0 to 2), —O—, —NH— or —$CH_2$—, and m' indicates an integer of 0 to 2), —CH=N— or the like, with starting the bonding indicated from ring A, is preferable, where a group such as —Y'—$(CH_2)m'$— (Y' indicates —$S(O)_m$— (m indicates an integer of 0 to 2), —O—, —NH— or —$CH_2$—, and m' indicates an integer of 0 to 2), —CH=, —CH=CH—, —N=CH— or the like, with starting the bonding indicated from ring A, is more preferable, and a group (ring B indicates a 7-membered ring) such as —Y'—$(CH_2)_2$— (Y' indicates —$S(O)_m$— (m indicates an integer of 0 to 2), —O—, —NH— or —$CH_2$—), with starting the bonding indicated from ring A, is most preferable.

"The substituent" that may be possessed by "a 5- to 7-membered cyclic ring" of "a 5- to 7-membered cyclic ring that may be substituted", which is indicated by B, is exemplified by a group similar to "the substituent" that may be possessed by "a 5- to 6-membered cyclic ring" of "a 5- to 6-membered cyclic ring that may be substituted", which is indicated by $R^1$. Also, such a substituent for B may be substituted at any positions of 1 to 4 (preferably, 1 to 2) of the same or different rings, but it is preferable that the position of $E_3$ is unsubstituted.

In the above-mentioned formula (I), it is preferable that each of $E_3$ and $E_4$ is the carbon atom that may be substituted (preferably, the carbon atom that is not substituted), and b indicates a double bond.

In the above-mentioned formula (I), "a bivalent cyclic ring group" indicated by $Z^1$ is exemplified by a group that is formed by removing two hydrogen atoms from a group similar to "a 5- to 6-membered cyclic ring" of "a 5- to 6-membered cyclic ring that may be substituted", or the like, where a bivalent cyclic ring group, which is formed by removing two hydrogen atoms from benzene, furan, thiophene, pyridine, cyclopentane, cyclohexane, pyrrolidine, piperidine, piperazine, morpholine, thiomorpholine or tetrahydropyran, is more preferable, and a bivalent cyclic ring group, which is formed by removing two hydrogen atoms from benzene, cyclohexane or piperidine (preferably, benzene) is most preferably used.

"A bivalent cyclic ring group" indicated by $Z^1$ may have a substituent similar to "a substituent" that is possessed by "a 5- to 6-membered cyclic ring" of "a 5- to 6-membered cyclic ring that may be substituted", but it is preferable not to have a substituent other than $X^2$ and $Z^2$, and also it is preferable that the substitution position for $Z^2$ is para to $X^2$ in the case where $Z^1$ is a 6-membered, bivalent cyclic ring group (preferably, phenylene).

In the above-mentioned formula (I), "a bivalent group, in which the number of atoms constituting the straight-chain portion is 1 to 4", which is indicated by $Z^2$, is exemplified by a bivalent group that has a hydrocarbon chain having the carbon number of 1 to 4, which may be substituted (for example, a $C_{1-4}$ alkylene, a $C_{2-4}$ alkenylene or the like, preferably a $C_{1-3}$ alkylene, more preferably methylene), or the like.

A bivalent group, which is indicated by $Z^2$, may be any group having a bivalent chain, in which the number of atoms constituting the straight-chain portion is 1 to 4, and is exemplified by, for example, an alkylene chain represented by $—(CH_2)_{k1}—$ (k1 is an integer of 1 to 4), an alkenylene chain represented by $—(CH_2)_{k2}—(CH=CH)—(CH_2)_{k3}—$ (each of k2 and k3 indicates an integer of 1 to 4 in the same or different manner. Hereupon, the sum of k2 and k3 is 2 or less) or the like.

A bivalent group, which is indicated by $X^1$, $X^2$ and $Z^2$, may have a substituent at an optional position (preferably, on the carbon atom), where such a substituent may be any one that is capable of being bonded to a bivalent chain constituting the straight-chain portion, is exemplified by, for example, a lower ($C_{1-6}$)alkyl (for example, methyl, ethyl, propyl, isopropyl, butyl, isobutyl, sec-butyl, tert-butyl, pentyl, isopentyl, neopentyl, hexyl or the like), a lower ($C_{3-7}$)cycloalkyl (for example, cyclopropyl, cyclobutyl, cyclopentyl, cyclohexyl, cycloheptyl or the like), formyl, a lower ($C_{2-7}$)alkanoyl (for example, acetyl, propionyl, butyryl or the like), a phosphono group that may be esterified, the carboxyl group that may be esterified, the hydroxyl group, oxo or the like, where preferably a lower alkyl having the carbon number of 1 to 6 (preferably a $C_{1-3}$ alkyl), the hydroxyl group, oxo or the like is exemplified.

Said phosphono group that may be esterified is exemplified by a group represented by $—P(O)(OR^7)(OR^8)$ [wherein each of $R^7$ and $R^8$ indicates hydrogen, an alkyl group having the carbon number of 1 to 6 or a cycloalkyl group having the carbon number of 3 to 7, and may be bonded together to form a 5- to 7-membered cyclic ring].

In the above-mentioned formula, an alkyl group having the carbon number of 1 to 6, which is represented by $R^7$ and $R^8$, is exemplified by methyl, ethyl, propyl, isopropyl, butyl, isobutyl, sec-butyl, tert-butyl, pentyl, isopentyl, neopentyl, hexyl or the like, and a cycloalkyl having the carbon number of 3 to 7 is exemplified by cyclopropyl, cyclobutyl, cyclopentyl, cyclohexyl, cycloheptyl or the like), where a lower alkyl having the carbon number of 1 to 6 is exemplified preferably, and a lower alkyl having the carbon number of 1 to 3 is exemplified more preferably. $R^7$ and $R^8$ may be the same or different, but it is preferable to be the same. Also, in the case where $R^7$ and $R^8$ are bonded together to form a 5- to 7-membered cyclic ring, $R^7$ and $R^8$ are bonded together to form a straight-chained $C_{2-4}$ alkylene side chain represented by $—(CH_2)_2—$, $—(CH_2)_3—$, $—(CH_2)_4—$. Said side chain may have substituents, and such a substituent is exemplified by, for example, the hydroxyl group, a halogen or the like.

The carboxyl group, which is esterified for the carboxyl group that may be esterified, is exemplified by a group, wherein the carboxyl group is bonded with an alkyl group having the carbon number of 1 to 6 or a cycloalkyl having the carbon number of 3 to 7, such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, hexyloxycarbonyl or the like.

A bivalent group, which is indicated by $Z^2$, is exemplified by a $C_{1-3}$ alkylene that may be substituted, where a $C_{1-3}$ alkylene that may be substituted with a $C_{1-3}$ alkyl, the hydroxyl group or oxo is more preferable.

Furthermore, as for a bivalent group, which is indicated by $Z^2$, a group represented by $—Z'—(CH_2)n—$ or $—(CH_2)n—Z'—$ (Z' indicates $—CH(OH)—$, $—C(O)—$ or $—CH_2—$, n indicates an integer of 0 to 2 and each methylene group may have 1 to 2 groups of the same or different substituent), with starting from the benzene ring, is preferable, a group represented by $—Z'—(CH_2)n—$ (Z' indicates $—CH(OH)—$, $—C(O)—$ or $—CH_2—$, n indicates an integer of 0 to 2 (preferably, n indicates 0) and each methylene group may have 1 to 2 groups of the same or different substituents), with starting from the benzene ring, is more preferable and methylene is most preferable.

In the above-mentioned formula (I), "an amino group" of "an amino group that may be substituted, where the nitrogen atom may be converted into a quaternary ammonium or the N-oxide" indicated by $R^2$, is exemplified by an amino group that may have 1 to 2 substituents, an amino group that has 4 substituents, where the nitrogen atom may be converted into a quaternary ammonium, or the like. In the case where the substituents on the nitrogen atom are 2 or more, these substituents may be the same or different, and in the case where the substituents on the nitrogen atom are 3, the amino group may be of any type of $—N^+R_3$, $—N^+R_2R'$, $—N^+RR'R''$ (each of R, R' and R'' indicates hydrogen or a substituent in a different manner). In addition, a counter anion for the amino group, in which the nitrogen atom is converted into a quaternary ammonium, is exemplified by, in addition to an anion of a halogen atom (for example, $Cl^-$, $Br^-$, $I^-$ or the like) or the like, an anion derived from an inorganic acid such as hydrochloric acid, hydrobromic acid, nitric acid, sulfuric acid, phosphoric acid and the like, an anion derived from an organic acid such as formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like and an anion derived from an acidic amino acid such as aspartic acid, glutamic acid and the like, where $Cl^-$, $Br^-$, $I^-$ or the like is more preferable.

Examples of substituents for said amino group include substituents such as, (1) an alkyl that may be substituted (for example, a $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl or the like, preferably a lower ($C_{1-6}$)alkyl or the like is exemplified);

(2) a cycloalkyl that may be substituted and may contain heteroatoms (for example, a $C_{3-7}$ cycloalkyl such as cyclopropyl, cyclobutyl, cyclopentyl, cyclohexyl, cycloheptyl or the like is exemplified);

(2-1) said cycloalkyl contains one heteroatom selected from the sulfur atom, the oxygen atom and the nitrogen atom, and may form oxirane, thiolane, aziridine, tetrahydrofuran, tetrahydrothiophene, pyrrolidine, tetrahydropyran, tetrahydrothiopyran, tetrahydrothiopyran 1-oxide, piperidine or the like (preferably, a 6-membred ring such as tetrahydropyran, tetrahydrothiopyran, piperidine or the like), where the binding position with the amino group is preferably position 3 or position 4 (preferably, position 4);

(2-2) also, said cycloalkyl may condensed with the benzene ring to form an indane (for example, indan-2-yl, indan-2-yl or the like), tetrahydronaphthalene, (for example, tetrahydronaphthalen-5-yl, tetrahydronaphthalen-6-yl or the like) or the like (preferably, indane);

(2-3) furthermore, said cycloalkyl may be crosslinked via a straight-chained, atom chain having the carbon number of 1 to 2 to form a crosslinked, cyclic hydrocarbon residue such as bicyclo[2.2.1]heptyl, bicyclo[2.2.2]octyl, bicyclo[3.2.1]octyl, bicyclo[3.2.2]nonyl or the like (preferably, a cycloalkyl having a crosslink via a straight-chained, atom chain having the carbon number of 1 to 2, or the like, more preferably bicyclo[2.2.1]heptyl or the like);

(3) an alkenyl that may be substituted (for example, an alkenyl that has the carbon number of 2 to 10 such as allyl, crotyl, 2-pentenyl, 3-hexenyl or the like, preferably a lower ($C_{2-6}$)alkenyl, or the like is exemplified);

(4) a cycloalkenyl that may be substituted (for example, an cycloalkenyl that has the carbon number of 3 to 7 such as 2-cyclopentenyl, 2-cyclohexenyl 2-cyclopentenylmethyl, 2-cyclohexenylmethyl or the like, or the like is exemplified);

(5) an aralkyl that may be substituted (for example, a phenyl-$C_{1-4}$ alkyl (for example, benzyl, phenethyl or the like) or the like is exemplified);

(6) formyl or an acyl that may be substituted (for example, an alkanoyl that has the carbon number of 2 to 4 (for example, acetyl, propionyl, butyryl, isobutyryl or the like), an alkylsulfonyl that has the carbon number of 1 to 4 (for example, methanesulfonyl, ethanesulfonyl or the like), an alkoxycarbonyl that has the carbon number of 1 to 4 (methoxycarbonyl, ethoxycarbonyl, tert-butoxycarbonyl or the like), an aralkyloxycarbonyl that has the carbon number of 7 to 10 (for example, benzyloxycarbonyl or the like) or the like is exemplified);

(7) an aryl that may be substituted (for example, phenyl, naphthyl or the like is exemplified); and (8) a heterocyclic ring group that may be substituted (a group that is formed by removing one hydrogen atom from a 5- to 6-membered, aromatic heterocyclic ring, which contains 1 to 4 heteroatoms of 1 to 2 kinds selected from the nitrogen atom, the sulfur atom and the oxygen atom, such as furan, thiophene, pyrrole, imidazole, pyrazole, thiazole, oxazole, isothiazole, isoxazole, tetrazole, pyridine, pyrazine, pyrimidine, pyridazine, triazole or the like, a group that is formed by removing one hydrogen atom from a 5- to 6-membered, non-aromatic heterocyclic ring, which contains 1 to 4 heteroatoms of 1 to 2 kinds selected from the nitrogen atom, the sulfur atom and the oxygen atom, such as tetrahydrofuran, tetrahydrothiophene, dithiolane, oxathiolane, pyrrolidine, pyrroline, imidazolidine, imidazoline, pyrazolidine, pyrazoline, piperidine, piperazine, oxazine, oxadiazine, thiazine, thiadiazine, morpholine, thiomorpholine, pyran, tetrahydropyran or the like, or the like; preferably, a group, which is formed by removing one hydrogen atom from a 5- to 6-membered, non-aromatic hetero-cyclic ring, or the like; and more preferably, a group, which is formed by removing one hydrogen atom from a 5- to 6-membered, non-aromatic heterocyclic ring, which has one heteroatom, such as tetrahydrofuran, piperidine, tetrahydropyran, tetrahydrothiopyran or the like) and the like. In addition, the substituents of said amino group may be bonded each other to form a 5- to 7-membered, cyclic amino such as piperidine, piperazine, morpholine, thiomorpholine or the like.

Examples of the substituents that may be possessed by (1) an alkyl that may be substituted, (2) a cycloalkyl that may be substituted, (3) an alkenyl that may be substituted, (4) a cycloalkenyl that may be substituted, (5) an aralkyl that may be substituted, (6) an acyl that may be substituted, (7) an aryl that may be substituted and (8) a heterocyclic ring group that may be substituted, which are described above, include a halogen (for example, fluorine, chlorine, bromine, iodine or the like), a lower ($C_{1-4}$)alkyl that may be halogenated, a $C_{1-4}$ alkoxyl that may be halogenated (for example, methoxy, ethoxy, propoxy, butoxy, trifluoromethoxy, trifluoroethoxy or the like), a $C_{1-4}$ alkylenedioxy (for example, —O—$CH_2$—O—, —O—$CH_2$—$CH_2$—O— or the like), formyl, a $C_{2-4}$ alkanoyl (for example, acetyl, propionyl or the like), a $C_{1-4}$ alkylsulfonyl (for example, methanesulfonyl, ethanesulfonyl or the like), a phenyl-lower ($C_{1-4}$)alkyl, a $C_{3-7}$ cycloalkyl, cyano, nitro, the hydroxyl group, the thiol group that may be substituted (for example, thiol, a $C_{1-4}$ alkylthio or the like), an amino group that may be substituted (for example, amino, a mono-$C_{1-4}$ alkylamino, a di-$C_{1-4}$ alkylamino, a 5- to 6-membered cyclic ring amino such as tetrahydropyrrole, piperazine, piperidine, morpholine, thiomorpholine, pyrrole, imidazole or the like, or the like), the carboxyl group that may be esterified or amidated (for example, carboxyl, a $C_{1-4}$ alkoxycarbonyl, carbamoyl, a mono-$C_{1-4}$ alkylcarbamoyl, a di-$C_{1-4}$ alkylcarbamoyl or the like), a lower ($C_{1-4}$) alkoxycarbonyl, a lower ($C_{7-10}$)aralkyloxycarbonyl, the oxo group (preferably, a halogen, a lower ($C_{1-4}$)alkyl that may be halogenated, a $C_{1-4}$ alkoxyl that may be halogenated, a phenyl-lower ($C_{1-4}$) alkyl, a $C_{3-7}$ cycloalkyl, cyano, the hydroxyl group or the like) and the like, where the number of the substituents is preferably 1 to 3.

In the above-mentioned formula (I), "an amino group that may be substituted, where the nitrogen atom may be converted into a quaternary ammonium or the N-oxide" indicated by $R^2$, is preferably an amino group that may have 1 to 3 substituents selected from, (1) a straight-chained or branched, lower ($C_{1-6}$)alkyl that may have 1 to 3 groups of a halogen, cyano, the hydroxyl group or a $C_{3-7}$ cycloalkyl;

(2) a $C_{5-8}$ cycloalkyl that may have 1 to 3 groups of a halogen, a lower ($C_{1-4}$)alkyl that may be halogenated or a phenyl-lower ($C_{1-4}$)alkyl, may contain one heteroatom selected from the sulfur atom, the oxygen atom and the nitrogen atom, may be condensed with the benzene ring and may be crosslinked via a straight-chained, atom chain having the carbon number of 1 to 2, (for example, cyclopentyl, cyclohexyl, cycloheptyl cyclooctyl, tetrahydropyranyl, tetrahydrothiapyranyl, piperidinyl, indanyl, tetrahydronaphthalenyl, bicyclo[2.2.1]heptyl or the like);

(3) a phenyl-lower ($C_{1-4}$)alkyl that may have 1 to 3 groups of a halogen, a lower ($C_{1-4}$)alkyl that may be halogenated or a $C_{1-4}$ alkoxyl that may be halogenated;

(4) a phenyl that may have 1 to 3 groups of a halogen, a lower ($C_{1-4}$)alkyl that may be halogenated or a $C_{1-4}$ alkoxyl that may be halogenated; and (5) a 5- to 6-membered, aromatic heterocyclic ring that may have 1 to 3 groups of a halogen, a lower ($C_{1-4}$) alkyl that may be halogenated, a $C_{1-4}$ alkoxyl that may be halogenated, a ($C_{1-4}$)alkoxy-($C_{1-4}$)alkoxyl that may be halogenated, a phenyl-lower ($C_{1-4}$)alkyl, cyano or the hydroxyl (for example, a group that is formed by removing one hydrogen atom from furan, thiophene, pyrrole, pyridine or the like).

In the above-mentioned formula (I), "a nitrogen-containing, heterocyclic ring" of "a nitrogen-containing, heterocyclic ring group that may be substituted and may contain the sulfur atom or the oxygen atom as a ring-constituting atom, where the nitrogen atom may be converted into a quaternary ammonium or the N-oxide" is exemplified by a 5- to 6-membered, aromatic heterocyclic ring, which may contain, in addition to one nitrogen atom, 1 to 3 heteroatoms of 1 to 2 kinds selected from the nitrogen atom, the sulfur atom and the oxygen atom, such as pyrrole, imidazole, pyrazole, thiazole, oxazole, isothiazole, isoxazole, tetrazole, pyridine, pyrazine, pyrimidine, pyridazine, triazole or the like, a 5- to 8-membered, non-aromatic heterocyclic ring, which may contain, in addition to one nitrogen atom, 1 to 3 heteroatoms of 1 to 2 kinds selected from the nitrogen atom, the sulfur atom and the oxygen atom, such as pyrrolidine, pyrroline, imidazolidine, imidazoline, pyrazolidine, pyrazoline, piperidine, piperazine, oxazine, oxadiazine, thiazine, thiadiazine, morpholine, thiomorpholine, azacycloheptane, azacyclooc-tane (azokane) or the like, or the like, where each of these nitrogen-containing, heterocyclic rings may be crosslinked via a straight-chained, atom chain having the carbon number of 1 to 2 and may form a crosslinked, nitrogen-containing, heterocyclic ring such as azabicyclo[2.2.1]heptane, azabicyclo[2.2.2]octane (quinuclidine) or the like (preferably, piperidine, which may have a crosslink via a straight-chained, atom chain having the carbon number of 1 to 2, or the like).

Among the specific examples of the above-mentioned, nitrogen-containing, heterocyclic ring, pyridine, imidazole, pyrrolidine, piperidine, piperazine, morpholine, thiomorpholine and azabicyclo[2.2.2]octane (preferably, 6-membered, cyclic rings) are preferable.

The nitrogen atom of said "nitrogen-containing, heterocyclic ring" may be converted into a quaternary ammonium, or may be oxidized. In the case where the nitrogen atom of said "nitrogen-containing, heterocyclic ring" is converted into a quaternary ammonium, a counter anion for "the nitrogen-containing, heterocyclic ring group, in which the nitrogen atom is converted into a quaternary ammonium", is exemplified by, in addition to an anion of a halogen atom (for example, $Cl^-$, $Br^-$, $I^-$ or the like) or the like, an anion derived from an inorganic acid such as hydrochloric acid, hydrobromic acid, nitric acid, sulfuric acid, phosphoric acid and the like, an anion derived from an organic acid such as formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like and an anion derived from an acidic amino acid such as aspartic acid, glutamic acid and the like, where $Cl^-$, $Br^-$, $I^-$ or the like is more preferable.

Said "nitrogen-containing, heterocyclic ring" may be bonded with a bivalent group, which is indicated by $Z^2$, via either of the carbon atom or the nitrogen atom and may be bonded on the carbon atom constituting the cyclic ring, as in the case of 2-pyridyl, 3-pyridyl, 2-piperidyl or the like, whereas a bonding as in the case of

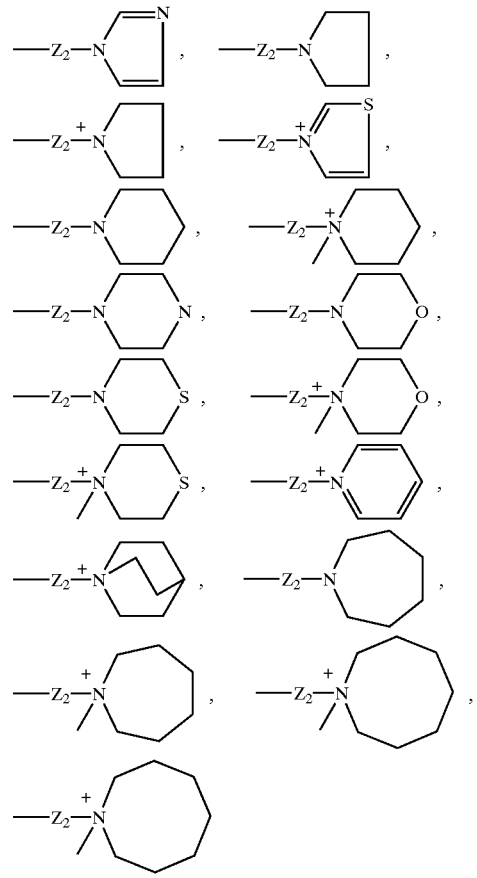

or the like is preferable.

Examples of substituents of said "nitrogen-containing, heterocyclic ring" include a halogen (for example, fluorine, chlorine, bromine, iodine or the like), a lower ($C_{1-4}$)alkyl that may be substituted, a lower ($C_{1-4}$)alkoxyl that may be substituted, a phenyl that may be substituted, a mono- or diphenyl-lower ($C_{1-4}$)alkyl that may be substituted, a $C_{3-7}$ cycloalkyl that may be substituted, cyano, nitro, the hydroxyl group, the thiol group that may be substituted (for example, thiol, a $C_{1-4}$ alkylthio or the like), an amino group that may be substituted (for example, amino, a mono-$C_{1-4}$ alkylamino, a di-$C_{1-4}$ alkylamino, a 5- to 6-membered cyclic ring amino such as tetrahydropyrrole, piperazine, piperidine, morpholine, thiomorpholine, pyrrole, imidazole or the like, or the like), the carboxyl group that may be esterified or amidated (for example, carboxyl, a $C_{1-4}$ alkoxycarbonyl, carbamoyl, a mono-$C_{1-4}$ alkylcarbamoyl, a di-$C_{1-4}$ alkylcarbamoyl or the like), a lower ($C_{1-4}$)alkoxycarbonyl, formyl, a ($C_{2-4}$)alkanoyl, a ($C_{1-4}$) alkylsulfonyl, a heterocyclic ring group that may be substituted (a group that is formed by removing one hydrogen atom from a 5- to 6-membered, aromatic heterocyclic ring, which contains 1 to 4 heteroatoms of 1 to 2 kinds selected from the nitrogen atom, the sulfur atom and the oxygen atom, such as furan, thiophene, pyrrole, imidazole, pyrazole, thiazole, oxazole, isothiazole, isoxazole, tetrazole, pyridine, pyrazine, pyrimidine, pyridazine, triazole or the like, a group that is formed by removing one hydrogen atom from a 5- to 6-membered, non-aromatic heterocyclic ring, which contains 1 to 4 heteroatoms of 1 to 2 kinds selected from the nitrogen atom, the sulfur atom and the oxygen atom, such as tetrahydrofuran, tetrahydrothiophene, dithiolane, oxathiolane, pyrrolidine, pyrroline, imidazolidine, imidazoline, pyrazolidine, pyrazoline, piperidine, piperazine, oxazine, oxadiazine, thiazine, thiadiazine, morpholine, thiomorpholine, pyran, tetrahydropyran, tetrahydrothiopyran or the like, or the like, where the number of the substituents is preferably 1 to 3. Also, the nitrogen in said "nitrogen-containing, heterocyclic ring" may be oxidized.

Examples of the substituents, which may be possessed by "a lower ($C_{1-4}$)alkyl that may be substituted", "a lower ($C_{1-4}$)alkoxyl that may be substituted", "a phenyl that may be substituted", "a mono- or diphenyl-lower ($C_{1-4}$) alkyl that may be substituted", "a $C_{3-7}$ cycloalkyl that may be substituted" and "a heterocyclic ring group that may be substituted", as the substituents that may be possessed by said "nitrogen-containing, heterocyclic ring", include, for example, a halogen (for example, fluorine, chlorine, bromine, iodine or the like), a lower ($C_{1-4}$)alkyl that may be halogenated, a lower ($C_{3-10}$)cycloalkyl, a lower ($C_{3-10}$) cycloalkenyl, a $C_{1-4}$ alkoxyl that may be halogenated (for example, methoxy, ethoxy, trifluoromethoxy, trifluoroethoxy or the like), formyl, a $C_{2-4}$ alkanoyl (for example, acetyl, propionyl or the like), a $C_{1-4}$ alkylsulfonyl (for example, methanesulfonyl, ethanesulfonyl or the like), a $C_{1-3}$ alkylenedioxy (for example, methylenedioxy, ethylenedioxy or the like), cyano, nitro, the hydroxyl group, the thiol group that may be substituted (for example, thiol, a $C_{1-4}$ alkylthio or the like), an amino group that may be substituted (for example, amino, a mono-$C_{1-4}$ alkylamino, a di-$C_{1-4}$ alkylamino, a 5- to 6-membered cyclic ring amino such as tetrahydropyrrole, piperazine, piperidine, morpholine, thiomorpholine, pyrrole, imidazole or the like, or the like), the carboxyl group that may be esterified or amidated (for example, carboxyl, a $C_{1-4}$ alkoxycarbonyl, carbamoyl, a mono-$C_{1-4}$ alkylcarbamoyl, a di-$C_{1-4}$ alkylcarbamoyl or the like), a lower ($C_{1-4}$)alkoxycarbonyl and the like, where the number of the substituents is preferably 1 to 3.

In the above-mentioned formula (I), the substituent, which may be possessed by "a nitrogen-containing, heterocyclic ring" of "a nitrogen-containing, heterocyclic ring group that may be substituted and may contain the sulfur atom or the oxygen atom as a ring-constituting atom, where the nitrogen atom may be converted into a quaternary ammonium or the N-oxide" is exemplified preferably by (1) a halogen, (2) cyano, (3) the hydroxyl group, (4) the carboxyl group, (5) a lower ($C_{1-4}$) alkoxycarbonyl, (6) a lower ($C_{1-4}$)alkyl that may be substituted with a halogen, the hydroxyl group or a lower ($C_{1-4}$)alkoxyl, (7) a lower ($C_{1-4}$)alkoxyl that may be substituted with a halogen, the hydroxyl group or a lower ($C_{1-4}$)alkoxyl, (8) a phenyl that may be substituted with a halogen, a lower ($C_{1-4}$)alkyl, the hydroxyl group, a lower ($C_{1-4}$)alkoxyl or a $C_{1-3}$ alkylenedioxy, (9) a mono- or diphenyl-lower ($C_{1-4}$)alkyl that may be substituted with a halogen, a lower ($C_{1-4}$)alkyl, the hydroxyl group, a lower ($C_{1-4}$)alkoxyl or a $C_{1-3}$ alkylenedioxy, (10) a group that is formed by removing one hydrogen atom from a 5- to 6-membered, aromatic heterocyclic ring, such as furan, thiophene, pyrrole, pyridine or the like, or the like.

In the above-mentioned formula (I), "a group that is bonded via the sulfur atom", which is indicated by $R^2$, is exemplified by a group represented by —S(O)m—$R^s$ (wherein m indicates an integer of 0 to 2 and $R^s$ indicates a substituent). In the above-mentioned formula, examples of the substituent indicated by $R^s$ include, for example, (1) an alkyl that may be substituted (for example, a $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl or the like, preferably a lower ($C_{1-6}$)alkyl, or the like is exemplified);

(2) a cycloalkyl that may be substituted and may contain heteroatoms (for example, a $C_{3-7}$ cycloalkyl such as cyclopropyl, cyclobutyl, cyclopentyl, cyclohexyl, cycloheptyl or the like is exemplified);

(3) an aralkyl that may be substituted (for example, a phenyl-$C_{1-4}$ alkyl (for example, benzyl, phenethyl or the like) or the like is exemplified); and (4) an aryl that may be substituted (for example, phenyl, naphthyl or the like is exemplified), where examples of the substituents that may be possessed by (1) an alkyl that may be substituted, (2) a cycloalkyl that may be substituted, (3) an aralkyl that may be substituted and (4) an aryl that may be substituted, which are described above, include a halogen (for example, fluorine, chlorine, bromine, iodine or the like), nitro, cyano, the hydroxyl group, the thiol group that may be substituted (for example, thiol, a $C_{1-4}$ alkylthio or the like), an amino group that may be substituted (for example, amino, a mono-$C_{1-4}$ alkylamino, a di-$C_{1-4}$ alkylamino, a 5- to 6-membered cyclic ring amino such as tetrahydropyrrole, piperazine, piperidine, morpholine, thiomorpholine, pyrrole, imidazole or the like, or the like), the carboxyl group that may be esterified or amidated (for example, carboxyl, a $C_{1-4}$ alkoxycarbonyl, carbamoyl, a mono-$C_{1-4}$ alkylcarbamoyl, a di-$C_{1-4}$ alkylcarbamoyl or the like), a $C_{1-4}$ alkyl that may be halogenated (for example, trifluoromethyl, methyl, ethyl or the like), a $C_{1-4}$ alkoxyl that may be halogenated (for example, methoxy, ethoxy, propoxy, butoxy, trifluoromethoxy, trifluoroethoxy or the like), formyl, a $C_{2-4}$ alkanoyl (for example, acetyl, propionyl or the like), a $C_{1-4}$ alkylsulfonyl (for example, methanesulfonyl, ethanesulfonyl or the like) or the like, where the number of the substituents is preferably 1 to 3.

In the above-mentioned formula (I), "the hydrocarbon atom" for the hydrocarbon atom that may be substituted, which is indicated by $R^{5'}$ and $R^{6'}$, in "a group represented by formula

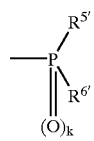

(wherein k indicates 0 or 1, the phosphorus atom may form a phosphonium salt when k is 0, and each of $R^{5'}$ and $R^{6'}$ indicates the hydrocarbon atom that may be substituted, the hydroxyl group that may be substituted or an amino group that may be substituted (preferably, the hydrocarbon atom that may be substituted or an amino group that may be substituted; more preferably the hydrocarbon atom that may be substituted) and $R^{5'}$ and $R^{6'}$ may bind each other to form a cyclic ring group together with the adjacent phosphorus atom)", which is indicated by $R^2$, is exemplified by, (1) an alkyl that may be substituted (for example, a $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl or the like, preferably a lower ($C_{1-6}$)alkyl, or the like is exemplified);

(2) a cycloalkyl that may be substituted (for example, a $C_{3-7}$ cycloalkyl such as cyclopropyl, cyclobutyl, cyclopentyl, cyclohexyl, cycloheptyl or the like);

(3) an alkenyl that may be substituted (for example, an alkenyl that has the carbon number of 2 to 10 such as allyl, crotyl, 2-pentenyl, 3-hexenyl or the like, preferably a lower ($C_{2-6}$)alkenyl, or the like is exemplified);

(4) a cycloalkenyl that may be substituted (for example, an cycloalkenyl that has the carbon number of 3 to 7 such as 2-cyclopentenyl, 2-cyclohexenyl 2-cyclopentenylmethyl, 2-cyclohexenylmethyl or the like, or the like is exemplified);

(5) an alkynyl that may be substituted (for example, an alkynyl that has the carbon number of 2 to 10 such as ethynyl, 1-propynyl, 2-propynyl, 1-butynyl, 2-pentynyl, 3-hexynyl or the like, preferably a lower ($C_{2-6}$)alkynyl, or the like is exemplified);

(6) an aralkyl that may be substituted (for example, a phenyl-$C_{1-4}$ alkyl (for example, benzyl, phenethyl or the like) or the like is exemplified); and (7) an aryl that may be substituted (for example, phenyl, naphthyl or the like is exemplified), where examples of the substituents that may be possessed by (1) an alkyl that may be substituted, (2) a cycloalkyl that may be substituted, (3) an alkenyl that may be substituted, (4) a cycloalkenyl that may be substituted, (5) an alkynyl that may be substituted, (6) an aralkyl that may be substituted and (7) an aryl that may be substituted, which are described above, include a halogen (for example, fluorine, chlorine, bromine, iodine or the like), nitro, cyano, the hydroxyl group, the thiol group that may be substituted (for example, thiol, a $C_{1-4}$ alkylthio or the like), an amino group that may be substituted (for example, amino, a mono-$C_{1-4}$ alkylamino, a di-$C_{1-4}$ alkylamino, a 5- to 6-membered cyclic ring amino such as tetrahydropyrrole, piperazine, piperidine, morpholine, thiomorpholine, pyrrole, imidazole or the like, or the like), the carboxyl group that may be esterified or amidated (for example, carboxyl, a $C_{1-4}$ alkoxycarbonyl, carbamoyl, a mono-$C_{1-4}$ alkylcarbamoyl, a di-$C_{1-4}$ alkylcarbamoyl or the like), a $C_{1-4}$ alkyl that may be halogenated (for example, trifluoromethyl, methyl, ethyl or the like), a $C_{1-6}$ alkoxyl that may be halogenated (for example, methoxy, ethoxy, propoxy, butoxy, trifluoromethoxy, trifluoroethoxy or the like, formyl, a $C_{2-4}$ alkanoyl (for example, acetyl, propionyl or the like), a $C_{1-4}$ alkylsulfonyl (for example, methanesulfonyl, ethanesulfonyl or the like) or the like, where the number of the substituents is preferably 1 to 3.

The hydroxyl group that may be substituted, which is indicated by $R^{5'}$ and $R^{6'}$, is exemplified by the hydroxyl group that may be possessed by, for example, (1) an alkyl that may be substituted (for example, a $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl or the like, preferably a lower ($C_{1-6}$)alkyl, or the like is exemplified);

(2) a cycloalkyl that may be substituted (for example, a $C_{3-7}$ cycloalkyl such as cyclopropyl, cyclobutyl, cyclopentyl, cyclohexyl, cycloheptyl or the like);

(3) an alkenyl that may be substituted (for example, an alkenyl that has the carbon number of 2 to 10 such as allyl, crotyl, 2-pentenyl, 3-hexenyl or the like, preferably a lower ($C_{2-6}$)alkenyl, or the like is exemplified);

(4) a cycloalkenyl that may be substituted (for example, an cycloalkenyl that has the carbon number of 3 to 7 such as 2-cyclopentenyl, 2-cyclohexenyl 2-cyclopentenylmethyl, 2-cyclohexenylmethyl or the like, or the like is exemplified);

(5) an aralkyl that may be substituted (for example, a phenyl-$C_{1-4}$ alkyl (for example, benzyl, phenethyl or the like) or the like is exemplified);

(6) formyl or an acyl that may be substituted (for example, an alkanoyl that has the carbon number of 2 to 4 (for example, acetyl, propionyl, butyryl, isobutyryl or the like), an alkylsulfonyl that has the carbon number of 1 to 4 (for example, methanesulfonyl, ethanesulfonyl or the like) or the like is exemplified); and (7) an aryl that may be substituted (for example, phenyl, naphthyl or the like is exemplified).

Examples of the substituents that may be possessed by (1) an alkyl that may be substituted, (2) a cycloalkyl that may be substituted, (3) an alkenyl that may be substituted, (4) a cycloalkenyl that may be substituted, (5) an aralkyl that may be substituted, (6) an acyl that may be substituted and (7) an aryl that may be substituted, which are described above, include a halogen (for example, fluorine, chlorine, bromine, iodine or the like), nitro, cyano, the hydroxyl group, the thiol group that may be substituted (for example, thiol, a $C_{1-4}$ alkylthio or the like), an amino group that may be substituted (for example, amino, a mono-$C_{1-4}$ alkylamino, a di-$C_{1-4}$ alkylamino, a 5- to 6-membered cyclic ring amino such as tetrahydropyrrole, piperazine, piperidine, morpholine, thiomorpholine, pyrrole, imidazole or the like, or the like), the carboxyl group that may be esterified or amidated (for example, carboxyl, a $C_{1-4}$ alkoxycarbonyl, carbamoyl, a mono-$C_{1-4}$ alkylcarbamoyl, a di-$C_{1-4}$ alkylcarbamoyl or the like), a $C_{1-4}$ alkyl that may be halogenated (for example, trifluoromethyl, methyl, ethyl or the like), a $C_{1-6}$ alkoxyl that may be halogenated (for example, methoxy, ethoxy, propoxy, butoxy, trifluoromethoxy, trifluoroethoxy or the like, formyl, a $C_{2-4}$ alkanoyl (for example, acetyl, propionyl or the like), a $C_{1-4}$ alkylsulfonyl (for example, methanesulfonyl, ethanesulfonyl or the like) and the like, where the number of the substituents is preferably 1 to 3.

Also, in the above-mentioned formula, $R^{5'}$ and $R^{6'}$ may bind each other to form a cyclic ring group together with the adjacent phosphorus atom (preferably, a 5- to 7-membered cyclic ring). Such a cyclic ring may have substituents and examples of said substituents include a halogen (for example, fluorine, chlorine, bromine, iodine or the like), nitro, cyano, the hydroxyl group, the thiol group that may be substituted (for example, thiol, a $C_{1-4}$ alkylthio or the like), an amino group that may be substituted (for example, amino, a mono-$C_{1-4}$ alkylamino, a di-$C_{1-4}$ alkylamino, a 5- to 6-membered cyclic ring amino such as tetrahydropyrrole, piperazine, piperidine, morpholine, thiomorpholine, pyrrole, imidazole or the like, or the like), the carboxyl group that may be esterified or amidated (for example, carboxyl, a $C_{1-4}$ alkoxycarbonyl, carbamoyl, a mono-$C_{1-4}$ alkylcarbamoyl, a di-$C_{1-4}$ alkylcarbamoyl or the like), a $C_{1-4}$ alkyl that may be halogenated (for example, trifluoromethyl, methyl, ethyl or the like), a $C_{1-6}$ alkoxyl that may be halogenated (for example, methoxy, ethoxy, propoxy, butoxy, trifluoromethoxy, trifluoroethoxy or the like, formyl, a $C_{2-4}$ alkanoyl (for example, acetyl, propionyl or the like), a $C_{1-4}$ alkylsulfonyl (for example, methanesulfonyl, ethanesulfonyl or the like) and the like, where the number of the substituents is preferably 1 to 3.

In the above-mentioned formula (I), a counter anion in the case where the phosphorus atom forms a phosphonium salt is exemplified by, in addition to an anion of a halogen atom (for example, $Cl^-$, $Br^-$, $I^-$ or the like) or the like, an anion derived from an inorganic acid such as hydrochloric acid, hydrobromic acid, nitric acid, sulfuric acid, phosphoric acid and the like, an anion derived from an organic acid such as formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like and an anion derived from an acidic amino acid such as aspartic acid, glutamic acid and the like, where Cl⁻, Br⁻, I⁻ or the like is more preferable.

An amino group that may be substituted, which is indicated by $R^{5'}$ and $R^{6'}$, is exemplified by an amino group that may have 1 to 2 groups such as, (1) an alkyl that may be substituted (for example, a $C_{1-10}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl or the like, preferably a lower ($C_{1-6}$)alkyl, or the like is exemplified);

(2) a cycloalkyl that may be substituted (for example, a $C_{3-7}$ cycloalkyl such as cyclopropyl, cyclobutyl, cyclopentyl, cyclohexyl, cycloheptyl or the like);

(3) an alkenyl that may be substituted (for example, an alkenyl that has the carbon number of 2 to 10 such as allyl, crotyl, 2-pentenyl, 3-hexenyl or the like, preferably a lower ($C_{2-6}$)alkenyl, or the like is exemplified);

(4) a cycloalkenyl that may be substituted (for example, an cycloalkenyl that has the carbon number of 3 to 7 such as 2-cyclopentenyl, 2-cyclohexenyl 2-cyclopentenylmethyl, 2-cyclohexenylmethyl or the like, or the like is exemplified);

(5) formyl or an acyl that may be substituted (for example, an alkanoyl that has the carbon number of 2 to 4 (for example, acetyl, propionyl, butyryl, isobutyryl or the like), an alkylsulfonyl that has the carbon number of 1 to 4 (for example, methanesulfonyl, ethanesulfonyl or the like) or the like is exemplified); and (6) an aryl that may be substituted (for example, phenyl, naphthyl or the like is exemplified).

Examples of the substituents that may be possessed by (1) an alkyl that may be substituted, (2) a cycloalkyl that may be substituted, (3) an alkenyl that may be substituted, (4) a cycloalkenyl that may be substituted, (5) an acyl that may be substituted and (6) an aryl that may be substituted, which are described above, include a halogen (for example, fluorine, chlorine, bromine, iodine or the like), nitro, cyano, the hydroxyl group, the thiol group that may be substituted (for example, thiol, a $C_{1-4}$ alkylthio or the like), an amino group that may be substituted (for example, amino, a mono-$C_{1-4}$ alkylamino, a di-$C_{1-4}$ alkylamino, a 5- to 6-membered cyclic ring amino such as tetrahydropyrrole, piperazine, piperidine, morpholine, thiomorpholine, pyrrole, imidazole or the like, or the like), the carboxyl group that may be esterified or amidated (for example, carboxyl, a $C_{1-4}$ alkoxycarbonyl, carbamoyl, a mono-$C_{1-4}$ alkylcarbamoyl, a di-$C_{1-4}$ alkylcarbamoyl or the like), a $C_{1-4}$ alkyl that may be halogenated (for example, trifluoromethyl, methyl, ethyl or the like), a $C_{1-6}$ alkoxyl that may be halogenated (for example, methoxy, ethoxy, propoxy, butoxy, trifluoromethoxy, trifluoroethoxy or the like, formyl, a $C_{2-4}$ alkanoyl (for example, acetyl, propionyl or the like), a $C_{1-4}$ alkylsulfonyl (for example, methanesulfonyl, ethanesulfonyl or the like) and the like, where the number of the substituents is preferably 1 to 3.

The substituents for "an amidino group that may be substituted" and "a guanidino group that may be substituted" are exemplified by substituents similar to those for "an amino group that may be substituted, where the nitrogen atom may be converted into a quaternary ammonium or the N-oxide" that is indicated by $R^2$.

It is preferable that $R^2$ is (1) an amino group that may be substituted, where the nitrogen atom may be converted into a quaternary ammonium or the N-oxide, (2) a nitrogen-containing, heterocyclic ring group that may be substituted and may contain the sulfur atom or the oxygen atom as a ring-constituting atom, where the nitrogen atom may be converted into a quaternary ammonium or the N-oxide, (3) an amidino group that may be substituted or (4) a guanidino group that may be substituted and it is more preferable that $R^2$ is an amino group that may be substituted, where the nitrogen atom may be converted into a quaternary ammonium or the N-oxide, or the like. Also, $R^2$ may be an amidino group that may be substituted or a guanidino group that may be substituted.

It is more preferable that $R^2$ is —NRR" or —N⁺RR'R" (wherein each of R, R' and R" indicates an aliphatic hydrocarbon group (an aliphatic-chain hydrocarbon group and an aliphatic, cyclic hydrocarbon group) that may be substituted or an alicyclic (non-aromatic), heterocyclic ring group that may be substituted).

In the above-mentioned formula, "an aliphatic hydrocarbon group that may be substituted" and "an alicyclic, heterocyclic ring group that may be substituted", which are indicated by R, R' and R', are exemplified by substituents similar to "an aliphatic hydrocarbon group that may be substituted (for example, an alkyl, a cycloalkyl, an alkenyl, a cycloalkenyl or the like, each of which may be substituted)" and "an alicyclic, heterocyclic ring group that may be substituted (for example, a 5- to 6-membered, non-aromatic, heterocyclic ring that may be substituted or the like)", which are exemplified by as the substituents that may be possessed by "an amino group that may be substituted" indicated by $R^2$.

Especially, as for R and R', an aliphatic hydrocarbon group that may be substituted (for example, an alkyl, an alkenyl or the like, each of which may be substituted) is preferable, a $C_{1-6}$ alkyl group that may be substituted is more preferable and the methyl that may be substituted is particularly preferable.

It is preferable that R" is an aliphatic hydrocarbon group that may be substituted (preferably, a $C_{3-8}$ cycloalkyl group that may be substituted; more preferably, a cyclohexyl that may be substituted) or an alicyclic, heterocyclic ring group that may be substituted (preferably, a saturated alicyclic, heterocyclic ring group that may be substituted (preferably, a 6-membered cyclic ring group); more preferably, tetrahydropyranyl that may be substituted, tetrahydrothiopyranyl that may be substituted or piperidyl that may be substituted; and particularly preferably, tetrahydropyranyl that may be substituted).

The following compounds are preferable as the compounds represented by formula (I).

N-[4-[N-Methyl-N-(tetrahydropyran-4-yl)aminomethyl] phenyl]-7-[2-(4-propoxyphenyl)ethoxy]-1,1-dioxo-2,3-dihydro-1-benzothiepine-4-carboxamide;

N-[4-[N-methyl-N-(tetrahydropyran-4-yl)aminomethyl] phenyl]-7-[(3-propoxybenzyl)oxy]-1,1-dioxo-2,3-dihydro-1-benzothiepine-4-carboxamide;

N-[4-[N-methyl-N-(tetrahydropyran-4-yl)aminomethyl] phenyl]-7-[(2-propoxybenzyl)oxy]-1,1-dioxo-2,3-dihydro-1-benzothiepine-4-carboxamide;

N-[4-[N-methyl-N-(tetrahydropyran-4-yl)aminomethyl] phenyl]-7-[(4-chlorobenzyl)oxy]-1,1-dioxo-2,3-dihydro-1-benzothiepine-4-carboxamide;

N-[4-[N-methyl-N-(tetrahydropyran-4-yl)aminomethyl] phenyl]-7-[(4-ethoxybenzyl)oxy]-1,1-dioxo-2,3-dihydro-1-benzothiepine-4-carboxamide;

N-[4-[N-methyl-N-(tetrahydropyran-4-yl)aminomethyl]
phenyl]-7-[[4-(propoxymethyl)benzyl]oxy]-1,1-dioxo-2,
3-dihydro-1-benzothiepine-4-carboxamide;

N-[1-(tetrahydropyran-4-yl)piperidin-4-yl]-7-(4-phenyl)-2,
3-dihydro-1-benzooxepine-4-carboxamide;

N-[4-[(2-imidazolin-2-yl)methyl]phenyl]-7-(4-
methylphenyl)-2,3-dihydro-1-benzooxepine-4-
carboxamide;

N-[4-[N-methyl-N-(tetrahydropyran-4-yl)aminomethyl]
phenyl]-7-[(4-propoxyphenyl)methoxy]-1,1-dioxo-2,3-
dihydro-1-benzothiepine-4-carboxamide;

N-[4-[N-methyl-N-(tetrahydropyran-4-yl)aminomethyl]
phenyl]-7-[(4-propoxyethoxyphenyl)methoxy]-1,1-
dioxo-2,3-dihydro-1-benzothiepine-4-carboxamide;

N-[4-[N-methyl-N-(tetrahydropyran-4-yl)aminomethyl]
phenyl]-7-[3-(4-propoxyphenyl)propoxy]-1,1-dioxo-2,3-
dihydro-1-benzothiepine-4-carboxamide; and the like.

As for a salt of any of the compounds represented by formula (I) of the present invention, a pharmaceutically permissible salt is preferable and is exemplified by a salt with an inorganic base, a salt with an organic base, a salt with an inorganic acid, a salt with an organic acid, a salt with a basic or acidic amino acid and the like. Preferable examples of a salt with an inorganic base include an alkali metal salt such as the sodium salt, the potassium salt and the like; an alkaline earth metal salt such as the calcium salt, the magnesium salt and the like; as well as the aluminum salt, the ammonium salt and the like. Preferable examples of a salt with an organic base include salts with any of trimethylamine, triethylamine, pyridine, picoline, ethanolamine, diethanolamine, triethanolamine, dicyclohexylamine, N,N'-dibenzylethylenediamine and the like. Preferable examples of a salt with an inorganic acid include salts with any of hydrochloric acid, hydrobromic acid, nitric acid, sulfuric acid, phosphoric acid and the like. Preferable examples of a salt with an organic acid include salts with any of formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of a salt with a basic amino acid include salts with any of arginine, lysine, ornithine and the like, and preferable examples of a salt with an acidic amino acid include salts with any of aspartic acid, glutamic acid and the like. The compounds represented by formula (I) of the present invention may be in the form of hydrates or may be in the form of non-hydrates. Also, in the case where any of the compounds represented by formula (I) of the present invention exists in configurational isomers, diastereomers, conformers or the like, they can be separated into each isomer according to a well-known, separation/purification means. Also, in the case where any of the compounds represented by formula (I) of the present invention is in the form of racemates, they may be separated according to a conventional optical resolution means into the (S) form and the (R) form, where each of the optically active compounds and the racemates is encompassed in the present invention.

The prodrug of any of the compounds represented by formula (I) to be employed in the present invention or a salt thereof [hereinafter, it may be designated as compound (I).] refers to a compound that is converted into compound (I) by a reaction with an enzyme, gastric acid or the like under a physiological condition in the living body, namely, a compound that is converted into compound (I) by oxidation, reduction, hydrolysis or the like, each of which is carried out enzymatically, and a compound that is converted into compound (I) by hydrolysis with gastric acid or the like. Examples of the prodrug of compound (I) include a compound, wherein the amino group in compound (I) is acylated, alkylated or phosphorylated (for example, a compound, wherein the amino group in compound (I) is converted into eicosanoylamino, alanylamino, pentylaminocarbonylamino, (5-methyl-2-oxo-1,3-dioxolan-4-yl)methoxycarbonylamino, tetrahydrofuranylamino, pyrrolidylmethylamino, pivaloyloxymethylamino or tert-butylamino, or the like); a compound, wherein the hydroxyl group in compound (I) is acylated, alkylated, phosphorylated or converted into the borate (for example, a compound, wherein the hydroxyl group in compound (I) is converted into acetyloxy, palmitoyloxy, propanoyloxy, pivaloyloxy, succinyloxy, fumaryloxy, alanyloxy, or dimethylaminomethylcarbonyloxy, or the like); a compound, wherein the carboxyl group in compound (I) is esterified or amidated (for example, a compound, wherein the carboxyl group in compound (I) is subjected to ethyl esterification, phenyl esterification, carboxyoxymethyl esterification, dimethylaminomethyl esterification, pivaloyloxymethyl esterification, ethoxycarbonyloxyethyl esterification, phthalidyl esterification, (5-methyl-2-oxo-1,3-dioxolan-4-yl)methyl esterification, cyclohexyloxycarbonyl esterification, or conversion into the methyl amide, or the like); and the like. These compounds can be produced from compound (I) according to a well-known method.

Moreover, the prodrug of compound (I) may be a compound that is converted into compound (I) under a physiological condition as described in "Development of Drugs", Volume 7, Molecular Design, Hirokawa Shoten, 1990; pages 163–198.

Also, compound (I) may be labeled with an isotope (for example, $^3$H, $^{14}$C, $^{35}$S, $^{125}$I or the like) or the like.

Any of the compounds represented by formula (I) of the present invention or a salt thereof (hereinafter, in the case where it abbreviated as compound (I), a salt thereof as well as any of the compounds represented by formula (I) and a salt thereof shall be included) can be alone, or by compounding with a pharmaceutically permissible carrier, orally or parenterally administered as a solid formulation such as a tablet, a capsule, a granule, a powder or the like; or a liquid formulation such as a syrup, an injection or the like.

The parenterally administered form is exemplified by an injection, a drip, a suppository, a pessary and the like, where a pessary is particularly useful for the prophylaxis of the HIV infectious diseases.

As for the pharmaceutically permissible carrier, any of a variety of organic or inorganic carrier substances, which have been conventionally employed as formulation materials, are used and compounded as a bulking agent, a lubricant, a binding agent and a disintegrator in a solid formulation; a vehicle, a solubilizing agent, a suspending agent, an isotonicity agent, a buffering agent and an analgesic in a liquid formulation. Also, as needed, formulation excipients such as a preservative, an antioxidant, a stabilizer, a coloring agent, a sweetening agent and the like can be used. Preferable examples of the bulking agent include, for example, lactose, sucrose, D-mannitol, starch, crystalline cellulose, light anhydrous silicic acid and the like. Preferable examples of the lubricant include, for example, magnesium stearate, potassium stearate, talc, colloidal silica and the like. Preferable examples of the binding agent include, for example, crystalline cellulose, sucrose, D-mannitol, dextrin, hydroxypropyl cellulose, hydroxypropylmethyl cellulose, polyvinyl pyrrolidone and the like. Preferable examples of the disintegrator include, for example, starch, carboxymethyl cellulose, calcium carboxymethyl cellulose, croscarmellose sodium, sodium carboxymethyl starch and the like. Preferable examples of the vehicle include, for example, water for injection, alcohol, propylene glycol, macrogol, sesame oil, corn oil and the like. Preferable examples of the solubilizing agent include, for example, polyethylene glycol, propylene glycol, D-mannitol, benzyl benzoate, ethanol, trisaminomethane, cholesterol, triethanolamine, sodium carbonate, sodium citrate and the like. Preferable examples of the suspending agent include, for example, a surface active agent such as stearyltriethanolamine, sodium lauryl sulfate, laurylaminopropionic acid, lecithin, benzalkonium chloride, benzethonium chloride, glycerin monostearate and the like; a hydrophilic, high molecular weight substance such as polyvinyl alcohol, polyvinyl pyrrolidone, sodium carboxymethyl cellulose, methyl cellulose, hydroxymethyl cellulose, hydroxyethyl cellulose, hydroxypropyl cellulose and the like, and the like. Preferable examples of the isotonicity agent include, for example, sodium chloride, glycerin, D-mannitol, and the like. Preferable examples of the buffering agent include, for example, a buffer solution of a phosphate, an acetate, a carbonate or a citrate and the like. Preferable examples of the analgesic include, for example, benzyl alcohol and the like. Preferable examples of the preservative include, for example, paraoxybenzoic acid esters, chlorobutanol, benzyl alcohol, phenethyl alcohol, dehydroacetic acid, sorbic acid and the like. Preferable examples of the antioxidant include, for example, sulfites, ascorbic acid and the like.

Any of the compounds represented by formula (I) of the present invention or a salt thereof may be employed in combination with another prophylactic/therapeutic agent of HIV infectious diseases (particularly a prophylactic/therapeutic agent of AIDS). In this case, these drugs can be formulated by compounding, separately or at the same time, with a pharmacologically permissible carrier, a bulking agent, a binding agent, a diluent and the like, and the resulting preparation can be orally or parenterally administered as the pharmaceutical composition for the prophylaxis and/or therapeutics. In the case where the drugs are formulated separately, the separately formulated preparations can be administered by admixing by the use of a diluent at the time of usage, whereas each of the separately formulated preparations may be administered to the same subject at the same time or separately with a time difference. A kit product for administering the separately formulated preparations by admixing by the use of a diluent at the time of usage (for example, a kit for injection comprising ampoules, each containing a particular drug, and a diluent for dissolving 2 or more kinds of drugs by admixing at the time of usage, or the like), a kit product for administering each of the separately formulated preparations to the same subject at the same time or separately with a time difference (for example, a kit for tablets, which encloses the tablets, each containing a particular drug, in a same bag or separate bags, as needed, fitted with a time field where the times for administration of the drugs are described, and allows to administer 2 or more kinds of drugs at the same time or separately with a time difference, or the like) and the like are encompassed in the pharmaceutical compositions of the present invention.

Specific examples of other prophylactic/therapeutic agents of HIV infectious diseases, which are to be employed in combination with the compounds represented by formula (I) of the present invention or salts thereof, include nucleic acid reverse transcriptase inhibitors such as zidovudine, didanosine, zalcitabine, lamivudine, stavudine, abacavir, adefovir, adefovir dipivoxil, fozivudine tidoxil and the like; non-nucleic acid reverse transcriptase inhibitors such as nevirapine, delavirdine, efavirenz, loviride, immunocal, olitipraz and the like (contain drugs, which have an antioxidant action, such as immunocal, olitipraz and the like); protease inhibitors such as saquinavir, ritonavir, indinavir, nelfinavir, amprenavir, palinavir, lasinavir and the like; and the like.

As for the nucleic acid reverse transcriptase inhibitors, zidovudine, didanosine, zalcitabine, lamivudine, stavudine and the like are preferable, as for non-nucleic acid reverse transcriptase inhibitors, nevirapine, delavirdine and the like are preferable and as for the protease inhibitors, saquinavir, ritonavir, indinavir, nelfinavir and the like are preferable.

Processes for the production of the compounds represented by formula (I) or salts thereof are shown in the following.

The compounds represented by formula (I) or salts thereof can be produced according to the well-known processes. For instance, they can be produced according to the following processes. Also, the compounds represented by formula (I) or salts thereof can be produced according to the process described in Japanese Patent Kokai Publication No. 1996-73476 or a modified process thereof.

Compounds, which are to be used in each of the following production processes, may form salts similar to compounds (I), as far as the reactions are not disturbed.

Also, in the case where a compound to be used as the raw material has an amino group, the carboxyl group and the hydroxyl group as substituents in each of the following reactions, such protective groups that are employed in general in the peptide chemistry may be introduced to these groups, where the objective compounds can be obtained by removal of the protecting groups after the reactions, as needed.

As for the protective group for an amino group, there is employed, for example, a $C_{1-6}$ alkylcarbonyl (for example, acetyl, propionyl or the like), formyl, a phenylcarbonyl, a $C_{1-6}$ alkyloxycarbonyl (for example, methoxycarbonyl, ethoxycarbonyl, t-butoxycarbonyl or the like), a phenyloxycarbonyl (for example, benzoxycarbonyl or the like), a $C_{7-10}$ aralkyloxycarbonyl (for example, benzyloxycarbonyl or the like), trityl, phthaloyl or the like, each of which may have substituents. As for these substituents, there is employed a halogen atom (for example, fluorine, chlorine, bromine, iodine or the like), a $C_{1-6}$ alkylcarbonyl (for example, acetyl, propionyl, butyryl or the like), the nitro group or the like, where the number of the substituents is about 1 to 3.

As for the protective group for the carboxyl group, there is employed, for example, a $C_{1-6}$ alkyl (for example, methyl, ethyl, propyl, isopropyl, butyl, tert-butyl or the like), phenyl, trityl, silyl or the like, each of which may have substituents. As for these substituents, there is employed a halogen atom (for example, fluorine, chlorine, bromine, iodine or the like), a $C_{1-6}$ alkylcarbonyl (for example, acetyl, propionyl, butyryl or the like), formyl, the nitro group or the like, where the number of the substituents is about 1 to 3.

As for the protective group for the hydroxyl group, there is employed, for example, a $C_{1-6}$ alkyl (for example, methyl, ethyl, propyl, isopropyl, butyl, tert-butyl or the like), phenyl, a $C_{7-10}$ aralkyl (for example, benzyl or the like), a $C_{1-6}$ alkylcarbonyl (for example, acetyl, propionyl or the like), formyl, a phenylcarbonyl, a $C_{7-10}$ aralkyloxycarbonyl (for example, benzyloxycarbonyl or the like), pyranyl, furanyl, silyl or the like, each of which may have substituents. As for these substituents, there is employed a halogen atom (for example, fluorine, chlorine, bromine, iodine or the like), a $C_{1-6}$ alkyl, phenyl, a $C_{7-10}$ aralkyl, the nitro group or the like, where the number of the substituents is about 1 to 4.

Also, as for the methods for introduction and removal of the protective groups, the well-known methods or modified methods thereof [for example, methods described in PROTECTIVE GROUPS IN ORGANIC SYNTHESIS (by J. F. W. McOmie et al., Plenum Press Company) are employed, where methods to treat with, for example, an acid, a base, a ultraviolet light, hydrazine, phenylhydrazine, sodium N-methyldithiocarbamate, tetrabutylammonium fluoride, palladium acetate or the like are employed as the methods for removal.

[Method A]

Compound (I) or a salt thereof can be produced, according to the reaction shown below, by reacting compound [II] or a salt thereof with compound [III] or a salt thereof.

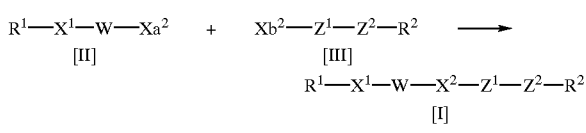

[wherein a group, which reacts with the substituent $Xb^2$ in compound [III] or a salt thereof to form $X^2$, is indicated by $Xa^2$ (for example, the carboxyl group or the like) and a group, which reacts with the substituent $Xa^2$ in compound [II] or a salt thereof to form $X^2$, is indicated by $Xb^2$ (for example, the amino group or the like) and other symbols have the same meanings as mentioned hereinabove.]

In the following is shown the production process in the case where $Xa^2$ is the carboxyl group, $Xb^2$ is the amino group and $X^2$ is —CO—NH—.

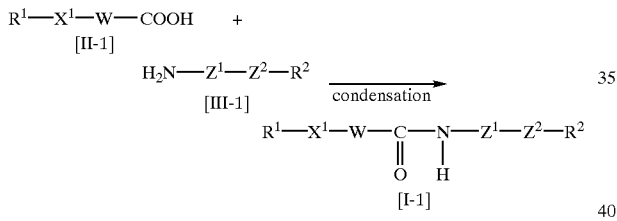

[each symbol of the formula has the same meaning as mentioned hereinabove]

In the present method, compound [I-1] is produced be reacting a carboxylic acid derivative [II-1] with an amine derivative.[III-1].

The condensation reaction of [II-1] and [III-1] is carried out according to a conventional means for peptide synthesis. Said means for peptide synthesis may be followed by an optional known method, a method described in, for example, M. Bodansky and M. A. Ondetti, Peptide Synthesis, Interscience, New York, 1996; F. M. Finn and K. Hofmann, The Proteins, Volume 2, H. Nenrath and R. L. Hillor, Ed., Academic Press Inc., New York, 1976; Nobuo Izumiya et al. "Bases and Experiments for Peptide Synthesis", Maruzen Kabushiki Kaisha, 1985, or the like, as exemplified by the azide method, the chloride method, the acid anhydride method, the mixed acid anhydride method, the DCC method, the active ester method, the method by the use of Woodward reagent K, the carbonyl diimidazole method, the oxidation-reduction method, the DCC/HONB method or the like, as well as the WSC method, the method by the use of diethyl cyanophosphonate or the like. The present condensation reaction can be carried out in a solvent. The solvent is exemplified by, for example, N,N-dimethylformamide, dimethyl sulfoxide, pyridine, chloroform, dichloromethane, tetrahydrofuran, dioxane, acetonitrile or an adequate mixture of these solvents. The reaction temperature is usually about –20° C. to about 50° C., preferably about –10° C. to about 30° C. The reaction time is usually about 2 hour to about 40 hours. The thus-obtained compound (I-1) can be subjected to isolation and purification according to the known separation and purification means such as concentration, concentration under reduced pressure, solvent extraction, crystallization, recrystallization, trans-solubilization, chromatography and the like.

[Method B]

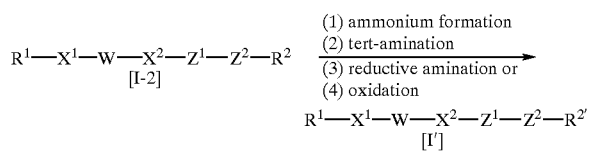

[1] In the case where $R^{2''}$ represented in compound [I-2] is, for example, a tertiary amine residue, quaternary compound

[I'] can be produced by reacting compound [I-2] with a halogenated alkyl or a halogenated aralkyl. Herein, the halogen atom is exemplified by chlorine, bromine, iodine or the like, and a halogenated alkyl (for example, a halogenated, lower ($C_{1-6}$)alkyl or the like) or a halogenated aralkyl (for example, a halogenated, lower ($C_{1-4}$)alkylphenyl or the like) is used usually in an amount of about 1 to 5 moles per one mole of compound [I-2]. The present reaction can be carried out in an inactive solvent, as exemplified by, for example, toluene, benzene, xylene, dichloromethane, chloroform, 1,2-dichloroethane, dimethylformamide (DMF), dimethyl acetamide or a mixed solvent thereof. The reaction temperature is a temperature range of about 10° C. to about 160° C., preferably about 20° C. to about 120° C. The reaction time is usually about one hour to about 100 hours, preferably, about 2 hours to about 40 hours. In addition, the present reaction is carried out preferably under an atmosphere of an inert gas (for example, nitrogen, argon or the like).

[2] In the case where $R^{2''}$ represented in compound [I-2] is, for example, a secondary amine residue, tertiary compound

[I'] can be produced by reacting compound [I-2] with a halogenated alkyl or a halogenated aralkyl. Herein, the halogen atom is exemplified by chlorine, bromine, iodine or the like, and a halogenated alkyl or a halogenated aralkyl is used usually in an amount of about 1 to 2 moles per one mole of compound [I-2]. This reaction can be allowed to proceed smoothly, as needed, by addition of an about equimolar amount to 3 molar amount of a base such as triethylamine, diisopropylethylamine, pyridine, lithium hydride, sodium hydride, sodium methoxide, sodium ethoxide, sodium carbonate, potassium carbonate, sodium hydrogen carbonate or the like, and further by addition of sodium iodide, potassium iodide or the like.

The present tertiary amination reaction can be carried out in an inactive solvent, as exemplified by, for example, methanol, ethanol, propanol, isopropanol, n-butanol, tetrahydrofuran, diethyl ether, dimethoxyethane, 1,4-dioxane, toluene, benzene, xylene, dichloromethane, chloroform, 1,2-dichloroethane, dimethylformamide (DMF), dimethyl sulfoxide (DMSO), pyridine or the like, or a mixed solvent thereof. The reaction temperature is a temperature range of about 0° C. to about 180° C. for about one hour to about 40 hours. In addition, the present reaction is carried out preferably under an atmosphere of an inert gas (for example, nitrogen, argon or the like).

[3] In the case where $R^{2''}$ represented in compound [I-2] is, for example, a secondary amine residue, tertiary compound [I'] can be produced by reacting compound [I-2] with an aldehyde compound in the presence of a reductive amination reagent such as sodium triacetoxyborohydride, sodium cyanoborohydride, sodium borohydride or the like. It is preferable that the reaction conditions of the present reductive amination reaction are altered depending on the reagent to be used, where, for instance, in the case where sodium triacetoxyborohydride is used, the reaction can be carried out in an inactive solvent, as exemplified by, for example, dichloromethane, chloroform, 1,2-dichloroethane, tetrahydrofuran (THF), diethyl ether, dioxane, acetonitrile, dimethylformamide (DMF) or the like, or a mixed solvent thereof. The present reagent is used in an amount of about 1 to 2 molar equivalents per one mole of compound [I-2]. The reaction is carried out usually at a temperature range of about 0° C. to about 80° C. for about one hour to about 40 hours. In addition, the present reaction is carried out preferably under an atmosphere of an inert gas (for example, nitrogen, argon or the like).

[4] In the case where $R^{2''}$ represented in compound [I-2] is, for example, a sulfide residue or a tertiary amine residue, compound [I'] having the sulfinyl group, the sulfonyl group or the amine oxide group can be produced by reacting compound [I-2] with an oxidizing agent such as m-chloroperbenzoic acid, perbenzoic acid, paranitroperbenzoic acid, magnesium monoperoxyphthalate, peracetic acid, hydrogen peroxide, sodium periodate, potassium periodate or the like. It is preferable that the reaction conditions of this oxidation reaction are altered depending on the oxidizing reagent to be used, where, for instance, in the case where m-chloroperbenzoic acid is used, the reaction can be carried out in an inactive solvent, as exemplified by, for example, dichloromethane, chloroform, 1,2-dichloroethane, tetrahydrofuran, acetone, ethyl acetate or the like, or a mixed solvent thereof. The oxidizing reagent is used in an amount of about 1 to 3 molar equivalents per one mole of compound [I-2]. The reaction is carried out usually at a temperature range of about −20° C. to about 80° C., (preferably, about −25° C. to about 25° C. for about one hour to about 40 hours.

[Method C]

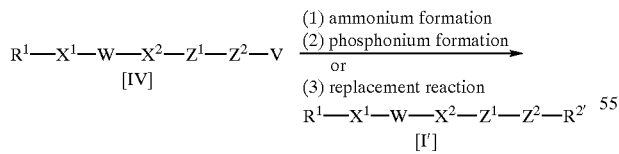

V in compound [IV] indicates a halogen atom (for example, chlorine, bromine, iodine or the like) or a sulfonyloxy group (the methanesulfonyloxy group, the trifluoromethanesulfonyloxy group, the benzenesulfonyloxy group or the toluenesulfonyloxy group) and other symbols indicate the same meanings as indicated hereinabove.

[1] Quaternary compound [I'] can be produced by reacting compound [IV] with a tertiary amine. The present reaction can be carried out in an inactive solvent, as exemplified by, for example, toluene, benzene, xylene, dichloromethane, chloroform, 1,2-dichloroethane, dimethylformamide (DMF), dimethyl acetamide or the like, or a mixed solvent thereof. The tertiary amine is used in an amount of about 1 to 3 moles per one mole of compound [IV]. The present reaction is carried out at a temperature range of about 10° C. to about 120° C. for about one hour to about 40 hours. In addition, the present reaction is carried out preferably under an atmosphere of an inert gas (for example, nitrogen, argon or the like).

[2] Quaternary compound [I'] can be produced by reacting compound [IV] with a tertiary phosphine. The present reaction can be carried out in an inactive solvent, as exemplified by, for example, toluene, benzene, xylene, dichloromethane, chloroform, 1,2-dichloroethane, acetonitrile, dimethylformamide (DMF) or the like, or a mixed solvent thereof. The tertiary phosphine is used in an amount of about 1 to 2 moles per one mole of compound [IV]. The present reaction is carried out at a temperature range of about 20° C. to about 150° C. for about one hour to about 50 hours. In addition, the present reaction is carried out preferably under an atmosphere of an inert gas (for example, nitrogen, argon or the like).

[3] Compound [I'] having a secondary or tertiary amino group or a thio group can be produced by reacting compound [IV] with a primary or secondary amine compound or a thiol compound. The primary or secondary amine compound or the thiol compound is used usually in an amount of about 1 to 3 moles per one mole of compound [IV]. This reaction can be allowed to proceed smoothly, as needed, by addition of an about equimolar amount to 3 molar amount of a base such as triethylamine, diisopropylethylamine, pyridine, lithium hydride, sodium hydride, sodium methoxide, sodium ethoxide, sodium carbonate, potassium carbonate, sodium hydrogen carbonate or the like, and further by addition of sodium iodide, potassium iodide or the like. The present substitution reaction can be carried out in an inactive solvent, as exemplified by, for example, methanol, ethanol, propanol, isopropanol, n-butanol, tetrahydrofuran, diethyl ether, dimethoxyethane, 1,4-dioxane, toluene, benzene, xylene, dichloromethane, chloroform, 1,2-dichloroethane, dimethylformamide (DMF), dimethyl sulfoxide (DMSO), pyridine or the like, or a mixed solvent thereof. The reaction is carried out at a temperature range of about −10° C. to about 180° C. for about one hour to about 40 hours. In addition, the present reaction is carried out preferably under an atmosphere of an inert gas (for example, nitrogen, argon or the like).

[Method D]

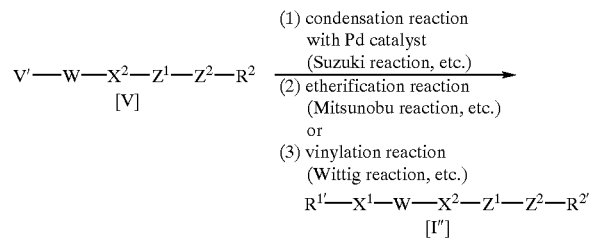

[1] Compound [V] [wherein V' indicates a halogen atom (for example, bromine, iodine or the like) or a sulfonyloxy group (the trifluoromethanesulfonyloxy group or the like) and other symbols indicate the same meanings as indicated hereinabove] is subjected to, for example, the Suzuki reaction [a cross condensation reaction of an arylboric acid and, for example, an aryl halide or an aryloxytrifluoromethanesulfonate by the use of a palladium catalyst; A. Suzuki, et al., Synth. Commun. 1981, 11, 513] to be able to produce compound [I"], wherein $X^1$ indicates a bond and $R^1$ indicates a 5- to 6-membered, cyclic ring aromatic group. Compound [I"] can be obtained by the use of an arylboric acid in an about equimolar amount to 1.5 molar amount per one mole of compound [V].

Also, compound [V] is subjected to, for example, a cross condensation reaction with an arylacetylene compound in the presence of a palladium catalyst [dichlorobis(triphenylphosphine)palladium or the like] [K. S. Y. Lau, et al., J. Org. Chem. 1981, 46, 2280; J. W. Tilley, S. Zawoisky, et al., J. Org. Chem. 1988, 53, 386] to be able to produce compound [I"] having an acetylenic bond, wherein $X^1$ indicates —C≡C—. Compound [I"] can be obtained by the use of an arylacetylene compound, usually, in an about equimolar amount to 2 molar amount per one mole of compound [V].

[2] Compound [V] [wherein V' indicates the hydroxyl group and other symbols indicate the same meanings as indicated hereinabove] is subjected to, for example, the Mitsunobu reaction [the etherification reaction by the use of a condensing agent such as, for example, triphenylphosphine and diethyl azodicarboxylate; O. Mitsunobu, et al., Synthesis, 1981, 1] to be able to produce compound [I"] having an ether bond. Compound [I"] can be obtained by the use of the corresponding alcohol compound or phenol compound in an about equimolar amount to 3 molar amount per one mole of compound [V].

In addition, compound [I"] having an ether bond can be produced also by the etherification reaction of compound [V] with a reactive compound such as a halo (chloro, iodo or the like) compound, a tosylate compound, a mesylate compound or the like. Said reactive compound is used usually in an about equimolar amount to 3 molar amount per one mole of compound [V]. This reaction can be allowed to proceed smoothly, as needed, by addition of an about equimolar amount to 3 molar amount of a base such as triethylamine, diisopropylethylamine, pyridine, lithium hydride, sodium hydride, sodium hydroxide, potassium hydroxide, sodium methoxide, sodium ethoxide, sodium carbonate, potassium carbonate, sodium hydrogen carbonate or the like, and further by addition of sodium iodide, potassium iodide or the like. The present substitution reaction can be carried out in an inactive solvent, as exemplified by, for example, tetrahydrofuran, diethyl ether, dimethoxyethane, 1,4-dioxane, toluene, benzene, xylene, dichloromethane, chloroform, 1,2-dichloroethane, dimethylformamide (DMF), dimethyl sulfoxide (DMSO), pyridine or the like, or a mixed solvent thereof. The reaction is carried out at a temperature range of about –10° C. to about 180° C. for about one hour to about 40 hours. In addition, the present reaction is carried out preferably under an atmosphere of an inert gas (for example, nitrogen, argon or the like).

[3] Compound [V] [wherein V' indicates the carbonyl group or a phosphonium salt, each of which may be substituted, or a phosphorous acid ester residue and other symbols indicate the same meanings as indicated hereinabove] is subjected to, for example, the Wittig reaction [A. Maercker, Org. React. 14, 270 (1965)] or the Wittig-Horner-Emmons reaction [J. Boutagy, R. Thomas, Chem. Rev., 74, 87 (1974)] to be able to produce compound [I"] having a vinyl bond. The corresponding carbonyl compound or phosphonium salt, or the phosphorous acid ester residue is used usually, in an about equimolar amount to 1.5 molar amount per one mole of compound [V].

[Method E]

$R^1—X^1—W—X^2—Z^1—Z^2—V''$
[VI]

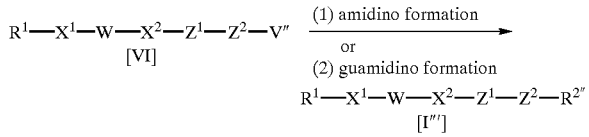

$R^1—X^1—W—X^2—Z^1—Z^2—R^{2''}$
[I''']

[1] First, compound [VI] [wherein V" indicates the cyano group and other symbols indicate the same meanings as indicated hereinabove] is reacted with a lower alcohol such as methanol, ethanol, propanol or the like in the presence of an acid such as hydrochloric acid or the like to obtain an imidate compound. The present reaction is carried out usually by the use of an excess amount of the above-mentioned alcohol at a temperature range of about –10° C. to about 50° C. for about one hour to about 40 hours. Also, the present reaction can be carried out in an inactive solvent, as exemplified by, for example, diethyl ether, 1,4-dioxane, toluene, benzene, xylene, dichloromethane, chloroform, 1,2-dichloroethane or the like, or a mixed solvent thereof.

Next, the thus-obtained imidate compound is subjected to the substitution reaction with a primary or secondary amine compound to be able to produce an amidine compound [I'"]. The primary or secondary amine compound is used usually in an amount of about 1 to 5 moles per one mole of the imidate compound. This reaction can be allowed to proceed smoothly, as needed, by addition of an about equimolar amount to 3 molar amount of a desalting agent such as triethylamine, pyridine, sodium hydroxide, potassium hydroxide, sodium methoxide, sodium ethoxide, sodium carbonate, potassium carbonate or the like. The present substitution reaction can be carried out in an inactive solvent, as exemplified by, for example, methanol, ethanol, propanol, isopropanol, n-butanol, tetrahydrofuran, diethyl ether, dimethoxyethane, 1,4-dioxane, toluene, benzene, xylene, dichloromethane, chloroform, 1,2-dichloroethane, dimethylformamide (DMF), dimethyl sulfoxide (DMSO), pyridine or the like, or a mixed solvent thereof. The reaction is carried out at a temperature range of about 0° C. to about 150° C. for about one hour to about 50 hours. In addition, the present reaction is carried out preferably under an atmosphere of an inert gas (for example, nitrogen, argon or the like).

[2] Compound [VI] [wherein V" indicates the amino group and other symbols indicate the same meanings as indicated hereinabove] is subjected to the substitution reaction with an S-alkyl (for example, methyl, ethyl or the like)-isothiourea compound to be able to produce a guanidine compound [I'"]. The S-alkyl-isothiourea compound is used usually in an equimolar amount to about 2 molar amount per one mole of compound [VI]. This reaction can be allowed to proceed smoothly, as needed, by addition of an about equimolar amount to 3 molar amount of a desalting agent such as triethylamine, pyridine, sodium hydroxide, potassium hydroxide, sodium methoxide, sodium ethoxide, sodium carbonate, potassium carbonate or the like. The present substitution reaction can be carried out in an inactive solvent, as exemplified by, for example, methanol, ethanol, propanol, isopropanol, n-butanol, tetrahydrofuran, diethyl ether, dimethoxyethane, 1,4-dioxane, toluene, benzene, xylene, dichloromethane, chloroform, 1,2-dichloroethane, dimethylformamide (DMF), dimethyl sulfoxide (DMSO), pyridine or the like, or a mixed solvent thereof. The reaction is carried out at a temperature range of about 0° C. to about 150° C. for about one hour to about 50 hours. In addition, the present reaction is carried out preferably under an atmosphere of an inert gas (for example, nitrogen, argon or the like).

The thus-obtained compound (I) can be subjected to isolation and purification according to the known separation and purification means such as concentration, concentration under reduced pressure, solvent extraction, crystallization, recrystallization, trans-solubilization, chromatography and the like.

Compound [II-1] to be used as the starting material can be produced according to a known process (for instance, the process described in Japanese Patent Kokai Publication No. 1996-73476 or the like) or a modified process thereof, where, for instance, the material can be produced according to the process shown in reaction scheme I as well as the process indicated in Reference Examples described hereinafter or a modified process thereof.

Reaction Scheme I

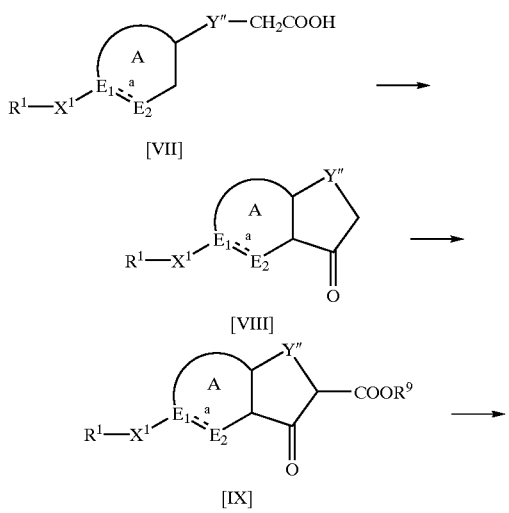

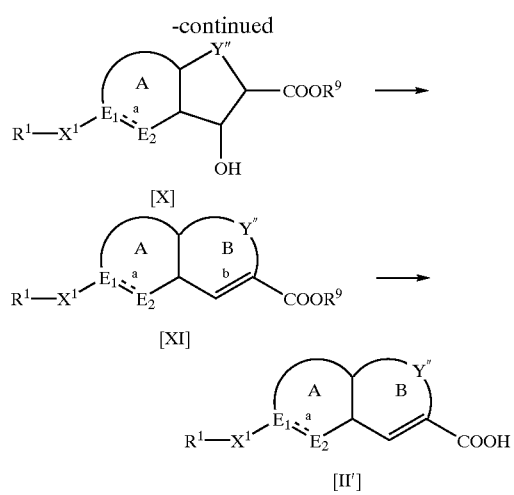

[wherein $R^9$ indicates a $C_{1-4}$ alkyl group, Y" indicates a bivalent group without an unsaturated bond, through which ring B forms a 5- to 7-membered cyclic ring, and other symbols indicate the same meanings as indicated hereinabove.]

In the present process, first, a compound represented by formula [VII] is heated with polyphosphoric acid, or compound [VII] is treated with thionyl chloride, oxalyl chloride, phosphorus pentachloride or the like to be converted into the corresponding acid chloride, which is then subjected to cyclization by the conventional Friedel-Crafts reaction to produce compound [III]. Next, compound [III] is reacted with a carbonic acid ester in the presence of a base to produce a keto ester [IX]. Compound [IX] is converted into compound [X] by catalytic hydrogenation or the reduction reaction with sodium borohydride or the like. Compound [X] is subjected to the dehydration reaction according to a conventional method to produce an unsaturated carboxylic acid ester [XI], which is then subjected to the ester-hydrolysis reaction to produce an unsaturated carboxylic acid [II'].

Of compound [II] to be used as the starting material, a compound wherein $Xa^2$ is not the carboxylic acid (for example, compound [II] wherein $Xa^2$ is the chlorosulfonyl group, the hydroxymethyl group, a halo (chloro or bromo) methyl group, the formyl group, the acetamido group or the like) can be produced according to the process shown in reaction scheme II as well as the process indicated in Reference Examples described hereinafter or a modified process thereof.

Reaction Scheme II

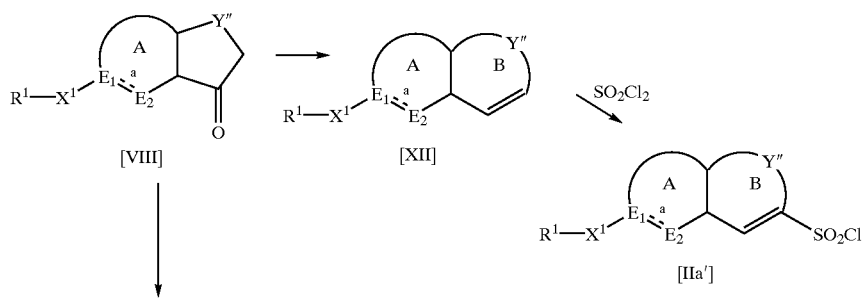

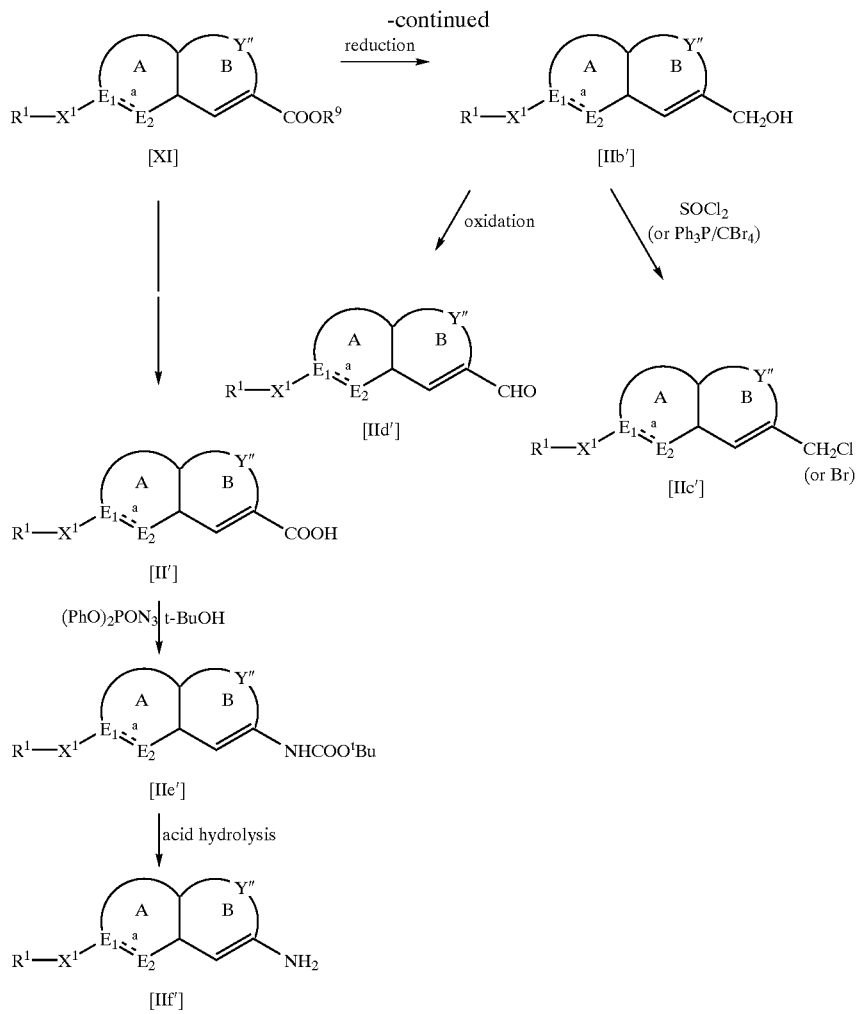

[each of the symbols in the formula indicates the same meaning as indicated hereinabove.]

The sulfonyl chloride compound [II'a] can be produced by subjecting a compound represented by formula [VIII] to the reduction according to a conventional method (the reduction with sodium borohydride or by catalytic hydrogenation or the like) followed by the dehydration reaction to produce compound [XII], which is subjected to the reaction with sulfuryl chloride.

The hydroxymethyl compound (II'b] can be produced by subjecting an ester compound represented by formula [XI] to the reduction according to a conventional method (the reduction with sodium borohydride, lithium aluminum hydride, diisobutylaluminum hydride (DIBAL) or the like). The thus-obtained hydroxymethyl compound [II'b] is subjected to the chlorination reaction with thionyl chloride or the like, or to the bromination reaction with triphenylphosphine-carbon tetrabromide or the like to be able to produce the halomethyl compound [II'c].

Also, the formyl compound [II'd] can be produced by subjecting a hydroxymethyl compound to the oxidation reaction with activated manganese dioxide or the like.

Furthermore, the amine compound [II'f] can be produced by subjecting a carboxylic acid compound represented by formula [II'] to the rearrangement reaction according to a conventional method with, for example, diphenylphosphoric acid amide (DPPA)-t-butanol to produce a urethane compound [II'e], which is then subjected to the acid-hydrolysis reaction.

The thus-obtained compound [II'a], [II'b], [II'c], [II'd], [II'e] or [II'f] and a compound represented by formula [III] are subjected to a variety of the above-mentioned reactions such as the amidation reaction, the tertiary amination reaction, the reductive amination reaction, the vinylation reaction, the etherification reaction, the alkylation (aralkylation) reaction and the like to be able to be converted into the compounds represented by formula (I) wherein $X^2$ is not the carbonylamido group.

In addition, compound [III-1] also can be produced according to a known process (for instance, the process described in Japanese Patent Kokai Publication No. 1996-73476 or the like) or a modified process thereof, where, for instance, the material can be produced according to the process shown in reaction scheme III as well as the process indicated in Reference Examples described hereinafter or a modified process thereof.

Reaction Scheme III

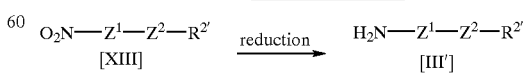

[each of the symbols in the formula indicates the same meaning as indicated hereinabove.]

The reduction reaction of compound [III] can be carried out according to the well-known methods. For instance, the reduction with a metal, the reduction with a metal hydride, the reduction with a metal hydride complex, the reduction with diborane and a substituted diborane, catalytic hydrogenation or the like. In other words, this reaction is carried out by treating compound [XIII] with a reducing agent. The reducing agent is exemplified by a metal and a metallic salt such as a metal such as reduced iron, zinc powder or the like, an alkaline metal borohydride (for example, sodium borohydride, lithium borohydride or the like), a metal hydride complex such as lithium aluminum hydride or the like, a metal hydride such as sodium hydride or the like, an organotin compound (such as triphenyltin hydride or the like), a nickel compound, a zinc compound or the like, a catalytic hydrogenation agent by the use of a transition-metal catalyst such as platinum, rhodium or the like and hydrogen, diborane and the like, where a catalytic hydrogenation agent by the use of a transition-metal catalyst such as platinum, rhodium or the like and hydrogen as well as the reduction with a metal such as reduced iron or the like are advantageously carried out. The reaction is carried out in an organic solvent that is inert to the reaction. As for said solvent to be used, there is selected appropriately, depending on the kind of the reducing agent, from, for example, benzene, toluene, xylene, chloroform, carbon tetrachloride, dichloromethane, 1,2-dichloroethane, 1,1,2,2-tetrachloroethane, diethyl ether, tetrahydrofuran, dioxane, methanol, ethanol, propanol, isopropanol, 2-methoxyethanol, N,N-dimethylformamide, acetic acid or a mixed solvent thereof. The reaction temperature is about −20° C. to about 150° C., particularly preferably, about −0° C. to about 100° C., and the reaction hour is about one hour to about 24 hours.

The thus-obtained compound (III') can be subjected to isolation and purification according to the known separation and purification means such as concentration, concentration under reduced pressure, solvent extraction, crystallization, recrystallization, trans-solubilization, chromatography and the like.

Because any of the compounds represented by formula (I) of the present invention or a salt thereof possesses a potent CCR5 antagonistic action, it is employed for the prophylaxis and the therapeutics of a variety of HIV infectious diseases in the human, for example, AIDS. Any of the compounds represented by formula (I) of the present invention or a salt thereof is of a low toxicity and can be employed safely.

Any of the compounds represented by formula (I) of the present invention or a salt thereof can be employed as a CCR5 antagonistic agent, for instance, as a prophylactic and therapeutic agent of AIDS and a depressant against the pathologic progress of AIDS.

The daily dosage of any of the compounds represented by formula (I) or a salt thereof is different depending on the condition and the weight of the patient as well as the administration method, where, in the case of the oral administration, the dosage as the active ingredient [any of the compounds represented by formula (I) or a salt thereof] per an adult (a body weight of 50 kg) is about 5 mg to 1000 mg, preferably about 10 mg to 600 mg, further preferably about 10 mg to 300 mg, particularly preferably about 15 to 150 mg, where the daily dosage is administered once or with being divided in 2 to 3 times.

Also, in the case where any of the compounds represented by formula (I) or a salt thereof is employed in combination with a reverse transcriptase inhibitor and/or a protease inhibitor, the dosage of the reverse transcriptase inhibitor or the protease inhibitor is appropriately selected, for example, in a range of more than about 1/200 to 1/2 fold and less than 2 to 3 fold on the basis of the ordinary dosage. Furthermore, in the case where 2 or more kinds of drugs are employed in combination, when a drug affects the metabolism of other drugs, the dosage of each of the drugs is appropriately modulated, but the dosage of each of the drugs in the case of the administration as a single formulation is employed in general.

The ordinary dosages of the representative reverse transcriptase inhibitors and protease inhibitors are indicated, for instances, in the following.

Zidovudine: 100 mg
Didanosine: 125 to 200 mg
Zalcitabine: 0.75 mg
Lamivudine: 150 mg
Stavudine: 30 to 40 mg
Saquinavir: 600 mg
Ritonavir: 600 mg
Indinavir: 800 mg
Nelfinavir: 750 mg In addition, in the following are shown the specific embodiments for the case where any of the compounds represented by formula (I) or a salt thereof is employed in combination with the reverse transcriptase inhibitor and/or the protease inhibitor.

[1] About 10 to 300 mg of any of the compounds represented by formula (I) or a salt thereof per an adult (a body weight of 50 kg) is administered to the same subject in a pattern of combination with about 50 to 200 mg of zidovudine. Each of the drugs may be administered respectively at the same time, or may be administered at a time difference within 12 hours.

[2] About 10 to 300 mg of any of the compounds represented by formula (I) or a salt thereof per an adult (a body weight of 50 kg) is administered to the same subject in a pattern of combination with about 300 to 1200 mg of saquinavir. Each of the drugs may be administered respectively at the same time, or may be administered at a time difference within 12 hours.

BEST FOR CARRYING OUT THE INVENTION

The present invention is embodied in more detail by the following Experimental Examples, Formulation Examples, Reference Examples and Examples, but this embodiment is merely illustrative, and is not intended to restrict the present invention.

The genetic engineering procedures described below were based on the methods described in the textbook (Maniatis, et al., Molecular Cloning, Cold Spring Harbor Laboratory, 1989) or the methods described in the protocols attached to the reagents.

EXAMPLES

Experimental Examples (1) Cloning of Human CCR5 Chemokine Receptor

CCR5 gene was cloned from human splenic cDNA by PCR method. With the use of 0.5 ng of splenic cDNA (Toyobo Co., Ltd., QUICK-Clone CDNA) as the template, the primer set, which were prepared by referring to the base sequence of the CCR5 gene reported by Samson et al. (Biochemistry 35 (11), 3362–3367 (1996)), Sequence Number 1 described in experimental example (1) of WO99/32100 [sequence length: 34; sequence type: nucleic acid; chain number: single chain; topology: linear; sequence species: other nucleic acid, synthetic DNA] and Sequence Number 2 described in experimental example (1) of WO99/32100 [sequence length: 34; sequence type: nucleic acid; chain number: single chain; topology: linear; sequence species: other nucleic acid, synthetic DNA] were added in amounts of 25 pmol each, and the PCR reaction was carried out in a DNA Thermal Cycler 480 (Perkin-Elmer Corp.) by the use of TaKaRa EX Taq (Takara Shuzo Co., Ltd.) (reaction conditions: 30 cycles of treatments at 95° C. for one minute, at 60° C. for one minute and at 75° C. for 5 minutes). The PCR product was electrophoresed on an agarose gel, a DNA fragment of about 1.0 kb was recovered and then CCR5 gene was cloned by the use of Original TA Cloning Kit (Funakoshi Co., Ltd.).

(2) Preparation of Expression Plasmid of Human CCR5

After the above-obtained plasmid was digested with restriction enzymes XbaI (Takara Shuzo Co., Ltd.) and BamHI (Takara Shuzo Co., Ltd.), the product was electrophoresed on an agarose gel to recover a DNA fragment of about 1.0 kb. This DNA fragment and a plasmid pcDNA3.1 (Funakoshi) expressible in animal cells, which is digested with XbaI and BamHI, were mixed and ligated by the use of DNA Ligation Kit Ver. 2 (Takara Shuzo Co., Ltd.), and competent cells of *Escherichia coli* JM109 (Takara Shuzo Co., Ltd.) were transformed with the ligation product to obtain plasmid pCKR5.

(3) Introduction of Expression Plasmid of Human CCR5 into CHO-K1 Cells and Expression thereof After CHO-K1 cells, which were grown in a 750-ml, tissue culture flask (Beckton, Dickinson and Company) using Ham F12 medium (Nihon Pharmaceutical Co., Ltd.) containing 10% fetal calf serum (Life Technologies Oriental, Inc.), were removed from the flask with 0.5/L trypsin-0.2 g/L EDTA (Life Technologies Oriental, Inc.), the cells were washed with PBS (Life Technologies Oriental, Inc.), were centrifuged (1000 rpm, 5 minutes) and were suspended in PBS. Next, DNA was introduced into the cells by the use of Gene Pulser (Bio-Rad Laboratories Inc.) under the following conditions. In other words, $8 \times 10^6$ cells and 10 $\mu$g human CCR5 expression plasmid pCKR5 were added into a cuvette with a 0.4-cm gap, and the cells were electroporated at 0.25 kV under a capacitance of 960 $\mu$F. Subsequently, the cells were transferred to Ham F12 medium containing 10% fetal calf serum, and were cultivated for 24 hours. The cells were then removed from the flask again for centrifugation, were then suspended in Ham F12 medium containing 10% fetal serum albumin containing geneticin (Life Technologies Oriental, Inc.) at a final concentration of 500 $\mu$g/ml, were diluted to $10^4$ cells/ml and were seeded into 96-well plates (Beckton, Dickinson and Company) to obtain geneticin-resistant strains.

Next, after the thus-obtained geneticin-resistant strains were cultivated in a 96-well plate (Beckton, Dickinson and Company), cells expressing CCR5 were selected from the resistant strains. In other words, the binding reaction was carried out at room temperature for 40 minutes in an assay buffer (Ham F12 medium containing 0.5% BSA and 20 mM HEPES (Wako Pure Chemical Industries, Ltd.)) that is supplemented with 200 pM [$^{125}$I]-RANTES (Amersham plc) as a ligand, and the cells were washed with ice-cold PBS, were then stirred after adding 50 $\mu$l/well of 1M NaOH and were counted for radioactivity in a $\gamma$-counter to select CHO/CCR5 strains, the cells to which the ligand was specifically bound.

(4) Evaluation of Compounds Based on CCR5-antagonistic Activity

CHO/CCR5 strains were seeded into 96-well microplates at a density of $5 \times 10^4$ cells/well, and were cultivated for 24 hours. After the culture fluid was removed by suction, the assay buffer containing a test compound (1 $\mu$M) was added to each well, and a ligand [$^{125}$I]-RANTES (Amersham Corporation) was added to a final concentration of 100 pM, after which the reaction was carried out at room temperature for 30 minutes. Next, after the assay buffer was removed by suction, the cells were washed twice with ice-cold PBS. Subsequently, 200 $\mu$l of MicroScint-20 (Packard Industry Company, Inc.) was added to each well, which was counted for radioactivity in a Top Count (Packard Industry Company, Inc.).

Percentages of CCR5-binding inhibition by test compounds were determined according to the method described above. The results are shown in Table 1.

TABLE 1

| Compound No. | Inhibition of binding (%) |
| --- | --- |
| 19 | 86 |
| 20 | 94 |
| 21 | 98 |
| 56 | 74 |
| 94 | 76 |
| 100 | 89 |
| 108 | 86 |
| 121 | 82 |

Preparations of a CCR5 antagonist (for example, prophylactic and therapeutic drugs of HIV infection, prophylactic and therapeutic drugs of AIDS or the like), which contains as the active ingredient any of the compounds represented by formula (1) of the present invention or salts thereof, may be manufactured, for example, according to the following formulations:

| 1. Capsule preparation | |
| --- | --- |
| (1) Compound obtained in Example 21 | 40 mg |
| (2) Lactose | 70 mg |
| (3) Microcrystalline cellulose | 9 mg |
| (4) Magnesium stearate | 1 mg |
| 1 capsule | 120 mg |

(1), (2), (3) and a half of (4) are mixed and are then granulated. Thereto is added the remaining (4), and the entire components are encapsulated.

| 2. Tablets | |
| --- | --- |
| (1) Compound obtained in Example 21 | 40 mg |
| (2) Lactose | 58 mg |
| (3) Corn starch | 18 mg |
| (4) Microcrystalline cellulose | 3.5 mg |
| (5) Magnesium stearate | 0.5 mg |
| 1 tablet | 120 mg |

(1), (2), (3), ⅔ of (4) and ½ of (5) are mixed and are then granulated. To the granules are added the remaining (4) and (5), and the resulting mixture is pressure-molded into tablets.

Reference Example 1

A solution of 4-methoxythiophenol (9.66 g), ethyl 4-bromobutyrate (13.5 g) and potassium carbonate (18.8 g) in DMF (200 ml) was stirred at room temperature for 4 hours. The reaction mixture was mixed with water and was extracted with ethyl acetate. The organic layer was washed with water and an aqueous saturated solution of sodium chloride, and was dried with magnesium sulfate. After concentration under reduced pressure, into a solution of the residue in ethanol (200 ml) was added at room temperature a 1 N aqueous solution of sodium hydroxide (85 ml), and the resulting mixture was stirred at room temperature for 4 hours. The reaction mixture was evaporated under reduced pressure to remove the ethanol and was then extracted with diethyl ether. The organic layer was washed with an aqueous saturated solution of sodium chloride and was dried with magnesium sulfate. After concentration under reduced pressure, the precipitated crystals were collected by filtration. The crystals were washed with hexane to obtain 4-[(4-methoxyphenyl)thio]butyric acid (13.09 g) as colorless crystals.

$^1$H-NMR (200 MHz, CDCl$_3$) δ1.81–1.96 (2H, m), 2.51 (2H, t, J=7.3 Hz), 2.87 (2H, t, J=7.1 Hz), 3.80 (3H, s), 6.85 (2H, d, J=8.8 Hz), 7.35 (2H, d, J=8.8 Hz).

Reference Example 2

A mixture of 4-[(4-methoxyphenyl)thio]butyric acid (10.0 g) and polyphosphoric acid (145 g) was stirred at 80–90° C. for 25 minutes. The reaction mixture was mixed with ice and was extracted with ethyl acetate. The organic layer was washed with water, an aqueous saturated solution of sodium bicarbonate and an aqueous saturated solution of sodium chloride, and was dried with magnesium sulfate. After concentration under reduced pressure, the residue was subjected to separation and purification using column chromatography (ethyl acetate/hexane 1:7) to obtain 7-methoxy-3,4-dihydro-1-benzothiepin-5(2H)-one (3.87 g) as a yellow oily substance.

$^1$H-NMR (200 MHz, CDCl$_3$) δ2.17–2.31 (2H, m), 2.94 (2H, t, J=6.8 Hz), 3.07 (2H, t, J=6.6 Hz), 3.83 (3H, s), 6.94 (1H, dd, J=8.6, 3.0 Hz), 7.383 (1H, d, J=8.6 Hz), 8.384 (1H, d, J=3.0 Hz).

Reference Example 3

A suspension of 7-methoxy-3,4-dihydro-1-benzothiepin-5(2H)-one (3.87 g) and sodium methoxide (5.0 g) in dimethyl carbonate (50 ml) was heated at reflux for 4 hours. The reaction mixture was mixed with 1 N hydrochloric acid (100 ml) and was then extracted with ethyl acetate. The organic layer was washed with an aqueous saturated solution of sodium chloride and was dried with magnesium sulfate. The resulting organic layer was concentrated under reduced pressure to obtain a yellow oily substance (4.96 g). Into a mixture of the thus-obtained oily substance, sodium borohydride (0.7 g) and THF (50 ml) was added dropwise at −40° C. methanol (5 ml), and the resulting mixture was stirred at −10° C. to −20° C. for one hour. The reaction mixture was mixed with water and was then extracted with ethyl acetate. The organic layer was washed with an aqueous saturated solution of sodium chloride and was dried with magnesium sulfate. The resulting organic layer was concentrated under reduced pressure to obtain a yellow oily substance (4.80 g). Into a solution of the thus-obtained oily substance and triethylamine (7.5 ml) in THF (50 ml) was added at 0° C. methanesulfonyl chloride (2.09 ml), and the resulting mixture was stirred at 0° C. for 0.5 hour and at room temperature for one hour. To this reaction mixture was added 1,8-diazabicyclo[5,4,0]-7-undecene (DBU) (4.0 ml), and the resulting mixture was stirred for 2.5 hours. The reaction mixture was mixed with water and was then extracted with ethyl acetate. The organic layer was washed with an aqueous saturated solution of sodium chloride and was dried with magnesium sulfate. After concentration under reduced pressure, the residue was subjected to separation and purification using column chromatography (ethyl acetate/hexane 1:5) to obtain methyl 7-methoxy-2,3-dihydro-1-benzothiepine-4-carboxylate (3.00 g) as a yellow oily substance.

$^1$H-NMR (200 MHz, CDCl$_3$) δ2.86–2.92 (2H, m), 3.18–3.24 (2H, m), 3.81 (3H, s), 3.84 (3H, s), 6.78 (1H, dd, J=8.4, 3.0 Hz), 6.90 (1H, d, J=3.0 Hz), 7.41 (1H, d, J=8.4 Hz), 7.77 (1H, s).

Reference Example 4

Into a solution of methyl 7-methoxy-2,3-dihydro-1-benzothiepine-4-carboxylate (3.00 g) in THF (30 ml) was added at 0° C. 70% 3-chloroperbenzoic acid (6.5 g), and the resulting mixture was stirred at 0° C. for 0.5 hour and at room temperature for one hour. The reaction mixture was mixed with an aqueous solution of sodium thiosulfate, was stirred for a few minutes and was then extracted with ethyl acetate. The organic layer was washed with an aqueous saturated solution of sodium bicarbonate (3 times) and an aqueous saturated solution of sodium chloride, and was dried with magnesium sulfate. After concentration under reduced pressure, the precipitated crystals were collected by filtration. The crystals were washed with diisopropyl ether to obtain methyl 7-methoxy-1,1-dioxo-2,3-dihydro-1-benzothiepine-4-carboxylate (3.15 g) as colorless crystals.

M. p. 144–145° C.

$^1$H-NMR (200 MHz, CDCl$_3$) δ3.04–3.10 (2H, m), 3.59–3.65 (2H, m), 3.86 (3H, s), 3.90 (3H, s), 6.96–7.02 (2H, m), 7.79 (1H, s), 8.10 (1H, d, J=10.0 Hz).

Elemental Analysis. Calcd. for C$_3$H$_{14}$O$_5$S: C, 55.31; H, 5.00. Found: C, 55.18; H, 5.01.

Reference Example 5

A mixture of methyl 7-methoxy-1,1-dioxo-2,3-dihydro-1-benzothiepine-4-carboxylate (300 mg), 48% hydrobromic acid (3 ml) and acetic acid (3 ml) was heated at reflux for 4 hours. After concentration under reduced pressure, 48% hydrobromic acid (3 ml) and acetic acid (3 ml) were further added to the reaction mixture, which was heated at reflux for 8 hours. After concentration under reduced pressure, the precipitated crystals were collected by filtration. The crystals were washed with diisopropyl ether to obtain 7-hydroxy-1,1-dioxo-2,3-dihydro-1-benzothiepine-4-carboxylic acid (224 mg) as light yellow crystals.

M. p. 260–265° C.

$^1$H-NMR (200 MHz, DMSO-d$_6$) δ2.84–2.90 (2H, m), 3.61–3.68 (2H, m), 6.92–7.02 (2H, m), 7.62 (1H, s), 7.85 (1H, d, J=8.4 Hz).

Elemental Analysis. Calcd. for C$_{11}$H$_{10}$O$_5$S.0.1 H$_2$O: C, 51.59; H, 4.02. Found: C, 51.38; H, 3.87.

Reference Example 6

To a solution of 7-hydroxy-1,1-dioxo-2,3-dihydro-1-benzothiepine-4-carboxylic acid (856 mg) in methanol (10 ml) was added sulfuric acid (0.1 ml), and the resulting mixture was heated at reflux for 23 hours. After concentration under reduced pressure, the reaction mixture was mixed with water and was then extracted with ethyl acetate. The organic layer was washed with an aqueous saturated solution of sodium chloride and was dried with magnesium sulfate. After concentration under reduced pressure, the precipitated crystals were collected by filtration. The crystals were washed with diisopropyl ether to obtain methyl 7-hydroxy-1,1-dioxo-2,3-dihydro-1-benzothiepine-4-carboxylate (848 mg) as light yellow crystals.

M. p. 176–178° C.

$^1$H-NMR (200 MHz, CDCl$_3$) δ3.04–3.10 (2H, m), 3.59–3.66 (2H, m), 3.86 (3H, s), 6.01 (1H, br s), 6.90–6.94 (2H, m), 7.74 (1H, s), 8.05 (1H, d, J=9.4 Hz).

Elemental Analysis. Calcd. for C$_{12}$H$_{12}$O$_5$S: C, 53.72; H, 4.51. Found: C, 53.67; H, 4.58.

Reference Example 7

A mixture of methyl 7-hydroxy-1,1-dioxo-2,3-dihydro-1-benzothiepine-4-carboxylate (300 mg), 4-chlorobenzyl chloride (210 mg), potassium carbonate (214 mg) and DMF (10 ml) was stirred at room temperature for 13 hours and at 50° C. for 3 hours. The reaction mixture was mixed with water and was then extracted with ethyl acetate. The organic layer was washed with an aqueous saturated solution of sodium chloride and was dried with magnesium sulfate. After concentration under reduced pressure, the residue was subjected to separation and purification using column chromatography (ethyl acetate/hexane 1:1) to obtain methyl 7-[(4-chlorobenzyl)oxy]-1,1-dioxo-2,3-dihydro-1-benzothiepine-4-carboxylate (272 mg) as colorless crystals.

M. p. 130–133° C.

$^1$H-NMR (200 MHz, CDCl$_3$) δ3.07 (2H, t, J=6.2 Hz), 3.58–3.65 (2H, m), 3.86 (3H, s), 5.12 (2H, s), 7.00–7.05 (2H, m), 7.32–7.42 (4H, m), 7.77 (1H, s), 8.10 (1H, d, J=8.4 Hz).

Elemental Analysis. Calcd. for C$_{19}$H$_{17}$O$_5$SCl: C, 58.09; H, 4.36. Found: C, 58.11; H, 4.61.

Reference Example 8

Into a solution of methyl 7-[(4-chlorobenzyl)oxy]-1,1-dioxo-2,3-dihydro-1-benzothiepine-4-carboxylate (200 mg) in THF/methanol (3/1.5 ml) was added at room temperature an aqueous solution (0.7 ml) of potassium carbonate (140 mg), and the resulting mixture was stirred at 65–70° C. for 23 hours. After cooling to room temperature, 1 N hydrochloric acid was added to the reaction mixture until the pH was adjusted to 5, and the precipitated crystals were collected by filtration. The crystals were washed with water, 2-propanol and diisopropyl ether to obtain 7-[(4-chlorobenzyl)oxy]-1,1-dioxo-2,3-dihydro-1-benzothiepine-4-carboxylic acid (149 mg) as light yellow crystals.

$^1$H-NMR (200 MHz, DMSO-d$_6$) δ2.91 (2H, t, J=6.6 Hz), 3.68 (2H, t, J=6.6 Hz), 5.26 (2H, s), 7.22 (1H, dd, J=8.8, 2.6 Hz), 7.37–7.54 (5H, m), 7.72 (1H, s), 7.95 (1H, d, J=8.8 Hz).

Reference Example 9

To a solution of methyl 7-hydroxy-1,1-dioxo-2,3-dihydro-1-benzothiepine-4-carboxylate (300 mg), 4-ethoxybenzyl alcohol (0.36 g) and triphenylphosphine (0.62 g) in THF (10 ml) was added at 0° C. diisopropyl azodicarboxylate (0.47 ml), and the resulting mixture was stirred at room temperature for 3.5 days. After concentration under reduced pressure, the residue was subjected to separation and purification using column chromatography (ethyl acetate/hexane 1:1) to obtain methyl 7-[(4-ethoxybenzyl)oxy]-1,1-dioxo-2,3-dihydro-1-benzothiepine-4-carboxylate (279 mg) as colorless crystals.

$^1$H-NMR (200 MHz, CDCl$_3$) δ1.43 (3H, t, J=7.0 Hz), 3.03–3.10 (2H, m), 3.58–3.65 (2H, m), 3.85 (3H, s), 4.05 (2H, q, J=7.0 Hz), 5.07 (2H, s), 6.92 (2H, d, J=8.8 Hz) 7.01–7.06 (2H, m), 7.33 (2H, d, J=8.8 Hz), 7.77 (1H, s), 8.08 (1H, d, J=9.2 Hz).

Reference Example 10

Into a suspension of methyl 7-[(4-ethoxybenzyl)oxy]-1,1-dioxo-2,3-dihydro-1-benzothiepine-4-carboxylate (200 mg) in THF/methanol (6/3 ml) was added at room temperature an aqueous solution (0.7 ml) of potassium carbonate (137 mg), and the resulting mixture was stirred at 70° C. for 16.5 hours. After cooling to room temperature, 1 N hydrochloric acid was added to the reaction mixture, which was extracted with ethyl acetate. The organic layer was washed with water and an aqueous saturated solution of sodium chloride, and was dried with magnesium sulfate. After concentration under reduced pressure, the precipitated crystals were collected by filtration. The crystals were washed with diisopropyl ether to obtain methyl 7-[(4-ethoxybenzyl)oxy]-1,1-dioxo-2,3-dihydro-1-benzothiepine-4-carboxylic acid (147 mg) as colorless crystals.

M. p. 180–184° C.

$^1$H-NMR (200 MHz, DMSO-d$_6$) δ1.33 (3H, t, J=7.0 Hz), 2.86–2.93 (2H, m), 3.65–3.71 (2H, m), 4.03 (2H, q, J=7.0 Hz), 5.15 (2H, s), 6.95 (2H, d, J=8.8 Hz), 7.21 (1H, dd, J=8.6, 2.4 Hz), 7.37–7.41 (3H, m), 7.72 (1H, m), 7.94 (1H, d, J=8.6 Hz).

Elemental Analysis. Calcd. for C$_{20}$H$_{20}$O$_6$S: C, 61.84; H, 5.19. Found: C, 61.85; H, 5.35.

Reference Example 11

A mixture of methyl 7-hydroxy-1,1-dioxo-2,3-dihydro-1-benzothiepine-4-carboxylate (200 mg), 4-fluorobenzyl chloride (0.090 ml), potassium carbonate (134 mg) and DMF (5 ml) was stirred at 55° C. for 7 hours. The reaction mixture was mixed with water and was extracted with ethyl acetate. The organic layer was washed with an aqueous saturated solution of sodium chloride and was dried with magnesium sulfate. After concentration under reduced pressure, the residue was subjected to separation and purification using column chromatography (ethyl acetate/hexane 1:1) to obtain methyl 7-[(4-fluorobenzyl)oxy]-1,1-dioxo-2,3-dihydro-1-benzothiepine-4-carboxylate (162 mg) as colorless crystals.

M. p. 141–143° C.

$^1$H-NMR (200 MHz, CDCl$_3$) δ3.03–3.10 (2H, m), 3.58–3.65 (2H, m), 3.85 (3H, s), 5.11 (2H, s), 7.01–7.14 (4H, m), 7.37–7.44 (2H, m), 7.77 (1H, m), 8.10 (1H, d, J=9.2 Hz).

Elemental Analysis. Calcd. for C$_{19}$H$_{17}$O$_5$SF: C, 60.63; H, 4.55. Found: C, 60.52; H, 4.66.

Reference Example 12

Into a suspension of methyl 7-[(4-fluorobenzyl)oxy]-1,1-dioxo-2,3-dihydro-1-benzothiepine-4-carboxylate (327.4 mg) in THF/methanol (4/2 ml) was added at room temperature an aqueous solution (1.0 ml) of potassium carbonate (240 mg), and the resulting mixture was stirred at 60° C. for 20 hours. After cooling to room temperature, 1 N hydrochloric acid (5 ml) was added to the reaction mixture, which was extracted with ethyl acetate. The organic layer was washed with an aqueous saturated solution of sodium chloride and was dried with magnesium sulfate. After concentration under reduced pressure, the precipitated crystals were collected by filtration. The crystals were washed with diisopropyl ether to obtain 7-[(4-fluorobenzyl)oxy]-1,1-dioxo-2,3-dihydro-1-benzothiepine-4-carboxylic acid (241 mg) as light yellow crystals.

M. p. 270–273° C.

¹H-NMR (200 MHz, DMSO-d₆) δ2.87–2.94 (2H, m), 3.65–3.72 (2H, m), 5.23 (2H, s), 7.20–7.29 (3H, m), 7.43 (1H, d, J=2.2 Hz), 7.50–7.57 (2H, m), 7.72 (1H, s), 7.95 (1H, d, J=8.8 Hz).

Elemental Analysis. Calcd. for $C_{18}H_{15}O_5SF$: C, 59.66; H, 4.17. Found: C, 59.43; H, 4.41.

Reference Example 13

Into a solution of methyl 7-hydroxy-1,1-dioxo-2,3-dihydro-1-benzothiepine-4-carboxylate (500 mg), 3-pyridinemethanol (405 mg) and triphenylphosphine (0.98 g) in THF (10 ml) was added at 0° C. diethyl azodicarboxylate (a 40% solution in toluene) (1.62 g), and the resulting mixture was stirred at room temperature for 20 hours. After concentration under reduced pressure, the residue was subjected to separation and purification using column chromatography (ethyl acetate) to obtain methyl 7-(3-pyridylmethoxy)-1,1-dioxo-2,3-dihydro-1-benzothiepine-4-carboxylate (694 mg) as colorless crystals.

Into a suspension of methyl 7-(3-pyridylmethoxy)-1,1-dioxo-2,3-dihydro-1-benzothiepine-4-carboxylate (650 mg) in THF/methanol (6/3 ml) was added at room temperature an aqueous solution (1.4 ml) of potassium carbonate (415 mg), and the resulting mixture was stirred at 60° C. for 19 hours. Into this reaction mixture was added further an aqueous solution (0.7 ml) of potassium carbonate (207 mg), and the resulting mixture was stirred further at 60° C. for 3 days. After cooling to room temperature, 1 N hydrochloric acid was added to the reaction mixture until the pH was adjusted to 7–8, and the precipitated crystals were collected by filtration. The crystals were washed with diisopropyl ether to obtain methyl 7-(3-pyridylmethoxy)-1,1-dioxo-2,3-dihydro-1-benzothiepine-4-carboxylic acid (493 mg) as colorless crystals.

¹H-NMR (200 MHz, DMSO-d₆) δ2.87–2.94 (2H, m), 3.66–3.72 (2H, m), 5.31 (2H, s), 7.25 (1H, dd, J=8.8, 2.6 Hz), 7.43–7.49 (2H, m), 7.73 (1H, s), 7.89–7.93 (1H, m), 7.96 (1H, d, J=8.8 Hz), 8.58 (1H, dd, J=4.8, 1.4 Hz), 8.70 (1H, d, J=1.4 Hz).

Reference Example 14

Into a solution of methyl 4-hydroxymethylbenzoate in DMF (100 ml) was added at 0° C. 60% sodium hydride (1.3 g), and the resulting mixture was stirred at room temperature for 4 days. The reaction mixture was mixed with water and was extracted with ethyl acetate. The organic layer was washed with water and an aqueous saturated solution of sodium chloride, and was dried with magnesium sulfate. After concentration under reduced pressure, the residue was subjected to separation and purification using column chromatography (ethyl acetate/hexane 1:9) to obtain methyl 4-propoxymethylbenzoate (2.09 g) as a colorless oily substance.

¹H-NMR (200 MHz, CDCl₃) δ0.95 (3H, t, J=7.3 Hz), 1.57–1.74 (2H, m), 3.46 (2H, t, J=6.6 Hz), 3.92 (3H, s), 4.56 (2H, s), 7.41 (2H, d, J=8.7 Hz), 8.02 (2H, d, J=8.7 Hz).

Reference Example 15

Into a suspension of lithium aluminum hydride (0.40 g) in diethyl ether (25 ml) was added dropwise at 0° C. a solution of methyl 4-(propoxymethyl)benzoate (2.09 g) in diethyl ether (25 ml) over a period of one hour. After stirring at room temperature for 2 hours, water (0.4 ml), a 15% aqueous solution of sodium hydroxide (0.4 ml) and water (0.4 ml) were added to the reaction mixture at 0° C., and the resulting mixture was stirred at room temperature for 2 hours. After addition of magnesium sulfate, the solid was removed by filtration. The filtrate was evaporated under reduced pressure to remove the solvent to obtain 4-(propoxymethyl)benzyl alcohol (1.81 g) as a colorless oily substance.

¹H-NMR (200 MHz, CDCl₃) δ0.94 (3H, t, J 7.3 Hz), 1.57–1.69 (3H, m), 3.43 (2H, t, J=6.6 Hz), 4.51 (2H, s), 4.69 (2H, d, J=5.8 Hz), 7.35 (4H, s).

Reference Example 16

Into a solution of methyl 7-hydroxy-1,1-dioxo-2,3-dihydro-1-benzothiepine-4-carboxylate (400 mg), 4-(propoxymethyl)benzyl alcohol (502 mg) and triphenylphosphine (782 mg) in THF (10 ml) was added at 0° C. diethyl azodicarboxylate (a 40% solution in toluene) (1.30 g), and the resulting mixture was stirred at room temperature for 68 hours. After concentration under reduced pressure, the residue was subjected to separation and purification using column chromatography (ethyl acetate/hexane 1:1) to obtain methyl 7-[[4-(propoxymethyl)benzyl]oxy]-1,1-dioxo-2,3-dihydro-1-benzothiepine-4-carboxylate (1.15 g) as colorless crystals.

Into a solution of methyl 7-[[4-(propoxymethyl)benzyl] oxy]-1,1-dioxo-2,3-dihydro-1-benzothiepine-4-carboxylate (1.15 g) in THF/methanol (10/5 ml) was added at room temperature an aqueous solution (2.1 ml) of potassium carbonate (622 mg), and the resulting mixture was stirred at 60° C. for 2 days. After cooling to room temperature, the reaction mixture was extracted with ethyl acetate. To the aqueous layer was added 1 N hydrochloric acid until the pH was adjusted to 2–3, and the resulting mixture was extracted with ethyl acetate. The organic layer was washed with an aqueous saturated solution of sodium chloride and was dried with magnesium sulfate. After concentration under reduced pressure, the precipitated crystals were collected by filtration. The crystals were washed with diisopropyl ether to obtain 7-[[4-(propoxymethyl)benzyl]oxy]-1,1-dioxo-2,3-dihydro-1-benzothiepine-4-carboxylic acid (425 mg) as colorless crystals.

M. p. 210–213° C.

¹H-NMR (200 MHz, DMSO-d₆) δ0.88 (3H, t, J=7.4 Hz), 1.46–1.64 (2H, m), 2.87–2.93 (2H, m), 3.38 (2H, t, J=6.6 Hz), 3.65–3.71 (2H, m), 4.46 (2H, s), 5.24 (2H, s), 7.22 (1H, dd, J=8.8, 2.6 Hz), 7.33–7.47 (5H, m), 7.72 (1H, s), 7.94 (1H, d, J=8.8 Hz).

Elemental Analysis. Calcd. for $C_{22}H_{24}O_6S$: C, 63.44; H, 5.81. Found: C, 63.29; H, 5.76.

Example 1 (Production of Compound 1)

Into a suspension of 7-[(4-chlorobenzyl)oxy]-1,1-dioxo-2,3-dihydro-1-benzothiepine-4-carboxylic acid (110 mg) in THF (5 ml) were added at room temperature thionyl chloride (0.042 ml) and one drop of DMF, and the resulting mixture was stirred for one hour. After concentration under reduced pressure to remove the solvent, the residue dissolved in THF (5 ml) was added dropwise to a solution of 4-[N-methyl-N-(tetrahydropyran-4-yl)aminomethyl]aniline (70 mg) and triethylamine (0.2 ml) in THF (5 ml) at room temperature. After being stirred at room temperature for 2.5 hours, the reaction mixture was mixed with water and was extracted with ethyl acetate. The organic layer was washed with an aqueous saturated solution of sodium chloride and was dried with magnesium sulfate. After concentration under reduced pressure, the residue was subjected to purification using column chromatography (ethanol/ethyl acetate 1:3) and to recrystallization (ethanol) to obtain 7-[[4-(chlorobenzyl)oxy]-N-[4-[N-methyl-N-(tetrahydropyran-4-yl)aminomethyl]phenyl]-1,1-dioxo-3,4-dihydro-1-benzothiepine-4-carboxamide (compound 1) (104 mg) as colorless crystals.

M. p. 237–239° C.

$^1$H-NMR (200 MHz, CDCl$_3$) δ1.67–1.82 (4H, m), 2.21 (3H, s), 2.55–2.72 (1H, m), 3.09 (2H, t, J=6.8 Hz), 3.30–3.44 (2H, m), 3.58 (2H, s), 3.69 (2H, t, J=6.8 Hz), 3.98–4.09 (2H, m), 5.12 (2H, s), 6.98–7.09 (2H, m), 7.21 (1H, s), 7.32 (2H, d, J=8.4 Hz), 7.37–7.42 (4H, m), 7.54 (2H, d, J=8.4 Hz), 7.91 (1H, s), 8.10 (1H, d, J=8.8 Hz).

Elemental Analysis. Calcd. for $C_{31}H_{33}N_2O_5SCl$: C, 64.07; H, 5.72, N, 4.82. Found: C, 64.03; H, 5.81, N, 5.00.

Example 2 (Production of Compound 2)

Into a solution of 7-[(4-ethoxybenzyl)oxy]-1,1-dioxo-2,3-dihydro-1-benzothiepine-4-carboxylic acid (110 mg) in THF (5 ml) were added at room temperature thionyl chloride (0.041 ml) and one drop of DMF, and the resulting mixture was stirred for one hour. After concentration under reduced pressure to remove the solvent, the residue dissolved in THF (5 ml) was added dropwise to a solution of 4-[N-methyl-N-(tetrahydropyran-4-yl)aminomethyl]aniline (69 mg) and triethylamine (0.2 ml) in THF (5 ml) at room temperature. After being stirred at room temperature for 1.5 hours, the reaction mixture was mixed with water and was extracted with ethyl acetate. The organic layer was washed with an aqueous saturated solution of sodium chloride and was dried with magnesium sulfate. After concentration under reduced pressure, the residue was subjected to purification using column chromatography (ethanol/ethyl acetate 1:3) and to recrystallization (ethanol) to obtain 7-[[4-(ethoxybenzyl)oxy]-N-[4-[N-methyl-N-(tetrahydropyran-4-yl)aminomethyl]phenyl]-1,1-dioxo-3,4-dihydro-1-benzothiepine-4-carboxamide (compound 2) (109 mg) as colorless crystals.

M. p. 211–213° C.

$^1$H-NMR (200 MHz, CDCl$_3$) δ1.43 (3H, t, J=7.2 Hz), 1.68–1.82 (4H, m), 2.21 (3H, s), 2.54–2.74 (1H, m), 3.05–3.12 (2H, m), 3.29–3.44 (2H, m), 3.58 (2H, s), 3.66–3.72 (2H, m), 3.98–4.10 (4H, m), 5.07 (2H, s), 6.92 (2H, d, J=8.8 Hz), 6.98 (1H, d, J=2.6 Hz), 7.04 (1H, dd, J=8.4, 2.6 Hz), 7.20 (1H, s), 7.30–7.35 (4H, m), 7.54 (2H, d, J=8.8 Hz), 7.91 (1H, s), 8.09 (1H, d, J=8.4 Hz).

Elemental Analysis. Calcd. for $C_{33}H_{38}N_2O_6S$: C, 67.10; H, 6.48, N, 4.74. Found: C, 66.94; H, 6.50, N, 4.89.

Example 3 (Production of Compound 3)

Into a suspension of 7-[(4-fluorobenzyl)oxy]-1,1-dioxo-2,3-dihydro-1-benzothiepine-4-carboxylic acid (170 mg) in THF (5 ml) were added at room temperature thionyl chloride (0.068 ml) and one drop of DMF, and the resulting mixture was stirred for one hour. After concentration under reduced pressure to remove the solvent, the residue dissolved in THF (10 ml) was added dropwise to a solution of 4-[N-methyl-N-(tetrahydropyran-4-yl)aminomethyl]aniline (114 mg) and triethylamine (0.2 ml) in THF (5 ml) at 0° C. After being stirred at room temperature for 20 hours, the reaction mixture was mixed with water and was extracted with ethyl acetate. The organic layer was washed with an aqueous saturated solution of sodium chloride and was dried with magnesium sulfate. After concentration under reduced pressure, the residue was subjected to purification using column chromatography (ethanol/ethyl acetate 1:3) and to recrystallization (ethanol) to obtain 7-(4-fluorobenzyloxy)-N-[4-[N-methyl-N-(tetrahydropyran-4-yl)aminomethyl]phenyl]-1,1-dioxo-3,4-dihydro-1-benzothiepine-4-carboxamide (compound 3) (206 mg) as colorless crystals.

M. p. 232–234° C.

$^1$H-NMR (200 MHz, CDCl$_3$) δ1.67–1.83 (4H, m), 2.20 (3H, s), 2.55–2.72 (1H, m), 3.06–3.13 (2H, m), 3.31–3.44 (2H, m), 3.57 (2H, s), 3.65–3.72 (2H, m), 3.99–4.10 (2H, m), 5.11 (2H, s), 6.98–7.15 (4H, m), 7.21 (1H, s), 7.32 (2H, d, J=8.4 Hz), 7.37–7.44 (2H, m), 7.53 (2H, d, J=8.4 Hz), 7.80 (1H, s), 8.10 (1H, d, J=8.8 Hz).

Elemental Analysis. Calcd. for $C_{31}H_{33}N_2O_5SF$: C, 65.94; H, 5.89, N, 4.96. Found: C, 65.59; H, 5.67, N, 4.97.

Example 4 (Production of Compound 4)

Into a solution of 7-(3-pyridylmethoxy)-1,1-dioxo-2,3-dihydro-1-benzothiepine-4-carboxylic acid (200 mg) in DMF (5 ml) was added at room temperature thionyl chloride (0.084 ml), and the resulting mixture was stirred for one hour. After concentration under reduced pressure to remove the solvent, the residue dissolved in DMF (5 ml) was added dropwise to a solution of 4-[N-methyl-N-(tetrahydropyran-4-yl)aminomethyl]aniline (141 mg) and triethylamine (0.4 ml) in THF (5 ml) at room temperature. After being stirred at room temperature for 18 hours, the reaction mixture was mixed with water and was extracted with ethyl acetate. The organic layer was washed with an aqueous saturated solution of sodium chloride and was dried with magnesium sulfate. After concentration under reduced pressure, the residue was subjected to purification using column chromatography (ethyl acetate) and to recrystallization (ethanol) to obtain N-[4-[N-methyl-N-(tetrahydropyran-4-yl)aminomethyl]phenyl]-7-(3-pyridylmethoxy)-1,1-dioxo-2,3-dihydro-1-benzothiepine-4-carboxamide (compound 4) (77 mg) as colorless crystals.

M. p. 225–229° C.

$^1$H-NMR (200 MHz, CDCl$_3$) δ1.67–1.80 (4H, m), 2.21 (3H, s), 2.55–2.74 (1H, m), 3.07–3.14 (2H, m), 3.30–3.44 (2H, m), 3.57 (2H, s), 3.67–3.73 (2H, m), 3.99–4.09 (2H, m), 5.17 (2H, s), 7.01–7.08 (2H, m), 7.22 (1H, s), 7.30–7.40 (3H, m), 7.53 (2H, d, J=8.4 Hz), 7.73–7.81 (1H, m), 7.83–7.89 (1H, m), 8.12 (1H, d, J=8.6 Hz), 8.62–8.72 (2H, m).

Elemental Analysis. Calcd. for $C_{30}H_{33}N_3O_5S$. 0.2 $H_2O$: C, 65.36; H, 6.11, N, 7.62. Found: C, 65.13; H, 6.07, N, 7.50.

Example 5 (Production of Compound 5)

Into a solution of 7-[[(4-(propoxymethyl)benzyl)oxy]-1,1-dioxo-2,3-dihydro-1-benzothiepine-4-carboxylic acid (200 mg) in THF (5 ml) were added at room temperature thionyl chloride (0.070 ml) and one drop of DMF, and the resulting mixture was stirred for one hour. After concentration under reduced pressure to remove the solvent, the residue dissolved in THF (10 ml) was added dropwise to a solution of 4-[N-methyl-N-(tetrahydropyran-4-yl)aminomethyl]aniline (116 mg) and triethylamine (0.27 ml) in THF (5 ml) at 0° C. After being stirred at room temperature for 2 days, the reaction mixture was mixed with water and was extracted with ethyl acetate. The organic layer was washed with an aqueous saturated solution of sodium chloride and was dried with magnesium sulfate. After concentration under reduced pressure, the residue was subjected to purification using column chromatography (ethanol/ethyl acetate 1:3) and to recrystallization (ethanol) to obtain N-[4-[N-methyl-N-(tetrahydropyran-4-yl)aminomethyl]phenyl]-7-[[(4-(propoxymethyl)benzyl)oxy]-1,1-dioxo-2,3-dihydro-1-benzothiepine-4-carboxamide (compound 5) (199 mg) as colorless crystals.

M. p. 201–203° C.

$^1$H-NMR (200 MHz, CDCl$_3$) δ0.95 (3H, t, J=7.5 Hz), 1.58–1.84 (6H, m), 2.20 (3H, s), 2.56–2.73 (1H, m), 3.05–3.12 (2H, m), 3.31–3.44 (2H, m), 3.46 (2H, t, J=6.6 Hz), 3.57 (2H, s), 3.65–3.72 (2H, m), 3.99–4.10 (2H, m), 4.52 (2H, s), 5.15 (2H, s), 6.98–7.07 (2H, m), 7.20 (1H, s), 7.32 (2H, d, J=8.6 Hz), 7.39 (4H, m), 7.53 (2H, d, J=8.6 Hz), 7.85 (1H, s), 8.09 (1H, d, J=8.8 Hz).

Elemental Analysis. Calcd. for C$_{35}$H$_{42}$N$_2$O$_6$S: C, 67.94; H, 6.84, N, 4.53. Found: C, 67.86; H, 6.69, N, 4.57.

Reference Example 17

A mixture of ethynylbenzene (511 mg, 5.00 mmol), methyl 7-bromo-2,3-dihydro-1-benzooxepine-4-carboxylate (708 mg, 2.50 mmol), dichlorobis(triphenylphosphine) palladium (176 mg, 0.25 mmol), copper iodide (48 mg, 0.25 mmol) and triethylamine (15 ml) was stirred at 80° C. for 17 hours. The reaction mixture was concentrated under reduced pressure and was mixed with ethyl acetate (70 ml), and the resulting mixture was washed successively with 1 N hydrochloric acid (5 ml×3) and an aqueous saturated solution of sodium chloride (5 ml). The organic layer was dried with anhydrous magnesium sulfate and was then concentrated under reduced pressure, and the residue was subjected to column chromatography (silica gel: 35 g, ethyl acetate/hexane=1/19). The objective fractions were concentrated under reduced pressure and were mixed with diisopropyl ether, and an insoluble material was collected by filtration. The insoluble material was washed with diisopropyl ether and was then dried under reduced pressure to obtain methyl 7-phenylethynyl-2,3-dihydro-1-benzooxepine-4-carboxylate (525 mg, 1.73 mmol, 69%).

IR (KBr): 1709, 1501 cm$^{-1}$.

$^1$H-NMR (CDCl$_3$) δ: 2.9–3.05 (2H, m), 3.83 (3H, s), 4.2–4.35 (2H, m), 6.96 (1H, d, J=8.6 Hz), 7.3–7.6 (8H, m).

Reference Example 18

To methyl 7-phenylethynyl-2,3-dihydro-1-benzooxepine-4-carboxylate (463 mg, 1.52 mmol) were added methanol (10 ml), THF (10 ml) and a 1 N aqueous solution of sodium hydroxide (4.56 ml), and the resulting mixture was stirred at room temperature for 24 hours. After addition of 1 N hydrochloric acid (4.56 ml), the reaction mixture was concentrated under reduced pressure and was mixed with water, and an insoluble material was collected by filtration. The insoluble material was successively washed with water and diisopropyl ether, and was then dried under reduced pressure to obtain 7-phenylethynyl-2,3-dihydro-1-benzooxepine-4-carboxylic acid (417 mg, 1.44 mmol, 94%).

$^1$H-NMR (DMSO-d$_6$) δ: 2.8–2.95 (2H, m), 4.2–4.35 (2H, m), 7.02 (1H, d, J=8.6 Hz), 7.35–7.6 (7H, m), 7.72 (1H, d, J=2.2 Hz).

Example 6 (Production of Compound 6)

To 7-phenylethynyl-2,3-dihydro-1-benzooxepine-4-carboxylic acid (140 mg, 0.48 mmol) dissolved in DMF (7 ml) were added at 0° C. 1-hydroxybenzotriazole (72 mg, 0.53 mmol), 4-[N-methyl-N-(tetrahydropyranyl)aminomethyl]aniline (117 mg, 0.53 mmol), 1-ethyl-3-(3-dimethylaminopropyl)carbodiimide hydrochloride (139 mg, 0.73 mmol), triethylamine (0.202 ml, 1.45 mmol) and 4-dimethylaminopyridine (3 mg), and the resulting mixture was stirred at room temperature for 14 hours. The reaction mixture was concentrated under reduced pressure and was mixed with ethyl acetate (60 ml), and the resulting mixture was washed successively with water (5 ml×3), an aqueous saturated solution of sodium bicarbonate (5 ml×3) and an aqueous saturated solution of sodium chloride (5 ml). The organic layer was dried with anhydrous magnesium sulfate and was then concentrated under reduced pressure, and the residue was subjected to column chromatography (silica gel: 15 g, ethyl acetate). The objective fractions were concentrated under reduced pressure and were mixed with diisopropyl ether, and an insoluble material was collected by filtration. The insoluble material was washed with diisopropyl ether and was then dried under reduced pressure to obtain N-[4-[N-methyl-N-(4-tetrahydropyranyl)aminomethyl]phenyl]-7-phenylethynyl-2,3-dihydro-1-benzooxepine-4-carboxamide (compound 6) (202 mg, 0.41 mmol, 85%).

IR (KBr): 1653, 1595, 1514, 1501 cm$^{-1}$.

$^1$H-NMR (CDCl$_3$) δ: 1.5–1.85 (4H, m), 2.22 (3H, s), 2.5–2.8 (1H, m), 3.0–3.15 (2H, m), 3.3–3.45 (2H, m), 3.58 (2H, s), 3.95–4.15 (2H, m), 4.3–4.45 (2H, m), 6.99 (1H, d, J=8.4 Hz), 7.15 (1H, s), 7.25–7.6 (11H, m).

Reference Example 19

To 3-hydroxy-5-oxo-6,7,8,9-tetrahydro-5H-benzocycloheptene (1.76 g, 10.0 mmol) dissolved in DMF (10 ml) were added potassium carbonate (2.76 g, 20.2 mmol) and benzyl bromide (1.308 ml, 11.0 mmol), and the resulting mixture was stirred at room temperature for 24 hours. The reaction mixture was concentrated under reduced pressure, and the residue was mixed with water (20 ml) and extracted with ethyl acetate (20 ml×3). The combined organic layers were dried with anhydrous magnesium sulfate and were then concentrated under reduced pressure, and the residue was subjected to column chromatography (silica gel: 35 g, ethyl acetate/hexane=1/9). The objective fractions were concentrated under reduced pressure to obtain 3-benzyloxy-5-oxo-6,7,8,9-tetrahydro-5H-benzocycloheptene (2.79 g).

IR (KBr): 1674 cm$^{-1}$.

$^1$H-NMR (CDCl$_3$) δ: 1.7–1.95 (4H, m), 2.65–2.8 (2H, m), 2.8–2.95 (2H, m), 5.08 (2H, s), 7.04 (1H, dd, J=2.6, 8.4 Hz), 7.13 (1H, d, J=8.4 Hz), 7.25–7.5 (6H, m).

Reference Example 20

To 3-benzyloxy-5-oxo-6,7,8,9-tetrahydro-5H-benzocycloheptene (2.72 g) dissolved in dimethyl carbonate (30 ml) was added sodium methoxide (2.70 g, 50.0 mmol), and the resulting mixture was stirred at reflux with heating (110° C.) for 6 hours. The reaction mixture was mixed with 1 N hydrochloric acid (60 ml) under ice cooling and was concentrated under reduced pressure to remove the organic solvent, and the aqueous layer was then extracted with ethyl acetate (30 ml×3). The combined organic layers were dried with anhydrous magnesium sulfate and were then concentrated under reduced pressure, and the residue was subjected to column chromatography (silica gel: 40 g, ethyl acetate/hexane=1/30). The objective fractions were concentrated under reduced pressure to obtain methyl 3-benzyloxy-5-oxo-6,7,8,9-tetrahydro-5H-benzocycloheptene-6-carboxylate (2.88 g, 8.88 mmol).

Reference Example 21

To methyl 3-benzyloxy-5-oxo-6,7,8,9-tetrahydro-5H-benzocycloheptene-6-carboxylate (2.81 g, 8.66 mmol) dissolved in a mixed solvent of dichloromethane (40 ml) and methanol (10 ml) was added at −40° C. (inner temperature) sodium borohydride (500 mg, 13.2 mmol), and the resulting mixture was stirred at −15° C. to −10° C. for 2 hours. The reaction mixture was cooled to −40° C., was mixed with water (20 ml) and extracted with dichloromethane (40 ml, 10 ml×2). The combined organic layers were dried with anhydrous magnesium sulfate and were then concentrated under reduced pressure. To the residue dissolved in THF (30 ml) were added at 0° C. triethylamine (6.04 ml, 43.3 mmol) and methanesulfonyl chloride (1.10 ml, 13.0 mmol), and the resulting mixture was stirred at room temperature for 20 hours. In order to complete the reaction, DBU (3.89 ml, 26.0 mmol) was added, and the resulting mixture was stirred at room temperature for 24 hours. The reaction mixture was concentrated under reduced pressure, was mixed with water and was extracted with ethyl acetate (30 ml×3). The combined organic layers were washed with 1 N hydrochloric acid (5 ml×3), were dried with anhydrous magnesium sulfate and were then concentrated under reduced pressure, and the residue was subjected to column chromatography (silica gel: 60 g, ethyl acetate/hexane=1/30 →1/9). The objective fractions were concentrated under reduced pressure to obtain methyl 2-benzyloxy-6,7-dihydro-5H-benzocycloheptene-8-carboxylate (2.32 g, 7.52 mmol, 87%).

IR (KBr): 1709 cm$^{-1}$.

$^1$H-NMR (CDCl$_3$) δ: 1.95–2.1 (2H, m), 2.55–2.65 (2H, m), 2.7–2.8 (2H, m), 3.81 (3H, s), 5.06 (2H, s), 6.84 (1H, dd, J=2.6, 8.4 Hz), 6.94 (1H, d, J=2.6 Hz), 7.06 (1H, d, J=8.4 Hz), 7.5–7.7 (5H, m), 7.64 (1H, s)

Reference Example 22

To methyl 2-benzyloxy-6,7-dihydro-5H-benzocycloheptene-8-carboxylate (2.28 g, 7.39 mmol) suspended in methanol (25 ml) was added a 1N aqueous solution of sodium hydroxide (23 ml), and the resulting mixture was stirred at room temperature for 13 hours. In order to complete the reaction, tetrahydrofuran (25 ml) was added, and the resulting mixture was stirred at 60° C. for 2 hours. The reaction mixture was mixed with 1 N hydrochloric acid (23 ml) at room temperature, was concentrated under reduced pressure and was mixed with water, and an insoluble material was collected by filtration. The insoluble material was washed with water and was dried under reduced pressure to obtain 2-benzyloxy-6,7-dihydro-5H-benzocycloheptene-8-carboxylic acid (2.09 g, 7.10 mmol, 96%).

$^1$H-NMR (CDCl$_3$) δ: 1.95–2.15 (2H, m), 2.55–2.7 (2H, m), 2.7–2.85 (2H, m), 5.07 (2H, s), 6.87 (1H, dd, J=2.7, 8.3 Hz), 6.96 (1H, d, J=2.7 Hz), 7.08 (1H, d, J=8.3 Hz), 7.25–7.5 (5H, m), 7.77 (1H, s).

Example 7 (Production of Compound 7)

To a mixture of 2-benzyloxy-6,7-dihydro-5H-benzocycloheptene-8-carboxylic acid (200 mg, 0.68 mmol), 4-[N-methyl-N-(tetrahydropyran-4-yl)aminomethyl]aniline (165 mg, 0.75 mmol), 1-hydroxybenzotriazole (101 mg, 0.75 mmol) and DMF (10 ml) were added at 0° C. 1-[3-(dimethylamino)propyl]-3-ethylcarbodiimide hydrochloride (235 mg, 1.23 mmol) and triethylamine (0.284 ml, 2.04 mmol), and the resulting mixture was stirred at room temperature for 3 days. The reaction mixture was concentrated under reduced pressure, ethyl acetate (40 ml) was added to the residue and the resulting mixture was washed successively with water (5 ml×3), an aqueous saturated solution of sodium bicarbonate (5 ml×3) and an aqueous saturated solution of sodium chloride (5 ml). The organic layer was dried with anhydrous magnesium sulfate and was then concentrated under reduced pressure, and the residue was subjected to column chromatography (silica gel: 15 g, ethyl acetate). The objective fractions were concentrated under reduced pressure and were mixed with diisopropyl ether, and an insoluble material was collected by filtration. The insoluble material was washed with diisopropyl ether and was then dried under reduced pressure to obtain 2-benzyloxy-N-[4-[N-methyl-N-(4-tetrahydropyran-4-yl)aminomethyl]phenyl]-6,7-dihydro-5H-benzocycloheptene-8-carboxamide (compound 7) (276 mg, 0.56 mmol, 82%).

IR (KBr): 1651, 1601, 1514 cm$^{-1}$.

$^1$H-NMR (CDCl$_3$) δ: 1.6–1.85 (4H, m), 2.0–2.25 (2H, m), 2.21 (3H, s), 2.5–2.85 (5H, m), 3.3–3.45 (2H, m), 3.57 (2H, s), 3.95–4.1 (2H, m), 5.07 (2H, s), 6.85 (1H, dd, J=2.7, 8.2 Hz), 6.92 (1H, d, J=2.7 Hz), 7.09 (1H, d, J=8.2 Hz), 7.25–7.5 (5H, m), 7.31 (2H, d, J=8.6 Hz), 7.55 (2H, d, J=8.6 Hz), 7.58 (1H, s).

Reference Example 23

To 3-hydroxy-5-oxo-6,7,8,9-tetrahydro-5H-benzocycloheptene (1.76 g, 10.0 mmol) dissolved in DMF (10 ml) were added potassium carbonate (2.76 g, 20.0 mmol) and 4-methylbenzyl bromide (2.04 g, 11.0 mmol), and the resulting mixture was stirred at room temperature for 24 hours. The reaction mixture was concentrated under reduced pressure, and the residue was mixed with water (20 ml) and extracted with ethyl acetate (20 ml×3). The combined organic layers were dried with anhydrous magnesium sulfate and were then concentrated under reduced pressure, and the residue was subjected to column chromatography (silica gel: 40 g, ethyl acetate/hexane=1/30). The objective fractions were concentrated under reduced pressure to obtain 3-(4-methylbenzyloxy)-5-oxo-6,7,8,9-tetrahydro-5H-benzocycloheptene (2.74 g, 9.77 mmol, 98%).

IR (KBr): 1674 cm$^{-1}$.

$^1$H-NMR (CDCl$_3$) δ: 1.7–1.95 (4H, m), 2.36 (3H, s), 2.7–2.8 (2H, m), 2.8–2.95 (2H, m), 5.04 (2H, s), 7.03 (1H, dd, J=2.8, 8.5 Hz), 7.12 (1H, d, J=8.5 Hz), 7.19 (2H, d, J=7.9 Hz), 7.32 (2H, d, J=7.9 Hz), 7.36 (1H, d, J=2.8 Hz).

Reference Example 24

To 3-(4-methylbenzyloxy)-5-oxo-6,7,8,9-tetrahydro-5H-benzocycloheptene (2.67 g, 9.52 mmol) dissolved in dimethyl carbonate (40 ml) was added sodium methoxide (2.57 g, 47.6 mmol), and the resulting mixture was stirred at reflux with heating (110° C.) for 6 hours. The reaction mixture was mixed with 1 N hydrochloric acid (60 ml) under ice cooling and was concentrated under reduced pressure to remove the organic solvent, and then the aqueous layer was extracted with ethyl acetate (30 ml×3). The combined organic layers were dried with anhydrous magnesium sulfate and were then concentrated under reduced pressure, and the residue was subjected to column chromatography (silica gel: 40 g, ethyl acetate/hexane=1/30). The objective fractions were concentrated under reduced pressure to obtain methyl 3-(4-methylbenzyloxy)-5-oxo-6,7,8,9-tetrahydro-5H-benzocycloheptene-6-carboxylate (2.84 g, 8.39 mmol, 88%).

Reference Example 25

To methyl 3-(4-methylbenzyloxy)-5-oxo-6,7,8,9-tetrahydro-5H-benzocycloheptene-6-carboxylate (2.77 g, 8.19 mmol) dissolved in a mixed solvent of dichloromethane (40 ml) and methanol (10 ml) was added at −40° C. (inner temperature) sodium borohydride (465 mg, 12.3 mmol), and the resulting mixture was stirred at −20° C. to −10° C. for 2 hours. The reaction mixture was cooled to −40° C., was mixed with water (20 ml) and extracted with dichloromethane (40 ml, 10 ml×2). The combined organic layers were dried with anhydrous magnesium sulfate and were then concentrated under reduced pressure. To the residue dissolved in THF (30 ml) were added at 0° C. triethylamine (5.70 ml, 40.9 mmol) and methanesulfonyl chloride (0.95 ml, 12.3 mmol), and the resulting mixture was stirred at room temperature for 12 hours. In order to complete the reaction, DBU (3.67 ml, 24.5 mmol) and dichloromethane (30 ml) were added, and the resulting mixture was stirred at room temperature for 3 hours. The reaction mixture was concentrated under reduced pressure, was mixed with water (30 ml) and was extracted with ethyl acetate (30 ml×3). The combined organic layers were washed with 1 N hydrochloric acid (5 ml×3), were dried with anhydrous magnesium sulfate and were then concentrated under reduced pressure, and the residue was subjected to column chromatography (silica gel: 60 g, ethyl acetate/hexane=1/30→1/9). The objective fractions were concentrated under reduced pressure to obtain methyl 2-(4-methylbenzyloxy)-6,7-dihydro-5H-benzocycloheptene-8-carboxylate (2.40 g, 7.44 mmol, 91%).

IR (KBr): 1709 cm$^{-1}$.

$^1$H-NMR (CDCl$_3$) δ: 1.95–2.1 (2H, m), 2.36 (3H, s), 2.55–2.65 (2H, m), 2.7–2.8 (2H, m), 3.81 (3H, s), 5.01 (2H, s), 6.83 (1H, dd, J=3.0, 8.4 Hz), 6.92 (1H, d, J=3.0 Hz), 7.05 (1H, d, J=8.4 Hz), 7.19 (2H, d, J=8.0 Hz), 7.32 (2H, d, J=8.0 Hz), 7.64 (1H, s).

Reference Example 26

To methyl 2-(4-methylbenzyloxy)-6,7-dihydro-5H-benzocycloheptene-8-carboxylate (2.34 g, 7.26 mmol) dissolved in a mixed solvent of methanol (25 ml) and THF (25 ml) was added a 1N aqueous solution of sodium hydroxide (23 ml), and the resulting mixture was stirred at room temperature for 18 hours. The reaction mixture was mixed with 1 N hydrochloric acid (23 ml) at room temperature, was concentrated under reduced pressure and was mixed with water, and an insoluble material was collected by filtration. The insoluble material was washed successively with water and hexane, and was dried under reduced pressure to obtain 2-(4-methylbenzyloxy)-6,7-dihydro-5H-benzocycloheptene-8-carboxylic acid (2.11 g, 6.84 mmol, 94%).

IR (KBr): 1663 cm$^{-1}$.

$^1$H-NMR (CDCl$_3$) δ: 1.95–2.1 (2H, m), 2.36 (3H, s), 2.55–2.67 (2H, m), 2.7–2.85 (2H, m), 5.02 (2H, s), 6.86 (1H, dd, J=2.7, 8.1 Hz), 6.95 (1H, d, J=2.7 Hz), 7.07 (1H, d, J=8.1 Hz), 7.19 (2H, d, J=8.1 Hz), 7.32 (2H, d, J=8.1 Hz), 7.77 (1H, s).

Example 8 (Production of Compound 8)

To a mixture of 2-(4-methylbenzyloxy)-6,7-dihydro-5H-benzocycloheptene-8-carboxylic acid (200 mg, 0.65 mmol), 4-[N-methyl-N-(tetrahydropyran-4-yl)aminomethyl]aniline (157 mg, 0.71 mmol), 1-hydroxybenzotriazole (96 mg, 0.71 mmol) and DMF (10 ml) were added at 0° C. 1-[3-(dimethylamino)propyl]-3-ethylcarbodiimide hydrochloride (186 mg, 0.97 mmol) and triethylamine (0.271 ml, 1.94 mmol), and the resulting mixture was stirred at room temperature for 4 days. The reaction mixture was concentrated under reduced pressure, ethyl acetate (40 ml) was added to the residue and the resulting mixture was washed successively with water (5 ml×3), an aqueous saturated solution of sodium bicarbonate (5 ml×3) and an aqueous saturated solution of sodium chloride (5 ml). The organic layer was dried with anhydrous magnesium sulfate and was then concentrated under reduced pressure, and the residue was subjected to column chromatography (silica gel: 15 g, ethyl acetate). The objective fractions were concentrated under reduced pressure and were mixed with diisopropyl ether, and an insoluble material was collected by filtration. The insoluble material was washed with diisopropyl ether and was then dried under reduced pressure to obtain 2-(4-methylbenzyloxy)-N-[4-[N-methyl-N-(4-tetrahydropyran-4-yl)aminomethyl]phenyl]-6,7-dihydro-5H-benzocycloheptene-8-carboxamide (compound 8) (273 mg, 0.53 mmol, 82%).

IR (KBr): 1651, 1601, 1518 cm$^{-1}$.

$^1$H-NMR (CDCl$_3$) δ: 1.6–1.85 (4H, m), 2.0–2.2 (2H, m), 2.21 (3H, s), 2.36 (3H, s), 2.5–2.85 (5H, m), 3.3–3.45 (2H, m), 3.57 (2H, s), 3.95–4.1 (2H, m), 5.02 (2H, s), 6.84 (1H, dd, J=2.5, 8.1 Hz), 6.91 (1H, d, J=2.5 Hz), 7.08 (1H, d, J=8.1 Hz), 7.19 (2H, d, J=8.3 Hz), 7.31 (2H, d, J=8.6 Hz), 7.32 (2H, d, J=8.3 Hz), 7.55 (2H, d, J=8.6 Hz), 7.60 (1H, s)

Reference Example 27

To 3-hydroxy-5-oxo-6,7,8,9-tetrahydro-5H-benzocycloheptene (1.76 g, 10.0 mmol) dissolved in DMF (20 ml) were added potassium carbonate (2.76 g, 20.0 mmol) and 4-phenylbenzyl bromide (2.72 g, 11.0 mmol), and the resulting mixture was stirred at room temperature for 24 hours. The reaction mixture was concentrated under reduced pressure, ethyl acetate (30 ml) and THF (30 ml) were added to the residue and the resulting mixture was washed with water (10 ml, 5 ml×3) and an aqueous saturated solution of sodium chloride (5 ml). The organic layer was dried with anhydrous magnesium sulfate and was then concentrated under reduced pressure, and the residue was mixed with diisopropyl ether, and an insoluble material was collected by filtration. The insoluble material was washed with diisopropyl ether and was then dried under reduced pressure to obtain 3-(4-phenylbenzyloxy)-5-oxo-6,7,8,9-tetrahydro-5H-benzocycloheptene (3.00 g, 8.76 mmol, 88%).

IR (KBr): 1674 cm$^{-1}$.

$^1$H-NMR (CDCl$_3$) δ: 1.7–1.95 (4H, m), 2.7–2.8 (2H, m), 2.8–2.95 (2H, m), 5.13 (2H, s), 7.06 (1H, dd, J=2.6, 8.4 Hz), 7.14 (1H, d, J=8.4 Hz), 7.3–7.65 (10H, m).

Reference Example 28

To 3-(4-phenylbenzyloxy)-5-oxo-6,7,8,9-tetrahydro-5H-benzocycloheptene (2.90 g, 8.47 mmol) dissolved in dimethyl carbonate (80 ml) was added sodium methoxide (2.29 g, 42.4 mmol), and the resulting mixture was stirred at reflux with heating (110° C.) for 6 hours. The reaction mixture was mixed with 1 N hydrochloric acid (60 ml) under ice cooling and was concentrated under reduced pressure to remove the organic solvent, and then the aqueous layer was extracted with a mixed solvent of ethyl acetate and THF ((30 ml/15 ml)×3). The combined organic layers were dried with anhydrous magnesium sulfate and were then concentrated under reduced pressure, and the residue was subjected to column chromatography (silica gel: 50 g, ethyl acetate/hexane=1/30). The objective fractions were concentrated under reduced pressure, diisopropyl ether was added to the residue and an insoluble material was collected by filtration. The insoluble material was washed with diisopropyl ether and was then dried under reduced pressure to obtain methyl 3-(4-phenylbenzyloxy)-5-oxo-6,7,8,9-tetrahydro-5H-benzocycloheptene-6-carboxylate (2.47 g, 6.17 mmol, 73%).

Reference Example 29

To methyl 3-(4-phenylbenzyloxy)-5-oxo-6,7,8,9-tetrahydro-5H-benzocycloheptene-6-carboxylate (2.31 g, 5.77 mmol) dissolved in a mixed solvent of dichloromethane (50 ml) and methanol (15 ml) was added at −40° C. (inner temperature) sodium borohydride (327 mg, 8.64 mmol), and the resulting mixture was stirred at −20° C. to −10° C. for 2 hours. The reaction mixture was cooled to −40° C., was mixed with water (20 ml) and extracted with dichloromethane (50 ml, 10 ml×2). The combined organic layers were dried with anhydrous magnesium sulfate and were then concentrated under reduced pressure. To the residue dissolved in dichloromethane (40 ml) were added at 0° C. triethylamine (4.02 ml, 28.8 mmol) and methanesulfonyl chloride (0.67 ml, 8.7 mmol), and the resulting mixture was stirred at room temperature for 16 hours. In order to complete the reaction, DBU (2.59 ml, 17.3 mmol) was added, and the resulting mixture was stirred at room temperature for 12 hours. The reaction mixture was concentrated under reduced pressure, was mixed with water (30 ml) and was extracted with ethyl acetate (40 ml, 15 ml×2). The combined organic layers were washed with 1 N hydrochloric acid (5 ml×3), were dried with anhydrous magnesium sulfate and were then concentrated under reduced pressure, and the residue was subjected to column chromatography (silica gel: 60 g, toluene). The objective fractions were concentrated under reduced pressure and the residue was mixed with ethyl acetate and diisopropyl ether, and an insoluble material was collected by filtration. The insoluble material was washed with diisopropyl ether and was then dried under reduced pressure to obtain methyl 2-(4-phenylbenzyloxy)-6,7-dihydro-5H-benzocycloheptene-8-carboxylate (1.31 g, 3.41 mmol, 59%).

IR (KBr): 1707 cm$^{-1}$.

$^1$H-NMR (CDCl$_3$) δ: 1.95–2.15 (2H, m), 2.55–2.7 (2H, m), 2.7–2.8 (2H, m), 3.82 (3H, s), 5.10 (2H, s), 6.87 (1H, dd, J=2.7, 8.3 Hz), 6.96 (1H, d, J=2.7 Hz), 7.08 (1H, d, J=8.3 Hz), 7.3–7.7 (10H, m).

Reference Example 30

To methyl 2-(4-phenylbenzyloxy)-6,7-dihydro-5H-benzocycloheptene-8-carboxylate (1.22 g, 3.17 mmol) dissolved in a mixed solvent of methanol (20 ml) and THF (35 ml) was added a 1N aqueous solution of sodium hydroxide (10 ml), and the resulting mixture was stirred at room temperature for 18 hours and 60° C. for 2 hours. The reaction mixture was mixed with 1 N hydrochloric acid (12 ml) at room temperature, was concentrated under reduced pressure and was mixed with water, and an insoluble material was collected by filtration. The insoluble material was washed successively with water and hexane, and was dried under reduced pressure to obtain 2-(4-phenylbenzyloxy)-6,7-dihydro-5H-benzocycloheptene-8-carboxylic acid (1.38 g).

$^1$H-NMR (DMSO-d$_6$) δ: 1.8–2.0 (2H, m). 2.4–2.55 (2H, m), 2.65–2.8 (2H, m), 5.16 (2H, s), 6.91 (1H, dd, J=2.6, 8.4 Hz), 7.08 (1H, d, J=2.6 Hz), 7.12 (1H, d, J=8.4 Hz), 7.3–7.75 (10H, m).

Example 9 (Production of Compound 9)

To a mixture of 2-(4-phenylbenzyloxy)-6,7-dihydro-5H-benzocycloheptene-8-carboxylic acid (200 mg, 0.54 mmol), 4-[N-methyl-N-(tetrahydropyran-4-yl)aminomethyl]aniline (131 mg, 0.59 mmol), 1-hydroxybenzotriazole (80 mg, 0.59 mmol) and DMF (10 ml) were added at 0° C. 1-[3-(dimethylamino)propyl]-3-ethylcarbodiimide hydrochloride (207 mg, 1.08 mmol) and triethylamine (0.226 ml, 1.62 mmol), and the resulting mixture was stirred at room temperature for 3 days. The reaction mixture was concentrated under reduced pressure, ethyl acetate (40 ml) was added to the residue and the resulting mixture was washed successively with water (5 ml×3), an aqueous saturated solution of sodium bicarbonate (5 ml×3) and an aqueous saturated solution of sodium chloride (5 ml). The organic layer was dried with anhydrous magnesium sulfate and was then concentrated under reduced pressure, and the residue was subjected to column chromatography (silica gel: 15 g, ethyl acetate). The objective fractions were concentrated under reduced pressure and were mixed with diisopropyl ether, and an insoluble material was collected by filtration. The insoluble material was washed with diisopropyl ether and was then dried under reduced pressure to obtain 2-(4-phenylbenzyloxy)-N-[4-[N-methyl-N-(4-tetrahydropyran-4-yl)aminomethyl]phenyl]-6,7-dihydro-5H-benzocycloheptene-8-carboxamide (compound 9) (243 mg, 0.42 mmol, 79%).

IR (KBr): 1651, 1601, 1516 cm$^{-1}$.

$^1$H-NMR (CDCl$_3$) δ: 1.55–1.85 (4H, m), 2.0–2.25 (2H, m), 2.21 (3H, s), 2.5–2.85 (5H, m), 3.25–3.45 (2H, m), 3.58 (2H, s), 3.95–4.15 (2H, m), 5.11 (2H, s), 6.87 (1H, dd, J=2.9, 8.0 Hz), 6.94 (1H, d, J=2.9 Hz), 7.10 (1H, d, J=8.0 Hz), 7.2–7.7 (14H, m).

Reference Example 31

To methyl 2-hydroxy-6,7-dihydro-5H-benzocycloheptene-8-carboxylate (327 mg, 1.50 mmol) dissolved in DMF (6 ml) were added potassium carbonate (415 mg, 3.00 mmol) and 4-fluorobenzyl bromide (0.206 ml, 1.65 mmol), and the resulting mixture was stirred at room temperature for 15 hours. The reaction mixture was concentrated under reduced pressure, ethyl acetate (40 ml) was added to the residue and the resulting mixture was washed with water (5 ml×3) and an aqueous saturated solution of sodium chloride (5 ml). The organic layer was dried with anhydrous magnesium sulfate and was then concentrated under reduced pressure, and the residue was subjected to column chromatography (silica gel: 15 g, ethyl acetate/hexane=1/25). The objective fractions were concentrated under reduced pressure to obtain methyl 2-(4-fluorobenzyloxy)-6,7-dihydro-5H-benzocycloheptene-8-carboxylate (485 mg, 1.49 mmol, 99%).

IR (KBr): 1707 cm$^{-1}$.

$^1$H-NMR (CDCl$_3$) δ: 1.95–2.15 (2H, m), 2.55–2.8 (4H, m), 3.82 (3H, s), 5.02 (2H, s), 6.83 (1H, dd, J=2.7, 8.2 Hz), 6.92 (1H, d, J=2.7 Hz), 7.0–7.15 (2H, m), 7.07 (1H, d, J=8.2 Hz), 7.35–7.45 (2H, m), 7.64 (1H, s).

Reference Example 32

To 2-(4-fluorobenzyloxy)-6,7-dihydro-5H-benzocycloheptene-8-carboxylate (462 mg, 1.42 mmol) dissolved in a mixed solvent of methanol (5 ml) and THF (5 ml) was added a 1N aqueous solution of sodium hydroxide (4.3 ml), and the resulting mixture was stirred at 50° C. for 2 hours. The reaction mixture was mixed with 1 N hydrochloric acid (4.3 ml) at 0° C., was concentrated under reduced pressure and was mixed with water, and an insoluble material was collected by filtration. The insoluble material was washed with water and was dried under reduced pressure to obtain 2-(4-fluorobenzyloxy)-6,7-dihydro-5H-benzocycloheptene-8-carboxylic acid (458 mg).

Example 10 (Production of Compound 10)

To a mixture of 2-(4-fluorobenzyloxy)-6,7-dihydro-5H-benzocycloheptene-8-carboxylic acid (170 mg, 0.54 mmol), 4-[N-methyl-N-(tetrahydropyran-4-yl)aminomethyl]aniline (144 mg, 0.65 mmol), 1-hydroxybenzotriazole (88 mg, 0.65 mmol) and DMF (6 ml) were added at 0° C. 1-[3-(dimethylamino)propyl]-3-ethylcarbodiimide hydrochloride (209 mg, 1.09 mmol) and triethylamine (0.228 ml, 1.64 mmol), and the resulting mixture was stirred at room temperature for 2 days. The reaction mixture was concentrated under reduced pressure, ethyl acetate (40 ml) was added to the residue and the resulting mixture was washed with an aqueous saturated solution of sodium bicarbonate (10 ml, 5 ml×2). The organic layer was dried with anhydrous magnesium sulfate and was then concentrated under reduced pressure, and the residue was subjected to column chromatography (silica gel: 15 g, ethyl acetate). The objective fractions were concentrated under reduced pressure, diisopropyl ether was added to the residue and an insoluble material was collected by filtration. The insoluble material was washed with diisopropyl ether and was then dried under reduced pressure to obtain 2-(4-fluorobenzyloxy)-N-[4-[N-methyl-N-(4-tetrahydropyran-4-yl)aminomethyl]phenyl]-6,7-dihydro-5H-benzocycloheptene-8-carboxamide (compound 10) (228 mg, 0.44 mmol, 81%).

IR (KBr): 1651, 1603, 1514 cm$^{-1}$.

$^{1}$H-NMR (CDCl$_3$) δ: 1.5–1.85 (4H, m), 2.0–2.25 (2H, m), 2.21 (3H, s), 2.55–2.85 (5H, m), 3.3–3.45 (2H, m), 3.58 (2H, s), 3.95–4.15 (2H, m), 5.02 (2H, s), 6.83 (1H, dd, J=2.7, 8.3 Hz), 6.90 (1H, d, J=2.7 Hz), 7.0–7.15 (2H, m), 7.09 (1H, d, J=8.3 Hz), 7.29 (1H, s), 7.31 (2H, d, J=8.5 Hz), 7.35–7.45 (2H, m), 7.55 (2H, d, J=8.5 Hz), 7.59 (1H, s).

Reference Example 33

To methyl 2-hydroxy-6,7-dihydro-5H-benzocycloheptene-8-carboxylate (327 mg, 1.50 mmol) dissolved in DMF (6 ml) were added potassium carbonate (415 mg, 3.00 mmol) and 2,4-difluorobenzyl bromide (0.212 ml, 1.65 mmol), and the resulting mixture was stirred at room temperature for 17 hours. The reaction mixture was concentrated under reduced pressure, ethyl acetate (40 ml) was added to the residue and the resulting mixture was washed with water (5 ml×2) and an aqueous saturated solution of sodium chloride (5 ml). The organic layer was dried with anhydrous magnesium sulfate and was then concentrated under reduced pressure, and the residue was subjected to column chromatography (silica gel: 15 g, ethyl acetate/hexane=1/25). The objective fractions were concentrated under reduced pressure to obtain methyl 2-(2,4-difluorobenzyloxy)-6,7-dihydro-5H-benzocycloheptene-8-carboxylate (500 mg, 1.45 mmol, 97%).

IR (KBr): 1709 cm$^{-1}$.

$^{1}$H-NMR (CDCl$_3$) δ: 1.95–2.1 (2H, m), 2.55–2.8 (4H, m), 3.82 (3H, s), 5.07 (2H, s), 6.75–7.0 (4H, m), 7.07 (1H, d, J=8.0 Hz), 7.4–7.55 (1H, m), 7.64 (1H, s).

Reference Example 34

To 2-(2,4-difluorobenzyloxy)-6,7-dihydro-5H-benzocycloheptene-8-carboxylate (477 mg, 1.39 mmol) dissolved in a mixed solvent of methanol (5 ml) and THF (5 ml) was added a 1N aqueous solution of sodium hydroxide (4.2 ml), and the resulting mixture was stirred at 50° C. for 2 hours. The reaction mixture was mixed with 1 N hydrochloric acid (4.2 ml) at 0° C., was concentrated under reduced pressure and was mixed with water, and an insoluble material was collected by filtration. The insoluble material was washed with water and was dried under reduced pressure to obtain 2-(2,4-difluorobenzyloxy)-6,7-dihydro-5H-benzocycloheptene-8-carboxylic acid (436 mg, 1.32 mmol, 95%).

Example 11 (Production of Compound 11)

To a mixture of 2-(2,4-difluorobenzyloxy)-6,7-dihydro-5H-benzocycloheptene-8-carboxylic acid (170 mg, 0.51 mmol), 4-[N-methyl-N-(tetrahydropyran-4-yl)aminomethyl]aniline (136 mg, 0.62 mmol), 1-hydroxybenzotriazole (83 mg, 0.61 mmol) and DMF (6 ml) were added at 0° C. 1-[3-(dimethylamino)propyl]-3-ethylcarbodiimide hydrochloride (197 mg, 1.03 mmol) and triethylamine (0.215 ml, 1.54 mmol), and the resulting mixture was stirred at room temperature for 2 days. The reaction mixture was concentrated under reduced pressure, ethyl acetate (40 ml) was added to the residue and the resulting mixture was washed with an aqueous saturated solution of sodium bicarbonate (10 ml, 5 ml×2). The organic layer was dried with anhydrous magnesium sulfate and was then concentrated under reduced pressure, and the residue was subjected to column chromatography (silica gel: 15 g, ethyl acetate). The objective fractions were concentrated under reduced pressure, diisopropyl ether was added to the residue and an insoluble material was collected by filtration. The insoluble material was washed with diisopropyl ether and was then dried under reduced pressure to obtain 2-(2,4-difluorobenzyloxy)-N-[4-[N-methyl-N-(4-tetrahydropyran-4-yl)aminomethyl]phenyl]-6,7-dihydro-5H-benzocycloheptene-8-carboxamide (compound 11) (228 mg, 0.43 mmol, 83%).

IR (KBr): 1651, 1601, 1510 cm$^{-1}$.

$^{1}$H-NMR (CDCl$_3$) δ: 1.5–1.85 (4H, m), 2.0–2.25 (2H, m), 2.21 (3H, s), 2.55–2.85 (5H, m), 3.25–3.45 (2H, m), 3.57 (2H, s), 3.95–4.1 (2H, m), 5.07 (2H, s), 6.75–7.0 (4H, m), 7.09 (1H, d, J=8.0 Hz), 7.29 (1H, s), 7.31 (2H, d, J=8.6 Hz), 7.4–7.65 (1H, m), 7.55 (2H, d, J=8.6 Hz), 7.59 (1H, s).

Reference Example 35

To methyl 2-hydroxy-6,7-dihydro-5H-benzocycloheptene-8-carboxylate (327 mg, 1.50 mmol) dissolved in DMF (6 ml) were added potassium carbonate (415 mg, 3.00 mmol) and 2,6-difluorobenzyl chloride (268 mg, 1.65 mmol), and the resulting mixture was stirred at room temperature for 24 hours. The reaction mixture was concentrated under reduced pressure, ethyl acetate (40 ml) was added to the residue and the resulting mixture was washed with water (5 ml×2) and an aqueous saturated solution of sodium chloride (5 ml). The organic layer was dried with anhydrous magnesium sulfate and was then concentrated under reduced pressure, and the residue was subjected to column chromatography (silica gel: 15 g, ethyl acetate/hexane=1/25). The objective fractions were concentrated under reduced pressure to obtain methyl 2-(2,6-difluorobenzyloxy)-6,7-dihydro-5H-benzocycloheptene-8-carboxylate (507 mg, 1.47 mmol, 98%).

IR (KBr): 1709 cm$^{-1}$.

$^{1}$H-NMR (CDCl$_3$) δ: 1.95–2.15 (2H, m), 2.55–2.8 (4H, m), 3.82 (3H, s), 5.11 (2H, s), 6.85–7.0 (2H, m), 6.87 (1H, dd, J=2.8, 8.2 Hz), 7.08 (1H, d, J=8.2 Hz), 7.25–7.45 (1H, m), 7.66 (1H, s).

Reference Example 36

To 2-(2,6-difluorobenzyloxy)-6,7-dihydro-5H-benzocycloheptene-8-carboxylate (486 mg, 1.41 mmol) dissolved in a mixed solvent of methanol (7 ml) and THF (7 ml) was added a 1N aqueous solution of sodium hydroxide (4.4 ml), and the resulting mixture was stirred at 50° C. for 6 hours. The reaction mixture was mixed with 1 N hydrochloric acid (4.4 ml) at 0° C., was concentrated under reduced pressure and was mixed with water, and an insoluble material was collected by filtration. The insoluble material was washed with water and was dried under reduced pressure to obtain 2-(2,6-difluorobenzyloxy)-6,7-dihydro-5H-benzocycloheptene-8-carboxylic acid (450 mg, 1.36 mmol, 97%).

Example 12 (Production of Compound 12)

To a mixture of 2-(2,6-difluorobenzyloxy)-6,7-dihydro-5H-benzocycloheptene-8-carboxylic acid (170 mg, 0.51 mmol), 4-[N-methyl-N-(tetrahydropyran-4-yl)aminomethyl]aniline (136 mg, 0.62 mmol), 1-hydroxybenzotriazole (83 mg, 0.61 mmol) and DMF (8 ml) were added at 0° C. 1-[3-(dimethylamino)propyl]-3-ethylcarbodiimide hydrochloride (197 mg, 1.03 mmol) and triethylamine (0.215 ml, 1.54 mmol), and the resulting mixture was stirred at room temperature for 3 days. The reaction mixture was concentrated under reduced pressure, ethyl acetate (40 ml) was added to the residue and the resulting mixture was washed with an aqueous saturated solution of sodium bicarbonate (10 ml, 5 ml×2). The organic layer was dried with anhydrous magnesium sulfate and was then concentrated under reduced pressure, and the residue was subjected to column chromatography (silica gel: 15 g, ethyl acetate). The objective fractions were concentrated under reduced pressure, and the residue was dissolved in ethyl acetate (10 ml). Thereto was added at 0° C. 4 N hydrogen chloride (a solution in ethyl acetate, 0.5 ml), and an insoluble material was collected by filtration. The insoluble material was washed with ethyl acetate and was then dried under reduced pressure to obtain 2-(2,6-difluorobenzyloxy)-N-[4-[N-methyl-N-(4-tetrahydropyran-4-yl)aminomethyl]phenyl]-6,7-dihydro-5H-benzocycloheptene-8-carboxamide hydrochloride (compound 12) (255 mg, 0.45 mmol, 87%).

IR (KBr): 1651, 1597, 1522 $cm^{-1}$.

$^1$H-NMR (DMSO-$d_6$) δ: 1.55–2.2 (6H, m), 2.45–2.65 (2H, m), 2.59 (3H, s), 2.65–2.85 (2H, m), 3.2–3.6 (3H, m), 3.9–4.1 (2H, m), 4.12 (1H, d, J=12.4 Hz), 4.44 (1H, d, J=12.4 Hz), 5.11 (2H, s), 6.93 (1H, dd, J=2.4, 8.1 Hz), 7.07 (1H, d, J=2.4 Hz), 7.1–7.3 (3H, m), 7.25 (1H, s), 7.45–7.65 (1H, m), 7.53 (2H, d, J=8.4 Hz), 7.82 (2H, d, J=8.4 Hz).

Reference Example 37

To methyl 2-hydroxy-6,7-dihydro-5H-benzocycloheptene-8-carboxylate (327 mg, 1.50 mmol) dissolved in DMF (6 ml) were added potassium carbonate (415 mg, 3.00 mmol) and 3,5-bis(trifluoromethyl)benzyl bromide (302 mg, 1.65 mmol), and the resulting mixture was stirred at room temperature for 17 hours. The reaction mixture was concentrated under reduced pressure, ethyl acetate (40 ml) was added to the residue and the resulting mixture was washed with water (5 ml×2) and an aqueous saturated solution of sodium chloride (5 ml). The organic layer was dried with anhydrous magnesium sulfate and was then concentrated under reduced pressure, and the residue was subjected to column chromatography (silica gel: 15 g, ethyl acetate/hexane=1/25). The objective fractions were concentrated under reduced pressure, hexane was added to the residue and an insoluble material was collected by filtration. The insoluble material was washed with hexane and was then dried under reduced pressure to obtain methyl 2-[3,5-bis(trifluoromethyl)benzyloxy]-6,7-dihydro-5H-benzocycloheptene-8-carboxylate (524 mg, 1.22 mmol, 81%).

IR (KBr): 1709 $cm^{-1}$.

$^1$H-NMR (CDCl$_3$) δ: 1.95–2.15 (2H, m), 2.55–2.7 (2H, m), 2.7–2.85 (2H, m), 3.82 (3H, s), 5.16 (2H, s), 6.85 (1H, dd, J=2.7, 8.2 Hz), 6.95 (1H, d, J=2.7 Hz), 7.11 (1H, d, J=8.2 Hz), 7.66 (1H, s), 7.86 (1H, s), 7.91 (2H, s).

Reference Example 38

To methyl 2-[3,5-bis(trifluoromethyl)benzyloxy]-6,7-dihydro-5H-benzocycloheptene-8-carboxylate (494 mg, 1.15 mmol) dissolved in a mixed solvent of methanol (7 ml) and THF (7 ml) was added a 1N aqueous solution of sodium hydroxide (3.5 ml), and the resulting mixture was stirred at 50° C. for 4 hours. The reaction mixture was mixed with 1 N hydrochloric acid (3.5 ml) at 0° C., was concentrated under reduced pressure and was mixed with water, and an insoluble material was collected by filtration. The insoluble material was washed with water and was dried under reduced pressure to obtain 2-[3,5-bis(trifluoromethyl)benzyloxy]-6,7-dihydro-5H-benzocycloheptene-8-carboxylic acid (475 mg, 1.10 mmol, 96%).

Example 13 (Production of Compound 13)

To a mixture of 2-[3,5-bis(trifluoromethyl)benzyloxy]-6,7-dihydro-5H-benzocycloheptene-8-carboxylic acid (170 mg, 0.40 mmol), 4-[N-methyl-N-(tetrahydropyran-4-yl)aminomethyl]aniline dihydrochloride (127 mg, 0.43 mmol), 1-hydroxybenzotriazole (64 mg, 0.47 mmol) and DMF (8 ml) were added at 0° C. 1-[3-(dimethylamino)propyl]-3-ethylcarbodiimide hydrochloride (151 mg, 0.79 mmol) and triethylamine (0.275 ml, 1.97 mmol), and the resulting mixture was stirred at room temperature for 3 days. The reaction mixture was concentrated under reduced pressure, ethyl acetate (40 ml) was added to the residue and the resulting mixture was washed with an aqueous saturated solution of sodium bicarbonate (10 ml, 5 ml×2). The organic layer was dried with anhydrous magnesium sulfate and was then concentrated under reduced pressure, and the residue was subjected to column chromatography (silica gel: 15 g, ethyl acetate). The objective fractions were concentrated under reduced pressure, diisopropyl ether was added to the residue and an insoluble material was collected by filtration. The insoluble material was washed with diisopropyl ether and was then dried under reduced pressure to obtain 2-[3,5-bis(trifluoromethyl)benzyloxy]-N-[4-[N-methyl-N-(4-tetrahydropyran-4-yl)aminomethyl]phenyl]-6,7-dihydro-5H-benzocycloheptene-8-carboxamide (compound 13) (189 mg, 0.30 mmol, 76%).

IR (KBr): 1653, 1601, 1514 $cm^{-1}$.

$^1$H-NMR (CDCl$_3$) δ: 1.6–1.85 (4H, m), 2.0–2.25 (2H, m), 2.21 (3H, s), 2.55–2.85 (5H, m), 3.25–3.45 (2H, m), 3.58 (2H, s), 3.95–4.1 (2H, m), 5.16 (2H, s), 6.85 (1H, dd, J=2.7, 8.2 Hz), 6.94 (1H, d, J=2.7 Hz), 7.13 (1H, d, J=8.2 Hz), 7.31 (1H, s), 7.32 (2H, d, J=8.6 Hz), 7.55 (2H, d, J=8.6 Hz), 7.60 (1H, s), 7.86 (1H, s), 7.91 (2H, s).

Reference Example 39

To triphenylphosphine (590 mg, 2.25 mmol), 4-ethoxybenzyl alcohol (342 mg, 2.25 mmol) and methyl 2-hydroxy-6,7-dihydro-5H-benzocycloheptene-8-carboxylate (327 mg, 1.50 mmol) dissolved in THF (6 ml) was added at 0° C. a solution of diisopropyl azodicarboxylate (0.439 ml, 2.23 mmol) in THF (2 ml), and the resulting mixture was stirred at room temperature for 6 hours. The reaction mixture was concentrated under reduced pressure and the residue was subjected to column chromatography (silica gel: 50 g, ethyl acetate/hexane=1/25→1/19). The objective fractions were concentrated under reduced pressure, diisopropyl ether was added to the residue and an insoluble material was collected by filtration. The insoluble material was washed with diisopropyl ether and was then dried under reduced pressure to obtain methyl 2-(4-ethoxybenzyloxy)-6,7-dihydro-5H-benzocycloheptene-8-carboxylate (308 mg, 0.87 mmol, 58%).

IR (KBr): 1709 cm$^{-1}$.

$^1$H-NMR (CDCl$_3$): δ1.42 (3H, t, J=7.0 Hz), 1.95–2.1 (2H, m), 2.55–2.8 (4H, m), 3.81 (3H, s), 4.05 (2H, q, J=7.0 Hz), 4.97 (2H, s), 6.84 (1H, dd, J=2.7, 8.3 Hz), 6.91 (2H, d, J=8.7 Hz), 6.92 (1H, d, J=2.7 Hz), 7.34 (2H, d, J=8.7 Hz), 7.65 (1H, s).

Reference Example 40

To methyl 2-(4-ethoxybenzyloxy)-6,7-dihydro-5H-benzocycloheptene-8-carboxylate (296 mg, 0.84 mmol) dissolved in a mixed solvent of methanol (4 ml) and THF (4 ml) was added a 1N aqueous solution of sodium hydroxide (2.5 ml), and the resulting mixture was stirred at 50° C. for 4 hours. The reaction mixture was mixed with 1 N hydrochloric acid (2.5 ml) at 0° C., was concentrated under reduced pressure and was mixed with water, and an insoluble material was collected by filtration. The insoluble material was washed with water, and was dried under reduced pressure to obtain 2-(4-ethoxybenzyloxy)-6,7-dihydro-5H-benzocycloheptene-8-carboxylic acid (283 mg, 0.84 mmol).

Example 14 (Production of Compound 14)

To a mixture of 2-(4-ethoxybenzyloxy)-6,7-dihydro-5H-benzocycloheptene-8-carboxylic acid (170 mg, 0.50 mmol), 4-[N-methyl-N-(tetrahydropyran-4-yl)aminomethyl]aniline (133 mg, 0.60 mmol), 1-hydroxybenzotriazole (81 mg, 0.60 mmol) and DMF (8 ml) were added at 0° C. 1-[3-(dimethylamino)propyl]-3-ethylcarbodiimide hydrochloride (193 mg, 1.01 mmol) and triethylamine (0.21 ml, 1.51 mmol), and the resulting mixture was stirred at room temperature for 24 hours. The reaction mixture was concentrated under reduced pressure, ethyl acetate (40 ml) was added to the residue and the resulting mixture was washed with an aqueous saturated solution of sodium bicarbonate (10 ml, 5 ml×2). The organic layer was dried with anhydrous magnesium sulfate and was then concentrated under reduced pressure, and the residue was subjected to column chromatography (silica gel: 15 g, ethyl acetate). The objective fractions were concentrated under reduced pressure, diisopropyl ether was added to the residue and an insoluble material was collected by filtration. The insoluble material was washed with diisopropyl ether and was then dried under reduced pressure to obtain 2-(4-ethoxybenzyloxy)-N-[4-[N-methyl-N-(4-tetrahydropyran-4-yl)aminomethyl]phenyl]-6,7-dihydro-5H-benzocycloheptene-8-carboxamide (compound 14) (234 mg, 0.43 mmol, 86%).

IR (KBr): 1651, 1601, 1514 cm$^{-1}$.

$^1$H-NMR (CDCl$_3$) δ: 1.42 (3H, t, J=7.0 Hz), 1.55–1.85 (4H, m), 2.0–2.25 (2H, m), 2.21 (3H, s), 2.55–2.85 (5H, m), 3.3–3.45 (2H, m), 3.57 (2H, s), 3.95–4.15 (2H, m), 4.04 (2H, q, J=7.0 Hz), 4.98 (2H, s), 6.84 (1H, dd, J=2.8, 8.4 Hz), 6.90 (1H, d, J=2.8 Hz), 6.91 (2H, d, J=8.8 Hz), 7.08 (1H, d, J=8.4 Hz), 7.28 (1H, s), 7.31 (2H, d, J=8.4 Hz), 7.34 (2H, d, J=8.8 Hz), 7.55 (2H, d, J=8.4 Hz), 7.61 (1H, s).

Reference Example 41

To 3-methoxy-5-oxo-6,7,8,9-tetrahydro-5H-benzocycloheptene (20.32 mg, 107 mmol) dissolved in dimethyl carbonate (500 ml) was added sodium methoxide (28.85 g, 534 mmol), and the resulting mixture was stirred at reflux with heating (110° C.) for 6 hours. The reaction mixture was mixed with 2 N hydrochloric acid (320 ml) under ice cooling and was concentrated under reduced pressure to remove the organic solvent, and then the aqueous layer was extracted with ethyl acetate (200 ml, 150 ml×3). The combined organic layers were dried with anhydrous magnesium sulfate and were then concentrated under reduced pressure, and the residue was subjected to column chromatography (silica gel: 150 g, ethyl acetate/hexane=1/19). The objective fractions were concentrated under reduced pressure to obtain methyl 3-methoxy-5-oxo-6,7,8,9-tetrahydro-5H-benzocycloheptene-6-carboxylate (24.20 g, 97.5 mmol, 91%).

Reference Example 42

To methyl 3-methoxy-5-oxo-6,7,8,9-tetrahydro-5H-benzocycloheptene-6-carboxylate (1079 mg, 4.35 mmol) dissolved in a mixed solvent of dichloromethane (10 ml) and methanol (2.5 ml) was added at −40° C. (inner temperature) sodium borohydride (300 mg, 7.93 mmol), and the resulting mixture was stirred at −15° C. to −10° C. for 1.5 hours. The reaction mixture was cooled to −40° C., was mixed with water (10 ml) and extracted with dichloromethane (×3). The combined organic layers were dried with anhydrous magnesium sulfate and were then concentrated under reduced pressure. To the residue dissolved in dichloromethane (15 ml) were added at 0° C. triethylamine (3.03 ml, 21.7 mmol) and methanesulfonyl chloride (0.505 ml, 6.52 mmol), and the resulting mixture was stirred at room temperature for 18 hours. In order to complete the reaction, DBU (1.95 ml, 13.0 mmol) was added, and the resulting mixture was stirred at room temperature for 3 hours. The reaction mixture was concentrated under reduced pressure, was mixed with water and was extracted with ethyl acetate (×3). The combined organic layers were washed with 1 N hydrochloric acid (×3) and an aqueous saturated solution of sodium chloride, were dried with anhydrous magnesium sulfate and were then concentrated under reduced pressure, and the residue was subjected to column chromatography (silica gel, ethyl acetate/hexane=1/9). The objective fractions were concentrated under reduced pressure to obtain methyl 2-methoxy-6,7-dihydro-5H-benzocycloheptene-8-carboxylate (730 mg, 3.14 mmol, 72%).

IR (KBr): 1709 cm$^{-1}$.

$^1$H-NMR (CDCl$_3$) δ: 1.95–2.1 (2H, m), 2.55–2.8 (4H, m), 3.80 (3H, s), 3.82 (3H, s), 6.77 (1H, dd, J=2.7, 8.3 Hz), 6.85 (1H, d, J=2.7 Hz), 7.06 (1H, d, J=8.3 Hz), 7.66 (1H, s).

Reference Example 43

To methyl 2-methoxy-6,7-dihydro-5H-benzocycloheptene-8-carboxylate (5.07 g, 21.8 mmol) dissolved in dichloromethane (100 ml) was added dropwise at −60° C. to −70° C. (inner temperature) boron tribromide (a 1 M solution in dichloromethane, 87 ml), and the resulting mixture was stirred for 5 hours while raising the temperature from −70° C. to room temperature. The reaction mixture was mixed with diethyl ether and water (100 ml) in the order, and was extracted with dichloromethane (100 ml, 50 ml×2). The combined organic layers were dried with anhydrous magnesium sulfate, and were then concentrated under reduced pressure. To the residue dissolved in methanol (150 ml) was added sulfuric acid (0.5 ml), and the resulting mixture was stirred under reflux with heating (100° C.) for 24 hours. The reaction mixture was concentrated under reduced pressure, was mixed with ethyl acetate (150 ml) and was washed with an aqueous saturated solution of sodium chloride (30 ml×3). After drying with anhydrous magnesium sulfate, the organic layer was concentrated under reduced pressure, diisopropyl ether was added to the residue and an insoluble material was collected by filtration. The insoluble material was washed with diisopropyl ether and was then dried under reduced pressure to obtain methyl 2-hydroxy-6,7-dihydro-5H-benzocycloheptene-8-carboxylate (4.31 g, 19.7 mmol, 90%).

IR (KBr): 1686 cm$^{-1}$.

$^1$H-NMR (CDCl$_3$) δ: 1.95–2.15 (2H, m), 2.55–2.8 (4H, m), 3.82 (3H, s), 6.71 (1H, dd, J=2.5, 8.1 Hz), 6.81 (1H, d, J=2.5 Hz), 7.02 (1H, d, J=8.1 Hz), 7.63 (1H, s).

Reference Example 44

To methyl 2-hydroxy-6,7-dihydro-5H-benzocycloheptene-8-carboxylate (400 mg, 1.83 mmol) dissolved in DMF (8 ml) were added potassium carbonate (507 mg, 3.67 mmol) and cyclohexylmethyl bromide (0.511 ml, 3.66 mmol), and the resulting mixture was stirred at room temperature for 23 hours and at 100° C. for 6 hours. The reaction mixture was concentrated under reduced pressure, water was added to the residue and the resulting mixture was extracted with ethyl acetate (×3). The combined organic layers were dried with anhydrous magnesium sulfate and were then concentrated under reduced pressure, and the residue was subjected to column chromatography (silica gel: 15 g, ethyl acetate/hexane=1/19). The objective fractions were concentrated under reduced pressure, hexane was added to the residue and an insoluble material was collected by filtration. The insoluble material was washed with hexane and was then dried under reduced pressure to obtain methyl 2-cyclohexylmethyloxy-6,7-dihydro-5H-benzocycloheptene-8-carboxylate (452 mg, 1.44 mmol, 78%).

IR (KBr): 1709 cm$^{-1}$.

$^1$H-NMR (CDCl$_3$) δ: 0.9–2.1 (13H, m), 2.55–2.8 (4H, m), 3.74 (2H, d, J=6.2 Hz), 3.81 (3H, s), 6.76 (1H, dd, J=2.5, 8.1 Hz), 6.84 (1H, d, J=2.5 Hz), 7.04 (1H, d, J=8.1 Hz), 7.65 (1H, s).

Reference Example 45

To methyl 2-cyclohexylmethyloxy-6,7-dihydro-5H-benzocycloheptene-8-carboxylate (425 mg, 1.35 mmol) dissolved in a mixed solvent of methanol (5 ml) and THF (5 ml) was added a 1N aqueous solution of sodium hydroxide (4 ml), and the resulting mixture was stirred at 50° C. for 6 hours. The reaction mixture was mixed with 1 N hydrochloric acid (4 ml) at 0° C., was concentrated under reduced pressure and was mixed with water, and an insoluble material was collected by filtration. The insoluble material was washed with water and was dried under reduced pressure to obtain 2-cyclohexylmethyloxy-6,7-dihydro-5H-benzocycloheptene-8-carboxylic acid (389 mg, 1.29 mmol, 96%).

Example 15 (Production of Compound 15)

To a mixture of 2-cyclohexylmethyloxy-6,7-dihydro-5H-benzocycloheptene-8-carboxylic acid (170 mg, 0.57 mmol), 4-[N-methyl-N-(tetrahydropyran-4-yl)aminomethyl]aniline (150 mg, 0.68 mmol), 1-hydroxybenzotriazole (84 mg, 0.62 mmol) and DMF (6 ml) were added at 0° C. 1-[3-(dimethylamino)propyl]-3-ethylcarbodiimide hydrochloride (217 mg, 1.13 mmol) and triethylamine (0.237 ml, 1.70 mmol), and the resulting mixture was stirred at room temperature for 4 days. The reaction mixture was concentrated under reduced pressure, ethyl acetate (40 ml) was added to the residue and the resulting mixture was washed with an aqueous saturated solution of sodium bicarbonate (10 ml, 5 ml×2). The organic layer was dried with anhydrous magnesium sulfate and was then concentrated under reduced pressure, and the residue was subjected to column chromatography (silica gel: 15 g, ethyl acetate). The objective fractions were concentrated under reduced pressure, and the residue was dissolved in ethyl acetate (10 ml). Thereto was added at 0° C. 4 N hydrogen chloride (a solution in ethyl acetate, 0.285 ml), and an insoluble material was collected by filtration. The insoluble material was washed with ethyl acetate and was then dried under reduced pressure to obtain 2-cyclohexylmethyloxy-N-[4-[N-methyl-N-(4-tetrahydropyran-4-yl)aminomethyl]phenyl]-6,7-dihydro-5H-benzocycloheptene-8-carboxamide hydrochloride (compound 15) (258 mg, 0.48 mmol, 85%).

IR (KBr): 1651, 1601, 1522 cm$^{-1}$.

$^1$H-NMR (DMSO-d$_6$) δ: 0.9–1.4 (5H, m), 1.5–2.2 (12H, m), 2.4–2.65 (2H, m), 2.59 (3H, s), 2.65–2.8 (2H, m), 3.2–3.6 (3H, m), 3.77 (2H, d, J=5.8 Hz), 3.9–4.1 (2H, m), 4.12 (1H, d, J=12.4 Hz), 4.43 (1H, d, J=12.4 Hz), 6.80 (1H, dd, J=2.5, 8.6 Hz), 6.94 (1H, d, J=2.5 Hz), 7.12 (1H, d, J=8.6 Hz), 7.25 (1H, s), 7.54 (2H, d, J=8.6 Hz), 7.81 (2H, d, J=8.6 Hz), 10.14 (1H, s).

Reference Example 46

To triphenylphosphine (1.18 g, 4.50 mmol), cyclohexanol (0.468 ml, 4.50 mmol) and methyl 2-hydroxy-6,7-dihydro-5H-benzocycloheptene-8-carboxylate (327 mg, 1.50 mmol) dissolved in THF (6 ml) was added at 0° C. a solution of diisopropyl azodicarboxylate (0.886 ml, 4.50 mmol) in THF (4 ml), and the resulting mixture was stirred at room temperature for 3 days. The reaction mixture was concentrated under reduced pressure and the residue was subjected to column chromatography (silica gel: 45 g, ethyl acetate/hexane=1/25). The objective fractions were concentrated under reduced pressure to obtain methyl 2-cyclohexyloxy-6,7-dihydro-5H-benzocycloheptene-8-carboxylate (434 mg, 1.44 mmol, 96%).

IR (KBr): 1709 cm$^{-1}$.

$^1$H-NMR (CDCl$_3$): δ1.15–2.1 (12H, m), 2.55–2.65 (2H, m), 2.65–2.8 (2H, m), 3.81 (3H, s), 4.1–4.3 (1H, m), 6.77 (1H, dd, J=2.7, 8.1 Hz), 6.85 (1H, d, J=2.7 Hz), 7.03 (1H, d, J=8.1 Hz), 7.64 (1H, s).

Reference Example 47

To methyl 2-cyclohexyloxy-6,7-dihydro-5H-benzocycloheptene-8-carboxylate (412 mg, 1.37 mmol) dissolved in a mixed solvent of methanol (5 ml) and THF (5 ml) was added a 1N aqueous solution of sodium hydroxide (4.0 ml), and the resulting mixture was stirred at 50° C. for 6 hours. The reaction mixture was mixed with 1 N hydrochloric acid (4.0 ml) at 0° C., was concentrated under reduced pressure and was mixed with water, and an insoluble material was collected by filtration. The insoluble material was washed with water and was dried under reduced pressure to obtain 2-cyclohexyloxy-6,7-dihydro-5H-benzocycloheptene-8-carboxylic acid (388 mg, 1.35 mmol, 99%).

Example 16 (Production of Compound 16)

To a mixture of 2-cyclohexyloxy-6,7-dihydro-5H-benzocycloheptene-8-carboxylic acid (170 mg, 0.59 mmol), 4-[N-methyl-N-(tetrahydropyran-4-yl)aminomethyl]aniline (157 mg, 0.71 mmol), 1-hydroxybenzotriazole (96 mg, 0.71 mmol) and DMF (8 ml) were added at 0° C. 1-[3-(dimethylamino)propyl]-3-ethylcarbodiimide hydrochloride (228 mg, 1.19 mmol) and triethylamine (0.248 ml, 1.78 mmol), and the resulting mixture was stirred at room temperature for 24 hours. The reaction mixture was concentrated under reduced pressure, ethyl acetate (40 ml) was added to the residue and the resulting mixture was washed with an aqueous saturated solution of sodium bicarbonate (10 ml, 5 ml×2). The organic layer was dried with anhydrous magnesium sulfate and was then concentrated under reduced pressure, and the residue was subjected to column chromatography (silica gel: 15 g, ethyl acetate). The objective fractions were concentrated under reduced pressure, diisopropyl ether was added to the residue and an insoluble material was collected by filtration. The insoluble material was washed with diisopropyl ether and was then dried under reduced pressure to obtain 2-cyclohexyloxy-N-[4-[N-methyl-N-(4-tetrahydropyran-4-yl)aminomethyl]phenyl]-6,7-dihydro-5H-benzocycloheptene-8-carboxamide (compound 16) (248 mg, 0.51 mmol, 85%).

IR (KBr): 1651, 1601, 1514 cm$^{-1}$.

$^1$H-NMR (CDCl$_3$) δ: 1.15–2.25 (16H, m), 2.21 (3H, s), 2.5–2.85 (5H, m), 3.25–3.45 (2H, m), 3.57 (2H, s), 3.95–4.1 (2H, m), 4.1–4.3 (1H, m), 6.77 (1H, dd, J=2.7, 8.2 Hz), 6.85 (1H, d, J=2.7 Hz), 7.06 (1H, d, J=8.2 Hz), 7.29 (1H, s), 7.31 (2H, d, J=8.4 Hz), 7.55 (2H, d, J=8.4 Hz), 7.60 (1H, s).

Reference Example 48

To triphenylphosphine (2361 mg, 9.00 mmol), 1-tert-butoxycarbonyl-4-hydroxypiperidine (1812 mg, 9.00 mmol) and methyl 2-hydroxy-6,7-dihydro-5H-benzocycloheptene-8-carboxylate (655 mg, 3.00 mmol) dissolved in THF (15 ml) was added at 0° C. a solution of diisopropyl azodicarboxylate (1.772 ml, 9.00 mmol) in THF (2 ml), and the resulting mixture was stirred at room temperature for 24 hours. The reaction mixture was concentrated under reduced pressure and the residue was subjected to column chromatography (silica gel: 70 g, ethyl acetate/hexane=1/9→1/7). The objective fractions were concentrated under reduced pressure to obtain methyl 2-[(1-tert-butoxycarbonylpiperidin-4-yl)oxy]-6,7-dihydro-5H-benzocycloheptene-8-carboxylate (1270 mg).

IR (KBr): 1698 cm$^{-1}$.

$^1$H-NMR (CDCl$_3$): δ1.47 (9H, s), 1.6–2.1 (6H, m), 2.55–2.7 (2H, m), 2.7–2.8 (2H, m), 3.2–3.45 (2H, m), 3.6–3.8 (2H, m), 3.82 (3H, s), 4.35–4.55 (1H, m), 6.78 (1H, dd, J=2.7, 8.3 Hz), 6.87 (1H, d, J=2.7 Hz), 7.05 (1H, d, J=8.3 Hz), 7.63 (1H, s).

Reference Example 49

To methyl 2-[(1-tert-butoxycarbonylpiperidin-4-yl)oxy]-6,7-dihydro-5H-benzocycloheptene-8-carboxylate (1245 mg, 3.10 mmol) dissolved in a mixed solvent of methanol (10 ml) and THF (10 ml) was added a 1N aqueous solution of sodium hydroxide (9.3 ml), and the resulting mixture was stirred at room temperature for 23 hours. The reaction mixture was mixed with 1 N hydrochloric acid (9.3 ml) at 0° C., was concentrated under reduced pressure and was mixed with water, and an insoluble material was collected by filtration. The insoluble material was washed with water, and was dried under reduced pressure to obtain 2-[(1-tert-butoxycarbonylpiperidin-4-yl)oxy]-6,7-dihydro-5H-benzocycloheptene-8-carboxylic acid (1150 mg, 2.97 mmol, 96%).

Example 17 (Production of Compound 17)

To a mixture of 2-[(1-tert-butoxycarbonylpiperidin-4-yl)oxy]-6,7-dihydro-5H-benzocycloheptene-8-carboxylic acid (1088 mg, 2.81 mmol), 4-[N-methyl-N-(tetrahydropyran-4-yl)aminomethyl]aniline hydrochloride (742 mg, 3.37 mmol), 1-hydroxybenzotriazole (455 mg, 3.37 mmol) and DMF (30 ml) were added at 0° C. 1-[3-(dimethylamino)propyl]-3-ethylcarbodiimide hydrochloride (1077 mg, 5.62 mmol) and triethylamine (1.174 ml, 8.42 mmol), and the resulting mixture was stirred at room temperature for 3 days. The reaction mixture was concentrated under reduced pressure, ethyl acetate (160 ml) was added to the residue and the resulting mixture was washed with an aqueous saturated solution of sodium bicarbonate (40 ml, 20 ml×2). The organic layer was dried with anhydrous magnesium sulfate and was then concentrated under reduced pressure, and the residue was subjected to column chromatography (silica gel: 70 g, ethyl acetate). The objective fractions were concentrated under reduced pressure to obtain 2-[(1-tert-butoxycarbonylpiperidin-4-yl)oxy]-N-[4-[N-methyl-N-(4-tetrahydropyran-4-yl)aminomethyl]phenyl]-6,7-dihydro-5H-benzocycloheptene-8-carboxamide (compound 17) (1446 mg, 2.45 mmol, 87%).

IR (KBr): 1694, 1667, 1599, 1514 cm$^{-1}$.

$^1$H-NMR (CDCl$_3$) δ: 1.47 (9H, s), 1.5–2.0 (8H, m), 2.0–2.25 (2H, m), 2.21 (3H, s), 2.5–2.85 (5H, m), 3.2–3.45 (4H, m), 3.57 (2H, s), 3.6–3.8 (2H, m), 3.95–4.1 (2H, m), 4.35–4.5 (1H, m), 6.78 (1H, dd, J=2.6, 8.2 Hz), 6.85 (1H, d, J=2.6 Hz), 7.07 (1H, d, J=8.2 Hz), 7.29 (1H, s), 7.31 (2H, d, J=8.4 Hz), 7.55 (2H, d, J=8.4 Hz), 7.61 (1H, s).

Reference Example 50

To triphenylphosphine (1.18 g, 4.50 mmol), tetrahydropyran-4-ol (0.429 g, 4.50 mmol) and methyl 2-hydroxy-6,7-dihydro-5H-benzocycloheptene-8-carboxylate (327 mg, 1.50 mmol) dissolved in THF (10 ml) was added at 0° C. a solution of diisopropyl azodicarboxylate (0.886 ml, 4.50 mmol) in THF (2 ml), and the resulting mixture was stirred at room temperature for 3 days. The reaction mixture was concentrated under reduced pressure and the residue was subjected to column chromatography (silica gel: 45 g, ethyl acetate/hexane=1/25). The objective fractions were concentrated under reduced pressure to obtain methyl 2-[(tetrahydropyran-4-yl)oxy]-6,7-dihydro-5H-benzocycloheptene-8-carboxylate (427 mg, 1.41 mmol, 94%).

IR (KBr): 1709 cm$^{-1}$.

$^1$H-NMR (CDCl$_3$): δ1.65–1.9 (2H, m), 1.9–2.1 (4H, m), 2.55–2.7 (2H, m), 2.7–2.8 (2H, m), 3.5–3.65 (2H, m), 3.82 (3H, s), 3.9–4.05 (2H, m), 4.35–4.55 (1H, m), 6.79 (1H, dd, J=2.4, 8.3 Hz), 6.87 (1H, d, J=2.4 Hz), 7.05 (1H, d, J=8.3 Hz), 7.63 (1H, s).

Reference Example 51

To methyl 2-[(tetrahydropyran-4-yl)oxy]-6,7-dihydro-5H-benzocycloheptene-8-carboxylate (406 mg, 1.34 mmol) dissolved in a mixed solvent of methanol (7 ml) and THF (7 ml) was added a 1N aqueous solution of sodium hydroxide (4.0 ml), and the resulting mixture was stirred at 60° C. for 5 hours. The reaction mixture was mixed with 1 N hydrochloric acid (4.0 ml) at 0° C., was concentrated under reduced pressure and was mixed with water, and an insoluble material was collected by filtration. The insoluble material was washed with water and was dried under reduced pressure to obtain 2-[(tetrahydropyran-4-yl)oxy]-6,7-dihydro-5H-benzocycloheptene-8-carboxylic acid (307 mg, 1.28 mmol, 96%).

Example 18 (Production of Compound 18)

To a mixture of 2-[(tetrahydropyran-4-yl)oxy]-6,7-dihydro-5H-benzocycloheptene-8-carboxylic acid (170 mg, 0.59 mmol), 4-[N-methyl-N-(tetrahydropyran-4-yl) aminomethyl]aniline dihydrochloride (190 mg, 0.65 mmol), 1-hydroxybenzotriazole (96 mg, 0.71 mmol) and DMF (8 ml) were added at 0° C. 1-[3-(dimethylamino)propyl]-3-ethylcarbodiimide hydrochloride (226 mg, 1.18 mmol) and triethylamine (0.411 ml, 2.95 mmol), and the resulting mixture was stirred at room temperature for 3 days. The reaction mixture was concentrated under reduced pressure, ethyl acetate (40 ml) was added to the residue and the resulting mixture was washed with an aqueous saturated solution of sodium bicarbonate (10 ml, 5 ml×2). The organic layer was dried with anhydrous magnesium sulfate and was then concentrated under reduced pressure, and the residue was subjected to column chromatography (silica gel: 15 g, ethyl acetate). The objective fractions were concentrated under reduced pressure, and the residue was dissolved in ethyl acetate (10 ml). Thereto was added at 0° C. 4 N hydrogen chloride (a solution in ethyl acetate, 0.6 ml), and an insoluble material was collected by filtration. The insoluble material was washed with ethyl acetate and was then dried under reduced pressure to obtain 2-[(tetrahydropyran-4-yl)oxy]-N-[4-[N-methyl-N-(4-tetrahydropyran-4-yl)aminomethyl]phenyl]-6,7-dihydro-5H-benzocycloheptene-8-carboxamide hydrochloride (compound 18) (264 mg, 0.50 mmol, 85%).

IR (KBr): 1649, 1597, 1522 $cm^{-1}$.

$^1$H-NMR (DMSO-$d_6$) δ: 1.45–2.2 (10H, m), 2.45–2.65 (2H, m), 2.59 (3H, s), 2.65–2.8 (2H, m), 3.2–3.55 (5H, m), 3.75–4.1 (4H, m), 4.12 (1H, d, J=13.1 Hz), 4.44 (1H, d, J=13.1 Hz), 4.45–4.65 (1H, m), 6.86 (1H, dd, J=2.4, 8.1 Hz), 7.02 (1H, d, J=2.4 Hz), 7.13 (1H, d, J=8.1 Hz), 7.25 (1H, s), 7.55 (2H, d, J=8.4 Hz), 7.82 (2H, d, J=8.4 Hz).

Reference Example 52

Into a solution of methyl 7-hydroxy-1,1-dioxo-2,3-dihydro-1-benzothiepine-4-carboxylate (400 mg), 4-propoxyphenethyl alcohol (537 mg) and triphenylphosphine (782 mg) in THF (10 ml) was added at 0° C. diethyl azodicarboxylate (a 40% solution in toluene) (1.36 ml), and the resulting mixture was stirred at room temperature for 24 hours. After concentration under reduced pressure, the residue was subjected to separation and purification using column chromatography (ethyl acetate/hexane 1:1) to obtain methyl 7-[[4-(propoxyphenethyl)oxy]-1,1-dioxo-2,3-dihydro-1-benzothiepine-4-carboxylate (1.2 g).

Into a solution of methyl 7-[[4-(propoxyphenethyl)oxy]-1,1-dioxo-2,3-dihydro-1-benzothiepine-4-carboxylate (1.2 g) in THF/methanol (10/5 ml) was added at room temperature an aqueous solution (2.1 ml) of potassium carbonate (622 mg), and the resulting mixture was stirred at 60° C. for 24 hours. After cooling to room temperature, the reaction mixture was extracted with ethyl acetate. To the aqueous layer was added 1 N hydrochloric acid (10 ml), and the resulting mixture was extracted with ethyl acetate. The organic layer was washed with an aqueous saturated solution of sodium chloride and was dried with magnesium sulfate. After concentration under reduced pressure, the precipitated crystals were collected by filtration. The crystals were washed with diisopropyl ether to obtain 7-[[4-(propoxyphenethyl)oxy]-1,1-dioxo-2,3-dihydro-1-benzothiepine-4-carboxylic acid (330 mg) as colorless crystals.

$^1$H-NMR (200 MHz, DMSO-$d_6$) δ0.97 (3H, t, J=7.5 Hz), 1.62–1.80 (2H, m), 2.86–2.92 (2H, m), 2.99 (2H, t, J=7.0 Hz), 3.63–3.70 (2H, m), 3.89 (2H, t, J=6.6 Hz), 4.28 (2H, t, J=7.0 Hz), 6.86 (2H, d, J=8.8 Hz), 7.13 (1H, dd, J=8.8, 2.6 Hz), 7.23 (2H, d, J=8.8 Hz), 7.33 (1H, d, J=2.6 Hz), 7.72 (1H, s), 7.91 (1H, d, J=8.8 Hz).

Reference Example 53

Into a solution of methyl 7-hydroxy-1,1-dioxo-2,3-dihydro-1-benzothiepine-4-carboxylate (400 mg), 3-propoxybenzyl alcohol (495 mg) and triphenylphosphine (782 mg) in THF (10 ml) was added at 0° C. diethyl azodicarboxylate (a 40% solution in toluene) (1.36 ml), and the resulting mixture was stirred at room temperature for 24 hours. After concentration under reduced pressure, the residue was subjected to separation and purification using column chromatography (ethyl acetate/hexane 1:2) to obtain methyl 7-(3-propoxybenzyl)oxy]-1,1-dioxo-2,3-dihydro-1-benzothiepine-4-carboxylate (650 mg).

Into a solution. of methyl 7-(3-propoxybenzyl)oxy]-1,1-dioxo-2,3-dihydro-1-benzothiepine-4-carboxylate (650 mg) in THF/methanol (5/2.5 ml) was added at room temperature an aqueous solution (2.1 ml) of potassium carbonate (622 mg), and the resulting mixture was stirred at 60° C. for 24 hours. After cooling to room temperature, the reaction mixture was extracted with ethyl acetate. To the aqueous layer was added 1 N hydrochloric acid (10 ml), and the resulting mixture was extracted with ethyl acetate. The organic layer was washed with an aqueous saturated solution of sodium chloride and was dried with magnesium sulfate. After concentration under reduced pressure, the precipitated crystals were collected by filtration. The crystals were washed with diisopropyl ether to obtain 7-(3-propoxybenzyl)oxy]-1,1-dioxo-2,3-dihydro-1-benzothiepine-4-carboxylic acid (379 mg) as colorless crystals.

M. p. 205–206° C.

$^1$H-NMR (200 MHz, DMSO-$d_6$) δ0.97 (3H, t, J=7.3 Hz), 1.63–1.82 (2H, m), 2.87–2.93 (2H, m), 3.65–3.71 (2H, m), 3.93 (2H, t, J=6.4 Hz), 5.22 (2H, s), 6.88–6.93 (1H, m), 6.99–7.03 (2H, m), 7.22 (1H, dd, J=8.7, 2.5 Hz), 7.30 (1H, t, J=8.8 Hz), 7.43 (1H, d, J=2.5 Hz), 7.72 (1H, s), 7.94 (1H, d, J=8.7 Hz).

Elemental Analysis. Calcd. for $C_{21}H_{22}O_6S$: C, 62.67; H, 5.51. Found: C, 62.35; H, 5.45.

Reference Example 54

Into a solution of methyl 7-hydroxy-1,1-dioxo-2,3-dihydro-1-benzothiepine-4-carboxylate (400 mg), 2-propoxybenzyl alcohol (537 mg) and triphenylphosphine (782 mg) in THF (10 ml) was added at 0° C. diethyl azodicarboxylate (a 40% solution in toluene) (1.36 ml), and the resulting mixture was stirred at room temperature for 24 hours. After concentration under reduced pressure, the residue was subjected to separation and purification using column chromatography (ethyl acetate/hexane 1:2) to obtain methyl 7-(2-propoxybenzyl)oxy]-1,1-dioxo-2,3-dihydro-1-benzothiepine-4-carboxylate (0.67 g).

Into a solution of methyl 7-(2-propoxybenzyl)oxy]-1,1-dioxo-2,3-dihydro-1-benzothiepine-4-carboxylate (0.67 g) in THF/methanol (10/5 ml) was added at room temperature an aqueous solution (2.1 ml) of potassium carbonate (622 mg), and the resulting mixture was stirred at 60° C. for 24 hours. After cooling to room temperature, the reaction mixture was extracted with ethyl acetate. To the aqueous layer was added 1 N hydrochloric acid (15 ml), and the resulting mixture was extracted with ethyl acetate. The organic layer was washed with an aqueous saturated solution of sodium chloride and was dried with magnesium sulfate. After concentration under reduced pressure, the precipitated crystals were collected by filtration. The crystals were washed with diisopropyl ether to obtain 7-(2-propoxybenzyl)oxy]-1,1-dioxo-2,3-dihydro-1-benzothiepine-4-carboxylic acid (270 mg) as light yellow crystals.

M. p. 157–160° C.

$^1$H-NMR (200 MHz, DMSO-d$_6$) δ0.96 (3H, t, J=7.4 Hz), 1.64–1.82 (2H, m), 2.91 (2H, t, J=6.4 Hz), 3.68 (2H, t, J=6.4 Hz), 4.00 (2H, t, J=6.4 Hz), 5.20 (2H, s), 6.96 (1H, t, J=7.2 Hz), 7.05 (1H, d, J=8.4 Hz), 7.20 (1H, dd, J=8.8, 2.4 Hz), 7.28–7.44 (3H, m), 7.72 (1H, s), 7.94 (1H, d, J=8.8 Hz).

Elemental Analysis. Calcd. for $C_{21}H_{22}O_6S$: C, 62.67; H, 5.51. Found: C, 62.40; H, 5.38.

Example 19 (Production of Compound 19)

Into a solution of 7-[(4-(propoxyphenethyl)oxy]-1,1-dioxo-2,3-dihydro-1-benzothiepine-4-carboxylic acid (180 mg) in THF (5 ml) were added at room temperature thionyl chloride (0.063 ml) and DMF (one drop), and the resulting mixture was stirred for one hour. After concentration under reduced pressure to remove the solvent, the residue dissolved in THF (10 ml) was added dropwise to a solution of 4-[N-methyl-N-(tetrahydropyran-4-yl)aminomethyl]aniline (105 mg) and triethylamine (0.18 ml) in THF (2 ml) at room temperature. After being stirred at room temperature for 5 hours, the reaction mixture was mixed with water and was extracted with ethyl acetate. The organic layer was washed with an aqueous saturated solution of sodium chloride and was dried with magnesium sulfate. After concentration under reduced pressure, the residue was subjected to purification using column chromatography (ethanol/ethyl acetate 1:2) and to recrystallization (ethanol) to obtain N-[4-[N-methyl-N-(tetrahydropyran-4-yl)aminomethyl]phenyl]-7-[4-(propoxyphenethyl)oxy]-1,1-dioxo-2,3-dihydro-1-benzothiepine-4-carboxamide (compound 19) (153 mg) as colorless crystals.

M. p. 157–158° C.

$^1$H-NMR (200 MHz, CDCl$_3$) δ1.03 (3H, t, J=7.3 Hz), 1.62–1.86 (6H, m), 2.21 (3H, s), 2.54–2.71 (1H, m), 2.99–3.13 (4H, m), 3.29–3.45 (2H, m), 3.57 (2H, s), 3.63–3.70 (2H, m), 3.90 (2H, t, J=6.6 Hz), 3.97–4.09 (2H, m), 4.19 (2H, t, J=7.0 Hz), 6.84–6.95 (4H, m), 7.18 (2H, d, J=8.4 Hz), 7.19 (1H, s), 7.32 (2H, d, J=8.4 Hz), 7.53 (2H, d, J=8.4 Hz), 7.79 (1H, s), 8.06 (1H, d, J=8.8 Hz).

Elemental Analysis. Calcd. for $C_{35}H_{42}N_2O_6S$: C, 67.94; H, 6.84, N, 4.35. Found: C, 68.13; H, 6.83, N, 4.49.

Example 20 (Production of Compound 20)

Into a solution of 7-[(3-(propoxybenzyl)oxy]-1,1-dioxo-2,3-dihydro-1-benzothiepine-4-carboxylic acid (180 mg) in THF (5 ml) were added at room temperature thionyl chloride (0.065 ml) and DMF (one drop), and the resulting mixture was stirred for one hour. After concentration under reduced pressure to remove the solvent, the residue dissolved in THF (10 ml) was added dropwise to a solution of 4-[N-methyl-N-(tetrahydropyran-4-yl)aminomethyl]aniline (108 mg) and triethylamine (0.19 ml) in THF (2 ml) at room temperature. After being stirred at room temperature for 67 hours, the reaction mixture was mixed with water and was extracted with ethyl acetate. The organic layer was washed with an aqueous saturated solution of sodium chloride and was dried with magnesium sulfate. After concentration under reduced pressure, the residue was subjected to purification using column chromatography (ethanol/ethyl acetate 1:3) and to recrystallization (ethanol) to obtain N-[4-[N-methyl-N-(tetrahydropyran-4-yl)aminomethyl]phenyl]-7-[(3-(propoxybenzyl)oxy]-1,1-dioxo-2,3-dihydro-1-benzothiepine-4-carboxamide (compound 20) (204 mg) as colorless crystals.

M. p. 197–199° C.

$^1$H-NMR (200 MHz, CDCl$_3$) δ1.04 (3H, t, J=7.3 Hz), 1.64–1.87 (6H, m), 2.20 (3H, s), 2.54–2.72 (1H, m), 3.06–3.13 (2H, m), 3.29–3.45 (2H, m), 3.57 (2H, s), 3.65–3.72 (2H, m), 3.93 (2H, t, J=6.4 Hz), 3.98–4.09 (2H, m), 5.12 (2H, s), 6.85–7.07 (4H, m), 7.20 (1H, s), 7.30–7.34 (4H, m), 7.53 (2H, d, J=8.4 Hz), 7.76 (1H, s), 8.09 (1H, d, J=8.8 Hz).

Elemental Analysis. Calcd. for $C_{34}H_{40}N_2O_6S$: C, 67.53; H, 6.67, N, 4.63. Found: C, 67.49; H, 6.63, N, 4.46.

Example 21 (Production of Compound 21)

Into a solution of 7-[(2-propoxybenzyl)oxy]-1,1-dioxo-2,3-dihydro-1-benzothiepine-4-carboxylic acid (180 mg) in THF (5 ml) were added at room temperature thionyl chloride (0.065 ml) and DMF (one drop), and the resulting mixture was stirred for one hour. After concentration under reduced pressure to remove the solvent, the residue dissolved in THF (10 ml) was added dropwise into a solution of 4-[N-methyl-N-(tetrahydropyran-4-yl)aminomethyl]aniline (108 mg) and triethylamine (0.18 ml) in THF (2 ml) at room temperature. After being stirred at room temperature for 2 days, the reaction mixture was mixed with water and was extracted with ethyl acetate. The organic layer was washed with an aqueous saturated solution of sodium chloride and was dried with magnesium sulfate. After concentration under reduced pressure, the residue was subjected to purification using column chromatography (silica gel: ethanol/ethyl acetate 1:3) and to recrystallization (ethanol) to obtain N-[4-[N-methyl-N-(tetrahydropyran-4-yl)aminomethyl]phenyl]-7-[(2-propoxybenzyl)oxy]-1,1-dioxo-2,3-dihydro-1-benzothiepine-4-carboxamide (compound 21) (139 mg) as colorless crystals.

M. p. 190–192° C.

$^1$H-NMR (200 MHz, CDCl$_3$) δ1.03 (3H, t, J=7.3 Hz), 1.63–1.87 (6H, m), 2.20 (3H, s), 2.55–2.73 (1H, m), 3.09 (2H, t, J=6.6 Hz), 3.31–3.43 (2H, m), 3.57 (2H, s), 3.68 (2H, t, J=6.6 Hz), 4.00 (2H, t, J=6.4 Hz), 3.98–4.10 (2H, m), 5.21 (2H, s), 6.90–7.02 (3H, m), 7.07 (1H, dd, J=8.8, 2.6 Hz), 7.21 (1H, s), 7.28–7.41 (4H, m), 7.53 (2H, d, J=8.4 Hz), 7.77 (1H, s), 8.08 (1H, d, J=8.4 Hz).

Elemental Analysis. Calcd. for $C_{34}H_{40}N_2O_6S$: C, 67.53; H, 6.67; N, 4.63. Found: C, 67.69; H, 6.65; N, 4.53.

Reference Example 55

A mixed solution of 2-hydroxy-5-bromobenzyl alcohol (3.00 g) and 2-bromo-4'-methylacetophenone (3.50 g) and potassium carbonate (2.45 g) in acetone (50 ml) was stirred at 80° C. for 4 hours. After cooling to room temperature, a solid material was removed by filtration and the filtrate was concentrated under reduced pressure. The residue was subjected to separation and purification using column chromatography (ethyl acetate/hexane 2:3→1:1) to obtain 2-[4-bromo-2-(hydroxymethyl)phenoxy]-1-(4-methylphenyl)-1-ethanone (3.60 g) as colorless crystals.

M. p. 125–127° C.

$^1$H-NMR (200 MHz, CDCl$_3$) δ2.44 (3H, s), 3.43 (1H, t, J=6.8 Hz), 4.73 (2H, d, J=6.8 Hz), 5.36 (2H, s), 6.72 (1H, d, J=8.8 Hz), 7.24–7.36 (3H, m), 7.45 (1H, d, J=2.6 Hz), 7.86 (2H, d, J=8.4 Hz)

IR (KBr) 3412, 1686, 1606, 1483, 1412, 1234, 1018, 810 cm$^{-1}$.

Elemental Analysis. Calcd. for C$_{16}$H$_{15}$O$_3$Br: C, 57.33; H, 4.51; Br, 23.84. Found: C, 57.33; H, 4.41; Br, 23.86.

Reference Example 56

Into a solution of 2-[4-bromo-2-(hydroxymethyl)phenoxy]-1-(4-methylphenyl)-1-ethanone (3.00 g) in acetonitrile (20 ml) was added at room temperature triphenylphosphine hydrobromide (3.17 g), and the resulting mixture was refluxed with heating for 2 days under a nitrogen atmosphere. After cooling to room temperature, the reaction mixture was mixed with diethyl ether, and the resulting crystals were collected by filtration to obtain [5-bromo-2-[2-(4-methylphenyl)-2-oxyoethoxy]benzyl](triphenyl)phosphonium bromide (5.94 g) as colorless crystals.

$^1$H-NMR (200 MHz, CDCl$_3$) δ2.44 (3H, s), 4.82 (2H, s), 5.29 (2H, d, J=14.0 Hz), 6.75 (1H, d, J=8.8 Hz), 7.25–7.39 (4H, m), 7.52–7.81 (15H, m), 7.88 (2H, d, J=8.2 Hz).

IR (KBr) 1691, 1489, 1437, 1234, 1120, 816, 748, 717, 689, 505 cm$^{-1}$.

Reference Example 57

Into a suspension of [5-bromo-2-[2-(4-methylphenyl)-2-oxoethoxy]benzyl](triphenyl)phosphonium bromide (5.53 g) in ethanol (20 ml) was added at room temperature a 20% solution of sodium ethoxide in ethanol (2.85 g), and the resulting mixture was stirred for 24 hours. After addition of water (15 ml) to the reaction mixture, a solid material was collected by filtration and was washed with water. The solid material were purified by recrystallization (ethanol) to obtain 6-bromo-3-(4-methylphenyl)-2H-1-benzopyran (2.16 g) as colorless crystals.

M. p. 143° C. (dec.)

$^1$H-NMR (200 MHz, CDCl$_3$) δ2.38 (3H, s), 5.15 (2H, d, J=1.4 Hz), 6.69–6.74 (2H, m), 7.16–7.28 (4H, m), 7.33 (2H, d, J=8.4 Hz)

IR (KBr) 1479, 1217, 898, 813 cm$^{-1}$.

Elemental Analysis. Calcd. for C$_{16}$H$_{13}$OBr: C, 63.81; H, 4.35; Br, 26.53. Found: C, 63.67; H, 4.37; Br, 26.50.

Reference Example 58

Into a solution of 6-bromo-3-(4-methylphenyl)-2H-1-benzopyran (0.5 g) in THF (15 ml) was added at −78° C. 1.6 M butyl lithium (a hexane solution) (1.14 ml) under a nitrogen atmosphere. The resulting mixture was stirred at −78° C. for one hour, was then mixed with dry ice and was stirred for additional one hour. After addition of 1 N hydrochloric acid (10 ml), the resulting mixture was extracted with ethyl acetate. The organic layer was washed with an aqueous saturated solution of sodium chloride and was dried with magnesium sulfate. After concentration under reduced pressure, the resulting crystals were collected by filtration, and the crystals were washed with diethyl ether and hexane to obtain 3-(4-methylphenyl)-2H-1-benzopyran-6-carboxylic acid (218 mg) as colorless crystals.

M. p. 255° C. (dec.)

$^1$H-NMR (200 MHz, CDCl$_3$) δ2.33 (3H, s), 5.27 (2H, d, J=1.0 Hz), 6.89 (1H, d, J=8.2 Hz), 7.10 (1H, s), 7.24 (2H, d, J=8.3 Hz), 7.48 (2H, d, J=8.3 Hz), 7.71 (1H, dd, J=8.2, 2.2 Hz), 7.77 (1H, d, J=2.2 Hz).

IR (KBr) 2976, 1676, 1302, 1223, 806 cm$^{-1}$.

Elemental Analysis. Calcd. for C$_{17}$H$_{14}$O$_3$: C, 76.68; H, 5.30. Found: C, 76.47; H, 5.37.

Example 22 (Production of Compound 22)

Into a solution of 3-(4-methylphenyl)-2H-1-benzopyran-6-carboxylic acid (130 mg) in THF (10 ml) were added at room temperature oxalyl chloride (0.07 ml) and one drop of DMF, and the resulting mixture was stirred for one hour. After concentration under reduced pressure to remove the solvent, to the residue dissolved in THF (20 ml) were added at 0° C. 4-[N-methyl-N-(tetrahydropyran-4-yl)aminomethyl]aniline (118 mg) and triethylamine (0.15 ml), and the reaction mixture was stirred at room temperature for 3 hours. The reaction mixture was poured into water with vigorous stirring to stop the reaction, and the resulting mixture was extracted with chloroform. The organic layer was washed with an aqueous saturated solution of sodium chloride and was dried with magnesium sulfate. After concentration under reduced pressure, the residue was purified by recrystallization (ethanol) to obtain 3-(4-methylphenyl)-N-[4-[N-methyl-N-(tetrahydropyran-4-yl)aminomethyl]phenyl]-2H-1-benzopyran-6-carboxamide (compound 22) (162 mg) as light yellow crystals.

M. p. 230–235° C.

$^1$H-NMR (200 MHz, CDCl$_3$) δ1.52–1.84 (4H, m), 2.21 (3H, s), 2.39 (3H, s), 2.56–2.74 (1H, m), 3.30–3.45 (2H, m), 3.58 (2H, s), 3.99–4.10 (2H, m), 5.26 (2H, d, J=1.6 Hz), 6.82 (1H, s), 6.90 (1H, d, J=9.2 Hz), 7.22 (2H, d, J=8.0 Hz), 7.30–7.37 (4H, m), 7.56–7.66 (4H, m), 7.72 (1H, br s).

IR (KBr) 3305, 2947, 2843, 1647, 1599, 1518, 1491, 1406, 1315, 1238, 1140, 810 cm$^{-1}$.

Elemental Analysis. Calcd. for C$_{30}$H$_{32}$N$_2$O$_3$·0.2 H$_2$O: C, 76.31; H, 6.92; N, 5.93. Found: C, 76.31; H, 7.02; N, 5.88.

Reference Example 59

Into a solution of sodium ethoxide (a 20% solution in ethanol, 22.2 g) in toluene (100 ml) was added at 0° C. over a period of more than 10 minutes a solution of 4-bromobenzaldehyde (10 g) and ethyl azidoacetate (7.0 g) in toluene (50 ml). After being stirred at room temperature for 2 hours, the reaction mixture was mixed with water and was extracted with ethyl acetate. The organic layer was washed with an aqueous saturated solution of sodium chloride and was dried with magnesium sulfate. After concentration under reduced pressure, the residue was subjected to separation and purification using column chromatography (ethyl acetate/hexane 1:19) to obtain ethyl (Z)-2-azido-3-(4-bromophenyl)acrylate (6.24 g) as a yellow oily substance.

$^1$H-NMR (200 MHz, CDCl$_3$) δ1.40 (3H, t, J=7.2 Hz), 4.38 (2H, q, J=7.2 Hz), 6.83 (1H, s), 7.51 (2H, d, J=8.6 Hz), 7.69 (2H, d, J=8.6 Hz).

IR (neat): 2121, 1713, 1398, 1379, 1315, 1281, 1250, 1076, 1011, 824 cm$^{-1}$.

Reference Example 60

A solution of ethyl (Z)-2-azido-3-(4-bromophenyl)acrylate (6.24 g) in xylene (200 ml) was heated at reflux for 4 hours. After cooling to room temperature, the reaction mixture was concentrated under reduced pressure, and the precipitated crystals were collected by filtration. The crystals were washed with xylene and hexane to obtain ethyl 6-bromo-1H-indole-2-carboxylate (3.21 g) as colorless crystals.

M. p. 187–188° C.

$^1$H-NMR (200 MHz, CDCl$_3$) δ1.43 (3H, t, J=7.2 Hz), 4.41 (2H, q, J=7.2 Hz), 7.18–7.28 (2H, m), 7.53–7.59 (2H, m), 8.78–8.97 (1H, m).

IR (KBr) 3321, 1695, 1522, 1315, 1240, 1201, 1020, 822, 763, 733 cm$^{-1}$.

Elemental Analysis. Calcd. for $C_{11}H_{10}NO_2Br$: C, 49.28; H, 3.76; N, 5.22. Found: C, 49.45; H, 3.63; N, 5.06.

Reference Example 61

A mixture of ethyl 6-bromo-1H-indole-2-carboxylate (2.5 g) and 4-methylphenylboric acid (1.39 g), potassium carbonate (2.58 g) and toluene/ethanol/water (90/9/9 ml) was stirred at room temperature for one hour. Into the reaction mixture was added tetrakis(triphenylphosphine)palladium (0.32 g), and the resulting mixture was heated at reflux for 18 hours. After cooling to room temperature, the mixture was extracted with ethyl acetate. The organic layer was washed with an aqueous saturated solution of sodium chloride and was dried with magnesium sulfate. After concentration under reduced pressure, the residue was subjected to purification using column chromatography (ethyl acetate/hexane 1:5→1:2→1:1) and to recrystallization (ethyl acetate/hexane) to obtain ethyl 6-(4-methylphenyl)-1H-indole-2-carboxylate (1.92 g) as colorless crystals.

M. p. 163–165° C.

$^1$H-NMR (200 MHz, CDCl$_3$) δ1.43 (3H, t, J=7.2 Hz), 2.41 (3H, s), 4.42 (2H, q, J=7.2 Hz), 7.23–7.27 (2H, m), 7.29 (1H, s), 7.41 (1H, dd, J=8.4, 1.6 Hz), 7.51–7.61 (3H, m), 7.73 (1H, d, J=8.4 Hz), 8.86–8.98 (1H, m).

IR (KBr) 3290, 1689, 1520, 1333, 1282, 1217, 820, 795 cm$^{-1}$.

Elemental Analysis. Calcd. for $C_{18}H_{17}NO_2$: C, 77.40; H, 6.13; N, 5.01. Found: C, 77.48; H, 6.21; N, 4.89.

Reference Example 62

Into a mixed solution of ethyl 6-(4-methylphenyl)-1H-indole-2-carboxylate (0.6 g) in ethanol/THF (10/10 ml) was added at room temperature a 2 N aqueous solution of sodium hydroxide (5 ml), and the resulting mixture was stirred for 64 hours. After addition of 1 N hydrochloric acid (15 ml), the reaction mixture was concentrated under reduced pressure. Water was added to the residue, and the resulting mixture was extracted with ethyl acetate. The organic layer was washed with an aqueous saturated solution of sodium chloride and was dried with magnesium sulfate. After concentration of the organic layer under reduced pressure, the precipitated crystals were collected by filtration. The crystals were washed with hexane to obtain 6-(4-methylphenyl)-1H-indole-2-carboxylic acid (509 mg) as colorless crystals.

M. p. 260° C. (dec.)

$^1$H-NMR (200 MHz, DMSO-d$_6$) δ2.35 (3H, s), 7.10 (1H, s), 7.28 (2H, d, J=8.0 Hz), 7.35 (1H, dd, J=8.4, 1.8 Hz), 7.56 (2H, d, J=8.0 Hz), 7.61 (1H, d, J=1.8 Hz), 7.71 (1H, d, J=8.4 Hz), 11.81 (1H, s).

IR (KBr) 3410, 1666, 1525, 1439, 1273, 1215, 800 cm$^{-1}$.

Elemental Analysis. Calcd. for $C_{16}H_{13}NO_2$: C, 76.48; H, 5.21; N, 5.57. Found: C, 76.66; H, 5.05; N, 5.34.

Example 23 (Production of Compound 23)

Into a solution of 6-(4-methylphenyl)-1H-indole-2-carboxylic acid (200 mg) in THF (10 ml) were added at room temperature oxalyl chloride (0.35 ml) and one drop of DMF, and the resulting mixture was stirred for one hour. After concentration under reduced pressure to remove the solvent, to the residue dissolved in THF (20 ml) were added at 0° C. 4-[N-methyl-N-(tetrahydropyran-4-yl)aminomethyl]aniline (193 mg) and triethylamine (0.22 ml) and the resulting mixture was stirred at room temperature for 18 hours. The reaction mixture was poured into water with vigorous stirring to stop the reaction, and the resulting mixture was extracted with ethyl acetate. The organic layer was washed with an aqueous saturated solution of sodium chloride and was dried with magnesium sulfate. After concentration of the organic layer under reduced pressure, the precipitated crystals were purified by recrystallization (ethanol) to obtain 6-(4-methylphenyl)-N-[4-[N-methyl-N-(tetrahydropyran-4-yl)aminomethyl]phenyl]-1H-indole-2-carboxamide (compound 23) (97 mg) as colorless crystals.

M. p. 246–250° C.

$^1$H-NMR (200 MHz, DMSO-d$_6$) δ1.45–1.79 (4H, m), 2.12 (3H, s), 2.36 (3H, s), 2.46–2.69 (1H, m), 3.19–3.38 (2H, m), 3.54 (2H, s), 3.84–3.96 (2H, m), 7.24–7.46 (6H, m), 7.57 (2H, d, J=8.0 Hz), 7.66 (1H, s), 7.69–7.80 (3H, m), 10.20 (1H, s), 11.78 (1H, s).

IR (KBr) 3298, 1655, 1601, 1537, 1333, 812 cm$^{-1}$.

Elemental Analysis. Calcd. for $C_{29}H_{31}N_3O_2 \cdot 0.2 H_2O$: C, 76.19; H, 6.92; N, 9.19. Found: C, 76.01; H, 6.81; N, 9.12.

Reference Example 63

Into a solution of ethyl 6-(4-methylphenyl)-1H-indole-2-carboxylate (0.9 g) in DMF (10 ml) was added at 0° C. sodium hydride (60%, 0.14 g), and the resulting mixture was stirred for 15 minutes. Into the reaction mixture was added methyl iodide (0.22 ml), and the resulting mixture was stirred at room temperature for 3 hours. The reaction mixture was mixed with water and was extracted with ethyl acetate. The organic layer was washed with an aqueous saturated solution of sodium chloride and was dried with magnesium sulfate. After concentration of the organic layer under reduced pressure, the residue was subjected to separation and purification using column chromatography (ethyl acetate/hexane 1:4) and further to recrystallization (ethyl acetate/hexane) to obtain ethyl 1-methyl-6-(4-methylphenyl)-1H-indole-2-carboxylate (0.80 g) as colorless crystals.

M. p. 98–99° C.

$^1$H-NMR (200 MHz, CDCl$_3$) δ1.42 (3H, t, J=7.0 Hz), 2.41 (3H, s), 4.12 (3H, s), 4.38 (2H, q, J=7.0 Hz), 7.26–7.32 (3H, m), 7.40 (1H, dd, J=8.4, 1.4 Hz), 7.54–7.60 (3H, m), 7.71 (1H, d, J=8.4 Hz).

IR (KBr) 1705, 1504, 1400, 1223, 1153, 1084, 822, 798 cm$^{-1}$.

Elemental Analysis. Calcd. for $C_{19}H_{19}NO_2$: C, 77.79; H, 6.53; N, 4.77. Found: C, 77.99; H, 6.50; N, 4.60.

Reference Example 64

Into a mixed solution of ethyl 1-methyl-6-(4-methylphenyl)-1H-indole-2-carboxylate (0.7 g) in ethanol/THF (20/10 ml) was added at room temperature a 2 N aqueous solution of sodium hydroxide (1.5 ml), and the resulting mixture was stirred for 24 hours. After addition of 1 N hydrochloric acid (5 ml), the reaction mixture was concentrated under reduced pressure. Water was added to the residue, and the resulting mixture was extracted with ethyl acetate. The organic layer was washed with an aqueous saturated solution of sodium chloride and was dried with magnesium sulfate. After concentration under reduced pressure, the precipitated crystals were collected by filtration. The crystals were washed with hexane to obtain 1-methyl-6-(4-methylphenyl)-1H-indole-2-carboxylic acid (600 mg) as colorless crystals.

M. p. 259° C. (dec.)

$^1$H-NMR (200 MHz, DMSO-d$_6$) δ2.36 (3H, s), 4.09 (3H, s), 7.23 (1H, s), 7.29 (2H, d, J=7.6 Hz), 7.42 (1H, dd, J=8.4, 1.4 Hz), 7.66–7.74 (3H, m), 7.80 (1H, s).

IR (KBr) 2916, 1680, 1512, 1470, 1433, 1257, 1228, 920, 820, 798 cm$^{-1}$.

Elemental Analysis. Calcd. for $C_{17}H_{15}NO_2$: C, 76.96; H, 5.70; N, 5.28. Found: C, 76.87; H, 5.76; N, 5.22.

Example 24 (Production of Compound 24)

Into a solution of 1-methyl-6-(4-methylphenyl)-1H-indole-2-carboxylic acid (200 mg) in THF (10 ml) were added at room temperature oxalyl chloride (0.20 ml) and one drop of DMF, and the resulting mixture was stirred for one hour. After concentration under reduced pressure to remove the solvent, to the residue dissolved in THF (30 ml) were added 4-[N-methyl-N-(tetrahydropyran-4-yl)aminomethyl] aniline (183 mg) and triethylamine (0.21 ml) at 0° C., and the resulting mixture was stirred at room temperature for 18 hours. After pouring into water with vigorous stirring to stop the reaction, the reaction mixture was concentrated under reduced pressure, and the precipitate was collected by filtration. The precipitate was washed with ethanol and ethyl acetate to obtain a crude product. The crude product was purified by recrystallization (ethanol) to obtain 1-methyl-6-(4-methylphenyl)-N-[4-[N-methyl-N-(tetrahydropyran-4-yl)aminomethyl]phenyl]-1H-indole-2-carboxamide (compound 24) (298 mg) as colorless crystals.

M. p. 225–226° C.

$^1$H-NMR (200 MHz, CDCl$_3$) δ1.62–1.83 (4H, m), 2.22 (3H, s), 2.42 (3H, s), 2.56–2.75 (1H, m), 3.29–3.45 (2H, m), 3.59 (2H, s), 3.98–4.11 (2H, m), 4.14 (3H, s), 7.02 (1H, s), 7.26–7.36 (4H, m), 7.43 (1H, dd, J=8.0, 1.4 Hz), 7.57–7.61 (5H, m), 7.71 (1H, d, J=8.8 Hz), 7.91 (1H, s).

IR (KBr) 3298, 1647, 1516, 1462, 1389, 1300, 1250, 1142, 810 cm$^{-1}$.

Elemental Analysis. Calcd. for $C_{30}H_{33}N_3O_2$: C, 77.06; H, 7.11; N, 8.99. Found: C, 76.98; H, 7.02; N, 8.99.

Reference Example 65

Into a suspension of 7-(4-methylphenyl)-2,3-dihydro-1-benzooxepine-4-carboxylic acid (280 mg) in methanol (20 ml)/ethyl acetate (10 ml) was added 10% palladium on charcoal (50% water content, 70 mg). Hydrogen gas was introduced, and the resulting mixture was stirred at room temperature for 17 hours and at 50° C. for 3 hours, and was then filtered to remove the catalyst. The filtrate was concentrated, and the residue was recrystallized from ethyl acetate/hexane to obtain 7-(4-methylphenyl)-2,3,4,5-tetrahydro-1-benzooxepine-4-carboxylic acid (187 mg) as colorless crystals.

M. p. 182–184° C.

$^1$H-NMR (200 MHz, CDCl$_3$) δ: 2.2–2.3 (2H, m), 2.38 (3H, s), 2.7–2.85 (1H, m), 3.05–3.3 (2H, m), 3.8–3.9 (1H, m), 4.3–4.4 (1H, m), 7.04 (1H, d, J=8.6), 7.22 (2H, d, J=8.2), 7.3–7.4 (2H, m), 7.44 (2H, d, J=8.4).

IR (KBr) 1692, 1491, 1310, 1250, 1227, 1051, 964, 814 cm$^{-1}$.

Elemental Analysis. Calcd. for $C_{18}H_{18}O_3$: C, 76.57; H, 6.43. Found: C, 76.48; H, 6.30.

Example 25 (Production of Compound 25)

Into a solution of 7-(4-methylphenyl)-2,3,4,5-tetrahydro-1-benzooxepine-4-carboxylic acid (141 mg) and 4-[N-methyl-N-(tetrahydropyran-4-yl)aminomethyl]aniline (110 mg) in DMF (4 ml) were added under ice cooling diethyl cyanophosphonate (0.08 ml) and triethylamine (0.08 ml). After being stirred at 0° C. for 30 minutes and at room temperature for 8 hours, an aqueous solution of sodium bicarbonate was added into the reaction mixture under ice cooling. The resulting mixture was extracted with ethyl acetate, and the extract was washed with an aqueous saturated solution of sodium chloride. The extract was dried with anhydrous magnesium sulfate and was then concentrated under reduced pressure. The residue was subjected to purification using silica gel column chromatography (ethyl acetate/hexane=4/1) and further to recrystallization from ethyl acetate/hexane to obtain N-[4-[(N-methyl-N-(tetrahydropyran-4-yl)aminomethyl)phenyl]-7-(4-methylphenyl)-2,3,4,5-tetrahydro-1-benzooxepine-4-carboxamide (compound 25) (43 mg) as colorless crystals.

M. p. 172–174° C.

$^1$H-NMR (200 MHz, CDCl$_3$) δ: 1.4–2.0 (4H, m), 2.15–2.45 (2H, m), 2.38 (6H, s), 2.65–2.85 (1H, m), 2.9–3.1 (2H, m), 3.2–3.4 (3H, m), 3.7–3.9 (3H, m), 3.9–4.1 (2H, m), 4.4–4.55 (1H, m), 7.05 (2H, d, J=8.8), 7.22 (2H, d, J=8.2), 7.3–7.5 (5H, m), 7.6–7.75 (2H, m).

IR (KBr) 1665, 1609, 1541, 1491, 1418, 1252, 1061, 818 cm$^{-1}$.

Reference Example 66

1,4-Dibromobenzene (25 g) was dissolved in concentrated sulfuric acid (30 ml). Thereto was added dropwise under ice cooling a mixed solution of concentrated sulfuric acid (30 ml)/nitric acid (8.9 ml). After 14 hours at room temperature, the reaction mixture was poured into ice water, was mixed with potassium carbonate and was extracted with ethyl acetate. The extract was washed successively with an aqueous solution of potassium bicarbonate and an aqueous saturated solution of sodium chloride, was dried (anhydrous magnesium sulfate) and was then concentrated. The residue was subjected to purification using silica gel column chromatography (hexane) to obtain 1,4-dibromo-2-nitrobenzene (13.3 g) as light yellow crystals.

$^1$H-NMR (200 MHz, CDCl$_3$) δ: 7.56 (dd, 1H, J=2.2, 8.6), 7.62 (d, 1H, J=8.6), 7.99 (d, 1H, J=2.2).

IR (KBr) 1537, 1458, 1352, 1034 cm$^{-1}$.

Reference Example 67

Into a solution of 1,4-dibromo-2-nitrobenzene (5.4 g) in THF (300 ml) was added phenyllithium (11.7 ml) under cooling at −100° C. in a liquid nitrogen/diethyl ether bath. After stirring for 30 minutes, DMF (5.9 ml) was added dropwise, and the resulting mixture was stirred for one hour in a dry ice/acetone bath. Thereto was added 1 N sulfuric acid (40 ml), and the resulting mixture was extracted with ethyl acetate. The organic layer was washed with an aqueous solution of sodium chloride, was dried (anhydrous magnesium sulfate) and was then concentrated. The residue was subjected to purification using silica gel column chromatography (ethyl acetate/hexane=1/8) to obtain 4-dibromo-2-nitrobenzaldehyde (3.53 g) as a brown solid.

$^1$H-NMR (200 MHz, CDCl$_3$) δ: 7.85 (d, 1H, J=8.2), 7.94 (dd, 1H, J=1.8, 8.2), 8.27 (d, 1H, J=1.8), 10.39 (s, 1H).

IR (KBr) 1699, 1595, 1559, 1534, 1346, 1190, 878, 820 cm$^{-1}$.

Reference Example 68

To 4-dibromo-2-nitrobenzaldehyde (1.89 g) were added 4-methylphenylboric acid (1.23 g), a 2 M aqueous solution of potassium carbonate (10 ml), ethanol (10 ml) and toluene (30 ml), and, after stirring at room temperature under an argon atmosphere for 30 minutes, tetrakis (triphenylphosphine)palladium (380 mg) was added thereto, and the resulting mixture was refluxed overnight. The reaction mixture was extracted with ethyl acetate, and the extract was washed successively with water and an aqueous solution of sodium chloride, was dried (anhydrous magnesium sulfate) and was then concentrated. The residue was subjected to purification using silica gel column chromatography (ethyl acetate/hexane=1/9) to obtain 4-(4-methylphenyl)-2-nitrobenzaldehyde (1.17 g) as a light brown powder.

$^1$H-NMR (200 MHz, CDCl$_3$) δ: 2.44 (s, 3H), 7.33 (d, 2H, J=8.4), 7.57 (d, 2H, J=8.4), 7.96 (dd, 1H, J=1.6, 8.2), 8.04 (d, 1H, J=8.2), 8.29 (d, 1H, J=1.6), 10.44 (s, 1H).

IR (KBr) 1696, 1609, 1534, 1520, 1350, 1188, 814 cm$^{-1}$.

Reference Example 69

Into a solution of 4-(4-methylphenyl)-2-nitrobenzaldehyde (590 mg) in THF (50 ml) was added a solution of sodium hydrosulfite (2.66 g)/water (25 ml). After being stirred at room temperature for 10 minutes, the reaction mixture was extracted with ethyl acetate, and the extract was washed with an aqueous solution of sodium chloride. The extract was dried (anhydrous magnesium sulfate) and was then concentrated to obtain 2-amino-4-(4-methylphenyl)benzaldehyde (0.26 g) as a light brown powder.

$^1$H-NMR (200 MHz, CDCl$_3$) δ: 2.41 (s, 3H), 5.8–6.4 (br, 2H), 6.84 (d, 1H, J=1.6), 6.98 (dd, 1H, J=1.6, 8.2), 7.26 (d, 2H, J=8.2), 7.45–7.6 (m, 3H), 9.89 (s, 1H).

IR (KBr) 1671, 1620, 1591, 1539, 1393, 1208, 1192, 795 cm$^{-1}$.

Reference Example 70

Into a solution of 2-amino-4-(4-methylphenyl) benzaldehyde (0.23 g) and pyruvic acid (192 mg) in methanol (20 ml) was added a solution of sodium hydroxide (349 mg)/methanol (20 ml), and the resulting mixture was stirred at 50–60° C. for 9 hours and was then concentrated. The concentrate was extracted with water, and the aqueous layer was washed twice with diethyl ether and was then mixed with 1 N hydrochloric acid to adjust the pH to 1–2. The resulting mixture was extracted with ethyl acetate, and the extract was washed with an aqueous solution of sodium chloride. The extract was dried (anhydrous magnesium sulfate) and was then concentrated. The residue was subjected to purification using silica gel column chromatography (ethyl acetate/methanol=4/1) to obtain 4-(4-methylphenyl)quinoline-2-carboxylic acid (117 mg) as an orange powder.

$^1$H-NMR (200 MHz, CDCl$_3$) δ: 2.40 (s, 3H), 7.37 (d, 2 H, J=8.2), 7.80 (d, 2H, J=8.2), 8.0–8.2 (m, 3H), 8.39 (s, 1H), 8.59 (d, 1H, J=8.0).

IR (KBr) 1620, 1555, 1454, 1404, 1173, 816 cm$^{-1}$.

Example 26 (Production of Compound 26)

Into a solution of 4-(4-methylphenyl)quinoline-2-carboxylic acid (100 mg) in THF (5 ml) were added under ice cooling DMF (one drop) and oxalyl chloride (0.04 ml), and the resulting mixture was stirred at 0° C. for 30 minutes. On the other hand, into a solution of 4-[N-methyl-N-(tetrahydropyran-4-yl)aminomethyl]aniline (92 mg) in THF (5 ml) were added under ice cooling triethylamine (0.33 ml) and then the above-prepared, acid chloride solution, and the resulting mixture was stirred at room temperature for one hour. The reaction mixture was mixed with water under ice cooling and was extracted with ethyl acetate. The extract was washed with an aqueous solution of sodium chloride, was dried (anhydrous magnesium sulfate) and was concentrated under reduced pressure. The residue was subjected to purification using silica gel column chromatography (ethyl acetate/methanol=9/1) and further to recrystallization from ethyl acetate/diethyl ether to obtain N-[4-[(N-methyl-N-(tetrahydropyran-4-yl))aminomethyl]phenyl]-7-(4-methylphenyl)quinoline-2-carboxamide (compound 26) (27 mg) as colorless crystals.

M. p. 148–150° C.

$^1$H-NMR (200 MHz, CD$_3$OD) δ: 1.6–1.9 (m, 4H), 2.25 (s, 3H), 2.43 (s, 3H), 2.6–2.8 (m, 1H), 3.3–3.5 (m, 2H), 3.66 (s, 2H), 3.9–4.1 (m, 2H), 7.35 (d, 2H, J=7.8), 7.39 (d, 2H, J=7.8), 7.74 (d, 2H, J=7.8), 7.85 (d, 2H, J=7.8), 7.95–8.05 (m, 1H), 8.08 (d, 1H, J=8.8), 8.26 (d, 1H, J=8.2), 8.45–8.5 (m, 1H), 8.51 (d, 1H, J=8.2).

IR (KBr) 1678, 1522, 1497, 1410, 812 cm$^{-1}$.

Elemental Analysis. Calcd. for C$_{30}$H$_{31}$N$_3$O$_2$.0.2 H$_2$O: C, 76.80; H, 6.75; N, 8.96. Found: C, 76.84; H, 6.59; N, 8.86.

Example 27 (Production of Compound 27)

Into a solution of 3-(4-methylphenyl)-2H-1-benzopyran-6-carboxylic acid (150 mg) in THF (10 ml) were added at room temperature oxalyl chloride (0.07 ml) and subsequently one drop of DMF, and the resulting mixture was stirred for one hour. After evaporation of the solvent under reduced pressure, to the residue dissolved in THF (20 ml) were added at 0° C. 1-(4-aminobenzyl)phosphorinane -1-oxide (138 mg) and triethylamine (0.16 ml), and the reaction mixture was stirred at room temperature for 4 hours. The reaction mixture was poured into water with vigorous stirring to stop the reaction and was extracted with chloroform. The organic layer was washed with an aqueous saturated solution of sodium chloride and was dried with magnesium sulfate. After concentration under reduced pressure, the residue was purified by recrystallization (ethanol) to obtain 3-(4-methylphenyl)-N-(4-pentamethylenephosphorylmethylphenyl)-2H-1-benzopyran-6-carboxamide (compound 27) (204 mg) as light yellow crystals.

M. p. 235° C. (dec.)

$^1$H-NMR (200 MHz, CDCl$_3$) δ1.40–2.16 (10H, m), 2.39 (3H, s), 3.15 (2H, d, J=13.6 Hz), 5.25 (2H, d, J=1.4 Hz), 6.82 (1H, s), 6.89 (1H, d, J=9.2 Hz), 7.18–7.29 (4H, m), 7.35 (2H, d, J=8.4 Hz), 7.62–7.70 (4H, m), 8.21–8.32 (1H, m).

IR (KBr) 3226, 1645, 1603, 1541, 1514, 1491, 1410, 1329, 1201, 1165, 1134, 837 cm$^{-1}$.

Elemental Analysis. Calcd. for C$_{29}$H$_{30}$NO$_3$P.0.3 H$_2$O: C, 73.03; H, 6.47; N, 2.94. Found: C, 73.07; H, 6.57; N, 2.87.

Example 28 (Production of Compound 28)

Into a solution of 3-(4-methylphenyl)-N-[4-[N-methyl-N-(tetrahydropyran-4-yl)aminomethyl]phenyl]-2H-1-benzopyran-6-carboxamide (80 mg) in DMF (30 ml) was added at room temperature methyl iodide (0.04 ml), and the resulting mixture was stirred for 3 days. After evaporation of the solvent under reduced pressure, ethyl acetate was added to the residue, and the precipitated crystals were collected by filtration to obtain N,N-dimethyl-N-[4-[[3-(4-methylphenyl)-2H-1-benzopyran-6-carbonyl]amino]benzyl]-4-tetrahydropyranylammonium iodide (compound 28) (87 mg) as light yellow crystals.

M. p. 215–218° C. (dec.)

$^1$H-NMR (200 MHz, DMSO-d$_6$) δ1.75–2.00 (2H, m), 2.10–2.23 (2H, m), 2.34 (3H, s), 2.89 (6H, s), 3.26–3.43 (2H, m), 3.49–3.68 (1H, m), 4.01–4.12 (2H, m), 4.47 (2H, s), 5.29 (2H, d, J=1.0 Hz), 6.96 (1H, d, J=8.0 Hz), 7.10 (1H, s), 7.26 (2H, d, J=8.0 Hz), 7.48–7.57 (4H, m), 7.75–7.80 (2H, m), 7.92 (2H, d, J=8.8 Hz), 10.34 (1H, s).

IR (KBr) 3273, 1647, 1597, 1524, 1493, 1323, 810 cm$^{-1}$.

Elemental Analysis. Calcd. for C$_{31}$H$_{35}$N$_2$O$_3$I.1.2 H$_2$O: C, 58.90; H, 5.96; N, 4.43. Found: C, 58.85; H, 5.66; N, 4.48.

Reference Example 71

Into acetic acid (42 ml) were added dropwise under ice cooling sulfuric acid (28 ml), subsequently N-(2-(4-bromophenyl)ethyl)trifluoroacetamide (7.8 g) and paraformamide (1.27 g) and the resulting mixture was stirred overnight under a nitrogen atmosphere. The reaction mixture was poured into ice water and was extracted with ethyl acetate. The organic layer was washed with an aqueous solution of sodium hydrogen carbonate, water and an aqueous saturated solution of sodium chloride, and was then dried with anhydrous magnesium sulfate. The resulting organic layer was evaporated under reduced pressure to remove the solvent to obtain 7-bromo-2-trifluoroacetyl-1,2,3,4-tetrahydroisoquinoline (8.1 g) as a colorless oil.

$^1$H-NMR (δ ppm, CDCl$_3$) 2.87–2.94 (2H, m), 3.81–3.91 (2H, m), 4.72 (0.7H, s), 4.77 (1.3H, s), 7.02–7.09 (1H, m), 7.27–7.37 (2H, m).

IR (neat) ν: 2907, 1696 cm$^{-1}$.

Reference Example 72

To 7-bromo-2-trifluoroacetyl-1,2,3,4-tetrahydroisoquinoline (8.1 g), 4-methylphenylboric acid (3.9 g), a 2 M aqueous solution of potassium carbonate (40 ml) and ethanol (40 ml) was added toluene (100 ml), and the resulting mixture was stirred at room temperature under an argon atmosphere for 30 minutes. Thereto was added tetrakis(triphenylphosphine)palladium (1.26 g), and the resulting mixture was refluxed under an argon atmosphere for 4.5 hours. The reaction mixture was extracted with ethyl acetate, and the organic layer was washed with water and an aqueous saturated solution of sodium chloride, and was then dried with anhydrous magnesium sulfate. After evaporation of the solvent under reduced pressure, methanol (200 ml) and a 2 M aqueous solution of potassium carbonate (50 ml) were added to the residue, and the resulting mixture was stirred overnight at room temperature. After concentration, the reaction mixture was extracted with ethyl acetate. The organic layer was washed with water and was then back-extracted with 1 N hydrochloric acid. The aqueous layer was made alkaline with a 1 N aqueous solution of sodium hydroxide, was then saturated with sodium chloride and was extracted with ethyl acetate. The organic layer was washed with an aqueous saturated solution of sodium chloride and was dried with anhydrous magnesium sulfate. The resulting organic layer was evaporated under reduced pressure to remove the solvent to obtain 7-(4-methylphenyl)-1,2,3,4-tetrahydroisoquinoline (4.2 g) as colorless crystals.

$^1$H-NMR (δ ppm, CDCl$_3$) 2.39 (3H, s), 2.83 (1.5H, t, J=6.0 Hz), 2.91–2.93 (1H, m), 3.17 (1.5H, t, J=6.0 Hz), 3.33 (0.5H, s), 3.82 (0.5H, s), 4.08 (1.5H, s), 7.13–7.25 (4H, m), 7.36 (1H, dd, J=1.8, 7.8), 7.44–7.49 (2H, m).

IR (KBr) ν: 2919, 1427 cm$^{-1}$.

Elemental Analysis. Calcd. for C$_{16}$H$_{17}$N.0.1 H$_2$O: C, 85.37; H, 7.70; N, 6.22. Found: C, 85.34; H, 7.57; N, 6.10.

Reference Example 73

A solution of 4-(chloromethyl)phenylisocyanate (0.38 g) in tetrahydrofuran was added dropwise under ice cooling into a solution of 7-(4-methylphenyl)-1,2,3,4-tetrahydroisoquinoline (0.5 g) in tetrahydrofuran. The resulting mixture was stirred for one hour and was then evaporated to remove the solvent to obtain 4-(7-(4-methylphenyl)-1,2,3,4-tetrahydroisoquinolin-2-ylcarbonylamino)benzyl chloride (0.82 g) as colorless crystals.

$^1$H-NMR (δ ppm, CDCl$_3$) 2.40 (3H, s), 2.98 (2H, t, J=5.8 Hz), 3.77 (2H, t, J=6.1 Hz), 4.57 (2H, s), 4.73 (2H, s), 6.48 (1H, br), 7.23–7.30 (4H, m), 7.34–7.49 (7H, m).

IR (KBr) ν: 3303, 3023, 1645 cm$^{-1}$.

Elemental Analysis. Calcd. for C$_{24}$H$_{23}$ClN$_2$O.0.2 H$_2$O: C, 73.07; H, 5.98; N, 7.10. Found: C, 73.04; H, 5.86; N, 7.10.

Reference Example 74

Oxalyl chloride (0.4 ml) was added under ice cooling into a suspension of 4-bromomethylphenylacetic acid (0.52 g) in dichloromethane (4 ml). Dimethylformamide (a catalytic amount) was then added thereto, and the resulting mixture was stirred at room temperature for 2 hours. After the reaction mixture was evaporated to remove the solvent, a solution of the residue in tetrahydrofuran was added dropwise under ice cooling into a solution of 7-(4-methylphenyl)-1,2,3,4-tetrahydroisoquinoline (0.5 g) and diisopropylethylamine (0.5 ml) in tetrahydrofuran. After being stirred at room temperature for 30 minutes, the resulting mixture was mixed with ethyl acetate, and the precipitate was removed by filtration. The filtrate was washed with water and an aqueous saturated solution of sodium chloride and was then dried with anhydrous magnesium sulfate. The resulting organic layer was evaporated under reduced pressure to remove the solvent to obtain 2-(4-bromomethylphenylacetyl)-7-(4-methylphenyl)-1,2,3,4-tetrahydroisoquinoline (0.7 g) as a light yellow oil.

$^1$H-NMR (δ ppm, CDCl$_3$) 2.39 (3H, s), 2.75 (1.1H, t, J=5.9 Hz), 2.89 (0.9H, t, J=6.0 Hz), 3.69 (1.1H, t, J=5.9 Hz), 3.82 (2H, s), 3.88 (0.9H, t, J=6.0 Hz), 4.44–4.57 (2H, m), 4.66 (0.9H, s), 4.82 (1.1H, s), 7.13–7.47 (11H, m).

IR (neat) ν: 3023, 2922, 1642 cm$^{-1}$.

Example 29 (Production of Compound 29)

A solution of 4-(7-(4-methylphenyl)-1,2,3,4-tetrahydroisoquinolin-2-ylcarbonylamino)benzyl chloride (0.2 g) and 1-methyl piperidine (0.19 ml) in dimethylformamide (5 ml) was stirred overnight at room temperature under a nitrogen atmosphere. The reaction mixture was evaporated to remove the solvent and was mixed with ethyl acetate, and the precipitate was collected by filtration. The precipitate was recrystallized from ethanol to obtain 1-methyl-1-(4-((7-(4-methylphenyl)-1,2,3,4-tetrahydroisoquinolin-2-yl)carbonylamino)benzyl)piperidinium chloride (compound 29) (0.23 g) as colorless crystals.

M. p. 179–180° C. (dec.)

$^1$H-NMR (δ ppm, DMSO-d$_6$) 1.45–1.65 (2H, m), 1.75–1.95 (4H, m), 2.34 (3H, s), 2.86–2.92 (5H, m), 3.24–3.32 (4H, m), 3.76 (2H, t, J=5.9 Hz), 4.48 (2H, s), 4.73 (2H, s), 7.25–7.29 (3H, m), 7.38–7.49 (4H, m), 7.55 (2H, d, J=8.2 Hz), 7.65 (2H, d, J=8.6 Hz), 8.91 (1H, br).

IR (KBr) ν: 3364, 3285, 2948, 1663 cm$^{-1}$.

Elemental Analysis. Calcd. for $C_{30}H_{36}ClN_3O \cdot H_2O$: C, 70.92; H, 7.54; N, 8.27. Found: C, 70.97; H, 7.80; N, 8.03.

Example 30 (Production of Compound 30)

A solution of 4-(7-(4-methylphenyl)-1,2,3,4-tetrahydroisoquinolin-2-ylcarbonylamino)benzyl chloride (0.2 g) and 1-ethylpiperidine (0.21 ml) in dimethylformamide (5 ml) was stirred overnight at room temperature under a nitrogen atmosphere. The reaction mixture was evaporated to remove the solvent and was mixed with ethyl acetate, and the precipitate was collected by filtration to obtain 1-ethyl-1-(4-((7-(4-methylphenyl)-1,2,3,4-tetrahydroisoquinolin-2-yl)carbonylamino)benzyl)piperidinium chloride (compound 30) (0.24 g) as a light red, amorphous substance.

$^1$H-NMR (δ ppm, DMSO-d$_6$) 1.33 (3H, t, J=7.2 Hz), 1.40–1.65 (2H, m), 1.75–1.95 (4H, m), 2.35 (3H, s), 2.89 (2H, t, J=5.6 Hz), 3.10–3.33 (6H, m), 3.76 (2H, t, J=5.6 Hz), 4.45 (2H, s), 4.73 (2H, s), 7.24–7.29 (3H, m), 7.35–7.48 (4H, m), 7.55 (2H, d, J=8.2 Hz), 7.65 (2H, d, J=8.4 Hz), 8.91 (1H, br).

IR (KBr) ν: 3236, 2948, 1651 cm$^{-1}$.

Elemental Analysis. Calcd. for $C_{31}H_{38}ClN_3O \cdot 0.8 H_2O$: C, 71.81; H, 7.70; N, 8.10. Found: C, 71.87; H, 7.79; N, 7.91.

Example 31 (Production of Compound 31)

A solution of 2-(4-bromomethylphenylacetyl)-7-(4-methylphenyl)-1,2,3,4-tetrahydroisoquinoline (0.2 g) and 1-methylpiperidine (0.17 ml) in dimethylformamide (5 ml) was stirred overnight at room temperature under a nitrogen atmosphere. The reaction mixture was evaporated to remove the solvent and was mixed with ethyl acetate, and the precipitate was collected by filtration. The precipitate was dissolved in ethanol, and the solvent was evaporated to obtain 1-methyl-1-(4-((7-(4-methylphenyl)-1,2,3,4-tetrahydroisoquinolin-2-yl)carbonylmethyl)benzyl)piperidinium bromide (compound 31) (0.24 g) as a colorless amorphous substance.

$^1$H-NMR (δ ppm, DMSO-d$_6$) 1.40–1.70 (2H, m), 1.78–1.91 (4H, m), 2.34 (3H, s), 2.77–2.88 (2H, m), 2.93 (3H, s), 3.21–3.27 (4H, m), 3.69–3.82 (2H, m), 3.90 (2H, s), 4.53 (2H, d, J=8.0 Hz), 4.76 (2H, d, J=20.8 Hz), 7.20–7.30 (3H, m), 7.39–7.56 (8H, m).

IR (KBr) ν: 3345, 2942, 1636 cm$^{-1}$.

Elemental Analysis. Calcd. for $C_{31}H_{37}BrN_2O \cdot 0.5 H_2O$: C, 68.63; H, 7.06; N, 5.16. Found: C, 68.54; H, 7.06; N, 4.95.

Example 32 (Production of Compound 32)

A solution of 2-(4-bromomethylphenylacetyl)-7-(4-methylphenyl)-1,2,3,4-tetrahydroisoquinoline (0.2 g) and 1-ethylpiperidine (0.19 ml) in dimethylformamide (5 ml) was stirred overnight at room temperature under a nitrogen atmosphere. The reaction mixture was evaporated to remove the solvent and was mixed with ethyl acetate, and the precipitate was collected by filtration. The precipitate was dissolved in ethanol, and the solvent was evaporated to obtain 1-ethyl-1-(4-((7-(4-methylphenyl)-1,2,3,4-tetrahydroisoquinolin-2-yl)carbonylmethyl)benzyl)piperidinium bromide (compound 32) (0.23 g) as a colorless amorphous substance.

$^1$H-NMR (δ ppm, DMSO-d$_6$) 1.34 (3H, t, J=7.2 Hz) 1.40–1.65 (2H, m), 1.75–1.90 (4H, m), 2.34 (3H, s), 2.75–2.85 (2H, m), 3.20–3.33 (6H, m), 3.70–3.80 (2H, m), 3.89 (2H, s), 4.49 (2H, d, J=8.4 Hz), 4.76 (2H, d, J=22.0 Hz), 7.23–7.27 (3H, m), 7.40–7.56 (8H, m).

IR (KBr) ν: 3353, 2942, 1638 cm$^{-1}$.

Elemental Analysis. Calcd. for $C_{32}H_{39}BrN_2O \cdot 0.5 H_2O$: C, 69.06; H, 7.24; N, 5.03. Found: C, 68.82; H, 7.38; N, 4.78.

Reference Example 75

Into a solution of 4-methoxybenzylamine (4.12 g) and tetrahydro-4H-pyran-4-one (3.00 g) in 1,2-dichloroethane (50 ml) was added sodium triacetoxyborohydride (6.99 g). After stirring at room temperature for 2 hours, 37% formalin solution (2.5 ml) and sodium triacetoxyborohydride (6.99 g) were added thereto. After stirring for additional one hour, the reaction mixture was mixed with an aqueous solution of sodium bicarbonate and was extracted with dichloromethane. The extract was washed with an aqueous solution of sodium chloride, was dried (anhydrous magnesium sulfate) and was then concentrated under reduced pressure. The residue was subjected to purification using silica gel column chromatography (ethyl acetate) to obtain N-methyl-N-(tetrahydropyran-4-yl)-4-methoxybenzylamine (3.56 g) as a light yellow, oily substance.

$^1$H-NMR (200 MHz, CDCl$_3$) δ: 1.6–1.8 (4H, m), 2.19 (3H, s), 2.55–2.75 (1H, m), 3.37 (2H, dt, J=3.0, 11.2), 3.53 (2H, s), 3.80 (3H, s), 4.0–4.1 (2H, m), 6.85 (2H, d, J=8.6), 7.22 (2H, d, J=8.6).

IR (KBr) 1613, 1510, 1456, 1300, 1246, 1173, 1142, 1038 cm$^{-1}$.

Reference Example 76

Into a solution of N-methyl-N-(tetrahydropyran-4-yl)-4-methoxybenzylamine (2.19 g) in dichloromethane (20 ml) was added at −78° C. a solution of boron tribromide in dichloromethane (11 ml). After gradually raising the temperature from −78° C. to room temperature, the resulting mixture was stirred for 2 hours, an additional solution of boron tribromide in dichloromethane (5 ml) was again added thereto, and the resulting mixture was stirred at room temperature for 30 minutes. The reaction mixture was mixed with an aqueous solution of sodium bicarbonate under ice cooling and was extracted with dichloromethane, and the extract was concentrated under reduced pressure. Thereto were added 1 N hydrochloric acid and diethyl ether to extract the aqueous layer. The extract was adjusted to pH 8 by adding an aqueous solution of potassium carbonate and was then extracted with ethyl acetate. The extract was washed with an aqueous solution of sodium chloride, was dried (anhydrous magnesium sulfate) and was then concentrated under reduced pressure. The residue was subjected to purification using silica gel column chromatography (ethyl acetate/methanol) to obtain N-methyl-N-(tetrahydropyran-4-yl)-4-hydroxybenzylamine (206 mg) as a light yellow, oily substance.

$^1$H-NMR (200 MHz, CDCl$_3$) δ: 1.6–1.8 (4H, m), 2.21 (3H, s), 2.55–2.75 (1H, m), 3.37 (2H, dt, J=2.8, 11.2), 3.54 (2H, s), 4.0–4.1 (2H, m), 6.74 (2H, d, J=8.6), 7.17 (2H, d, J=8.6).

IR (KBr) 1613, 1520, 1458, 1246 cm$^{-1}$.

Reference Example 77

Into a solution of 7-(4-methylphenyl)-2,3-dihydro-1-benzooxepine-4-carboxylic acid (841 mg) and triethylamine (0.42 ml) in THF (15 ml) was added dropwise at −5° C. a solution of ethyl chloroformate (0.29 ml)/THF (2 ml). The resulting mixture was stirred at −5° C. for 30 minutes, and an insoluble material was removed by filtration. Into the filtrate was added dropwise under ice cooling a solution of sodium borohydride (284 mg)/water (6 ml). After stirring at room temperature for 1.5 hours, the reaction mixture was mixed with 1 N hydrochloric acid and was extracted with ethyl acetate. The extract was washed successively with water, a 1 N aqueous solution of sodium hydroxide, water and an aqueous solution of sodium chloride, was dried (anhydrous magnesium sulfate) and was then concentrated under reduced pressure. The residue was recrystallized from ethyl acetate/diethyl ether/hexane to obtain 4-hydroxymethyl-7-(4-methylphenyl)-2,3-dihydro-1-benzooxepine (708 mg) as colorless crystals.

M. p. 91–92° C.

$^1$H-NMR (200 MHz, CDCl$_3$) δ: 2.39 (3H, s), 2.71 (2H, t, J=4.8), 4.25 (2H, s), 4.30 (2H, t, J=4.8), 6.46 (1H, s), 7.00 (1H, d, J=8.4 z), 7.23 (2H, d, J=8.2), 7.3–7.5 (4H, m).

IR (KBr) 1497, 1331, 1265, 1231, 1125, 1040, 1028, 918, 901, 806 cm$^{-1}$.

Elemental Analysis. Calcd. for C$_{18}$H$_{18}$O$_2$: C, 81.17; H, 6.81. Found: C, 81.29; H, 6.88.

Example 33 (Production of Compound 33)

To 4-hydroxymethyl-7-(4-methylphenyl)-2,3-dihydro-1-benzooxepine (89 mg), N-methyl-N-(tetrahydropyran-4-yl)-4-hydroxybenzylamine (92 mg) and tributylphosphine (0.13 ml) was added under ice cooling 1,1-(azodicarbonyl)dipiperidine (129 mg). After the resulting mixture was stirred at 0° C. for 10 minutes and at room temperature for one hour, an insoluble material was removed by filtration. The filtrate was extracted with ethyl acetate, and the extract was washed twice with an aqueous solution of sodium chloride. The extract was dried (anhydrous magnesium sulfate) and then was concentrated under reduced pressure. The residue was subjected to purification using silica gel column chromatography (ethyl acetate/hexane=4/1) and further to recrystallization from ethyl acetate/hexane to obtain 4-[4-[(N-methyl-N-(tetrahydropyran-4-yl)aminomethyl]phenoxymethyl]-7-(4-methylphenyl)-2,3-dihydro-1-benzooxepine (compound 33) (45 mg) as colorless crystals.

M. p. 135–136° C.

$^1$H-NMR (200 MHz, CDCl$_3$) δ: 1.6–1.8 (4H, m), 2.20 (3H, s), 2.39 (3H, s), 2.55–2.75 (1H, m), 2.75–2.8 (2H, m), 3.36 (2H, dt, J=2.8, 11.2), 3.53 (2H, s), 4.0–4.1 (2H, m), 4.32 (2H, t, J=4.6), 4.61 (2H, s), 6.55 (1H, s), 6.91 (2H, d, J=8.8), 7.00 (1H, d, J=8.0), 7.2–7.3 (4H, m), 7.3–7.4 (2H, m), 7.44 (2H, d, J=8.2).

IR (KBr) 1508, 1493, 1235, 1161, 1003, 816 cm$^{-1}$.

Elemental Analysis. Calcd. for C$_{31}$H$_{35}$NO$_2$.H$_2$O: C, 78.95; H, 7.91; N, 2.97. Found: C, 78.83; H, 7.55; N, 2.88.

Reference Example 78

Into a solution of 4-hydroxymethyl-7-(4-methylphenyl)-2,3-dihydro-1-benzooxepine (320 mg) in dichloromethane (10 ml) were added triphenylphosphine (378 mg) and carbon tetrabromide (597 mg), and the resulting mixture was stirred at room temperature for 2 hours. Thereto were additionally added triphenylphosphine (157 mg) and carbon tetrabromide (249 mg), and the resulting mixture was stirred further for 30 minutes, was then mixed with an aqueous solution of sodium bicarbonate under ice cooling and was extracted with ethyl acetate. The extract was washed with an aqueous solution of sodium chloride, was dried (anhydrous magnesium sulfate) and was then concentrated under reduced pressure.

The residue was subjected to purification using silica gel column chromatography (ethyl acetate/hexane=1/9) and further to washing with diethyl ether/hexane to obtain 4-bromomethyl-7-(4-methylphenyl)-2,3-dihydro-1-benzooxepine (286 mg) as a white powder.

$^1$H-NMR (200 MHz, CDCl$_3$) δ: 2.39 (3H, s), 2.85 (2H, t, J=4.6), 4.20 (2H, s), 4.30 (2H, t, J=4.6), 6.59 (1H, s), 7.00 (1H, d, J=8.8), 7.23 (2H, d, J=8.2), 7.3–7.4 (2H, m), 7.43 (2H, d, J=8.2).

IR (KBr) 1493, 1265, 1236, 1196, 912, 808 cm$^{-1}$.

Reference Example 79

Into a solution of 4-[N-methyl-N-(tetrahydropyran-4-yl)aminomethyl]aniline (551 mg) in THF (50 ml) were added triethylamine (0.42 ml) and acetic anhydride (0.26 ml), and the resulting mixture was stirred at room temperature for 3 hours. After evaporation of THF, the residue was extracted with ethyl acetate. The extract was washed successively with an aqueous solution of sodium bicarbonate and an aqueous solution of sodium chloride, was dried with anhydrous magnesium sulfate and was then concentrated under reduced pressure. The residue was recrystallized from ethyl acetate/hexane to obtain N-[4-[N-methyl-N-(tetrahydropyran-4-yl)aminomethyl]phenyl]acetamide (472 mg) as light yellow crystals.

M. p. 105–106° C.

$^1$H-NMR (200 MHz, CDCl$_3$) δ: 1.6–1.8 (4H, m), 2.17 (3H, s), 2.19 (3H, s), 2.55–2.7 (1H, m), 3.36 (2H, dt, J=3.2, 11.4), 3.55 (2H, s), 3.95–4.1 (2H, m), 7.1–7.2 (1H, br), 7.27 (2H, d, J=8.8), 7.44 (2H, d, J=8.8).

IR (KBr) 1665, 1601, 1537, 1408, 1316, 1140, 1009, 839 cm$^{-1}$.

Elemental Analysis. Calcd. for C$_{15}$H$_{22}$N$_2$O$_2$: C, 68.67; H, 8.45; N, 10.68. Found: C, 68.56; H, 8.38; N, 10.76.

Example 34 (Production of Compound 91)

Into a solution of N-[4-[N-methyl-N-(tetrahydropyran-4-yl)aminomethyl]phenyl]acetamide (227 mg) in DMF (4 ml) was added under ice cooling sodium hydride (36 mg). The resulting mixture was stirred at room temperature for 20 minutes, and 4-bromomethyl-7-(4-methylphenyl)-2,3-dihydro-1-benzooxepine (285 mg) was then added under ice cooling. After stirring at room temperature for one hour, the reaction mixture was mixed with water under ice cooling. The resulting mixture was salted out and was extracted with ethyl acetate/THF. The extract was dried (anhydrous magnesium sulfate) and was then concentrated under reduce pressure. The residue was subjected to purification using silica gel column chromatography (ethyl acetate/methanol=40/1), and the resulting product was triturated with diisopropyl ether. The powder was collected by filtration and was washed with diisopropyl ether to obtain N-[4-[(N-methyl-N-(tetrahydropyran-4-yl)aminomethyl]phenyl]-N-[[7-(4-methylphenyl)-2,3-dihydro-1-benzooxepin-4-yl]methyl] acetamide (compound 91) (209 mg) as a light yellow, amorphous substance.

$^1$H-NMR (200 MHz, CDCl$_3$) 1.6–1.8 (4H, m), 1.91 (3H, s), 2.16 (3H, s), 2.37 (3H, s), 2.5–2.65 (1H, brm), 2.65–2.75 (2H, m), 3.25–3.45 (2H, m), 3.55 (2H, s), 3.9–4.1 (2H, m), 4.23 (2H, d, J=4.8), 4.50 (2H, s), 6.06 (1H, s), 6.96 (1H, d, J=8.6), 7.08 (2H, d, J=7.6), 7.15–7.4 (8H, m).

IR (KBr): 1661, 1508, 1491, 1387, 1235, 814 cm$^{-1}$.

Reference Example 80

Into a solution of 4-hydroxymethyl-7-(4-methylphenyl)-2,3-dihydro-1-benzooxepine (0.21 g) in dichloromethane (10 ml) were added manganese dioxide (687 mg), and the resulting mixture was stirred at room temperature for 3 hours. An insoluble material was removed by filtration, and the filtrate was evaporated to remove dichloromethane. The residue was recrystallized from ethyl acetate/hexane to obtain 7-(4-methylphenyl)-2,3-dihydro-1-benzooxepine-4-carbaldehyde (192 mg) as colorless crystals.

M. p. 132–133° C.

$^1$H-NMR (200 MHz, CDCl$_3$) δ: 2.40 (3H, s), 2.90 (2H, t, J=4.4), 4.31 (2H, t, J=4.4), 7.09 (1H, d, J=8.4), 7.2–7.3 (3H, m), 7.4–7.6 (4H, m), 9.58 (1H, s).

IR (KBr) 1672, 1626, 1495, 1296, 1242, 1163, 1134, 1080, 1028, 810 cm$^{-1}$.

Elemental Analysis. Calcd. for C$_{18}$H$_{16}$O$_2$.0.1 H$_2$O: C, 81.24; H, 6.14. Found: C, 81.43; H, 6.09.

Example 35 (Production of Compound 34)

Into a solution of 7-(4-methylphenyl)-2,3-dihydro-1-benzooxepine-4-carbaldehyde (191 mg)) and 4-[N-methyl-N-(tetrahydropyran-4-yl)aminomethyl]aniline (159 mg) in 1,2-dichloroethane (5 ml) was added sodium triacetoxyborohydride (168 mg). The resulting mixture was stirred at room temperature for 4.5 hours, additional sodium triacetoxyborohydride (76 mg) was added thereto and the resulting mixture was stirred further for 4 days. The reaction mixture was mixed with an aqueous solution of sodium bicarbonate under ice cooling and was extracted with dichloromethane, and the extract was washed with an aqueous solution of sodium chloride. The extract was dried (anhydrous magnesium sulfate) and was then concentrated under reduced pressure. The residue was subjected to purification using silica gel column chromatography (ethyl acetate/methanol=10/1), 4 N hydrochloric acid was added to the resulting product and the precipitate was collected by filtration and was washed with ethyl acetate to obtain N-[4-[(N-methyl-N-(tetrahydropyran-4-yl)aminomethyl)]phenyl]-N-[7-(4-methylphenyl)-2,3-dihydro-1-benzooxepin-4-yl]methylamine (compound 34) (88 mg) as a light yellow powder.

M. p. 158–160° C.

$^1$H-NMR (200 MHz, DMSO-d$_6$) δ: 1.6–2.1 (4H, m), 2.33 (3H, s), 2.56 (3H, s), 2.6–2.7 (2H, m), 3.2–3.4 (3H, m), 3.8–4.0 (5H, m), 4.15–4.3 (3H, m), 6.50 (1H, s), 6.67 (2H, d, J=8.8), 6.94 (1H, d, J=8.0), 7.2–7.3 (4H, m), 7.3–7.45 (2H, m), 7.48 (2H, d, J=8.2), 8.32 (1H, s), 9.8–10.0 (1H, br).

IR (KBr) 1493, 1456, 1238, 816 cm$^{-1}$.

Reference Example 81

Into a solution of 4-bromomethyl-7-(4-methylphenyl)-2,3-dihydro-1-benzooxepine (329 mg) in toluene (10 ml) was added triphenylphosphine (393 mg), and the resulting mixture was refluxed for 2 hours. After gradual cooling, the precipitate was collected by filtration and was washed with toluene. The precipitate was dried under reduced pressure to obtain [7-(4-methylphenyl)-2,3-dihydro-1-benzooxepin-4-yl]methyltriphenylphosphonium bromide (549 mg) as a white powder.

$^1$H-NMR (200 MHz, CDCl$_3$) δ: 2.35 (3H, s), 2.35–2.45 (2H, m), 4.07 (2H, t, J=4.4), 4.48, 4.55 (1H, s), 6.22, 6.25 (1H, s), 6.93 (1H, d, J=8.0), 6.95–7.05 (1H, m), 7.21 (2H, d, J=8.6), 7.3–7.4 (3H, m), 7.7–8.0 (15H, m).

IR (KBr) 1489, 1435, 1235, 1115, 810, 723 cm$^{-1}$.

Reference Example 82

Into a solution of N-methyl-N-(tetrahydropyran-4-yl)-4-hydroxybenzylamine (0.94 g) in dichloromethane (20 ml) was added manganese dioxide (3.48 g), and the resulting mixture was stirred at room temperature for 24 hours. Manganese dioxide was removed by filtration, and the filtrate was evaporated. The residue was subjected to purification using silica gel column chromatography (ethyl acetate/hexane=2/1) to obtain 4-[N-methyl-N-(tetrahydropyran-4-yl)aminomethyl]benzaldehyde (931 mg) as a colorless oily substance.

$^1$H-NMR (200 MHz, CDCl$_3$) δ: 1.5–1.85 (4H, m), 2.22 (3H, s), 2.55–2.75 (1H, m), 3.38 (2H, dt, J=2.8, 11.4), 3.67 (2H, s), 3.95–4.15 (2H, m), 7.51 (2H, d, J=8.0), 7.84 (2H, d, J=8.0), 10.01 (1H, s).

IR (KBr) 1699, 1607, 1209, 1142, 1086 cm$^{-1}$.

Example 36 (Production of Compounds 35 and 36)

Into a solution of [7-(4-methylphenyl)-2,3-dihydro-1-benzooxepin-4-yl]methyltriphenylphosphonium bromide (549 mg) and 4-[N-methyl-N-(tetrahydropyran-4-yl) aminomethyl]benzaldehyde (217 mg) in THF (10 ml) was added under ice cooling potassium t-butoxide (104 mg). After stirring at 0° C. for one hour, the reaction mixture was mixed with water under ice cooling, was salted out and was extracted with ethyl acetate. The extract was dried (anhydrous magnesium sulfate) and was then concentrated under reduced pressure. The residue was subjected to purification using silica gel column chromatography (ethyl acetate/hexane=2/1), and the product from the first eluent was recrystallized from ethyl acetate/hexane to obtain (Z)-4-[2-[4-[(N-methyl-N-(tetrahydropyran-4-yl)aminomethyl]phenyl]ethenyl]-7-(4-methylphenyl)-2,3-dihydro-1-benzooxepine (compound 35) (80 mg) as colorless crystals. The product from the second eluent was recrystallized from ethyl acetate/hexane to obtain (E)-4-[2-[4-[(N-methyl-N-(tetrahydropyran-4-yl)aminomethyl]phenyl]ethenyl]-7-(4-methylphenyl)-2,3-dihydro-1-benzooxepine (compound 36) (22 mg) as colorless crystals, Compound 35: M. p. 115–116° C.

$^1$H-NMR (200 MHz, CDCl$_3$) δ: 1.5–1.8 (4H, m), 2.18 (3H, s), 2.38 (3H, s), 2.5–2.7 (3H, m), 3.36 (2H, dt, J=2.2, 11.2), 3.56 (2H, s), 3.95–4.1 (2H, m), 4.16 (2H, t, J=4.6), 6.32 (1H, d, J=12.2), 6.49 (1H, d, J=12.2), 6.52 (1H, s), 6.97 (1H, d, J=8.4), 7.15–7.35 (8H, m), 7.42 (2H, d, J=8.4).

IR (KBr) 1493, 1264, 1240, 1136, 1080, 1028, 1007, 912, 862, 845, 816 cm$^{-1}$.

Elemental Analysis. Calcd. for C$_{32}$H$_{35}$NO$_2$: C, 82.54; H, 7.58; N, 3.01. Found: C, 82.38; H, 7.75; N, 2.84.

Compound 36: M. p. 119–120° C.

$^1$H-NMR (200 MHz, CDCl$_3$) δ: 1.6–1.8 (4H, m), 2.23 (3H, s), 2.40 (3H, s), 2.6–2.8 (1H, m), 2.95 (2H, t, J=4.6), 3.38 (2H, dt, J=3.0, 11.2), 3.59 (2H, s), 4.0–4.1 (2H, m), 4.38 (2H, t, J=4.6), 6.58 (1H, d, J=17.0), 6.59 (1H, s), 6.98 (1H, d, J=17.0), 7.01 (1H, d, J=8.4), 7.2–7.45 (8H, m), 7.46 (2H, d, J=8.4).

IR (KBr) 1491, 1377, 1262, 1231, 1140, 1086, 963, 810 cm$^{-1}$.

Elemental Analysis. Calcd. for C$_{32}$H$_{35}$NO$_2$: C, 82.54; H, 7.58; N, 3.01. Found: C, 82.19; H, 7.33; N, 2.85.

Reference Example 83

A mixture of 7-(4-methylphenyl)-2,3-dihydro-1-benzooxepine-4-carboxylic acid (561 mg), diphenylphosphoryl azide (0.43 ml), triethylamine (0.28 ml) and methanol (10 ml) was refluxed for 5 hours. The reaction mixture was evaporated to remove the solvent and was then extracted with ethyl acetate. The extract was washed successively with a 5% aqueous solution of citric acid, water, an aqueous solution of sodium bicarbonate, water and an aqueous solution of sodium chloride, was dried (anhydrous magnesium sulfate) and was then concentrated under reduced pressure. The residue was subjected to purification using silica gel column chromatography (ethyl acetate/hexane=1/4) to obtain 4-methoxycarbonylamino-7-(4-methylphenyl)-2,3-dihydro-1-benzooxepine (180 mg) as a light yellow solid.

$^1$H-NMR (200 MHz, CDCl$_3$) δ: 2.38 (3H, s), 2.93 (2H, t, J=5.2), 3.74 (3H, s), 4.28 (2H, t, J=5.2), 6.13 (1H, brs), 6.62 (1H, s), 6.96 (1H, d, J=8.2), 7.2–7.4 (4H, m), 7.44 (2H, d, J=8.2).

IR (KBr) 1715, 1489, 1269, 1186, 1047, 1026, 959, 812 cm$^{-1}$.

Reference Example 84

Into a solution of N-methyl-N-(tetrahydropyran-4-yl)-4-(hydroxymethyl)benzylamine (0.68 g) and triphenylphosphine (0.91 g) in dichloromethane (10 ml) was added under ice cooling carbon tetrabromide (1.44 g), and the resulting mixture was stirred at room temperature for 2 hours. The reaction mixture was mixed with an aqueous solution of sodium bicarbonate under ice cooling and was extracted with ethyl acetate. The extract was washed with an aqueous solution of sodium chloride, was dried (anhydrous magnesium sulfate) and was concentrated under reduced pressure. The residue was subjected to purification using silica gel column chromatography (ethyl acetate/hexane 1/9) and further to washing with diethyl ether/hexane to obtain N-methyl-N-(tetrahydropyran-4-yl)-4-(bromomethyl)benzylamine (687 mg) as a white solid.

$^1$H-NMR (200 MHz, CDCl$_3$) δ: 1.6–1.8 (4H, m), 2.20 (3H, s), 2.55–2.75 (1H, m), 3.37 (2H, dt, J=3.0, 11.4), 3.58 (2H, s), 4.0–4.1 (2H, m), 4.50 (2H, s), 7.3–7.6 (4H, m).

IR (KBr) 1474, 1456, 1431, 1387, 1248, 1142, 1084, 1013, 853 cm$^{-1}$.

Example 37 (Production of Compound 37)

Into a solution of 4-methoxycarbonylamino-7-(4-methylphenyl)-2,3-dihydro-1-benzooxepine (179 mg) in DMF (4 ml) was added under ice cooling sodium hydride (27 mg). After stirring at room temperature for 30 minutes, N-methyl-N-(tetrahydropyran-4-yl)-4-(bromomethyl)benzylamine (273 mg) was added into the resulting mixture under ice cooling. After stirring at room temperature for one hour. the reaction mixture was mixed with water under ice cooling. The resulting mixture was salted out and was extracted with ethyl acetate. The extract was dried (anhydrous magnesium sulfate) and was then concentrated under reduced pressure. The residue was subjected to purification using silica gel column chromatography (ethyl acetate/hexane 4/1) and the resulting product was triturated with diisopropyl ether/hexane. The powder was collected by filtration and was washed with diisopropyl ether to obtain N-methoxycarbonyl-N-[7-(4-methylphenyl)-2,3-dihydro-1-benzooxepin-4-yl]-N-[[4-[N-methyl-N-(tetrahydropyran-4-yl)]aminomethyl]phenylmethyl]amine (compound 37) (25 mg) as a light yellow, amorphous substance.

$^1$H-NMR (200 MHz, CDCl$_3$) δ: 1.5–1.8 (4H, m), 2.23 (3H, brs), 2.2–2.3 (1H, m), 2.6–2.7 (2H, m), 3.25–3.4 (2H, m), 3.6–3.7 (2H, m), 3.76 (3H, s), 4.0–4.1 (2H, m), 4.1–4.2 (2H, m), 4.72 (2H, s), 6.24 (1H, s), 6.96 (1H, d, J=8.4), 7.2–7.7 (10H, m).

IR (KBr) 1701, 1493, 1449, 1375, 1264, 1236, 1121 cm$^{-1}$.

Example 38 (Production of Compound 38)

To N-methyl-N-(tetrahydropyran-4-yl)-4-((7-(4-methylphenyl)-2,3-dihydro-1-benzooxepin-4-yl)-methylamino)benzylamine dihydrochloride (0.25 g) dissolved in 1,2-dichloroethane (5 ml) were added triethylamine (0.13 ml) and a 37% aqueous solution of formaldehyde (0.05 ml), and thereto was added under ice cooling sodium triacetoxyborohydride (0.14 g). The resulting mixture was stirred at room temperature overnight under a nitrogen atmosphere. The reaction mixture was evaporated to remove the solvent, was neutralized with a 1 N aqueous solution of sodium hydroxide and was extracted with ethyl acetate. The organic layer was washed with water and an aqueous saturated solution of sodium chloride, and was then dried with anhydrous magnesium sulfate. The organic layer was evaporated under reduced pressure to remove the solvent to obtain crude crystals. The crude crystals were recrystallized from ethyl acetate/hexane to obtain N-methyl-N-(tetrahydropyran-4-yl)-4-((N-methyl-N-(7-(4-methylphenyl)-2,3-dihydro-1-benzooxepin-4-yl)-methyl)amino)benzylamine (compound 38) (0.11 g) as colorless crystals.

M. p. 110–114° C.

$^1$H-NMR (δ ppm, CDCl$_3$) 1.60–1.75 (4H, m), 2.21 (3H, s), 2.37 (3H, s), 2.61 (2H, t, J=4.8 Hz), 2.63–2.75 (1H, m), 2.97 (3H, s), 3.36 (2H, dt, J=3.0, 9.7 Hz), 3.52 (2H, s), 3.98 (2H, s), 3.98–4.05 (2H, m), 4.29 (2H, t, J=4.8 Hz), 6.33 (1H, s), 6.72 (2H, d, J=8.8 Hz), 6.99 (1H, d, J=9.2 Hz), 7.15–7.23 (4H, m), 7.28–7.33 (2H, m), 7.43 (2H, d, J=8.2 Hz).

IR (KBr) ν: 2949, 1615, 1520, 1491 cm$^{-1}$.

Elemental Analysis. Calcd. for $C_{32}H_{38}N_2O_2 \cdot 0.2\ H_2O$: C, 79.04; H, 7.96; N, 5.76. Found: C, 79.18; H, 7.89; N, 5.75.

Reference Example 85

To 7-(4-methylphenyl)-2,3,4,5-tetrahydro-1-benzooxepin-5-one (1 g) dissolved in ethanol (50 ml) was added under ice cooling sodium borohydride (0.3 g). The resulting mixture was stirred at room temperature for 30 minutes, was mixed with water and was concentrated. The residue was extracted with ethyl acetate, and the organic layer was washed with water and was then concentrated. To the residue dissolved in bis(2-methoxyethyl)ether (20 ml) was added hydrochloric acid (5 ml), and the resulting mixture was stirred with heating at 75° C. for one hour. The reaction mixture was poured into water and was extracted with ethyl acetate. The organic layer was washed with water and an aqueous saturated solution of sodium chloride, was then dried with anhydrous magnesium sulfate and was evaporated to remove the solvent. The precipitate was collected by filtration using hexane to obtain 7-(4-methylphenyl)-2,3-dihydro-1-benzooxepine (0.78 g) as colorless crystals.

M. p. 98–100° C.

$^1$H-NMR (δ ppm, CDCl$_3$) 2.38 (3H, s), 2.65–2.74 (2H, m), 4.27 (2H, t, J=4.9 Hz), 6.01 (1H, dt, J=11.7, 4.4 Hz), 6.39 (1H, d, J=11.7 Hz), 7.01 (1H, d, J=8.0 Hz), 7.23 (2H, d, J=8.2 Hz), 7.31–7.38 (2H, m), 7.45 (2H, d, J=8.0 Hz).

IR (KBr) ν: 3025, 1491 cm$^{-1}$.

Elemental Analysis. Calcd. for $C_{17}H_{16}O$: C, 86.41; H, 6.82. Found: C, 86.17; H, 6.61.

Reference Example 86

Into dimethylformamide (0.2 ml) was added dropwise under ice cooling sulfuryl chloride (0.17 ml), and the resulting mixture was stirred at room temperature for 10 minutes under a nitrogen atmosphere. Thereto was added 7-(4-methylphenyl)-2,3-dihydro-1-benzooxepine (0.3 g), and the resulting mixture was heated at 90° C. for 3 hours under a nitrogen atmosphere. The reaction mixture was mixed with ice water and was extracted with ethyl acetate. The organic layer was washed with water and an aqueous saturated solution of sodium chloride, was then dried with anhydrous magnesium sulfate and was evaporated to remove the solvent to obtain 7-(4-methylphenyl)-2,3-dihydro-1-benzooxepine-4-sulfonyl chloride (0.36 g) as light yellow crystals.

M. p. 162–166° C.

$^1$H-NMR (δ ppm, CDCl$_3$) 2.40 (3H, s), 3.27 (2H, t, J=4.7 Hz), 4.41 (2H, t, J=4.7 Hz), 7.11 (1H, d, J=9.6 Hz), 7.26 (2H, d, J=8.2 Hz), 7.44 (2H, d, J=8.2 Hz), 7.57–7.62 (2H, m), 7.70 (1H, s).

IR (KBr) ν: 3027, 1634, 1493 cm$^{-1}$.

Elemental Analysis. Calcd. for C$_{17}$H$_{15}$ClO$_3$S: C, 60.98; H, 4.52. Found: C, 61.14; H, 4.26.

Example 39 (Production of Compound 39)

To 4-(N-methyl-N-(tetrahydropyran-4-yl)aminomethyl) aniline (0.13 g) and triethylamine (0.22 ml) dissolved in tetrahydrofuran (10 ml) was added under ice cooling 7-(4-methylphenyl)-2,3-dihydro-1-benzooxepine-4-sulfonyl chloride (0.18 g), and the resulting mixture was stirred at room temperature overnight under a nitrogen atmosphere. The reaction mixture was evaporated to remove the solvent, was then mixed with water and was extracted with ethyl acetate. The organic layer was washed with water and an aqueous saturated solution of sodium chloride, was then dried with anhydrous magnesium sulfate and was evaporated to remove the solvent. The residue was subjected to purification using silica gel column (ethyl acetate) to obtain crude crystals. The crude crystals were recrystallized from ethyl acetate/hexane to obtain 7-(4-methylphenyl)-N-(4-((N-methyl-N-tetrahydropyran-4-yl)aminomethyl)phenyl)-2,3-dihydro-1-benzooxepine-4-sulfonamide (compound 39) (0.19 g) as colorless crystals.

M. p. 157–162° C.

$^1$H-NMR (δ ppm, CDCl$_3$) 1.54–1.71 (4H, m), 2.12 (3H, s), 2.39 (3H, s), 2.50–2.65 (1H, m), 2.98 (2H, t, J=4.5 Hz), 3.31 (2H, dt, J=0.8, 11.0 Hz), 3.49 (2H, s), 3.97–4.11 (2H, m), 4.25 (2H, t, J=4.5 Hz), 7.02 (1H, d, J=9.2 Hz), 7.11 (2H, d, J=8.8 Hz), 7.22–7.26 (4H, m), 7.40–7.50 (5H, m).

IR (KBr) ν: 2949, 2847, 1493 cm$^{-1}$.

Elemental Analysis. Calcd. for C$_{30}$H$_{34}$N$_2$O$_4$S: C, 69.47; H, 6.61; N, 5.40. Found: C, 69.27; H, 6.50; N, 5.37.

Reference Example 87

A solution of 4-nitrobenzylamine (5.24 g, 34.4 mmol) and S-methyl-N,N'-bis(tert-butoxycarbonyl)isothiourea (5.00 g, 17.2 mmol) in THF (60 ml) was stirred at 55° C. for 9 hours and at room temperature for 11 hours. The reaction mixture was concentrated under reduced pressure, was then mixed with ethyl acetate (150 ml) and was washed with 1 N hydrochloric acid (30 ml×3) and an aqueous saturated solution of sodium chloride (30 ml) in the order. The organic layer was dried with anhydrous magnesium sulfate and was then concentrated under reduced pressure, and the residue was subjected to column chromatography (silica gel, 150 g: ethyl acetate/hexane 1/9→1/6). The objective fractions were concentrated under reduced pressure, diisopropyl ether was added and an insoluble material was collected by filtration. The insoluble material was washed with diisopropyl ether and was then dried under reduced pressure to obtain N-(4-nitrobenzyl)-N',N"-bis(tert-butoxycarbonyl) guanidine (5.67 g, 14.4 mmol, 83%)

IR (KBr): 1723, 1644, 1620, 1570, 1524 cm$^{-1}$.

$^1$H-NMR (CDCl$_3$) δ: 1.50 (18H, s), 4.7–4.8 (2H, m), 7.48 (2H, d, J=8.5 Hz), 8.21 (2H, d, J=8.5 Hz).

Reference Example 88

To N-(4-nitrobenzyl)-N',N"-bis(tert-butoxycarbonyl) guanidine (1.97 g, 4.99 mmol) dissolved in a mixed solvent of THF (25 ml) and methanol (25 ml) were added at 0° C. nickel bromide (109 mg, 0.50 mmol) and sodium borohydride (757 mg, 20.0 mmol) in the order, and the resulting mixture was stirred at room temperature for 30 minutes. The reaction mixture was mixed with 1 N hydrochloric acid (40 ml) at 0° C., and the resulting mixture was stirred at the same temperature for 5 minutes. The resulting mixture was adjusted to about pH 8 by adding an aqueous saturated solution of sodium bicarbonate and was extracted with ethyl acetate. The organic layer was dried with anhydrous sodium sulfate and was then concentrated under reduced pressure, diisopropyl ether was added to the residue, and an insoluble material was collected by filtration. The insoluble material was washed with diisopropyl ether and was then dried under reduced pressure to obtain 4-[N',N"-bis(tert-butoxycarbonyl)guanidinomethyl]aniline (1.21 g, 3.32 mmol, 66%).

IR (KBr): 1622, 1516 cm$^{-1}$.

$^1$H-NMR (CDCl$_3$) δ: 1.47(9H, s), 1.52 (9H, s), 4.45–4.55 (2H, m), 6.66 (2H, d, J=8.6 Hz), 7.11 (2H, d, J=8.6 Hz).

Example 40 (Production of Compound 40)

To 7-(4-methylphenyl)-2,3-dihydro-1-benzooxepine-4-carboxylic acid (300 mg, 1.07 mmol) dissolved in DMF (10 ml) were added at 0° C. 1-hydroxybenzotriazole (159 mg, 1.18 mmol), 4-[N',N"-bis(tert-butoxycarbonyl) guanidinomethyl]aniline (429 mg, 1.18 mmol), 1-ethyl-3-(3-dimethylaminopropyl)carbodiimide hydrochloride (308 mg, 1.61 mmol), triethylamine (0.447 ml, 3.21 mmol) and 4-dimethylaminopyridine (6 mg), and the resulting mixture was stirred at room temperature for 48 hours. The reaction mixture was concentrated under reduced pressure and was mixed with ethyl acetate (70 ml) and the resulting mixture was washed with water (5 ml×3), an aqueous saturated solution of sodium bicarbonate (5 ml×3) and an aqueous saturated solution of sodium chloride (5 ml) in the order. The organic layer was dried with anhydrous sodium sulfate and was concentrated under reduced pressure, and the residue was subjected to column chromatography (silica gel: 15 g, ethyl acetate/hexane=1/4). The objective fractions were concentrated under reduced pressure, a mixed solvent (ethyl acetate/hexane=1/1) was added to the residue and an insoluble material was collected by filtration. The insoluble material was washed with the mixed solvent (ethyl acetate/hexane=1/1) and was then dried under reduced pressure to obtain N-[4-[N',N"-bis(tert-butoxycarbonyl) guanidinomethyl]phenyl]-7-(4-methylphenyl)-2,3-dihydro-1-benzooxepine-4-carboxamide (compound 40) (390 mg, 0.62 mmol, 58%).

IR (KBr): 1723, 1647, 1617, 1576, 1518 cm$^{-1}$.

$^1$H-NMR (CDCl$_3$) δ: 1.48 (9H, s), 1.52 (9H, s), 2.40 (3H, s), 3.0–3.15 (2H, m), 4.3–4.45 (2H, m), 4.55–4.7 (2H, m), 7.06 (1H, d, J=8.4 Hz), 7.2–7.7 (11H, m).

Example 41 (Production of Compound 41)

To N-[4-[N',N"-bis(tert-butoxycarbonyl) guanidinomethyl]phenyl]-7-(4-methylphenyl)-2,3-dihydro- 1-benzooxepine-4-carboxamide (170 mg, 0.27 mmol) was added 4 N hydrogen chloride (a solution in ethyl acetate), and the resulting mixture was stirred at room temperature for 18 hours. The reaction mixture was concentrated under reduced pressure and was mixed with diethyl ether to collect an insoluble material by filtration. The insoluble material was washed with diethyl ether and was then dried under reduced pressure to obtain N-(4-guanidinomethylphenyl)-7-(4-methylphenyl)-2,3-dihydro-1-benzooxepine-4-carboxamide hydrochloride (compound 41) (130 mg, 0.28 mmol).

IR (KBr): 1655, 1613, 1597, 1522 cm$^{-1}$.

$^1$H-NMR (DMSO-d$_6$) δ: 2.35 (3H, s), 2.9–3.05 (2H, m), 4.2–4.4 (4H, m), 7.06 (1H, d, J=8.4 Hz), 7.2–7.8 (7H, m).

Reference Example 89

Into a solution of 7-(4-methylphenyl)-2,3-dihydro-1-benzooxepine-4-carboxylic acid (0.93 g) in dichloromethane (20 ml) were added under ice cooling DMF (4 drops) and oxalyl chloride (0.34 ml). After 2 hours at room temperature, the reaction mixture was concentrated, and the residue was dissolved in THF (20 ml). In addition, into a solution of 4-aminobenzonitrile (412 mg) in THF (10 ml) were added under ice cooling triethylamine (1.38 ml) and then the above-prepared acid chloride solution, and the resulting mixture was stirred at room temperature for 17 hours. The reaction mixture was mixed with water under ice cooling and was extracted with ethyl acetate. The extract was washed with an aqueous solution of sodium chloride, was dried (anhydrous magnesium sulfate) and was then evaporated under reduced pressure to remove the solvent. The residue was subjected to purification using silica gel column chromatography (ethyl acetate/hexane=1/4) and further to recrystallization from ethyl acetate/hexane to obtain N-(4-cyanophenyl)-7-(4-methylphenyl)-2,3-dihydro-1-benzooxepine-4-carboxamide (986 mg) as colorless crystals.

M. p. 187–189° C.

$^1$H-NMR (200 MHz, CDCl$_3$) δ: 2.40 (s, 3H), 3.07 (t, 2H, J=4.6), 4.36 (t, 2H, J=4.6), 7.07 (d, 1H, J=8.0), 7.2–7.3 (m, 3H), 7.4–7.55 (m, 4H), 7.64 (d, 2H, J=8.8), 7.74 (d, 2H, J=8.8).

IR (KBr) 2222, 1671, 1588, 1514, 1404, 1316, 1225, 1175, 837, 812 cm$^{-1}$.

Elemental Analysis. Calcd. for C$_{25}$H$_{20}$N$_2$O$_2$: C, 78.93; H, 5.30; N, 7.36. Found: C, 78.98; H, 5.24; N, 7.26.

Reference Example 90

To N-(4-cyanophenyl)-7-(4-methylphenyl)-2,3-dihydro-1-benzooxepine-4-carboxamide (347 mg) was added a solution of 28% hydrogen chloride/ethanol/dioxane (5 ml). After the resulting mixture was stirred at room temperature for 20 hours, the precipitate was collected by filtration and was washed with ethyl acetate to obtain N-[4-(ethoxycarbonimidoyl)phenyl]-7-(4-methylphenyl)-2,3-dihydro-1-benzooxepine-4-carboxamide hydrochloride (369 mg) as yellow crystals.

$^1$H-NMR (DMSO-d$_6$) δ: 1.50 (t, 2H, J=7.0), 2.34 (s, 3H), 2.9–3.1 (m, 2H), 4.1–4.4 (m, 2H), 4.60 (q, 2H, J=7.0), 7.06 (d, 1H, J=8.8), 7.26 (d, 2H, J=8.4), 7.45–7.65 (m, 4H), 7.7–7.85 (m, 1H), 8.01 (d, 2H, J=8.8), 8.12 (d, 2H, J=8.8), 10.59 (s, 1H), 10.8–11.2 (br, 1H).

Example 42 (Production of Compound 42)

To N-[4-(ethoxycarbonimidoyl)phenyl]-7-(4-methylphenyl)-2,3-dihydro-1-benzooxepine-4-carboxamide hydrochloride (364 mg) was added a solution of 14% ammonia/ethanol (5 ml). The resulting mixture was stirred at room temperature overnight and then at 50° C. for 3 hours. The reaction mixture was concentrated, the residue was suspended in ethyl acetate and 4 N hydrochloric acid/ethyl acetate was added. The precipitate was collected by filtration, was washed with ethyl acetate and further was recrystallized from acetonitrile/methanol/ethyl acetate to obtain N-(4-amidinophenyl)-7-(4-methylphenyl)-2,3-dihydro-1-benzooxepine-4-carboxamide hydrochloride (compound 42) (127 mg) as colorless crystals.

M. p. 294–296° C.

$^1$H-NMR (200 MHz, DMSO-d$_6$) δ: 2.35 (s, 3H), 2.95–3.05 (m, 2H), 4.25–4.35 (m, 2H), 7.06 (d, 1H, J=8.4), 7.26 (d, 2H, J=8.0), 7.45 (s, 1H), 7.56 (d, 2H, J=8.0), 7.5–7.6 (m, 1H), 7.75–7.85 (m, 1H), 7.84 (d, 2H, J=8.8), 7.96 (d, 2H, J=8.8), 8.8–9.0 (brm, 2H), 9.2–9.3 (brm, 2H), 10.45 (s, 1H).

IR (KBr) 1676, 1644, 1597, 1493, 1329, 1258, 845, 814 cm$^{-1}$.

Elemental Analysis. Calcd. for C$_{25}$H$_{23}$N$_3$O$_2$.HCl.0.3 H$_2$O: C, 68.35; H, 5.64; N, 9.56. Found: C, 68.09; H, 5.56; N, 9.87.

Example 43 (Production of Compound 43)

Into a suspension (4 ml) of N-[4-(ethoxycarbonimidoyl)phenyl]-7-(4-methylphenyl)-2,3-dihydro-1-benzooxepine-4-carboxamide hydrochloride (169 mg) in ethanol was added ethylamine (1 ml). The resulting mixture was stirred at room temperature for 4 days and was then concentrated. The residue was suspended in ethyl acetate, 4 N hydrochloric acid/ethyl acetate was added and the precipitate was collected by filtration. The precipitate was recrystallized from ethyl acetate/methanol to obtain N-(4-ethylamidinophenyl)-7-(4-methylphenyl)-2,3-dihydro-1-benzooxepine-4-carboxamide hydrochloride (compound 43) (25 mg) as colorless crystals.

M. p. >300° C.

$^1$H-NMR (200 MHz, DMSO-d$_6$) δ: 1.25 (t, 3H, J=7.2), 2.34 (s, 3H), 2.9–3.1 (m, 2H), 3.3–3.5 (m, 2H), 4.25–4.4 (m, 2H), 7.06 (d, 1H, J=8.6), 7.26 (d, 2H, J=7.6), 7.46 (s, 1H), 7.5–7.65 (m, 3H), 7.75 (d, 2H, J=8.6), 7.7–7.8 (m, 1H), 7.95 (d, 2H, J=8.6), 8.9 (brs, 1H), 9.33 (brs, 1H), 9.6–9.7 (m, 1H), 10.12 (s, 1H).

IR (KBr) 1671, 1518, 1456, 1318, 1231, 816 cm$^{-1}$.

Elemental Analysis. Calcd. for C$_{27}$H$_{27}$N$_3$O$_2$.HCl.0.5 H$_2$O: C, 68.85; H, 6.21; N, 8.92. Found: C, 68.61; H, 6.21; N, 8.94.

Example 44 (Production of Compound 44)

Into a solution of N-[4-(ethoxycarbonimidoyl)phenyl]-7-(4-methylphenyl)-2,3-dihydro-1-benzooxepine-4-carboxamide hydrochloride (200 mg) in ethanol (4 ml) was added morpholine (1 ml). The resulting mixture was stirred at room temperature overnight, was then concentrated and was mixed with an aqueous solution of sodium bicarbonate. The resulting mixture was extracted with ethyl acetate, and the extract was washed with an aqueous solution of sodium chloride. The extract was dried (anhydrous magnesium sulfate) and was then mixed with 4 N hydrochloric acid/ethyl acetate, and the precipitate was collected by filtration and was washed with ethyl acetate to obtain N-[4-(4-morpholino) carbonimidoylphenyl]-7-(4-methylphenyl)-2,3-dihydro-1-benzooxepine-4-carboxamide hydrochloride (compound 44) (104 mg) as colorless crystals.

M. p. 209–211° C.

$^1$H-NMR (200 MHz, DMSO-d$_6$) δ: 2.3 (s, 3H), 2.9–3.1 (m, 2H), 3.3–3.55 (m, 2H), 3.6–3.75 (m, 2H), 3.75–3.9 (m, 4H), 4.25–4.4 (m, 2H), 7.07 (d, 1H, J=8.6), 7.27 (d, 2H, J=7.6), 7.45 (s, 1H), 7.5–7.7 (m, 3H), 7.60 (d, 2H, J=7.6), 7.75–7.8 (m, 1H), 7.98 (d, 2H, J=8.6), 9.30 (s, 1H), 9.54 (s, 1H), 10.43 (s, 1H).

IR (KBr) 1663, 1603, 1522, 1493, 1460, 1318, 1248, 1184, 1115, 850, 812 cm$^{-1}$.

Elemental Analysis. Calcd. for C$_{29}$H$_{29}$N$_3$O$_3$.HCl.0.6 H$_2$O: C, 67.66; H, 6.11; N, 8.16. Found: C, 67.45; H, 5.96; N, 7.94.

Example 45 (Production of Compound 45)

To N-(4-cyanomethylphenyl)-7-(4-methylphenyl)-2,3-dihydro-1-benzooxepine-4-carboxamide hydrochloride (200 mg) was added a solution of 28% hydrogen chloride/ethanol/dioxane (2 ml). The resulting mixture was kept overnight in a refrigerator and then was concentrated, and ethanol (4 ml) and morpholine (1 ml) were added to the residue. After being stirred at room temperature for one hour, the reaction mixture was concentrated and was mixed with an aqueous solution of sodium bicarbonate. The resulting mixture was extracted with ethyl acetate. The extract was dried (magnesium sulfate) and was concentrated, and the residue was recrystallized from methanol/ethyl acetate/hexane to obtain N-[4-[(4-morpholino)carbonimidoylmethyl]phenyl]-7-(4-methylphenyl)-2,3-dihydro-1-benzooxepine-4-carboxamide (compound 45) (93 mg) as colorless crystals.

M. p. 196–198° C.

$^1$H-NMR (200 MHz, CDCl$_3$) δ: 2.39 (3H, s), 3.07 (2H, t, J=4.8), 3.4–3.55 (4H, m), 3.6–3.7 (6H, m), 4.34 (2H, t, J=4.8), 7.04 (1H, d, J=8.4), 7.19 (2H, d, J=8.8), 7.2–7.3 (2H, m), 7.4–7.55 (5H, m), 7.60 (2H, d, J=8.0), 7.79 (1H, brs).

IR (KBr) 1659, 1582, 1522, 1493, 1318, 1171, 1123, 1030, 814 cm$^{-1}$.

Elemental Analysis. Calcd. for C$_{30}$H$_{31}$N$_3$O$_3$.0.5 H$_2$O: C, 73.45; H, 6.57; N, 8.57. Found: C, 73.46; H, 6.43; N, 8.48.

Example 46 (Production of Compound 46)

To N-(4-cyanomethylphenyl)-7-(4-methylphenyl)-2,3-dihydro-1-benzooxepine-4-carboxamide (200 mg) was added a solution of a 28% hydrogen chloride/ethanol/dioxane (2 ml). The resulting mixture was kept overnight in a refrigerator and then was concentrated, and ethanol (4 ml) and piperidine (1 ml) were added to the residue. After being stirred at room temperature for one hour, the reaction mixture was concentrated and was mixed with an aqueous solution of sodium bicarbonate. The mixture was extracted with ethyl acetate/methanol. The extract was dried (magnesium sulfate) and was then concentrated. To the residue was added 4 N hydrochloric acid/ethyl acetate, and the precipitate was collected by filtration and was washed with ethyl acetate to obtain N-[4-(1-piperidino)carbonimidoylmethyl]phenyl]-7-(4-methylphenyl)-2,3-dihydro-1-benzooxepine-4-carboxamide (compound 46) (103 mg) as a white powder.

M. p. 195–197° C.

$^1$H-NMR (200 MHz, DMSO-d$_6$) δ: 1.2–1.35 (2H, m), 1.5–1.65 (4H, m), 2.34 (3H, s), 2.95–3.05 (2H, m), 3.42 (4H, s), 3.5–3.7 (2H, m), 3.95–4.05 (2H, m), 4.25–4.35 (2H, m), 7.05 (1H, d, J=8.6), 7.2–7.4 (5H, m), 7.5–7.6 (3H, m), 7.7–7.8 (3H, m), 8.88 (1H, brs), 9.4–9.5 (1H, m), 10.07 (1H, s).

IR (KBr) 1647, 1630, 1518, 1491, 1321, 1264, 814 cm$^{-1}$.

Elemental Analysis. Calcd. for C$_{31}$H$_{33}$N$_3$O$_2$.HCl.H$_2$O: C, 69.71; H, 6.79; N, 7.87. Found: C, 69.67; H, 6.84; N, 7.81.

Reference Example 91

To 7-(4-methylphenyl)-2,3-dihydro-1-benzooxepine-4-carboxylic acid (1402 mg, 5.00 mmol) dissolved in DMF (30 ml) were added at 0° C. 1-hydroxybenzotriazole (743 mg, 5.50 mmol), 2-[1-(tert-butoxycarbonyl)piperidin-4-yl]ethylamine (1256 mg, 5.50 mmol) and 1-[3-(dimethylamino)propyl]-3-ethylcarbodiimide hydrochloride (1438 mg, 7.50 mmol), and the resulting mixture was stirred at room temperature for 8 hours. The reaction mixture was concentrated, ethyl acetate (120 ml) was added to the residue and the resulting mixture was washed successively with water (30 ml), an aqueous saturated solution of sodium bicarbonate (20 ml×3) and an aqueous saturated solution of sodium chloride (20 ml). The organic layer was dried with anhydrous magnesium sulfate and was then concentrated under reduced pressure, and the residue was subjected to column chromatography (silica gel, ethyl acetate/hexane=1/2→1/1). The objective fractions were concentrated under reduced pressure and were mixed with diisopropyl ether to collect an insoluble material by filtration. The insoluble material was washed with diisopropyl ether and was dried under reduced pressure to obtain N-[2-[1-(tert-butoxycarbonyl)piperidin-4-yl]ethyl]-7-(4-methylphenyl)-2,3-dihydro-1-benzooxepine-4-carboxamide (1.64 g, 3.34 mmol, 67%).

IR (KBr): 1694, 1674, 1653, 1617, 1539 cm$^{-1}$.

$^1$H-NMR (CDCl$_3$) δ: 1.0–1.8 (7H, m), 1.46 (9H, s), 2.39 (3H, s), 2.6–2.8 (2H, m), 2.9–3.05 (2H, m), 3.35–3.5 (2H, m), 4.0–4.2 (2H, m), 4.25–4.35 (2H, m), 5.75–5.85 (1H, m), 7.03 (1H, d, J=8.2 Hz), 7.16 (1H, s), 7.24 (2H, d, J=8.0 Hz), 7.43 (1H, dd, J=2.5, 8.2 Hz), 7.45 (2H, d, J=8.0 Hz), 7.49 (1H, d, J=2.5 Hz).

Example 47 (Production of Compound 47)

To N-[2-[1-(tert-butoxycarbonyl)piperidin-4-yl]ethyl]-7-(4-methylphenyl)-2,3-dihydro-1-benzooxepine-4-carboxamide (491 mg, 1.00 mmol) was added 4 N hydrogen chloride (an ethyl acetate solution, 10 ml), and the resulting mixture was stirred at room temperature for 3 hours. The reaction mixture was concentrated under reduced pressure, ethyl acetate (15 ml) was added to the residue and the resulting mixture was extracted with water (10 ml) and 1 N hydrochloric acid (5 ml×2). The aqueous layer was adjusted to pH>11 with an 8 N aqueous solution of sodium hydroxide and was extracted with dichloromethane (15 ml×3). The combined organic layers were dried with anhydrous sodium sulfate, were then concentrated under reduced pressure and were mixed with diethyl ether to collect an insoluble material by filtration. The insoluble material was washed with diethyl ether and was then dried under reduced pressure to obtain N-[2-(4-piperidyl)ethyl]-7-(4-methylphenyl)-2,3-dihydro-1-benzooxepine-4-carboxamide (compound 47) (361 mg, 0.92 mmol, 92%).

IR (KBr): 1649, 1607, 1537 cm$^{-1}$.

$^1$H-NMR (CDCl$_3$) δ: 1.05–1.8 (7H, m), 2.39 (3H, s), 2.5–2.7 (2H, m), 2.9–3.15 (4H, m), 3.35–3.5 (2H, m), 4.25–4.4 (2H, m), 5.75–5.85 (1H, m), 7.03 (1H, d, J=8.3 Hz), 7.16 (1H, s), 7.24 (2H, d, J=8.2 Hz), 7.43 (1H, dd, J=2.5, 8.3 Hz), 7.45 (2H, d, J=8.2 Hz), 7.49 (1H, d, J=2.5 Hz).

Example 48 (Production of Compound 48)

To N-[2-(4-piperidyl)ethyl]-7-(4-methylphenyl)-2,3-dihydro-1-benzooxepine-4-carboxamide (150 mg, 0.38 mmol) and tetrahydropyran-4-one (38 mg, 0.38 mmol) dissolved in 1,2-dichloroethane (6 ml) were added sodium triacetoxyborohydride (122 mg, 0.58 mmol) and acetic acid (0.022 ml, 0.38 mmol), and the resulting mixture was stirred at room temperature for 23 hours. The reaction mixture was mixed with a 1 N aqueous solution of sodium hydroxide (20 ml) and was extracted with dichloromethane (20 ml, 10 ml×2). The combined organic layers were dried with anhydrous sodium sulfate and were concentrated under reduced pressure, and the residue was subjected to column chromatography (silica gel 15 g: dichloromethane/methanol=1/0→9/1). The objective fractions were concentrated under reduced pressure and were mixed with diisopropyl ether to collect an insoluble material by filtration. The insoluble material was washed with diisopropyl ether and was dried under reduced pressure to obtain N-[2-[1-(tetrahydropyran-4-yl)piperidin-4-yl]ethyl]-7-(4-methylphenyl)-2,3-dihydro-1-benzooxepine-4-carboxamide (compound 48) (119 mg, 0.25 mmol, 65%).

IR (KBr): 1651, 1615, 1539 cm$^{-1}$.

$^1$H-NMR (CDCl$_3$) δ: 1.2–1.9 (11H, m), 2.1–2.3 (2H, m), 2.39 (3H, s), 2.4–2.65 (1H, m), 2.9–3.1 (4H, m), 3.25–3.5 (4H, m), 3.95–4.1 (2H, m), 4.35–4.4 (2H, m), 5.75–5.9 (1H, m), 7.03 (1H, d, J=8.3 Hz), 7.16 (1H, s), 7.24 (2H, d, J=8.2 Hz), 7.43 (1H, dd, J=2.4, 8.3 Hz), 7.45 (2H, d, J=8.2 Hz), 7.49 (1H, d, J=2.4 Hz).

Example 49 (Production of Compound 49)

To N-[2-(4-piperidyl)ethyl]-7-(4-methylphenyl)-2,3-dihydro-1-benzooxepine-4-carboxamide (150 mg, 0.38 mmol) dissolved in DMF (4 ml) were added potassium carbonate (106 mg, 0.77 mmol) and benzyl bromide (0.046 ml, 0.39 mmol), and the resulting mixture was stirred at room temperature for 20 hours. The reaction mixture was concentrated under reduced pressure, and the residue was mixed with water (15 ml) and was extracted with ethyl acetate (15 ml×3). The combined organic layers were dried with anhydrous sodium sulfate and were then concentrated under reduced pressure, and the residue was subjected to column chromatography (silica gel 15 g, ethyl acetate/methanol=1/0→95/5). The objective fractions were concentrated under reduced pressure and were mixed with diisopropyl ether to collect an insoluble material by filtration, and the insoluble material was washed with diisopropyl ether and then was dried under reduced pressure to obtain N-[2-(1-benzylpiperidin-4-yl)ethyl]-7-(4-methylphenyl)-2,3-dihydro-1-benzooxepine-4-carboxamide (compound 49) (154 mg, 0.32 mmol, 83%).

IR (KBr): 1651, 1615, 1537 cm$^{-1}$.

$^1$H-NMR (CDCl$_3$) δ: 1.15–1.8 (7H, m), 1.85–2.1 (2H, m), 2.39 (3H, s), 2.8–3.0 (4H, m), 3.3–3.5 (2H, m), 3.50 (2H, s), 4.25–4.35 (2H, m), 5.7–5.85 (1H, m), 7.03 (1H, d, J=8.5 Hz), 7.15 (1H, s), 7.2–7.35 (5H, m), 7.24 (2H, d, J=8.0 Hz), 7.43 (1H, dd, J=2.4, 8.5 Hz), 7.45 (2H, d, J=8.0 Hz), 7.48 (1H, d, J=2.4 Hz).

Reference Example 92

To 7-(4-methylphenyl)-2,3-dihydro-1-benzooxepine-4-carboxylic acid (1402 mg, 5.00 mmol) dissolved in DMF (30 ml) were added at 0° C. 1-hydroxybenzotriazole (743 mg, 5.50 mmol), [1-(tert-butoxycarbonyl)piperidin-4-yl]methylamine (1393 mg, 6.50 mmol) and 1-[3-(dimethylamino)propyl]-3-ethylcarbodiimide hydrochloride (1438 mg, 7.50 mmol), and the resulting mixture was stirred at room temperature for 61 hours. The reaction mixture was concentrated under reduced pressure, ethyl acetate (100 ml) was added to the residue, and the resulting mixture was washed successively with water (10 ml×3), a 10% aqueous solution of potassium hydrogensulfate (10 ml×3), an aqueous saturated solution of sodium bicarbonate (10 ml×3) and an aqueous saturated solution of sodium chloride (10 ml). The organic layer was dried with anhydrous magnesium sulfate and then was concentrated under reduced pressure, and the residue was subjected to column chromatography (silica gel 80 g, ethyl acetate/hexane 1/2→1/1). The objective fractions were concentrated under reduced pressure to obtain N-[1-(tert-butoxycarbonyl)piperidin-4-yl]methyl]-7-(4-methylphenyl)-2,3-dihydro-1-benzooxepine-4-carboxamide (2409 mg).

IR (KBr): 1671, 1617, 1537 cm$^{-1}$.

$^1$H-NMR (CDCl$_3$) δ: 1.0–1.85 (5H, m), 1.46 (9H, s), 2.39 (3H, s), 2.6–2.8 (2H, m), 2.9–3.05 (2H, m), 3.2–3.35 (2H, m), 4.0–4.25 (2H, m), 4.25–4.4 (2H, m), 5.85–6.05 (1H, m), 7.03 (1H, d, J=8.3 Hz), 7.17 (1H, s), 7.24 (2H, d, J=8.0 Hz), 7.44 (1H, dd, J=2.3, 8.3 Hz), 7.45 (2H, d, J=8.0 Hz), 7.49 (1H, d, J=2.3 Hz).

Example 50 (Production of Compound 50)

To N-[1-(tert-butoxycarbonyl)piperidin-4-yl]methyl-7-(4-methylphenyl)-2,3-dihydro-1-benzooxepine-4-carboxamide (1430 mg, 3.00 mmol) was added 4 N hydrogen chloride (an ethyl acetate solution, 50 ml), and the resulting mixture was stirred at room temperature for 13 hours. The reaction mixture was concentrated under reduced pressure, ethyl acetate (50 ml) was added to the residue, and an insoluble material was collected by filtration. The insoluble material was washed with ethyl acetate and then was dried under reduced pressure to obtain N-(4-piperidylmethyl)-7-(4-methylphenyl)-2,3-dihydro-1-benzooxepine-4-carboxamide hydrochloride (compound 50) (1195 mg, 2.89 mmol, 96%).

IR (KBr): 1647, 1609, 1535 cm$^{-1}$.

$^1$H-NMR (DMSO-d$_6$) δ: 1.2–1.55 (2H, m), 1.65–1.95 (3H, m), 2.34 (3H, s), 2.65–2.95 (4H, m), 3.05–3.35 (4H, m), 4.15–4.3 (2H, m), 7.02 (1H, d, J=8.4 Hz), 7.26 (1H, s), 7.26 (2H, d, J=8.1 Hz), 7.51 (1H, dd, J=2.2, 8.4 Hz), 7.55 (2H, d, J=8.1 Hz), 7.67 (1H, d, J=2.2 Hz), 8.15–8.3 (1H, m).

Example 51 (Production of Compound 51)

To N-(4-piperidylmethyl)-7-(4-methylphenyl)-2,3-dihydro-1-benzooxepine-4-carboxamide hydrochloride (250 mg, 0.61 mmol) suspended in 1,2-dichloroethane (10 ml were added successively triethylamine (0.101 ml, 0.72 mmol), tetrahydropyran-4-one (0.067 ml, 0.73 mmol), sodium triacetoxyborohydride (205 mg, 0.97 mmol) and acetic acid (0.042 ml, 0.73 mmol), and the resulting mixture was stirred at room temperature for 23 hours. The reaction mixture was mixed with a 1 N aqueous solution of sodium hydroxide (10 ml) and was extracted with dichloromethane (10 ml×3). The combined organic layers were dried with anhydrous sodium sulfate and were concentrated under reduced pressure, and the residue was subjected to column chromatography (silica gel 15 g, dichloromethane/methanol=1/0→9/1). The objective fractions were concentrated under reduced pressure and were mixed with diisopropyl ether to collect an insoluble material by filtration. The insoluble material was washed with diisopropyl ether and then was dried under reduced pressure to obtain N-[1-(tetrahydropyran-4-yl)piperidin-4-yl]methyl-7-(4-methylphenyl)-2,3-dihydro-1-benzooxepine-4-carboxamide (compound 51) (183 mg, 0.40 mmol, 66%).

IR (KBr): 1651, 1615, 1537 cm$^{-1}$.

$^1$H-NMR (CDCl$_3$) δ: 1.2–1.9 (9H, m), 2.15–2.3 (2H, m), 2.39 (3H, s), 2.45–2.65 (1H, m), 2.9–3.1 (4H, m), 3.2–3.45 (4H, m), 3.95–4.1 (2H, m), 4.25–4.35 (2H, m), 5.9–6.05 (1H, m), 7.03 (1H, d, J=8.4 Hz), 7.18 (1H, s), 7.24 (2H, d, J=8.2 Hz), 7.43 (1H, dd, J=2.4, 8.4 Hz), 7.45 (2H, d, J=8.2 Hz), 7.50 (1H, d, J=2.4 Hz).

Reference Example 93

To 7-(4-methylphenyl)-2,3-dihydro-1-benzooxepine-4-carboxylic acid (1402 mg, 5.00 mmol) dissolved in DMF (30 ml) were added at 0° C. 1-hydroxybenzotriazole (743 mg, 5.50 mmol), 3-[1-(tert-butoxycarbonyl)piperidin-4-yl]propylamine (1333 mg, 5.50 mmol) and 1-[3-(dimethylamino)propyl]-3-ethylcarbodiimide hydrochloride (1438 mg, 7.50 mmol), and the resulting mixture was stirred at room temperature for 18 hours. The reaction mixture was concentrated under reduced pressure, ethyl acetate (100 ml) was added to the residue and the resulting mixture was washed successively with water (10×3 ml), a 10% aqueous solution of potassium hydrogensulfate (10 ml×3), an aqueous saturated solution of sodium bicarbonate (10 ml×3) and an aqueous saturated solution of sodium chloride (10 ml). The organic layer was dried with anhydrous magnesium sulfate and was then concentrated under reduced pressure, and the residue was subjected to column chromatography (silica gel 80g, ethyl acetate/hexane=1/3→1/1)]. The objective fractions were concentrated under reduced pressure to obtain N-[3-[1-(tert-butoxycarbonyl)piperidin-4-yl]propyl]-7-(4-methylphenyl)-2,3-dihydro-1-benzooxepine-4-carboxamide (2498 mg, 4.95 mmol, 99%).

IR (KBr): 1694, 1671, 1653, 1620, 1537 cm$^{-1}$.

$^1$H-NMR (CDCl$_3$) δ: 0.9–1.8 (9H, m), 2.39 (3H, s), 2.55–2.8 (2H, m), 2.9–3.0 (2H, m), 3.3–3.45 (2H, m), 4.0–4.15 (2H, m), 4.25–4.4 (2H, m), 5.8–5.9 (1H, m), 7.03 (1H, d, J=8.2 Hz), 7.16 (1H, s), 7.24 (2H, d, J=8.0 Hz), 7.43 (1H, dd, J=2.3, 8.2 Hz), 7.45 (2H, d, J=8.0 Hz), 7.49 (1H, d, J=2.3 Hz)

Example 52 (Production of Compound 52)

To N-[3-[1-(tert-butoxycarbonyl)piperidin-4-yl]propyl]-7-(4-methylphenyl)-2,3-dihydro-1-benzooxepine-4-carboxamide (1514 mg, 3.00 mmol) was added 4 N hydrogen chloride (an ethyl acetate solution, 50 ml), and the resulting mixture was stirred at room temperature for 16 hours. The reaction mixture was concentrated under reduced pressure, and the residue was mixed with ethyl acetate (50 ml) to collect an insoluble material by filtration. The insoluble material was washed with ethyl acetate and was then dried under reduced pressure to obtain N-[3-(4-piperidyl)propyl]-7-(4-methylphenyl)-2,3-dihydro-1-benzooxepine-4-carboxamide hydrochloride (compound 52) (1286 mg, 2.92 mmol, 97%).

IR (KBr): 1647, 1599, 1545 cm$^{-1}$.

$^1$H-NMR (DMSO-d$_6$) δ: 1.1–1.9 (9H, m), 2.34 (3H, s), 2.7–2.95 (4H, m), 3.05–3.4 (4H, m), 4.15–4.3 (2H, m), 7.02 (1H, d, J=8.4 Hz), 7.24 (1H, s), 7.26 (2H, d, J=8.0 Hz), 7.51 (1H, dd, J=2.2, 8.4 Hz), 7.55 (2H, d, J=8.0 Hz), 7.64 (1H, d, J=2.2 Hz), 8.0–8.15 (1H, m).

Example 53 (Production of Compound 53)

To N-[3-(4-piperidyl)propyl]-7-(4-methylphenyl)-2,3-dihydro-1-benzooxepine-4-carboxamide hydrochloride (250 mg, 0.57 mmol) suspended in 1,2-dichloroethane (10 ml) were added successively triethylamine (0.095 ml, 0.68 mmol), tetrahydropyran-4-one (0.084 ml, 0.91 mmol), sodium triacetoxyborohydride (192 mg, 0.91 mmol) and acetic acid (0.039 ml, 0.68 mmol), and the resulting mixture was stirred at room temperature for 16 hours. The reaction mixture was mixed with a 1 N aqueous solution of sodium hydroxide (10 ml) and was extracted with dichloromethane (10 ml×3). The combined organic layers were dried with anhydrous sodium sulfate and were then concentrated under reduced pressure, and the residue was subjected to column chromatography (silica gel 15 g, dichloromethane/methanol=1/0→9/1) The objective fractions were concentrated under reduced pressure and were mixed with diisopropyl ether to collect an insoluble material by filtration. The insoluble material was washed with diisopropyl ether and were then dried under reduced pressure to obtain N-[3-[1-(4-tetrahydropyranyl)piperidin-4-yl]propyl]-7-(4-methylphenyl)-2,3-dihydro-1-benzooxepine-4-carboxamide (compound 53) (198 mg, 0.41 mmol, 71%).

IR (KBr): 1649, 1605, 1541 cm$^{-1}$.

$^1$H-NMR (CDCl$_3$) δ: 1.15–1.9 (13H, m), 2.05–2.3 (2H, m), 2.39 (3H, s), 2.4–2.65 (1H, m), 2.9–3.1 (4H, m), 3.25–3.5 (4H, m), 3.95–4.1 (2H, m), 4.25–4.4 (2H, m), 5.8–5.95 (1H, m), 7.03 (1H, d, J=8.3 Hz), 7.16 (1H, s), 7.24 (2H, d, J=8.2 Hz), 7.43 (1H, dd, J=2.3, 8.3 Hz), 7.45 (2H, d, J=8.2 Hz), 7.49 (1H, d, J=2.3 Hz).

Reference Example 94

To 7-(4-methylphenyl)-2,3-dihydro-1-benzooxepine-4-carboxylic acid (1.0 g) suspended in dichloromethane (14 ml) were added under ice cooling oxalyl chloride (0.93 ml) and DMF (one drop), and the resulting mixture was stirred at room temperature for 1.5 hours. After the reaction mixture was evaporated to remove the solvent, the residue dissolved in THF (20 ml) was added dropwise into a solution of 1-(t-butoxycarbonyl)piperidine (1.4 g) and triethylamine (1.5 ml) in tetrahydrofuran (10 ml) under ice cooling. The resulting mixture was stirred at room temperature overnight under a nitrogen atmosphere. The reaction mixture was evaporated to remove the solvent, was mixed with water and was extracted with ethyl acetate. The organic layer was washed with water and an aqueous saturated solution of sodium chloride and then was dried with anhydrous magnesium sulfate. The resulting organic layer was evaporated to remove the solvent to obtain crude crystals. The crude crystals were recrystallized from ethyl acetate/hexane to obtain N-[1-(t-butoxycarbonyl)piperidin-4-yl]-7-(4-methylphenyl)-2,3-dihydro-1-benzooxepine-4-carboxamide (1.54 g) as colorless prisms.

M. p. 205–208° C.

$^1$H-NMR (δ ppm, CDCl$_3$) 1.37–1.42 (2H, m), 1.47 (9H, s), 1.96–2.04 (2H, m), 2.39 (3H, s), 2.84–2.98 (4H, m), 3.99–4.11 (3H, m), 4.31 (2H, t, J=4.7 Hz), 5.72 (1H, d, J=7.4 Hz), 7.03 (1H, d, J=8.4 Hz), 7.13 (1H, s), 7.24 (2H, d, J=9.2 Hz), 7.41–7.49 (4H, m).

IR (KBr) ν: 2976, 1694 cm$^{-1}$.

Anal. Calcd. for C$_{28}$H$_{34}$N$_2$O$_4$: C, 72.70; H, 7.41; N, 6.06. Found: C, 72.51; H, 7.20; N, 6.20.

Reference Example 95

To cyclooctanone (4.07 g) and p-toluenesulfonyl hydrazide (6 g) suspended in methanol (40 ml) was added hydrochloric acid (1 ml), and the resulting mixture was stirred at room temperature for 3 days. The reaction mixture was concentrated, and the precipitated crystals were collected by filtration and were washed with methanol, hexane and diethyl ether to obtain cyclooctanone p-toluenesulfonyl hydrazone (7.29 g) as colorless crystals.

M. p. 140–143° C.

$^1$H-NMR (δ ppm, CDCl$_3$) 1.10–1.25 (2H, m), 1.35–1.45 (4H, m), 1.55–1.73 (4H, m), 1.88 (1H, br), 2.19–2.35 (4H, m), 2.42 (3H, s), 7.30 (2H, d, J=8.3 Hz), 7.84 (2H, d, J=8.3 Hz).

IR (KBr) ν: 3221, 2926, 2857 cm$^{-1}$.

Anal. Calcd. for C$_{15}$H$_{22}$N$_2$O$_2$S: C, 61.19; H, 7.53; N, 9.52. Found: C, 61.22; H, 7.31; N, 9.66.

Reference Example 96

To cyclooctanone p-toluenesulfonyl hydrazone (4.5 g) suspended in N,N,N',N'-tetraethylenediamine (46 ml) was added dropwise at −55° C. a 1.6 M solution of n-butyllithium in hexane (38 ml). The resulting mixture was stirred at room temperature for 30 minutes under an argon atmosphere, was then cooled with ice, was mixed with DMF (5.9 ml) and was stirred at room temperature for one hour. The reaction mixture was poured into water and was extracted with ethyl acetate. The organic layer was washed with 1 N hydrochloric acid, water and an aqueous saturated solution of sodium chloride, and was then dried with anhydrous magnesium sulfate. The resulting organic layer was evaporated under reduced pressure to remove the solvent. The residue was subjected to purification using a silica gel column (ethyl acetate:hexane=1:9) to obtain cyclooctene-1-carbaldehyde (1.5 g) as a light yellow oil.

$^1$H-NMR (δ ppm, CDCl$_3$) 1.39–1.69 (8H, m), 2.38–2.52 (4H, m), 6.72 (1H, t, J=8.3 Hz), 9.41 (1H, s).

IR (neat) ν: 2932, 2859, 1675 cm$^{-1}$.

Reference Example 97

To cyclononanone (1.36 g) and p-toluenesulfonyl hydrazide (1.81 g) suspended in methanol (12 ml) was added hydrochloric acid (0.3 ml), and the resulting mixture was stirred at room temperature overnight. The reaction mixture was evaporated to remove the solvent, and the precipitated crystals were collected by filtration and were washed with cold methanol, and diethyl ether-hexane to obtain cyclononanone p-toluenesulfonyl hydrazone (2.29 g) as colorless crystals.

M. p. 135–138° C.

$^1$H-NMR (δ ppm, CDCl$_3$) 1.00–1.10 (2H, m), 1.10–1.25 (2H, m), 1.38–1.76 (8H, m), 2.18–2.24 (2H, m), 2.28–2.34 (2H, m), 2.41 (3H, s), 7.30 (2H, d, J=8.0 Hz), 7.32 (1H, br), 7.85 (2H, d, J=8.0 Hz).

IR (KBr) ν: 3223, 2922 cm$^{-1}$.

Anal. Calcd. for C$_{16}$H$_{24}$N$_2$O$_2$S: C, 62.30; H, 7.84; N, 9.08. Found: C, 62.42; H, 7.66; N, 9.21

Reference Example 98

To cyclononanone p-toluenesulfonyl hydrazone (2.0 g) suspended in N,N,N',N'-tetraethylenediamine (20 ml) was added dropwise at −55° C. a 1.6 M solution of n-butyllithium in hexane (16.2 ml). The resulting mixture was stirred at room temperature for 30 minutes under an argon atmosphere, was then cooled with ice, was mixed with DMF (2.5 ml) and was stirred at room temperature for one hour. The reaction mixture was poured into ice water and was extracted with ethyl acetate. The organic layer was washed with 1 N hydrochloric acid, water and an aqueous saturated solution of sodium chloride, and was then dried with anhydrous magnesium sulfate. The resulting organic layer was evaporated under reduced pressure to remove the solvent. The residue was subjected to purification using a silica gel column (ethyl acetate:hexane=1:10) to obtain cyclononene-1-carbaldehyde (0.7 g) as a light yellow oil.

$^1$H-NMR (δ ppm, CDCl$_3$): 1.35–1.60 (8H, m), 1.60–1.75 (2H, m), 2.36–2.54 (4H, m), 6.61 (1H, t, J=8.8 Hz), 9.41 (1H, s).

IR (neat) ν: 2928, 2857, 1684 cm$^{-1}$.

Example 54 (Production of Compound 54)

To N-[1-(t-butoxycarbonyl)piperidin-4-yl]-7-(4-methylphenyl)-2,3-dihydro-1-benzooxepine-4-carboxamide (1.56 g) dissolved in ethyl acetate (100 ml) was added 4 N hydrochloric acid/ethyl acetate (25 ml), and the resulting mixture was stirred at room temperature overnight. The reaction mixture was mixed with a 1 N aqueous solution of sodium hydroxide and was extracted with ethyl acetate. The organic layer was washed with water and an aqueous saturated solution of sodium chloride, and then was dried with anhydrous magnesium sulfate. The resulting organic layer was evaporated under reduced pressure to remove the solvent to obtain N-(4-piperidinyl)-7-(4-methylphenyl)-2,3-dihydro-1-benzooxepine-4-carboxamide (compound 54) (1.1 g) as colorless prisms.

M. p. 183–185° C.

$^1$H-NMR (δ ppm, CDCl$_3$) 1.31–1.50 (2H, m), 1.98–2.06 (2H, m), 2.39 (3H, s), 2.75 (2H, dt, J=2.6, 12.0 Hz), 2.97 (2H, t, J=4.5 Hz), 3.12 (2H, dt, J=12.8, 3.4 Hz), 3.90–4.10 (1H, m), 4.32 (2H, t, J=4.5 Hz), 5.75 (1H, d, J=8.2 Hz), 7.03 (1H, d, J=8.2 Hz), 7.14 (1H, s), 7.24 (2H, d, J=8.0 Hz), 7.40–7.50 (4H, m).

IR (KBr) ν: 3299, 2938, 1651 cm$^{-1}$.

Anal. Calcd. for C$_{23}$H$_{26}$N$_2$O$_2$.0.2 H$_2$O: C, 75.46; H, 7.27; N, 7.65. Found: C, 75.49; H, 7.15; N, 7.56.

Example 55 (Production of Compound 55)

To N-(4-piperidinyl)-7-(4-methylphenyl)-2,3-dihydro-1-benzooxepine-4-carboxamide (0.15 g) and cyclohexane carbaldehyde (0.056 g) dissolved in 1,2-dichloroethane (10 ml) was added sodium triacetoxyborohydride (0.13 g) under ice cooling, and the resulting mixture was stirred at room temperature overnight under a nitrogen atmosphere. The reaction mixture was neutralized with a 1 N aqueous solution of sodium hydroxide, was then concentrated and was extracted with ethyl acetate. The organic layer was washed with water and an aqueous saturated solution of sodium chloride, and was then dried with anhydrous magnesium sulfate. The resulting organic layer was evaporated under reduced pressure to remove the solvent to obtain crude crystals. The crude crystals were recrystallized from ethyl acetate/hexane to obtain N-(1-cyclohexylmethylpiperidin-4-yl)-7-(4-methylphenyl)-2,3-dihydro-1-benzooxepine-4-carboxamide (compound 55) (0.13 g) as colorless prisms.

M. p. 180–181° C.

$^1$H-NMR (δ ppm, CDCl$_3$) 0.80–1.00 (2H, m), 1.10–1.17 (4H, m), 1.40–1.80 (7H, m), 1.95–2.14 (4H, m), 2.16 (2H, d, J=7.0 Hz), 2.39 (3H, s), 2.81–2.88 (2H, m), 2.96 (2H, t, J=4.5 Hz), 3.80–4.00 (1H, m), 4.31 (2H, t, J=4.5 Hz), 5.74 (1H, br), 7.02 (1H, d, J=8.4 Hz), 7.14 (1H, s), 7.24 (2H, d, J=8.8 Hz), 7.36–7.50 (4H, m).

IR (KBr) ν: 2924, 2851, 1651 cm$^{-1}$.

Anal. Calcd. for C$_{30}$H$_{38}$N$_2$O$_2$: C, 78.56; H, 8.35; N, 6.11. Found: C, 78.31; H, 8.17; N, 6.16.

Example 56 (Production of Compound 56)

To N-(4-piperidinyl)-7-(4-methylphenyl)-2,3-dihydro-1-benzooxepine-4-carboxamide (0.15 g) and tetrahydro-4H- pyran-4-one (0.06 g) dissolved in 1,2-dichloroethane (7 ml) was added under ice cooling sodium triacetoxyborohydride (0.13 g), and the resulting mixture was stirred at room temperature overnight under a nitrogen atmosphere. The reaction mixture was neutralized with a 1 N aqueous solution of sodium hydroxide, was then concentrated and was extracted with ethyl acetate. The organic layer was washed with water and an aqueous saturated solution of sodium chloride, and was then dried with anhydrous magnesium sulfate. The resulting organic layer was evaporated under reduced pressure to remove the solvent to obtain crude crystals. The crude crystals were recrystallized from ethyl acetate/hexane to obtain N-(1-(tetrahydropyran-4-yl)piperidin-4-yl)-7-(4-methylphenyl)-2,3-dihydro-1-benzooxepine-4-carboxamide (compound 56) (0.13 g) as colorless prisms.

M. p. 199–204° C. (dec.)

$^1$H-NMR ($\delta$ ppm, CDCl$_3$) 1.40–1.80 (6H, m), 2.00–2.15 (2H, m), 2.25–2.39 (2H, m), 2.39 (3H, s), 2.43–2.55 (1H, m), 2.90–3.00 (4H, m), 3.28 (2H, dt, J=1.8, 11.6 Hz), 3.80–4.00 (1H, m), 4.00–4.10 (2H, m), 4.31 (2H, t, J=4.7 Hz), 5.72 (1H, d, J=9.2 Hz), 7.03 (1H, d, J=8.0 Hz), 7.14 (1H, s), 7.24 (2H, d, J=9.2 Hz), 7.40–7.50 (4H, m).

IR (KBr) $\nu$: 3287, 2951, 1651 cm$^{-1}$.

Anal. Calcd. for C$_{28}$H$_{34}$N$_2$O$_3$.0.2 H$_2$O: C, 74.70; H, 7.70; N, 6.22. Found: C, 74.90; H, 7.89; N, 6.39.

Example 57 (Production of Compound 57)

To N-(4-piperidinyl)-7-(4-methylphenyl)-2,3-dihydro-1-benzooxepine-4-carboxamide (0.15 g) and cyclooctene-1-carbaldehyde (0.08 g) dissolved in 1,2-dichloroethane (10 ml) was added sodium triacetoxyborohydride (0.12 g) under ice cooling, and the resulting mixture was stirred at room temperature overnight under a nitrogen atmosphere. The reaction mixture was neutralized with a 1 N aqueous solution of sodium hydroxide, was then concentrated and was extracted with ethyl acetate. The organic layer was washed with water and an aqueous saturated solution of sodium chloride, and was then dried with anhydrous magnesium sulfate. The resulting organic layer was evaporated under reduced pressure to remove the solvent. The residue was subjected to purification using a silica gel column (ethyl acetate) to obtain crude crystals. The crude crystals were recrystallized from ethyl acetate/diethyl ether/hexane to obtain N-(1-(cyclooctcn-1-yl)methylpiperidin-4-yl)-7-(4-methylphenyl)-2,3-dihydro-1-benzooxepine-4-carboxamide (compound 57) (0.11 g) as colorless prisms.

M. p. 148–151° C.

$^1$H-NMR ($\delta$ ppm, CDCl$_3$) 1.48–1.65 (10H, m), 1.69–2.20 (8H, m), 2.39 (3H, s), 2.78–2.84 (4H, m), 2.96 (2H, t, J=4.6 Hz), 3.80–4.00 (1H, m), 4.31 (2H, t, J=4.6 Hz), 5.49 (1H, t, J=8.0 Hz), 5.72 (1H, d, J=7.8 Hz), 7.03 (1H, d, J=8.2 Hz), 7.14 (1H, s), 7.24 (2H, d, J=8.8 Hz), 7.40–7.50 (4H, m).

IR (KBr) $\nu$: 3295, 2924, 1647, 1609 cm$^{-1}$.

Anal. Calcd. for C$_{32}$H$_{40}$N$_2$O$_2$: C, 79.30; H, 8.32; N, 5.78. Found: C, 79.02; H, 8.12; N, 5.71.

Example 58 (Production of Compound 58)

To N-(4-piperidinyl)-7-(4-methylphenyl)-2,3-dihydro-1-benzooxepine-4-carboxamide (0.15 g) and benzaldehyde (0.05 g) dissolved in 1,2-dichloroethane (10 ml) was added under ice cooling sodium triacetoxyborohydride (0.12 g), and the resulting mixture was stirred at room temperature overnight under a nitrogen atmosphere. The reaction mixture was evaporated to remove the solvent, was neutralized with a 1 N aqueous solution of sodium hydroxide and was extracted with ethyl acetate. The organic layer was washed with water and an aqueous saturated solution of sodium chloride, and then was dried with anhydrous magnesium sulfate. The resulting organic layer was evaporated under reduced pressure to remove the solvent to obtain crude crystals. The crude crystals were recrystallized from ethyl acetate/hexane to obtain N-(1-benzylpiperidin-4-yl)-7-(4-methylphenyl)-2,3-dihydro-1-benzooxepine-4-carboxamide (compound 58) (0.17 g) as colorless prisms.

M. p. 161–162° C. (dec.)

$^1$H-NMR ($\delta$ ppm, CDCl$_3$) 1.45–1.60 (2H, m), 1.95–2.05 (2H, m), 2.18 (2H, t, J=11.5 Hz), 2.39 (3H, s), 2.83–2.89 (2H, m), 2.96 (2H, t, J=4.7 Hz), 3.53 (2H, s), 3.80–4.00 (1H, m), 4.31 (2H, t, J=4.7 Hz), 5.71 (1H, d, J=8.0 Hz), 7.03 (1H, d, J=8.4 Hz), 7.13 (1H, s), 7.22–7.30 (3H, m), 7.32–7.34 (4H, m), 7.40–7.50 (4H, m).

IR (KBr) $\nu$: 3250, 2942, 1649, 1609 cm$^{-1}$.

Anal. Calcd. for C$_{30}$H$_{32}$N$_2$O$_2$.0.2 H$_2$O: C, 78.99; H, 7.16; N, 6.14. Found: C, 78.97; H, 7.10; N, 6.20.

Example 59 (Production of Compound 59)

To N-(4-piperidinyl)-7-(4-methylphenyl)-2,3-dihydro-1-benzooxepine-4-carboxamide (0.15 g) and cyclononene-1-carbaldehyde (0.085 g) dissolved in 1,2-dichloroethane (10 ml) was added under ice cooling sodium triacetoxyborohydride (0.12 g), and the resulting mixture was stirred at room temperature overnight under a nitrogen atmosphere. The reaction mixture was evaporated to remove the solvent, was neutralized with a 1 N aqueous solution of sodium hydroxide, was then concentrated and was extracted with ethyl acetate. The organic layer was washed with water and an aqueous saturated solution of sodium chloride, and was then dried with anhydrous magnesium sulfate. The resulting organic layer was evaporated under reduced pressure to remove the solvent. The residue was subjected to purification using a silica gel column (ethyl acetate) to obtain crude crystals. The crude crystals were recrystallized from ethyl acetate/hexane to obtain N-(1-(cyclononen-1-yl)methylpiperidin-4-yl)-7-(4-methylphenyl)-2,3-dihydro-1-benzooxepine-4-carboxamide (compound 59) (0.08 g) as colorless prisms.

M. p. 128–130° C.

$^1$H-NMR ($\delta$ ppm, CDCl$_3$) 1.46–1.67 (12H, m), 1.96–2.25 (8H, m), 2.39 (3H, s), 2.75–2.85 (2H, m), 2.84 (2H, s), 2.96 (2H, t, J=4.5 Hz), 3.80–4.00 (1H, m), 4.31 (2H, t, J=4.5 Hz), 5.43 (1H, t, J=8.6 Hz), 5.74 (1H, d, J=8.0 Hz), 7.03 (1H, d, J=8.4 Hz), 7.14 (1H, s), 7.24 (2H, d, J=8.8 Hz), 7.40–7.50 (4H, m).

IR (KBr) $\nu$: 3299, 2926, 1647, 1609 cm$^{-1}$.

Anal. Calcd. for C$_{33}$H$_{42}$N$_2$O$_2$: C, 79.48; H, 8.49; N, 5.62. Found: C, 79.60; H, 8.44; N, 5.61.

Example 60 (Production of Compound 60)

To N-(4-piperidinyl)-7-(4-methylphenyl)-2,3-dihydro-1-benzooxepine-4-carboxamide (0.15 g) and cyclohexylactaldehyde (0.07 g) dissolved in 1,2-dichloroethane (10 ml) was added under ice cooling sodium triacetoxyborohydride (0.12 g), and the resulting mixture was stirred at room temperature overnight under a nitrogen atmosphere. The reaction mixture was evaporated to remove the solvent, was mixed with a 1 N aqueous solution of sodium hydroxide and was extracted with ethyl acetate. The organic layer was washed with water and an aqueous saturated solution of sodium chloride, and was then dried with anhydrous magnesium sulfate. The resulting organic layer was evaporated under reduced pressure to remove the solvent to obtain crude crystals. The crude crystals were recrystallized from ethyl acetate/hexane to obtain N-(1-(2-cyclohexylethyl)piperidin-4-yl)-7-(4-methylphenyl)-2,3-dihydro-1-benzooxepine-4-carboxamide (compound 60) (0.16 g) as colorless prisms.

M. p. 193–196° C.

$^1$H-NMR (δ ppm, CDCl$_3$) 0.80–1.00 (2H, m), 1.10–1.50 (6H, m), 1.50–1.74 (7H, m), 1.95–2.19 (4H, m), 2.34–2.42 (2H, m), 2.39 (3H, s), 2.86–2.98 (4H, m), 3.80–4.00 (1H, m), 4.32 (2H, t, J=4.7 Hz), 5.74 (1H, d, J=7.6 Hz), 7.03 (1H, d, J=8.4 Hz), 7.14 (1H, s), 7.25 (2H, d, J=9.2 Hz), 7.40–7.51 (4H, m).

IR (KBr) ν: 3287, 2924, 2851, 1651 cm$^{-1}$.

Anal. Calcd. for $C_{31}H_{40}N_2O_2$: C, 78.77; H. 8.53; N, 5.93. Found: C, 78.76; H, 8.42; N, 6.05.

Example 61 (Production of Compound 61)

To N-(4-piperidinyl)-7-(4-methylphenyl)-2,3-dihydro-1-benzooxepine-4-carboxamide (0.13 g) and a 37% aqueous solution of formaldehyde (0.04 ml) suspended in 1,2-dichloroethane (5 ml) was added under ice cooling sodium triacetoxyborohydride (0.11 g), and the resulting mixture was stirred at room temperature overnight under a nitrogen atmosphere. The reaction mixture was evaporated to remove the solvent, was then neutralized with a 1 N aqueous solution of sodium hydroxide and was extracted with ethyl acetate. The organic layer was washed with water and an aqueous saturated solution of sodium chloride, and was then dried with anhydrous magnesium sulfate. The resulting organic layer was evaporated under reduced pressure to remove the solvent to obtain crude crystals. The crude crystals were recrystallized from ethyl acetate/hexane to obtain N-(1-methylpiperidin-4-yl)-7-(4-methylphenyl)-2,3-dihydro-1-benzooxepine-4-carboxamide (compound 61) (0.11 g) as colorless prisms.

M. p. 180–182° C.

$^1$H-NMR (δ ppm, CDCl$_3$) 1.47–1.64 (2H, m), 1.99–2.10 (2H, m), 2.16 (2H, dt, J=2.2, 11.5 Hz), 2.31 (3H, s), 2.39 (3H, s), 2.81–2.87 (2H, m), 2.96 (2H, t, J=4.6 Hz), 3.83–3.94 (1H, m), 4.32 (2H, t, J=4.6 Hz), 5.72 (1H, d, J=6.8 Hz), 7.03 (1H, d, J=8.6 Hz), 7.14 (1H, s), 7.24 (2H, d, J=9.2 Hz), 7.40–7.51 (4H, m).

IR (KBr) ν: 3287, 2940, 1647, 1607 cm$^{-1}$.

Anal. Calcd. for $C_{24}H_{28}N_2O_2 \cdot 0.1 H_2O$: C, 76.20; H, 7.51; N, 7.41. Found: C, 76.19; H, 7.53; N, 7.38.

Reference Example 99

Into a solution of 2-bromoethylamine hydrobromide (5.0 g) and potassium carbonate (5.06 g) in THF/water (20/5 ml) was added at 0° C. benzyl chloroformate (4.16 g), and the resulting mixture was stirred at room temperature for 16 hours. The reaction mixture was mixed with water and was extracted with ethyl acetate. The organic layer was washed with an aqueous saturated solution of sodium chloride and was dried with anhydrous magnesium sulfate. The resulting organic layer was evaporated under reduced pressure to obtain benzyl 2-bromoethylcarbamate (7.32 g). A solution of benzyl 2-bromoethylcarbamate (7.23 g), tert-butyl 4-piperidinyl-carbamate formic acid salt (4.63 g) and tri-ethylamine (8 ml) in acetonitrile (30 ml) was heated at reflux for 24 hours. After the reaction mixture was concentrated under reduced pressure, water was added to the residue, and the resulting mixture was extracted with ethyl acetate. The organic layer was washed with an aqueous saturated solution of sodium chloride and was dried with magnesium sulfate. After concentration under reduced pressure, the residue was subjected to purification using column chromatography (ethyl acetate/hexane) to obtain benzyl 2-[4-(tert-butoxycarbonylamino)piperidin-1-yl]ethylcarbamate (5.5 g) as colorless crystals.

$^1$H-NMR (200 MHz, CDCl$_3$) δ1.22–1.43 (2H, m), 1.44 (9H, s), 1.84–1.97 (2H, m), 2.01–2.16 (2H, m), 2.39–2.49 (2H, m), 2.71–2.85 (2H, m), 3.23–3.35 (2H, m), 3.36–3.54 (1H, m), 4.29–4.54 (1H, m), 5.10 (2H, s), 5.18–5.32 (1H, m), 7.29–7.42 (5H, m).

Reference Example 100

A mixture of benzyl 2-[4-(tert-butoxycarbonylamino)piperidin-1-yl]ethylcarbamate (3.0 g), Pd-C (0.3 g), and ethanol (100 ml) was stirred vigorously for 3 days under a hydrogen atmosphere. Pd-C was removed by filtration, and the filtrate was concentrated under reduced pressure to obtain tert-butyl 1-(2-aminoethyl)-4-piperidinylcarbamate (2.4 g) as a colorless oily substance.

$^1$H-NMR (200 MHz, CDCl$_3$) δ1.28–1.46 (2H, m), 1.45 (9H, s), 1.84–2.00 (2H, m), 2.02–2.15 (2H, m), 2.39 (2H, t, J=6.3 Hz), 2.67–2.88 (4H, m), 3.30–3.56 (1H, m), 4.36–4.57 (1H, m).

Reference Example 101

Into a solution of tert-butyl 1-(2-aminoethyl)-4-piperidinylcarbamate (2.4 g) and tetrahydro-4H-pyran-4-one (0.79 g) in dichloroethane (35 ml) was added at room temperature sodium triacetoxyborohydride (2.19 g), and the resulting mixture was stirred for 2.5 hours. To the reaction mixture were added 37% formalin (0.65 g) and sodium triacetoxyborohydride (2.19 g), and the resulting mixture was stirred for 64 hours. The reaction mixture was mixed with an aqueous solution of sodium bicarbonate and was extracted with chloroform. The organic layer was washed with an aqueous saturated solution of sodium chloride and was dried with magnesium sulfate. The resulting organic layer was concentrated under reduced pressure to obtain tert-butyl 1-[2-[N-methyl-N-(tetrahydropyran-4-yl)amino]ethyl]-4-piperidinylcarbamate (2.72 g) as a yellow oil.

Into a solution of tert-butyl 1-[2-[N-methyl-N-(tetrahydropyran-4-yl)amino]ethyl]-4-piperidinylcarbamate (2.72 g) in ethanol (30 ml) was added concentrated hydrochloric acid (10 ml), and the resulting mixture was stirred for 7 hours. After the reaction mixture was concentrated under reduced pressure, ethanol and methanol are added to the residue, and the resulting mixture was concentrated further. The precipitate was collected by filtration and was washed with ethanol and methanol to obtain 4-amino-1-[2-[N-methyl-N-(tetrahydropyran-4-yl)amino]ethyl]piperidine dihydrochloride (1.65 g) as a light yellow powder.

$^1$H-NMR (200 MHz, DMSO-d$_6$) δ1.64–2.30 (8H, m), 2.76 (3H, s), 2.96–3.84 (12H, m), 3.90–4.06 (2H, m), 8.30–8.54 (1H, m).

Example 62 (Production of Compound 62)

Into a solution of 7-(4-methylphenyl)-2,3-dihydro-1-benzooxepine-4-carboxylic acid (150 mg) and 1-hydroxybenzotriazole (0.14 g) in acetonitrile (10 ml) was added at room temperature 1-ethyl-3-(3'-dimethylaminopropyl)carbodiimide hydrochloride (0.20 g), and the resulting mixture was stirred for one hour. Into the reaction mixture was added a solution of 4-amino-1-[2-[N-methyl-N-(tetrahydropyran-4-yl)amino]ethyl]piperidine dihydrochloride (282 mg), triethylamine (0.15 ml.) and diazabicyclo[5,4,0]-7-undecene (0.37 g) in acetonitrile (15 ml), and the resulting mixture was stirred for 18 hours. After the reaction mixture was concentrated under reduced pressure, water was added to the residue and the resulting mixture was extracted with ethyl acetate. The organic layer was washed with an aqueous saturated solution of sodium chloride and was dried with magnesium sulfate. The resulting organic layer was evaporated to remove the solvent, and then the residue was subjected to purification using column chromatography (triethylamine/ethanol/ethyl acetate 1:10:10) and further to recrystallization (ethyl acetate/hexane) to obtain 7-(4-methylphenyl)-N-[1-[2-[N-methyl-N-(tetrahydropyran-4-yl)amino]ethyl]piperidin-4-yl]-2,3-dihydro-1-benzooxepine-4-carboxamide (compound 62) (99 mg) as colorless crystals.

$^1$H-NMR (200 MHz, CDCl$_3$) δ1.51–1.87 (8H, m), 1.95–2.08 (2H, m), 2.17–2.32 (2H, m), 2.34 (3H, s), 2.39 (3H, s), 2.52–2.76 (4H, m), 2.89–3.04 (3H, m), 3.29–3.44 (2H, m), 3.80–4.10 (3H, m), 4.32 (2H, t, J=4.8 Hz), 5.69–5.79 (1H, m), 7.03 (1H, d, J=8.4 Hz), 7.15 (1H, s), 7.24 (2H, d, J=8.8 Hz), 7.41–7.51 (4H, m).

IR (KBr) 3317, 1641, 1616, 1530, 1493, 1331, 1238, 1140, 816 cm$^{-1}$.

Elemental Analysis. Calcd. for C$_{31}$H$_{41}$N$_3$O$_3$.0.5 H$_2$O:

C, 72.63; H, 8.26; N, 8.20. Found: C, 72.53; H, 8.26; N, 8.20.

Reference Example 102

A solution of trans-4-(tert-butoxycarbonylaminomethyl)cyclohexanecarboxylic acid (19.76 g), diphenylphosphoryl azide (25.36 g) and triethylamine (12 ml) in toluene (210 ml) was stirred at room temperature for 30 minutes and at 100° C. for 30 minutes. Into the reaction mixture was added benzyl alcohol (9.7 ml), and the resulting mixture was heated at reflux for 24 hours. After cooling to room temperature, the reaction mixture was mixed with water and was extracted with ethyl acetate. The organic layer was washed with 1 N hydrochloric acid, water, an aqueous saturated solution of sodium bicarbonate and an aqueous saturated solution of sodium chloride, and was dried with magnesium sulfate. After the resulting organic layer was concentrated under reduced pressure, the residue was subjected to purification using column chromatography (ethyl acetate/hexane 1:2) and to recrystallization (ethyl acetate/hexane) to obtain benzyl trans-4-(tert-butoxycarbonylaminomethyl)cyclohexylcarbamate (18.93 g) as colorless crystals.

M. p. 130–131° C.

$^1$H-NMR (200 MHz, CDCl$_3$) δ0.95–1.16 (4H, m), 1.44 (9H, s), 1.32–1.50 (1H, m), 1.70–1.83 (2H, m), 1.98–2.12 (2H, m), 2.97 (2H, t, J=6.4 Hz), 3.31–3.56 (1H, m), 4.48–4.65 (2H, m), 5.08 (2H, s), 7.27–7.39 (5H, m).

IR (KBr) 3369, 3344, 1689, 1529, 1282, 1250, 1176 cm$^{-1}$.

Elemental Analysis. Calcd. for C$_{20}$H$_{30}$N$_2$O$_4$: C, 66.27; H, 8.34; N, 7.73. Found: C, 66.16; H, 8.11; N, 7.97.

Reference Example 103

To benzyl trans-4-(tert-butoxycarbonylaminomethyl)cyclohexylcarbamate (18.93 g) was added concentrated hydrochloric acid (60 ml), and the resulting mixture was stirred at room temperature for 16 hours. The reaction mixture was mixed with ethanol and was then concentrated under reduced pressure. The residue was mixed with diethyl ether, and the precipitated crystals were collected by filtration. The crystals were washed with diethyl ether to obtain benzyl trans-4-aminomethylcyclohexylcarbamate hydrochloride (11.76 g) as colorless crystals.

$^1$H-NMR (200 MHz, DMSO-d$_6$) δ0.86–1.32 (4H, m), 1.39–1.62 (1H, m), 1.69–1.91 (4H, m), 2.53–2.70 (2H, m), 3.12–3.31 (1H, m), 5.00 (2H, s), 7.20 (1H, d, J=7.8 Hz), 7.29–7.46 (5H, m), 7.92–8.28 (3H, m).

IR (KBr) 3365, 1693, 1527, 1267, 1232, 1041, 698 cm$^{-1}$.

Reference Example 104

To a solution of benzyl trans-4-aminomethylcyclohexylcarbamate hydrochloride (11.56 g), tetrahydro-4H-pyran-4-one (3.85 g), triethylamine (8 ml) and 1,8-diazabicyco[5,4,0]-7-undecene (5.85 g) in 1,2-dichloroethane (100 ml) was added at room temperature sodium triacetoxyborohydride (8.96 g), and the resulting mixture was stirred for 14 hours. To the reaction mixture were added 37% formalin (3.43 g) and sodium triacetoxyborohydride, and the resulting mixture was stirred further for 7 hours. The reaction mixture was mixed with water and was extracted with dichloromethane. The organic layer was washed with an aqueous saturated solution of sodium chloride and was dried with anhydrous magnesium sulfate. After the resulting organic layer was concentrated under reduced pressure, the residue was subjected to separation and purification using column chromatography (ethanol/ethyl acetate 1:4→1:2) to obtain benzyl trans-4-[N-methyl-N-(tetrahydropyran-4-yl)aminomethyl]cyclohexylcarbamate (8.45 g) as colorless crystals.

M. p. 81–84° C.

$^1$H-NMR (200 MHz, CDCl$_3$) δ0.81–1.16 (4H, m), 1.22–1.42 (2H, m), 1.48–1.71 (3H, m), 1.76–1.91 (2H, m), 1.96–2.10 (2H, m), 2.19 (2H, d, J=7.0 Hz), 2.23 (3H, s), 2.41–2.59 (1H, m), 3.25–3.55 (1H, m), 3.35 (2H, dt, J=2.8, 11.4 Hz), 3.93–4.07 (2H, m), 4.50–4.64 (1H, m), 5.09 (2H, s), 7.26–7.39 (5H, m).

IR (KBr) 3317, 1713, 1682, 1539, 1265, 1232, 1041, 741 cm$^{-1}$.

Elemental Analysis. Calcd. for C$_{21}$H$_{32}$N$_2$O$_3$: C, 69.97; H, 8.95; N, 7.77. Found: C, 69.57; H, 8.80; N, 7.81.

Reference Example 105

To a mixture of benzyl trans-4-[N-methyl-N-(tetrahydropyran-4-yl)aminomethyl]cyclohexylcarbamate (6.00 g) and 10% Pd-C (0.6 g) in ethanol (100 ml) was added dropwise at room temperature formic acid (2.5 ml), and the resulting mixture was stirred for 16 hours. Pd-C was removed by filtration, and the filtrate was concentrated under reduced pressure. Ethanol (100 ml) and concentrated hydrochloric acid (6 ml) were added to the residue, and the resulting mixture was then concentrated under reduced pressure. The residue was mixed with diethyl ether, and the resulting powder was collected by filtration and was washed with ethanol and diethyl ether to obtain trans-4-[N-methyl-N-(tetrahydropyran-4-yl)aminomethyl]cyclohexylamine dihydrochloride (4.07 g) as colorless crystals.

$^1$H-NMR (200 MHz, DMSO-d$_6$) δ0.89–1.19 (2H, m), 1.22–1.50 (2H, m), 1.59–2.21 (9H, m), 2.65–3.12 (6H, m), 3.25–3.52 (2H, m), 3.89–4.03 (2H, m), 8.00–8.21 (3H, m), 10.00–10.19 (1H, m).

IR (KBr) 3440, 1462, 1086, 1012 cm$^{-1}$.

Example 63 (Production of Compound 63)

Into a suspension of 7-(4-methylphenyl)-2,3-dihydrobenzooxepine-4-carboxylic acid (200 mg) and 1-hydroxybenzotriazole (145 mg) in acetonitrile (10 ml) was added at room temperature 1-ethyl-3-(3'-dimethylaminopropyl)carbodiimide hydrochloride (205 mg), and the resulting mixture was stirred for 2 hours. To the reaction mixture was added a solution of trans-4-[N-methyl-N-(tetrahydropyran-4-yl)aminomethyl]cyclohexylamine dihydrochloride (320 mg), 1,8-diazabicyclo[5,4,0]-7-undecene (326 mg) and triethylamine (0.2 ml) in acetonitrile (10 ml), and the resulting mixture was stirred for 4 hours. After the reaction mixture was concentrated under reduced pressure, water was added to the residue, and the resulting mixture was extracted with ethyl acetate. The organic layer was washed with an aqueous saturated solution of sodium chloride and was dried with magnesium sulfate. The resulting organic layer was evaporated under reduced pressure to remove the solvent and the residue was then subjected to purification using column chromatography (ethanol/ethyl acetate 1:1) and to recrystallization (ethyl acetate/hexane) to obtain trans-7-(4-methylphenyl)-N-[4-[N-methyl-N-(tetrahydropyran-4-yl)aminomethyl]cyclohexyl]-2,3-dihydro-1-benzooxepine-4-carboxamide (compound 63) (233 mg) as colorless crystals.

M. p. 144–146° C.

$^1$H-NMR (200 MHz, CDCl$_3$) δ0.92–1.26 (4H, m), 1.46–1.73 (5H, m), 1.82–1.96 (2H, m), 2.02–2.17 (2H, m), 2.23 (2H, d, J=8.4 Hz), 2.25 (3H, s), 2.39 (3H, s), 2.43–2.63 (1H, m), 2.96 (2H, t, J=4.8 Hz), 3.29–3.45 (2H, m), 3.73–3.92 (1H, m), 3.96–4.09 (2H, m), 4.31 (2H, t, J=4.8 Hz), 5.64 (1H, d, J=7.4 Hz), 7.02 (1H, d, J=8.4 Hz), 7.12 (1H, s), 7.24 (2H, d, J=9.2 Hz), 7.40–7.50 (4H, m).

IR (KBr) 3323, 1612, 1527, 1493, 1319, 1238, 812 cm$^{-1}$.

Elemental Analysis. Calcd. for C$_{31}$H$_{40}$N$_2$O$_3$: C, 76.19; H, 8.25; N, 5.73. Found: C, 75.90; H, 8.10; N, 5.75.

Example 64 (Production of Compound 64)

Into a suspension of 2-(4-methylphenyl)-6,7-dihydro-5H-benzocycloheptene-8-carboxylic acid (200 mg) and 1-hydroxybenzotriazole (146 mg) in acetonitrile (10 ml) was added at room temperature 1-ethyl-3-(3'-dimethylaminopropyl)carbodiimide hydrochloride (207 mg), and the resulting mixture was stirred for 2 hours. Into the reaction mixture was added a solution of trans-4-[N-methyl-N-(tetrahydropyran-4-yl)aminomethyl]cyclohexylamine dihydrochloride (323 mg), 1,8-diazabicyclo[5,4,0]-7-undecene (326 mg) and triethylamine (0.2 ml) in acetonitrile (15 ml), and the resulting mixture was stirred for 10 hours. After the reaction mixture was concentrated under reduced pressure, water was added to the residue, and the resulting mixture was extracted with ethyl acetate. The organic layer was washed with an aqueous saturated solution of sodium chloride and was dried with anhydrous magnesium sulfate. The resulting organic layer was evaporated under reduced pressure to remove the solvent and the residue was then subjected to purification using column chromatography (ethanol/ethyl acetate 1:1) and to recrystallization (ethyl acetate/hexane) to obtain trans-2-(4-methylphenyl)-N-[4-[N-methyl-N-(tetrahydropyran-4-yl)aminomethyl]cyclohexyl]-6,7-dihydro-5H-benzocycloheptene-8-carboxamide (compound 64) (253 mg) as colorless crystals.

M. p. 163–165° C.

$^1$H-NMR (200 MHz, CDCl$_3$) δ0.88–1.23 (4H, m), 1.31–1.71 (5H, m), 1.80–1.95 (2H, m), 1.99–2.18 (4H, m), 2.23 (2H, d, J=8.4 Hz), 2.25 (3H, s), 2.39 (3H, s), 2.43–2.65 (3H, m), 2.76–2.88 (2H, m), 3.26–3.43 (2H, m), 3.69–3.92 (1H, m), 3.95–4.06 (2H, m), 5.64–5.75 (1H, m), 7.17–7.26 (3H, m), 7.38–7.50 (5H, m).

IR (KBr) 3354, 1641, 1616, 1514, 1446, 812 cm$^{-1}$.

Elemental Analysis. Calcd. for C$_{32}$H$_{42}$N$_2$O$_2$.0.1 H$_2$O: C, 78.68; H, 8.71; N, 5.73. Found: C, 78.44; H, 8.64; N, 5.70.

Reference Example 106

To a solution of benzyl trans-4-aminomethylcyclohexylcarbamate hydrochloride (5.0 g), tert-butyl 4-piperidone-1-carboxylate (3.31 g) and 1,8-diazabicyco[5,4,0]-7-undecene (2.53 g) in acetonitrile/THF (50/100 ml) was added at room temperature sodium triacetoxyborohydride (3.87 g), and the resulting mixture was stirred for 9 hours. To the reaction mixture were added 37% formalin (1.48 g) and sodium triacetoxyborohydride (3.9 g), and the resulting mixture was stirred further for 64 hours. The reaction mixture was evaporated to remove the solvent, was then mixed with water and was extracted with ethyl acetate. The organic layer was washed with an aqueous saturated solution of sodium chloride and was dried with magnesium sulfate. After the resulting organic layer was concentrated under reduced pressure, the precipitated crystals were collected by filtration. The crystals were washed with diethyl ether to obtain tert-butyl trans-4-[N-[4-(N-benzyloxycarbonylamino)cyclohexylmethyl]-N-methylamino]piperidine-1-carboxylate (5.28 g) as colorless crystals.

$^1$H-NMR (200 MHz, CDCl$_3$) δ1.04–1.28 (4H, m), 1.46 (9H, s), 1.53–1.72 (4H, m), 1.80–2.44 (5H, m), 2.52–3.00 (4H, m), 2.77 (3H, s), 3.19–3.56 (2H, m), 4.19–4.41 (2H, m), 4.61–4.71 (1H, m), 5.08 (2H, s), 7.29–7.42 (5H, m).

IR (KBr) 3242, 1713, 1687, 1537, 1422, 1248, 1169, 1045, 746 cm$^{-1}$.

Reference Example 107

A mixture of tert-butyl trans-4-[N-[4-(N-benzyloxycarbonylamino)cyclohexylmethyl]-N-methylamino]piperidine-1-carboxylate (4.5 g), Pd-C (0.43 g) and ethanol (300 ml) was stirred vigorously for 24 hours under a hydrogen atmosphere. The catalyst was removed by filtration, and the filtrate was concentrated under reduced pressure. The precipitated crystals were collected by filtration. The crystals were washed with diethyl ether to obtain tert-butyl trans-4-[N-(4-aminocyclohexylmethyl)-N-methylamino]piperidine-1-carboxylate (2.80 g) as colorless crystals.

$^1$H-NMR (200 MHz, CDCl$_3$) δ0.75–1.00 (2H, m), 1.24–1.56 (5H, m), 1.45 (9H, s), 1.59–1.74 (2H, m), 1.79–1.95 (2H, m), 2.00–2.26 (4H, m), 2.21 (3H, s), 2.33–2.52 (1H, m), 2.55–2.76 (2H, m), 2.81–3.04 (1H, m), 3.45–4.00 (2H, m), 4.04–4.28 (2H, m).

IR (KBr) 2925, 1687, 1433, 1267, 1246, 1169 cm$^{-1}$.

Example 65 (Production of Compound 65)

Into a suspension of 7-(4-methylphenyl)-2,3-dihydro-1-benzooxepine-4-carboxylic acid (400 mg) and 1-hydroxybenzotriazole (289 mg) in acetonitrile (20 ml) was added at room temperature 1-ethyl-3-(3-dimethylaminopropyl)carbodiimide hydrochloride (0.41 g), and the resulting mixture was stirred for 2 hours. Into the reaction mixture was added a solution of tert-butyl trans-4-[N-(4-aminocyclohexylmethyl)-N-methylamino]piperidine-1-carboxylate (698 mg) and triethylamine (0.4 ml) in acetonitrile (30 ml), and the resulting mixture was stirred for 20 hours. After the reaction mixture was concentrated under reduced pressure, water was added to the residue, and the resulting mixture was extracted with ethyl acetate. The organic layer was washed with an aqueous saturated solution of sodium chloride and was dried with magnesium sulfate. After the resulting organic layer was concentrated under reduced pressure to remove the solvent, the residue was subjected to purification using column chromatography (ethanol/ethyl acetate 1:3→1:2) and to recrystallization (ethyl acetate/hexane) to obtain trans-N-[4-[N-(1-tert-butoxycarbonylpiperidin-4-yl)-N-methylaminomethyl]cyclohexyl]-7-(4-methylphenyl)-2,3-dihydro-1-benzooxepine-4-carboxamide (compound 65) (560 mg) as colorless crystals.

M. p. 146–150° C.

$^1$H-NMR (200 MHz, CDCl$_3$) δ0.94–1.32 (4H, m), 1.46 (9H, s), 1.55–1.79 (5H, m), 1.81–1.96 (2H, m), 2.01–2.12 (2H, m), 2.22 (2H, d, J=9.0 Hz), 2.25 (3H, s), 2.39 (3H, s), 2.36–2.54 (1H, m), 2.57–2.76 (2H, m), 2.96 (2H, t, J=4.4 Hz), 3.72–3.93 (1H, m), 4.04–4.22 (2H, m), 4.31 (2H, t, J=4.4 Hz), 5.66 (1H, d, J=7.8 Hz), 7.02 (1H, d, J=8.4 Hz), 7.12 (1H, s), 7.19–7.28 (2H, m), 7.38–7.52 (4H, m).

IR (KBr) 3352, 1701, 1686, 1618, 1527, 1491, 1425, 1240, 1163, 1043, 812 cm$^{-1}$.

Elemental Analysis. Calcd. for C$_{36}$H$_{49}$N$_3$O$_4$: C, 73.56; H, 8.40; N, 7.15. Found: C, 73.38; H, 8.13; N, 7.16.

Example 66 (Production of Compound 66)

Into a solution of trans-N-[4-[N-(1-tert-butoxycarbonylpiperidin-4-yl)-N-methylaminomethyl]cyclohexyl]-7-(4-methylphenyl)-2,3-dihydro-1-benzooxepine-4-carboxamide (0.41 g) in ethanol (30 ml) was added at room temperature concentrated hydrochloric acid (5 ml), and the resulting mixture was stirred for 2 days. After the reaction mixture was concentrated under reduced pressure, the resulting crystals were purified by recrystallization (ethanol/diethyl ether) to obtain trans-N-[4-[N-(piperidin-4-yl)-N-methylaminomethyl]cyclohexyl]-7-(4-methylphenyl)-2,3-dihydro-1-benzooxepine-4-carboxamide dihydrochloride (compound 66) (381 mg) as colorless crystals.

M. p. 249° C. (dec.)

$^1$H-NMR (200 MHz, DMSO-d$_6$) δ0.93–1.47 (4H, m), 1.62–2.28 (9H, m), 2.34 (3H, s), 2.73 (3H, s), 2.79–3.10 (4H, m), 3.25–3.71 (3H, m), 4.15–4.54 (5H, m), 7.01 (1H, d, J=8.4 Hz), 7.19–7.28 (3H, m), 7.48–7.57 (3H, m), 7.62–7.68 (1H, m), 7.91 (1H, d, J=7.8 Hz), 8.98–9.29 (1H, m).

IR (KBr) 3390, 2939, 1639, 1493, 1460, 1352, 1267 cm$^{-1}$.

Elemental Analysis. Calcd. for C$_{43}$H$_{43}$N$_3$O$_2$.2.5 H$_2$O: C, 61.48; H, 7.99; N, 6.94. Found: C, 61.68; H, 7.54; N, 6.91.

Example 67 (Production of Compound 67)

Into a suspension of 6-(4-methylphenyl)-2H-1-benzopyran-3-carboxylic acid (150 mg) and 1-hydroxybenzotriazole (114 mg) in acetonitrile (15 ml) was added at room temperature 1-ethyl-3-(340-dimethylaminopropyl)carbodiimide hydrochloride (162 mg), and the resulting mixture was stirred for 2 hours. Into the reaction mixture was added a solution of trans-4-[N-methyl-N-(tetrahydropyran-4-yl)aminomethyl]cyclohexylamine dihydrochloride (253 mg), 1,8-diazabicyclo[5,4,0]-7-undecene (257 mg) and triethylamine (0.16 ml) in acetonitrile (20 ml), and the resulting mixture was stirred for 5 hours. After the reaction mixture was concentrated under reduced pressure, water was added to the residue, and the resulting mixture was extracted with ethyl acetate. The organic layer was washed with an aqueous saturated solution of sodium chloride and was dried with magnesium sulfate. After the resulting organic layer was concentrated under reduced pressure to remove the solvent, the residue was subjected to purification using column chromatography (ethanol/ethyl acetate 1:1) and to recrystallization (ethyl acetate/hexane) to obtain trans-6-(4-methylphenyl)-N-[4-[N-methyl-N-(tetrahydropyran-4-yl)aminomethyl]cyclohexyl]-2H-1-benzopyran-3-carboxamide (compound 67) (144 mg) as colorless crystals.

M. p. 141–143° C.

$^1$H-NMR (200 MHz, CDCl$_3$) δ0.92–1.31 (4H, m), 1.49–1.71 (5H, m), 1.82–1.95 (2H, m), 1.98–2.13 (2H, m), 2.24 (2H, d, J=8.8 Hz), 2.26 (3H, s), 2.39 (3H, s), 2.44–2.63 (1H, m), 3.28–3.42 (2H, m), 3.70–3.92 (1H, m), 3.95–4.06 (2H, m), 5.02 (2H, s), 5.65 (1H, d, J=8.8 Hz), 6.90 (1H, d, J=8.6 Hz), 6.97 (1H, s), 7.21–7.30 (3H, m), 7.40–7.44 (3H, m).

IR (KBr) 3315, 1647, 1606, 1545, 1487, 1336, 1240, 1142, 808 cm$^{-1}$.

Elemental Analysis. Calcd. for C$_{30}$H$_{38}$N$_2$O$_3$: C, 75.92; H, 8.07; N, 5.90. Found: C, 75.22; H, 7.96; N, 5.90.

Example 68 (Production of Compound 68)

Into a suspension of 3-(4-methylphenyl)-2H-1-benzopyran-6-carboxylic acid (150 mg) and 1-hydroxybenzotriazole (114 mg) in acetonitrile (15 ml) was added at room temperature 1-ethyl-3-(3'-dimethylaminopropyl)carbodiimide hydrochloride (162 mg), and the resulting mixture was stirred for 2 hours. Into the reaction mixture was added a solution of trans-4-[N-methyl-N-(tetrahydropyran-4-yl)aminomethyl]cyclohexylamine dihydrochloride (253 mg), 1,8-diazabicyclo[5,4,0]-7-undecene (257 mg) and triethylamine (0.16 ml) in acetonitrile (20 ml), and the resulting mixture was stirred for 4 hours. After the reaction mixture was concentrated under reduced pressure, water was added to the residue, and the resulting mixture was extracted with chloroform. The organic layer was washed with an aqueous saturated solution of sodium chloride and was dried with magnesium sulfate. After the resulting organic layer was concentrated under reduced pressure to remove the solvent, the residue was subjected to purification using column chromatography (ethanol/ethyl acetate 1:2) and to recrystallization (ethanol) to obtain trans-3-(4-methylphenyl)-N-[4-[N-methyl-N-(tetrahydropyran-4-yl)aminomethyl]cyclohexyl]-2H-1-benzopyran-6-carboxamide (compound 68) (190 mg) as colorless crystals.

M. p. 205–207° C.

$^1$H-NMR (200 MHz, CDCl$_3$) δ0.96–1.27 (4H, m), 1.52–1.76 (5H, m), 1.83–1.96 (2H, m), 2.04–2.20 (2H, m), 2.24 (2H, d, J=7.8 Hz), 2.26 (3H, s), 2.38 (3H, s), 2.45–2.62 (1H, m), 3.29–3.45 (2H, m), 3.83–4.09 (3H, m), 5.22 (2H, d, J=1.4 Hz), 5.82 (1H, d, J=6.8 Hz), 6.79 (1H, s), 6.84 (1H, d, J=7.8 Hz), 7.21 (2H, d, J=8.0 Hz), 7.34 (2H, d, J=8.0 Hz), 7.46–7.51 (2H, m).

IR (KBr) 3356, 1633, 1529, 1493, 1331, 1221, 1140, 808 cm$^{-1}$.

Elemental Analysis. Calcd. for C$_{30}$H$_{38}$N$_2$O$_3$: C, 75.92; H, 8.07; N, 5.90. Found: C, 75.82; H, 8.08; N, 5.93.

Example 69 (Production of Compound 69)

Into a suspension of 2-(4-methylphenyl)-7,8-dihydro-6H-cyclohepta[b]thiophene-5-carboxylic acid (150 mg) and 1-hydroxybenzotriazole (107 mg) in acetonitrile (15 ml) was added at room temperature 1-ethyl-3-(3'- dimethylaminopropyl)carbodiimide hydrochloride (152 mg), and the resulting mixture was stirred for 2 hours. Into the reaction mixture was added a solution of trans-4-[N-methyl-N-(tetrahydropyran-4-yl)aminomethyl]cyclohexylamine dihydrochloride (236 mg), 1,8-diazabicyclo[5,4,0]-7-undecene (240 mg) and triethylamine (0.15 ml) in acetonitrile (20 ml), and the resulting mixture was stirred for 20 hours. After the reaction mixture was concentrated under reduced pressure, water was added to the residue, and the resulting mixture was extracted with ethyl acetate. The organic layer was washed with an aqueous saturated solution of sodium chloride and was dried with magnesium sulfate. After the resulting organic layer was concentrated under reduced pressure to remove the solvent, the residue was subjected to purification using column chromatography (ethanol/ethyl acetate 1:2→2:3) and to recrystallization (ethyl acetate/hexane) to obtain trans-2-(4-methylphenyl)-N-[4-[N-methyl-N-(tetrahydropyran-4-yl)aminomethyl]cyclohexyl-7,8-dihydro-6H-cyclohepta[b]thiophene-5-carboxamide (compound 69) (137 mg) as light yellow crystals.

M. p. 192–197° C.

$^1$H-NMR (200 MHz, CDCl$_3$) δ0.81–1.23 (4H, m), 1.52–1.72 (5H, m), 1.80–1.95 (2H, m), 2.00–2.15 (4H, m), 2.24 (2H, d, J=8.8 Hz), 2.26 (3H, s), 2.36 (3H, s), 2.43–2.63 (1H, m), 2.65–2.77 (2H, m), 3.01–3.10 (2H, m), 3.27–3.44 (2H, m), 3.66–3.92 (1H, m), 3.96–4.07 (2H, m), 5.62 (1H, d, J=8.0 Hz), 7.05 (2H, s), 7.17 (2H, d, J=7.8 Hz), 7.42 (2H, d, J=7.8 Hz).

IR (KBr) 3278, 1641, 1608, 1535, 1452, 1319, 1236, 1140, 810 cm$^{-1}$.

Elemental Analysis. Calcd. for $C_{30}H_{40}N_2O_2S.0.2 H_2O$: C, 72.60; H, 8.20; N, 5.64. Found: C, 72.58; H, 8.03; N, 5.65.

Example 70 (Production of Compound 70)

Into a suspension of 2-methyl-6-(4-methylphenyl)-quinoline-3-carboxylic acid (150 mg) and 1-hydroxybenzotriazole (109 mg) in acetonitrile (15 ml) was added at room temperature 1-ethyl-3-(3-dimethylaminopropyl)carbodiimide hydrochloride (156 mg), and the resulting mixture was stirred for 2 hours. Into the reaction mixture was added a solution of trans-4-[N-methyl-N-(tetrahydropyran-4-yl)aminomethyl]cyclohexylamine dihydrochloride (242 mg), 1,8-diazabicyclo[5,4,0]-7-undecene (246 mg) and triethylamine (0.15 ml) in acetonitrile (15 ml), and the resulting mixture was stirred for 4 days. After the reaction mixture was concentrated under reduced pressure, water was added to the residue, and the resulting mixture was extracted with ethyl acetate. The organic layer was washed with an aqueous saturated solution of sodium chloride and was dried with magnesium sulfate. After the resulting organic layer was concentrated under reduced pressure to remove the solvent, the residue was subjected to purification using column chromatography (ethanol/ethyl acetate 1:2→1:1) and to recrystallization (ethyl acetate/hexane) to obtain trans-2-methyl-6-(4-methylphenyl)-N-[4-[N-methyl-N-(tetrahydropyran-4-yl)aminomethyl]cyclohexyl]quinoline-3-carboxamide (compound 70) (142 mg) as colorless crystals.

M. p. 163–165° C.

$^1$H-NMR (200 MHz, CDCl$_3$) δ0.93–1.34 (4H, m), 1.52–1.75 (5H, m), 1.86–2.00 (2H, m), 2.12–2.32 (2H, m), 2.26 (2H, d, J=5.4 Hz), 2.27 (3H, s), 2.43 (3H, s), 2.45–2.65 (1H, m), 2.83 (3H, s), 3.29–3.43 (2H, m), 3.86–4.09 (3H, m), 5.84 (1H, d, J=8.8 Hz), 7.30 (2H, d, J=8.1 Hz), 7.59 (2H, d, J=8.1 Hz), 7.91 (1H, d, J=2.2 Hz), 7.98 (1H, dd, J=8.8, 2.2 Hz), 8.04–8.09 (2H, m).

IR (KBr) 3277, 1639, 1539, 1491, 1448, 1140, 812 cm$^{-1}$.

Elemental Analysis. Calcd. for $C_{31}H_{39}N_3O_2.0.2 H_2O$: C, 76.10; H, 8.12; N, 8.59. Found: C, 76.00; H, 8.03; N, 8.60.

Example 71 (Production of Compound 71)

Into a suspension of (E)-3-[5-(4-methylphenyl)-thiophen-2-yl]acrylic acid (200 mg) and 1-hydroxybenzotriazole (166 mg) in acetonitrile (10 ml) was added at room temperature 1-ethyl-3-(3'-dimethylaminopropyl)carbodiimide hydrochloride (235 mg), and the resulting mixture was stirred for 2 hours. Into the reaction mixture was added a solution of trans-4-[N-methyl-N-(tetrahydropyran-4-yl)aminomethyl]cyclohexylamine dihydrochloride (368 mg), triethylamine (0.23 ml) and 1,8-diazabicyclo[5,4,0]-7-undecene (374 mg) in acetonitrile (10 ml), and the resulting mixture was stirred further for 18 hours. After the reaction mixture was concentrated under reduced pressure, water was added to the residue, and the resulting mixture was extracted with ethyl acetate. The organic layer was washed with an aqueous saturated solution of sodium chloride and was dried with magnesium sulfate. After the resulting organic layer was concentrated under reduced pressure to remove the solvent, the residue was subjected to purification using column chromatography (ethanol/ethyl acetate 1:1) and to recrystallization (ethanol/ethyl acetate) to obtain trans-(E)-N-[4-(N-methyl-N-(tetrahydropyran-4-yl)aminomethylcyclohexyl]-3-[5-(4-methylphenyl)thiophen-2-yl]acrylamide (compound 71) (246 mg) as yellow crystals.

M. p. 199–201° C.

$^1$H-NMR (200 MHz, CDCl$_3$) δ0.95–1.27 (4H, m), 1.48–1.70 (5H, m), 1.80–1.93 (2H, m), 2.02–2.14 (2H, m), 2.23 (2H, dd, J=8.8 Hz), 2.25 (3H, s), 2.37 (3H, s), 2.42–2.61 (1H, m), 3.28–3.43 (2H, m), 3.74–3.93 (1H, m), 3.96–4.06 (2H, m), 5.35 (1H, d, J=8.2 Hz), 6.13 (1H, d, J=15.2 Hz), 7.14–7.22 (4H, m), 7.49 (2H, d, J=8.0 Hz), 7.69 (1H, d, J=15.2 Hz).

IR (KBr) 3273, 1645, 1603, 1549, 1456, 1236, 1211, 797 cm$^{-1}$.

Elemental Analysis. Calcd. for $C_{27}H_{36}N_2O_2S.0.2 H_2O$: C, 71.08; H, 8.04; N, 6.14. Found: C, 71.11; H, 7.99; N, 6.17.

Example 72 (Production of Compound 72)

Into a suspension of (E)-3-[4-(4-methylphenyl)-thiophen-2-yl]acrylic acid (150 mg) and 1-hydroxybenzotriazole (124 mg) in acetonitrile (10 ml) was added at room temperature 1-ethyl-3-(3-dimethylaminopropyl)carbodiimide hydrochloride (177 mg), and the resulting mixture was stirred for 2 hours. Into the reaction mixture was added a solution of trans-4-[N-methyl-N-(tetrahydropyran-4-yl)aminomethyl]cyclohexylamine dihydrochloride (276 mg), 1,8-diazabicyclo[5,4,0]-7-undecene (281 mg) and triethylamine (0.17 ml) in acetonitrile (15 ml), and the resulting mixture was stirred for 16 hours. After the reaction mixture was concentrated under reduced pressure, water was added to the residue, and the resulting mixture was extracted with ethyl acetate. The organic layer was washed with an aqueous saturated solution of sodium chloride and was dried with magnesium sulfate. After the resulting organic layer was concentrated under reduced pressure to remove the solvent, the residue was subjected to purification using column chromatography (ethanol/ethyl acetate 1:2) and to recrystallization (ethanol) to obtain (trans, E)-3-[4-(4-methylphenyl)thiophen-2-yl]-N-[4-[N-methyl-N-(tetrahydropyran-4-yl)

aminomethyl]cyclohexyl]acrylamide (compound 72) (191 mg) as colorless crystals.

M. p. 180–183° C.

$^1$H-NMR (200 MHz, CDCl$_3$) δ0.94–1.26 (4H, m), 1.50–1.74 (5H, m), 1.79–1.94 (2H, m), 2.01–2.15 (2H, m), 2.23 (2H, d, J=8.4 Hz), 2.25 (3H, s), 2.37 (3H, s), 2.42–2.62 (1H, m), 3.36 (2H, dt, J=2.8, 11.0 Hz), 3.75–3.94 (1H, m), 3.96–4.06 (2H, m), 5.41 (1H, d, J=8.4 Hz), 6.18 (1H, d, J=15.4 Hz), 7.21 (2H, d, J=8.0 Hz), 7.36 (1H, s), 7.43–7.48 (3H, m), 7.75 (1H, d, J=15.4 Hz).

IR (KBr) 3317, 1649, 1614, 1539, 1333, 1201, 816 cm$^{-1}$.

Elemental Analysis. Calcd. for C$_{27}$H$_{36}$N$_2$O$_2$S: C, 71.64; H, 8.02; N, 6.19. Found: C, 71.34; H, 7.97; N, 6.29.

Example 73 (Production of Compound 73)

Into a suspension of (E)-3-[5-(4-methylphenyl)pyridin-3-yl]acrylic acid (150 mg) and 1-hydroxybenzotriazole (134 mg) in acetonitrile (15 ml) was added at room temperature 1-ethyl-3-(3'-dimethylaminopropyl)carbodiimide hydrochloride (0.19 g), and the resulting mixture was stirred for 2 hours. Into the reaction mixture was added a solution of trans-4-[N-methyl-N-(tetrahydropyran-4-yl)aminomethyl] cyclohexylamine dihydrochloride (198 mg), 1,8-diazabicyclo[5,4,0]-7-undecene (0.2 g) and triethylamine (0.18 ml) in acetonitrile (20 ml), and the resulting mixture was stirred for 64 hours. After the reaction mixture was concentrated under reduced pressure, water was added to the residue, and the resulting mixture was extracted with chloroform. The organic layer was washed with an aqueous saturated solution of sodium chloride and was dried with magnesium sulfate. After the resulting organic layer was concentrated under reduced pressure to remove the solvent, the precipitated crystals were purified by recrystallization (ethanol/ethyl acetate) to obtain (trans, E)-3-[5-(4-methylphenyl)pyridin-3-yl]-N-[4-[N-methyl-N-(tetrahydropyran-4-yl)aminomethyl]cyclohexyl]acrylamide (compound 73) (226 mg) as colorless crystals.

M. p. 233–236° C.

$^1$H-NMR (200 MHz, CDCl$_3$) δ0.96–1.30 (4H, m), 1.51–1.71 (5H, m), 1.81–1.95 (2H, m), 2.03–2.18 (2H, m), 2.23 (2H, d, J=8.0 Hz), 2.25 (3H, s), 2.42 (3H, s), 2.45–2.61 (1H, m), 3.36 (2H, dt, J=3.0, 11.4 Hz), 3.77–4.08 (3H, m), 5.53 (1H, d, J=9.2 Hz), 6.50 (1H, d, J=15.4 Hz), 7.30 (2H, d, J=8.1 Hz), 7.49 (2H, d, J=8.1 Hz), 7.67 (1H, d, J=15.4 Hz), 7.93 (1H, dd, J=2.2, 2.2 Hz), 8.69 (1H, d, J=2.2 Hz), 8.78 (1H, d, J=2.2 Hz).

IR (KBr) 3302, 1659, 1612, 1541, 1344, 976, 822 cm$^{-1}$.

Elemental Analysis. Calcd. for C$_{28}$H$_{37}$N$_3$O$_2$: C, 75.13; H, 8.33; N, 9.39. Found: C, 75.06; H, 8.11; N, 9.34.

Example 74 (Production of Compound 74)

Into a suspension of (E)-3-[4-(4-methylphenyl) furan-2-yl]acrylic acid (150 mg) and 1-hydroxybenzotriazole (133 mg) in acetonitrile (15 ml) was added at room temperature 1-ethyl-3-(3'-dimethylaminopropyl)carbodiimide hydrochloride (189 mg), and the resulting mixture was stirred for 2 hours. Into the reaction mixture was added a solution of trans-4-[N-methyl-N-(tetrahydropyran-4-yl)aminomethyl] cyclohexylamine dihydrochloride (295 mg), 1,8-diazabicyclo[5,4,0]-7-undecene (0.3 g) and triethylamine (0.18 ml) in acetonitrile (15 ml), and the resulting mixture was stirred for 4 days. After the reaction mixture was concentrated under reduced pressure, water was added to the residue, and the resulting mixture was extracted with ethyl acetate. The organic layer was washed with an aqueous saturated solution of sodium chloride and was dried with magnesium sulfate. After the resulting organic layer was concentrated under reduced pressure to remove the solvent, the residue was subjected to purification using column chromatography (ethanol/ethyl acetate 1:3→1:2) and to recrystallization (ethyl acetate/hexane) to obtain (trans, E)-3-[4-(4-methylphenyl)furan-2-yl]-N-[4-[N-methyl-N-(tetrahydropyran-4-yl)aminomethyl]cyclohexyl]acrylamide (compound 74) (137 mg) as light yellow crystals.

M. p. 165–167° C.

$^1$H-NMR (200 MHz, CDCl$_3$) δ0.87–1.28 (4H, m), 1.47–1.66 (5H, m), 1.76–1.96 (2H, m), 2.02–2.15 (2H, m), 2.22 (2H, d, J=8.4 Hz), 2.24 (3H, s), 2.38 (3H, s), 2.42–2.60 (1H, m), 3.28–3.42 (2H, m), 3.73–3.92 (1H, m), 3.95–4.06 (2H, m), 5.40 (1H, d, J=8.8 Hz), 6.33 (1H, d, J=15.4 Hz), 6.60 (1H, d, J=3.4 Hz), 6.65 (1H, d, J=3.4 Hz), 7.20 (2H, d, J=8.0 Hz), 7.39 (1H, d, J=15.4 Hz), 7.60 (2H, d, J=8.0 Hz).

IR (KBr) 3319, 1651, 1614, 1541, 1989, 1219, 1142, 955, 779 cm$^{-1}$.

Elemental Analysis. Calcd. for C$_{27}$H$_{36}$N$_2$O$_3$: C, 74.28; H, 8.31; N, 6.42. Found: C, 74.13; H, 8.07; N, 6.36.

Example 75 (Production of Compound 75)

Into a solution of trans-(E)-N-[4-(N-methyl-N-(tetrahydropyran-4-yl)aminomethylcyclohexyl)-3-[5-(4-methylphenyl)thiophen-2-yl]acrylamide (100 mg) in DMF (3 ml) was added at room temperature methyl iodide (0.03 ml), and the resulting mixture was stirred for 24 hours. The reaction mixture was evaporated under reduced pressure to remove the solvent, and the residue was mixed with ethanol. The precipitated crystals were collected by filtration to obtain N,N-dimethyl-N-[trans-4-[(E)-3-[5-(4-methylphenyl)-2-thienyl]-2-propenoylamino] cyclohexylmethyl]-4-tetrahydropyranylammonium iodide (compound 75) (87 mg) as light yellow crystals.

M. p. 229–232° C.

$^1$H-NMR (200 MHz, DMSO-d$_6$) δ1.12–1.37 (4H, m), 1.63–2.05 (8H, m), 2.33 (3H, s), 2.99 (6H, s), 3.10–3.23 (2H, m), 3.26–3.42 (3H, m), 3.46–3.80 (2H, m), 3.97–4.11 (2H, m), 6.35 (1H, d, J=15.4 Hz), 7.25 (2H, d, J=8.0 Hz), 7.34 (1H, d, J=4.1 Hz), 7.44 (1H, d, J=4.1 Hz), 7.53 (1H, d, J=15.4 Hz), 7.56 (2H, d, J=8.0 Hz), 8.03 (1H, d, J=7.6 Hz).

IR (KBr) 3442, 3240, 2933, 1653, 1606, 1543, 1452, 808 cm$^{-1}$.

Elemental Analysis. Calcd. for C$_{28}$H$_{39}$N$_2$O$_2$sI.0.3 H$_2$O: C, 56.05; H, 6.65; N, 4.67. Found: C, 55.95; H, 6.50; N, 4.70.

Reference Example 108

Into a suspension of 7-(4-methylphenyl)-2,3-dihydro-1-benzooxepine-4-carboxylic acid (1.2 g) in dichloromethane (10 ml) were added under ice cooling oxalyl chloride (1.1 ml) and dimethylformamide (a catalytic amount), and the resulting mixture was stirred at room temperature for 2 hours. After evaporation of the solvent, the residue dissolved in tetrahydrofuran (15 ml) was added dropwise under ice cooling to a solution of 4-trifluoroacetamidopiperidine (0.85 g) and triethylamine (1.8 ml) in THF (10 ml). The resulting mixture was stirred at room temperature overnight under a nitrogen atmosphere. After the reaction mixture was concentrated under reduced pressure, water was added to the residue, and the resulting mixture was extracted with ethyl acetate. The organic layer was washed with an aqueous saturated solution of sodium chloride and was dried with magnesium sulfate. The resulting organic layer was concentrated under reduced pressure to remove the solvent to obtain crude crystals. The crude crystals were recrystallized from ethyl acetate/hexane to obtain 1-(7-(4-methylphenyl)-2,3-dihydro-1-benzooxepine-4-carbonyl)-4-trifluoroacetamidopiperidine as colorless prisms.

M. p. 189–192° C.

$^1$H-NMR (δ ppm, CDCl$_3$) 1.40–1.62 (2H, m), 2.05–2.15 (2H, m), 2.39 (3H, s), 2.90 (2H, t, J=4.4 Hz), 2.98–3.15 (2H, m), 4.00–4.20 (1H, m), 4.34 (2H, t, J=4.4 Hz), 4.34–4.45 (2H, m), 6.30 (1H, d, J=8.0 Hz), 6.47 (1H, s), 7.04 (1H, d, J=8.0 Hz), 7.24 (2H, d, J=7.8 Hz), 7.35–7.45 (4H, m).

IR (KBr) ν: 3250, 2926, 1715 cm$^{-1}$.

Anal. Calcd. for C$_{25}$H$_{25}$F$_3$N$_2$O$_3$: C, 65.49; H, 5.50; N, 6.11. Found: C, 65.32; H, 5.57; N, 6.08.

Example 76 (Production of Compound 76)

To 1-(7-(4-methylphenyl)-2,3-dihydro-1-benzooxepine-4-carbonyl)-4-trifluoroacetamidopiperidine (1.6 g) dissolved in methanol (100 ml) was added a 1 N aqueous solution of sodium hydroxide (7 ml), and the resulting mixture was stirred at room temperature overnight. The reaction mixture was concentrated and was then extracted with ethyl acetate. The organic layer was washed with water and an aqueous saturated solution of sodium chloride, and was then dried with anhydrous magnesium sulfate. The resulting organic layer was evaporated under reduced pressure to remove the solvent to obtain crude crystals. The crude crystals were recrystallized from ethyl acetate/hexane to obtain 4-amino-1-(7-(4-methylphenyl)-2,3-dihydro-1-benzooxepine-4-carbonyl)piperidine (compound 76) (1.1 g) as colorless prisms.

M. p. 123–127° C.

$^1$H-NMR (δ ppm, CDCl$_3$) 1.22–1.40 (2H, m), 1.80–1.95 (2H, m), 2.39 (3H, s), 2.90 (2H, t, J=4.4 Hz), 2.92–3.05 (3H, m), 4.14–4.36 (2H, m), 4.34 (2H, t, J=4.4 Hz), 6.46 (1H, s), 7.04 (1H, d, J=8.0 Hz), 7.24 (2H, d, J=8.0 Hz), 7.37–7.46 (4H, m).

IR (KBr) ν: 2938, 1605 cm$^{-1}$.

Anal. Calcd. for C$_{23}$H$_{26}$N$_2$O$_2$: C, 76.21; H, 7.23; N, 7.73. Found: C, 75.92; H, 7.14; N, 7.77.

Example 77 (Production of Compound 77)

To 4-amino-1-(7-(4-methylphenyl)-2,3-dihydro-1-benzooxepine-4-carbonyl)piperidine (0.3 g) and tetrahydro-4H-pyran-4-one (0.083 g) dissolved in 1,2-dichloroethane (6 ml) was added under ice cooling sodium triacetoxyborohydride (0.25 g), and the resulting mixture was stirred at room temperature overnight under a nitrogen atmosphere. The reaction mixture was evaporated to remove the solvent, was neutralized with a 1 N aqueous solution of sodium hydroxide and was extracted with ethyl acetate. The organic layer was washed with water and an aqueous saturated solution of sodium chloride, and then was dried with anhydrous magnesium sulfate. The resulting organic layer was evaporated under reduced pressure to remove the solvent, and the residue dissolved in ethyl acetate was mixed with 4 N hydrochloric acid/ethyl acetate (0.5 ml) to collect the precipitated powder by filtration. The powder was washed with hexane to obtain 1-(7-(4-methylphenyl)-2,3-dihydro-1-benzooxepine-4-carbonyl)-4-((tetrahydropyran-4-yl)amino)piperidine hydrochloride (compound 77) (0.35 g) as a colorless amorphous substance.

$^1$H-NMR (δ ppm, DMSO-d$_6$) 1.62 (4H, br), 1.93–2.13 is (4H, m), 2.34 (3H, s), 2.80 (2H, s-like), 2.98 (2H, br), 3.40–3.53 (4H, m), 3.89–3.94 (2H, m), 4.17–4.28 (4H, m), 6.54 (1H, s), 7.02 (1H, d, J=8.4 Hz), 7.24 (2H, d, J=7.8 Hz), 7.46–7.61 (4H, m), 9.07 (2H, br).

IR (KBr) ν: 2951, 2791, 2737, 2693, 1620 cm$^{-1}$.

Anal. Calcd. for C$_{28}$H$_{34}$N$_2$O$_3$.HCl.0.2 H$_2$O: C, 69.11; H, 7.33; N, 5.76. Found: C, 69.08; H, 7.20; N, 5.97.

Example 78 (Production of Compound 78)

To 1-(7-(4-methylphenyl)-2,3-dihydro-1-benzooxepine-4-carbonyl)-4-((tetrahydropyran-4-yl)amino)piperidine hydrochloride (0.2 g), 37% formalin (0.05 ml) and triethylamine (0.06 ml) suspended in 1,2-dichloroethane (5 ml) was added under ice cooling sodium triacetoxyborohydride (0.13 g), and the resulting mixture was stirred at room temperature overnight under a nitrogen atmosphere. The reaction mixture was evaporated to remove the solvent, was neutralized with a 1 N aqueous solution of sodium hydroxide and was extracted with ethyl acetate. The organic layer was washed with water and an aqueous saturated solution of sodium chloride, and was then dried with anhydrous magnesium sulfate. The resulting organic layer was evaporated under reduced pressure to remove the solvent, and the residue dissolved in ethyl acetate was mixed with 4 N hydrochloric acid/ethyl acetate (0.5 ml) to collect the precipitated powder by filtration. The powder was washed with diethyl ether to obtain 1-(7-(4-methylphenyl)-2,3-dihydro-1-benzooxepine-4-carbonyl)-4-((N-methyl-N-(tetrahydropyran-4-yl))amino)piperidine hydrochloride (compound 78) (0.19 g) as a colorless amorphous substance.

$^1$H-NMR (δ ppm, DMSO-d$_6$) 1.60–1.85 (4H, m), 1.85–2.20 (4H, m), 2.34 (3H, s), 2.67 (3H, d, J=4.6 Hz), 2.80 (2H, t-like), 2.96 (2H, br), 3.29–3.46 (3H, m), 3.70 (1H, br), 3.94–4.00 (2H, m), 4.25 (2H, br), 4.28 (2H, t-like), 6.59 (1H, s), 7.03 (1H, d, J=8.4 Hz), 7.25 (2H, d, J=8.0 Hz), 7.46–7.55 (3H, m), 7.64 (1H, d, J=2.6 Hz), 10.07 (1H, br)

IR (KBr) ν: 2963, 2649, 1605 cm$^{-1}$.

Anal. Calcd. for C$_{29}$H$_{36}$N$_2$O$_3$.HCl.H$_2$O: C, 67.62; H, 7.63; N, 5.44. Found: C, 67.48; H, 7.65; N, 5.43.

Reference Example 109

To 7-(4-methylphenyl)-2,3-dihydro-1-benzooxepine-4-carbaldehyde (2.0 g) and 4-trifluoroacetamidopiperidine (1.56 g) dissolved in 1,2-dichloroethane (50 ml) was added under ice cooling sodium triacetoxyborohydride (1.8 g), and the resulting mixture was stirred at room temperature overnight under a nitrogen atmosphere. Thereto were added triethylamine (1.1 ml) and sodium triacetoxyborohydride (0.8 g), and the resulting mixture was stirred at room temperature overnight under a nitrogen atmosphere. The reaction mixture was evaporated to remove the solvent, was neutralized with a 1 N aqueous solution of sodium hydrogen carbonate and was extracted with ethyl acetate. The organic layer was washed with water and an aqueous saturated solution of sodium chloride, and then was dried with anhydrous magnesium sulfate. The resulting organic layer was evaporated under reduced pressure to remove the solvent to obtain crude crystals (3.0 g). A portion of the crystals was recrystallized from ethyl acetate/hexane to obtain 1-(7-(4-methylphenyl)-2,3-dihydro-1-benzooxepin-4-ylmethy)-4-trifluoroacetamidopiperidine as light yellow crystals.

M. p. 94–96° C.

$^1$H-NMR (δ ppm, CDCl$_3$) 1.43–1.61 (2H, m), 1.96–2.17 (4H, m), 2.38 (3H, s), 2.69 (2H, t, J=4.8 Hz), 2.82–2.88 (2H, m), 3.05 (2H, s), 3.75–3.95 (1H, m), 4.26 (2H, t, J=4.8 Hz), 6.13 (1H, d, J=7.2 Hz), 6.35 (1H, s), 6.99 (1H, d, J=8.0 Hz), 7.22 (2H, d, J=8.1 Hz), 7.29–7.36 (2H, m), 7.44 (2H, d, J=8.1 Hz)

IR (KBr) ν: 3299, 2948, 1703 cm$^{-1}$.

Anal. Calcd. for $C_{25}H_{27}F_3N_2O_2 \cdot 0.2\ H_2O$: C, 67.01; H, 6.16; N, 6.25. Found: C, 67.16; H, 6.13; N, 6.07

Example 79 (Production of Compound 79)

To 1-(7-(4-methylphenyl)-2,3-dihydro-1-benzooxepin-4-yl)-methy-4-(trifluoroacetamido)piperidine (2.7 g) dissolved in methanol (200 ml) was added a 1 N aqueous solution of sodium hydroxide (20 ml), and the resulting mixture was stirred at room temperature for 2 days. The reaction mixture was concentrated and then was extracted with ethyl acetate. The organic layer was washed with water and an aqueous saturated solution of sodium chloride and then was dried with anhydrous magnesium sulfate. The resulting organic layer was evaporated to remove the solvent under reduced pressure to obtain 4-amino-1-(7-(4-methylphenyl)-2,3-dihydro-1-benzooxepin-4-yl) methylpiperidine (compound 79) (1.44 g) as a colorless amorphous substance.

$^1$H-NMR (δ ppm, CDCl$_3$) 1.26–1.47 (2H, m), 1.77–1.83 (2H, m), 1.92–2.05 (2H, m), 2.38 (3H, s), 2.61–2.69 (1H, m), 2.71 (2H, t, J=4.8 Hz), 2.80–2.85 (2H, m), 3.03 (2H, s), 4.26 (2H, t, J=4.8 Hz), 6.34 (1H, s), 6.99 (1H, d, J=8.4 Hz), 7.22 (2H, d, J=8.0 Hz), 7.28–7.36 (2H, m), 7.45 (2H, d, J=8.0 Hz).

IR (KBr) ν: 2936, 1576, 1493 cm$^{-1}$.

Anal. Calcd. for $C_{28}H_{23}N_2O \cdot 0.2\ H_2O$: C, 78.46; H, 8.13; N, 7.96. Found: C, 78.35; H, 7.97; N, 7.56.

Example 80 (Production of Compound 80)

To 4-amino-1-(7-(4-methylphenyl)-2,3-dihydro-1-benzooxepin-4-yl)methylpiperidine (0.4 g) and tetrahydro-4H-pyran-4-one (0.12 g) dissolved in 1,2-dichloroethane (10 ml) was added under ice cooling sodium triacetoxyborohydride (0.34 g), and the resulting mixture was stirred at room temperature overnight under a nitrogen atmosphere. The reaction mixture was evaporated to remove the solvent, was neutralized with a 1 N aqueous solution of sodium hydroxide and was then extracted with ethyl acetate. The organic layer was washed with water and an aqueous saturated solution of sodium chloride, was then dried with anhydrous magnesium sulfate, and was evaporated under reduced pressure to remove the solvent. The residue was subjected to purification using a silica gel column (methanol/triethylamine/ethyl acetate) to obtain crude crystals. The crude crystals were recrystallized from ethyl acetate/hexane to obtain 1-(7-(4-methylphenyl)-2,3-dihydro-1-benzooxepin-4-yl)methyl-4-((tetrahydropyran-4-yl)amino) piperidine (compound 80) (0.17 g) as colorless crystals.

M. p. 101–103° C.

$^1$H-NMR (δ ppm, CDCl$_3$) 1.26–1.50 (4H, m), 1.78–2.05 (6H, m), 2.38 (3H, s), 2.60–2.72 (3H, m), 2.76–2.89 (3H, m), 3.04 (2H, s), 3.40 (2H, dt, J=2.2, 11.7 Hz), 3.94–4.00 (2H, m), 4.26 (2H, t, J=5.0 Hz), 6.34 (1H, s), 6.99 (1H, d, J=8.0 Hz), 7.22 (2H, d, J=8.1 Hz), 7.28–7.36 (2H, m), 7.45 (2H, d, J=8.1 Hz).

IR (KBr) ν: 2936, 1493 cm$^{-1}$.

Anal. Calcd. for $C_{28}H_{36}N_2O_2$: C, 77.74; H, 8.39; N, 6.48. Found: C, 77.49; H, 8.44; N, 6.71.

Example 81 (Production of Compound 81)

To 4-amino-1-(7-(4-methylphenyl)-2,3-dihydro-1-benzooxepin-4-yl)methylpiperidine (0.3 g) and tetrahydro-4H-pyran-4-one (0.09 g) dissolved in 1,2-dichloroethane (10 ml) was added under ice cooling sodium triacetoxyborohydride (0.26 g). The resulting mixture was stirred at room temperature overnight under a nitrogen atmosphere. Thereto was added a 37% aqueous solution of formaldehyde (0.1 ml) and was then added under ice cooling sodium triacetoxyborohydride (0.3 g), and the resulting mixture was stirred at room temperature overnight under a nitrogen atmosphere. The reaction mixture was evaporated to remove the solvent, was neutralized with a 1 N aqueous solution of sodium hydroxide and was then extracted with ethyl acetate. The organic layer was washed with water and an aqueous saturated solution of sodium chloride and was then dried with anhydrous magnesium sulfate, and the solvent was evaporated. The residue was subjected to purification using a silica gel column (methanol/triethylamine/ethyl acetate). The purified material dissolved in ethyl acetate was mixed with 4 N hydrochloric acid/ethyl acetate (0.4 ml) and hexane to collect the precipitated powder by filtration. The powder was washed with hexane to obtain 1-(7-(4-methylphenyl)-2,3-dihydro-1-benzooxepin-4-yl)methyl-4-(N-methyl-N-(tetrahydropyran-4-yl)amino)piperidine dihydrochloride (compound 81) (0.21 g) as a colorless amorphous substance.

$^1$H-NMR (δ ppm, DMSO-d$_6$) 1.70–1.99 (2H, m), 2.07–2.24 (2H, m), 2.34 (3H, s), 2.34–2.39 (2H, m), 2.63–2.74 (3H, m), 2.91 (2H, br), 3.00–3.20 (2H, m), 3.26–3.40 (2H, m), 3.45–3.61 (2H, m), 3.70–3.90 (3H, m), 3.90–4.20 (3H, m), 4.25 (2H, br), 6.77 (1H, s), 7.02 (1H, d, J=8.4 Hz), 7.26 (2H, d, J=8.2 Hz), 7.45–7.53 (4H, m), 11.06 (2H, br).

IR (KBr) ν: 2940, 2654, 1493 cm$^{-1}$.

Reference Example 110

To 7-phenyl-3,4-dihydronaphthalene-2-carboxylic acid (1.00 g) dissolved in methanol (25 ml) was added a concentrated sulfuric acid (0.1 ml), and the resulting mixture was heated at reflux for 48 hours. After cooling to room temperature, the reaction mixture was mixed with a 5% aqueous solution of sodium hydrogen carbonate and was extracted with ethyl acetate. The organic layer was washed with an aqueous saturated solution of sodium chloride, was dried with anhydrous sodium sulfate and was then evaporated under reduced pressure to remove the solvent. To the resulting residue dissolved in ethanol (50 ml) was added dried 10% palladium on charcoal (0.05 g), and the resulting mixture was stirred at an ordinary temperature and under an atmospheric pressure for 48 hours. The palladium on charcoal was removed by a filtration operation, the filtrate was concentrated and the residue was then subjected to purification using column chromatography (ethyl acetate/hexane=1/2) to obtain an oily material. To this material dissolved in methanol (15 ml) was added a 1 N aqueous solution of sodium hydroxide (10 ml), and the resulting mixture was heated at reflux for 3 hours. After cooling to room temperature, the reaction mixture was acidified by the addition of a diluted hydrochloric acid and was extracted with ethyl acetate. The organic layer was washed with an aqueous saturated solution of sodium chloride and was dried with anhydrous magnesium sulfate, and then the solvent was evaporated under reduced pressure. The resulting residue was recrystallized from ethyl acetate/hexane to obtain 7-phenyl-1,2,3,4-tetrahydronaphthalene-2-carboxylic acid (677 mg) as colorless crystals.

M. p. 164–166° C.

Elemental Analysis. Calcd. for $C_{17}H_{16}O_2$: C, 80.93; H, 6.39. Found: C, 80.83; H, 6.30.

IR (KBr) cm$^{-1}$: 3030, 2924, 1693, 1483, 1294, 1234, 764, 700.

$^1$H-NMR (200 MHz, CDCl$_3$) δ: 1.83–2.05 (1H, m), 2.22–2.35 (1H, m), 2.75–3.05 (3H, m), 3.12 (2H, d, J=7.4 Hz), 7.18 (1H, d, J=7.8 Hz), 7.27–7.46 (5H, m), 7.52–7.60 (2H, m).

Example 82 (Production of Compound 82)

To 7-phenyl-1,2,3,4-tetrahydronaphthalene-2-carboxylic acid (400 mg) dissolved in THF (7 ml) were added oxalyl chloride (207 μl) and one drop of DMF, and the resulting mixture was stirred at room temperature for one hour. After the reaction mixture was evaporated under reduced pressure to remove the solvent, to the residue dissolved in THF (7 ml) were added at room temperature 1-(4-aminobenzyl) piperidine (333 mg) and triethylamine (267 μl). The resulting mixture was stirred at room temperature for 17 hours, water (100 ml) was then added and the resulting mixture was extracted with ethyl acetate. The organic layer was washed with an aqueous saturated solution of sodium chloride and was dried with anhydrous magnesium sulfate, and the solvent was then evaporated under reduced pressure. The resulting residue was recrystallized from ethyl acetate/ diisopropyl ether to obtain N-[4-(piperidinomethyl)phenyl]-7-phenyl-1,2,3,4-tetrahydronaphthalene-2-carboxamide (compound 82) (604 mg) as light brown crystals.

M. p. 185–187° C.

Elemental Analysis. Calcd. for C$_{29}$H$_{32}$N$_2$O: C, 82.04; H, 7.60; N, 6.60. Found: C, 81.98; H, 7.45; N, 6.63.

IR (KBr) cm$^{-1}$: 3288, 2933, 1657, 1603, 1537, 1485, 1410, 1321, 760, 696.

$^1$H-NMR (200 MHz, CDCl$_3$) δ: 1.35–1.75 (6H, m), 1.90–2.15 (1H, m), 2.18–2.42 (5H, m), 2.60–2.78 (1H, m), 2.88–3.05 (2H, m), 3.08–3.30 (2H, m), 3.44 (2H, m), 7.15–7.60 (13H, m).

Example 83 (Production of Compound 83)

To N-[4-(piperidinomethyl)phenyl]-7-phenyl-1,2,3,4-tetrahydronaphthalene-2-carboxamide (300 mg) dissolved in DMF (3 ml) was added methyl iodide (132 μl), and the resulting mixture was stirred at room temperature for 17 hours. The reaction mixture was mixed with ethyl acetate (100 ml), and the resulting precipitate was collected by filtration to obtain 1-[4-(7-phenyl-1,2,3,4-tetrahydronaphthalene-2-carboxamido)benzyl]-1-methylpiperidinium iodide (compound 83) (374 mg) as colorless crystals.

M. p. 205–208° C.

Elemental Analysis. Calcd. for C$_{30}$H$_{35}$N$_2$OI·0.5 H$_2$O: C, 62.61; H, 6.30; N, 4.87. Found: C, 62.94; H, 6.08; N, 5.05.

IR (KBr) cm$^{-1}$: 3439, 1660, 1599, 1531, 1485, 1417, 1321, 760.

$^1$H-NMR (200 MHz, DMSO-d$_6$) δ: 1.40–1.95 (6H, m), 2.05–2.20 (1H, m), 2.75–3.10 (9H, m), 3.20–3.35 (4H, m), 4.52 (2H, s), 7.20 (1H, d, J=8.4 Hz), 7.35–7.55 (7H, m), 7.64 (2H, d, J=7.6 Hz), 7.78 (2H, d, J=8.2 Hz), 10.28 (1H, s).

Reference Example 111

A mixture comprising ethyl 3-hydroxybenzoate (5.00 g), benzyl bromide (4.29 ml), potassium carbonate (6.24 g) and acetone (50 ml) was stirred at room temperature for 16 hours. After the reaction mixture was evaporated under reduced pressure to remove the solvent, water (200 ml) was added to the residue, and the resulting mixture was extracted with ethyl acetate. After the organic layer was concentrated, a 1 N aqueous solution of sodium hydroxide (50 ml) was added to the residue dissolved in methanol (50 ml), and the resulting mixture was heated at reflux for 2 hours. After cooling to room temperature, the reaction mixture was acidified by the addition of concentrated hydrochloric acid and was then extracted with ethyl acetate. The organic layer was washed with an aqueous saturated solution of sodium chloride, was dried with anhydrous sodium sulfate and was then evaporated under reduced pressure to remove the solvent. The resulting residue was recrystallized from ethyl acetate/hexane to obtain 3-benzyloxybenzoic acid (5.10 g) as colorless crystals.

M. p. 140–141° C.

Elemental Analysis. Calcd. for C$_{14}$H$_{12}$O$_3$: C, 73.67; H, 5.30. Found: C, 73.70; H, 5.32.

IR (KBr) cm$^{-1}$: 3030, 2897, 1684, 1603, 1450, 1323, 1296, 1250, 1039, 760, 733.

$^1$H-NMR (200 MHz, CDCl$_3$) δ: 5.13 (2H, s), 7.18–7.28 (1H, m), 7.28–7.48 (6H, m), 7.70–7.77 (2H, m).

Reference Example 112

A mixture comprising ethyl 3-hydroxybenzoate (5.00 g), 4-methylbenzyl chloride (4.78 ml), potassium carbonate (6.24 g), methyl iodide (5.41 g) and acetone (50 ml) was heated at reflux for 15 hours. After the reaction mixture was evaporated under reduced pressure to remove the solvent, the residue was mixed with water (200 ml) and was extracted with ethyl acetate. After the organic layer was concentrated, a 1 N aqueous solution of sodium hydroxide (50 ml) was added to the residue dissolved in methanol (50 ml), and the resulting mixture was heated at reflux for 3 hours. After cooling to room temperature, the reaction mixture was acidified by the addition of concentrated hydrochloric acid and then was extracted with ethyl acetate. The organic layer was washed with an aqueous saturated solution of sodium chloride, was dried with anhydrous sodium sulfate and was evaporated under reduced pressure to remove the solvent. The resulting residue was recrystallized from ethyl acetate/hexane to obtain 3-(4-methylbenzyloxy) benzoic acid (5.92 g) as colorless crystals.

M. p. 152–154° C.

Elemental Analysis. Calcd. for C$_{15}$H$_{14}$O$_3$: C, 74.36; H, 5.82. Found: C, 74.16; H, 5.77.

IR (KBr) cm$^{-1}$: 3010, 2897, 1684, 1605, 1454, 1298, 1248, 1041, 802, 760.

$^1$H-NMR (200 MHz, CDCl$_3$) δ: 2.37 (3H, s), 5.08 (2H, s), 7.17–7.27 (3H, m), 7.31–7.43 (3H, m), 7.70–7.77 (2H, m).

Reference Example 113

A mixture comprising ethyl 3-hydroxybenzoate (5.00 g), 1-(chloromethyl)naphthalene (5.40 ml), potassium carbonate (6.24 g), methyl iodide (a catalytic amount) and acetone (50 ml) was heated at reflux for 24 hours. After the reaction mixture was concentrated under reduced pressure to remove the solvent, the residue was mixed with water (200 ml) and was extracted with ethyl acetate. After the organic layer was concentrated, a 1 N aqueous solution of sodium hydroxide (50 ml) was added to the residue dissolved in methanol (50 ml), and the resulting mixture was heated at reflux for 2 hours. After being cooled to room temperature, the reaction mixture was acidified by the addition of concentrated hydrochloric acid and was then extracted with ethyl acetate. The organic layer was washed with an aqueous saturated solution of sodium chloride, was dried with anhydrous sodium sulfate and was then evaporated under reduced pressure to remove the solvent. The resulting residue was recrystallized from ethyl acetate/hexane to obtain 3-(1-naphthylmethoxy) benzoic acid (7.14 g) as colorless crystals.

M. p. 177–179° C.

Elemental Analysis. Calcd. for $C_{18}H_{14}O_3$: C, 77.68; H, 5.07. Found: C, 77.41; H, 4.89.

IR (KBr) cm$^{-1}$: 3049, 2887, 1714, 1691, 1595, 1439, 1308, 1277, 1238, 1014, 781, 756.

$^1$H-NMR (200 MHz, CDCl$_3$) δ: 5.55 (2H, s), 7.24–7.32 (1H, m), 7.35–7.65 (5H, m), 7.73–7.95 (4H, m), 8.02–8.10 (1H, m).

Example 84 (Production of Compound 84)

To 3-benzyloxybenzoic acid (800 mg) dissolved in THF (10 ml) were added oxalyl chloride (397 μl) and one drop of DMF, and the resulting mixture was stirred at room temperature for one hour. After the reaction mixture was evaporated to remove the solvent, to the residue dissolved in THF (15 ml) were added dropwise at room temperature 1-(4-aminobenzyl)piperidine (733 mg) and triethylamine (589 μl). This reaction mixture was stirred at room temperature for 17 hours, was then mixed with water (100 ml) and was extracted with ethyl acetate. The organic layer was washed with an aqueous saturated solution of sodium chloride, was dried with anhydrous sodium sulfate and was then evaporated under reduced pressure to remove the solvent. The resulting residue was recrystallized from ethyl acetate/hexane to obtain 3-benzyloxy-4'-(piperidinomethyl)benzanilide (compound 84) (1.06 g) as colorless crystals.

M. p. 137–138° C.

Elemental Analysis. Calcd. for $C_{26}H_{28}N_2O_2$: C, 77.97; H, 7.05; N, 6.99. Found: C, 77.73; H, 7.15; N, 6.91.

IR (KBr) cm$^{-1}$: 3348, 2929, 1645, 1597, 1524, 1319, 1273, 750, 698.

$^1$H-NMR (200 MHz, CDCl$_3$) δ: 1.38–1.70 (6H, m), 2.32–2.43 (4H, m), 3.46 (2H, s), 5.13 (2H, s), 7.11–7.20 (1H, m), 7.28–7.60 (12H, m), 7.77 (1H, S).

Example 85 (Production of Compound 85)

To 3-(4-methylbenzyloxy)benzoic acid (1.00 g) dissolved in THE (15 ml) were added oxalyl chloride (468 oil) and one drop of DMF, and the resulting mixture was stirred at room temperature for one hour. After the reaction mixture was evaporated under reduced pressure to remove the solvent, to the residue dissolved in THF (15 ml) were added at room temperature 1-(4-aminobenzyl)piperidine (864 mg) and triethylamine (695 μl). The resulting mixture was stirred at room temperature for 3 hours, was then mixed with water (100 ml) and was extracted with ethyl acetate. The organic layer was washed with an aqueous saturated solution of sodium chloride, was dried with anhydrous sodium sulfate and was then evaporated under reduced pressure to remove the solvent. The resulting residue was recrystallized from ethyl acetate/hexane to obtain 3-(4-methylbenzyloxy)-4'-(piperidinomethyl)benzanilide (compound 85) (1.25 g) as colorless crystals.

M. p. 153–155° C.

Elemental Analysis. Calcd. for $C_{27}H_{30}N_2O_2$: C, 78.23; H, 7.29; N, 6.76. Found: C, 78.05; H, 7.25; N, 6.75.

IR (KBr) cm$^{-1}$: 3348, 2941, 1655, 1597, 1581, 1524, 1410, 1321, 1269, 1051, 800.

$^1$H-NMR (200 MHz, CDCl$_3$) δ: 1.35–1.75 (6H, m), 2.30–2.45 (7H, m), 3.47 (2H, s), 5.09 (2H, s), 7.10–7.40 (9H, m), 7.47–7.60 (3H, m), 7.78 (1H, s).

Example 86 (Production of Compound 86)

To 3-(1-naphthylmethoxy)benzoic acid (1.00 g) dissolved in THF (10 ml) were added oxalyl chloride (407 μl) and one drop of DMF, and the resulting mixture was stirred at room temperature for one hour. After the reaction mixture was evaporated to remove the solvent, to the residue dissolved in THF (15 ml) were added at room temperature 1-(4-aminobenzyl)piperidine (751 mg) and triethylamine (604 μl). The resulting mixture was stirred at room temperature for 96 hours, was then mixed with water (100 ml) and was extracted with ethyl acetate. The organic layer was washed with an aqueous saturated solution of sodium chloride, was dried with anhydrous sodium sulfate and was then evaporated under reduced pressure to remove the solvent. The resulting residue was recrystallized from ethyl acetate/hexane to obtain 3-(1-naphthylmethoxy)-4'-(piperidinomethyl)benzanilide (compound 86) (1.25 g) as colorless crystals.

M. p. 171–173° C.

Elemental Analysis. Calcd. for $C_{30}H_{30}N_2O_2 \cdot 0.1\ H_2O$: C, 79.65; H, 6.73; N, 6.19. Found: C, 79.55; H, 6.76; N, 6.19.

IR (KBr) cm$^{-1}$: 3350, 2929, 1655, 1597, 1581, 1522, 1410, 1321, 1290, 1269, 793.

$^1$H-NMR (200 MHz, CDCl$_3$) δ: 1.35–1.70 (6H, m), 2.33–2.43 (4H, m), 3.47 (2H, s), 5.57 (2H, s), 7.20–7.65 (12H, m), 7.78 (1H, s), 7.84–7.93 (2H, m), 8.03–8.08 (1H, m).

Example 87 (Production of Compound 87)

To 3-benzyloxy -4'-(piperidinomethyl)benzanilide (560 mg) dissolved in DMF (3 ml) was added methyl iodide (261 μl), and the resulting mixture was stirred at room temperature for 14 hours. Ethyl acetate (100 ml) was added to this reaction mixture, and the resulting precipitate was collected by filtration to obtain 1-[4-(3-benzyloxybenzoylamino)benzyl]-1-methylpiperidinium iodide (compound 87) (724 mg) as colorless crystals.

M. p. 192–194° C.

Elemental Analysis. Calcd. for $C_{27}H_{31}N_2O_2I$: C, 59.78; H, 5.76; N, 5.16. Found: C, 59.51; H, 5.67; N, 5.46.

IR (KBr) cm$^{-1}$: 3437, 3317, 1662, 1593, 1520, 1317, 1273, 1016, 750, 700.

$^1$H-NMR (200 MHz, DMSO-d$_6$) δ: 1.40–2.00 (6H, m), 2.92 (3H, s), 3.20–3.40 (4H, m), 4.54 (2H, s), 5.20 (2H, s), 7.23–7.60 (11H, m), 7.92 (2H, d, J=8.4 Hz), 10.42 (1H, s).

Example 88 (Production of Compound 88)

To 3-(4-methylbenzyloxy)-4'-(piperidinomethyl)benzanilide (900 mg) dissolved in DMF (5 ml) was added methyl iodide (405 μl), and the resulting mixture was stirred at room temperature for 15 hours. Ethyl acetate (200 ml) was added to this reaction mixture, and the resulting precipitate was collected by filtration to obtain 1-methyl-1-[4-[3-(4-methylbenzyloxy)benzoylamino]benzyl]piperidinium iodide (compound 88) (1.05 g) as colorless crystals.

M. p. 210–212° C.

Elemental Analysis. Calcd. for $C_{28}H_{33}N_2O_2I \cdot 0.5\ H_2O$: C, 59.47; H, 6.06; N, 4.95. Found: C, 59.77; H, 5.94; N, 5.10.

IR (KBr) cm$^{-1}$: 3298, 2949, 1657, 1595, 1520, 1483, 1416, 1321, 1275, 1213, 1012, 804.

$^1$H-NMR (200 MHz, DMSO-d$_6$) δ: 1.40–2.00 (6H, m), 2.32 (3H, s), 2.93 (3H, s), 3.20–3.40 (4H, m), 4.56 (2H, s), 5.15 (2H, s), 7.17–7.60 (10H, m), 7.93 (2H, d, J=8.4 Hz), 10.43 (1H, s).

Example 89 (Production of Compound 89)

To 3-(1-naphthylmethoxy)-4'-(piperidinomethyl)benzanilide (950 mg) dissolved in DMF (8 ml) was added methyl iodide (394 μl), and the resulting mixture was stirred at room temperature for 38 hours. Ethyl acetate (200 ml) was added to this reaction mixture, and the resulting precipitate was collected by filtration to obtain 1-methyl-1-[4-[3-(1-naphthylmethoxy)benzoylamino]benzyl]piperidinium iodide (compound 89) (1.21 g) as colorless crystals.

M. p. 211–213° C.

Elemental Analysis. Calcd. for $C_{31}H_{33}N_2O_2I$: C, 62.84; H, 5.61; N, 4.73. Found: C, 62.47; H, 5.61; N, 4.73.

IR (KBr) $cm^{-1}$: 3442, 3282, 1655, 1597, 1520, 1485, 1417, 1325, 1273, 793.

$^1$H-NMR (200 MHz, DMSO-$d_6$) δ: 1.40–2.00 (6H, m), 2.92 (3H, s), 3.20–3.40 (4H, m), 4.54 (2H, s), 5.66 (2H, s), 7.35–7.75 (10H, m), 7.80–8.05 (4H, m), 8.07–8.17 (1H, m), 10.44 (1H, s).

Example 90 (Production of Compound 90)

To 3-(4-methylbenzyloxy)-4'-(piperidinomethyl)benzanilide (150 mg) dissolved in THF (5 ml) was added at 0° C. 70% mCPBA (m-chloroperbenzoic acid) (116 mg), and the resulting mixture was stirred at 0° C. for one hour. An aqueous saturated solution of sodium thiosulfate (10 ml) and an aqueous saturated solution of potassium carbonate were added to this reaction mixture, and the resulting mixture was stirred at room temperature for 30 minutes and was then extracted with ethyl acetate. The organic layer was washed with an aqueous saturated solution of sodium chloride, was dried with anhydrous sodium sulfate and was then evaporated under reduced pressure to remove the solvent. The resulting residue was recrystallized from ethyl acetate/methanol to obtain 3-(4-methylbenzyloxy)-4'-(1-oxypiperidinomethyl)benzanilide (compound 90) (77 mg) as colorless crystals.

M. p. 128–130° C.

Elemental Analysis. Calcd. for $C_{27}H_{30}N_2O_3 \cdot 1.0\ H_2O$: C, 72.30; H, 7.19; N, 6.25. Found: C, 72.53; H, 6.96; N, 6.28.

IR (KBr) $cm^{-1}$: 3388, 2939, 1662, 1597, 1520, 1414, 1321, 1271, 1211, 806, 748.

$^1$H-NMR (200 MHz, CDCl$_3$) δ: 1.15–1.80 (4H, m), 2.10–2.50 (5H, m), 3.00–3.18 (4H, m), 4.33 (2H, s), 5.09 (2H, s), 7.09–7.60 (10H, m), 7.77 (2H, d, J=8.0 Hz), 8.69 (1H, s).

Example 91 (Production of Compound 92)

Into a solution of N-[4-(ethoxycarbonimidoyl)phenyl]-7-(4-methylphenyl)-2,3-dihydro-1-benzooxepine-4-carboxamide hydrochloride (200 mg) in ethanol (4 ml) was added ethylenediamine (0.09 ml). The resulting mixture was stirred at room temperature overnight, was then concentrated and was mixed with an aqueous solution of sodium bicarbonate. The resulting mixture was extracted with ethyl acetate/tetrahydrofuran, and the extract was washed with an aqueous solution of sodium chloride. The extract was dried (anhydrous magnesium sulfate) and was then concentrated, and the residue was recrystallized from ethyl acetate/methanol to obtain N-[4-(2-imidazolin-2-yl)phenyl]-7-(4-methylphenyl)-2,3-dihydro-1-benzooxepine-4-carboxamide (compound 92) (60 mg) as colorless crystals.

M. p. 282–283° C.

$^1$H-NMR (200 MHz, DMSO-$d_6$) δ: 2.34 (s, 3H), 2.9–3.1 (m, 2H), 3.60 (brs, 4H), 4.2–4.4 (m, 2H), 6.87 (brs, 1H), 7.06 (d, 1H, J=8.0), 7.27 (d, 2H, J=8.4), 7.37 (s, 1H), 7.5–7.6 (m, 3H), 7.7–7.8 (m, 5H), 10.15 (s, 1H).

IR (KBr) 1649, 1605, 1525, 1508, 1489, 1321, 1260, 810 $cm^{-1}$.

Elemental Analysis. Calcd. for $C_{27}H_{25}N_3O_2$: C, 76.57; H, 5.95; N, 9.92. Found: C, 76.45; H, 6.08; N, 9.97.

Example 92 (Production of Compound 93)

Into a solution of N-[4-(imidazolin-2-yl)phenyl]-7-(methylphenyl)-2,3-dihydro-1-benzooxepine-4-carboxamide (120 mg) in THF/DMF (10 ml/1 ml) were added triethylamine (0.09 ml) and acetyl chloride (0.024 ml), and the resulting mixture was stirred at room temperature for one hour. The reaction mixture was mixed with water under ice cooling and was extracted with ethyl acetate. The extract was washed with an aqueous solution of sodium chloride, was dried (anhydrous magnesium sulfate) and was then concentrated. The residue was subjected to purification using silica gel column chromatography (ethyl acetate/methanol) and further to recrystallization from ethyl acetate/methanol to obtain N-[4-(acetyl-2-imidazolin-2-yl)phenyl]-2,3-dihydro-1-benzooxepine-4-carboxamide (compound 93) (56 mg) as colorless crystals.

M. p. 222–224° C.

$^1$H-NMR (200 MHz, CDCl$_3$) δ: 1.90 (3H, s), 2.39 (3H, s), 3.05–3.15 (2H, m), 3.85–4.15 (4H, m), 4.36 (2H, t, J=4.6), 7.06 (1H, d, J=8.6), 7.2–7.3 (2H, m), 7.4–7.6 (6H, m), 7.67 (2H, d, J=8.8), 7.78 (1H, brs).

IR (KBr): 1665, 1649, 1530, 1512, 1391, 1279, 841, 814 $cm^{-1}$.

Elemental Analysis. Calcd. for $C_{29}H_{27}N_3O_3$: C, 74.82; H, 5.85; N, 9.03. Found: C, 74.58; H, 5.67; N, 8.95.

Example 93 (Production of Compound 94)

To N-(4-cyanomethylphenyl)-7-(4-methylphenyl)-2,3-dihydro-1-benzooxepine-4-carboxamide (789 mg) was added under ice cooling a solution of 24% hydrogen chloride/ethanol/dioxane (10 ml). The resulting mixture was stirred at room temperature for one hour and was then concentrated. To the residue suspended in ethanol (20 ml) was added ethylenediamine (0.4 ml) under ice cooling. The resulting mixture was stirred at room temperature for 15 hours, was then concentrated and was mixed with an aqueous solution of sodium bicarbonate. The resulting mixture was extracted with ethyl acetate, and the extract was washed with an aqueous solution of sodium chloride. After drying (magnesium sulfate), the extract was concentrated, and the residue was recrystallized from ethyl acetate/methanol to obtain N-(4-imidazolin-2-yl)methyl]phenyl]-7-(4-methylphenyl)-2,3-dihydro-1-benzooxepine-4-carboxamide (compound 94) (580 mg) as colorless crystals.

M. p. 210–212° C.

$^1$H-NMR (200 MHz, CDCl$_3$) δ: 2.38 (3H, s), 3.0–3.1 (2H, m), 3.49 (2H, s), 3.59 (4H, s), 4.25–4.35 (2H, m), 7.03 (d, 1H, J=8.2), 7.15–7.35 (5H, m), 7.4–7.6 (6H, m).

IR (KBr): 1649, 1603, 1516, 1493, 1327, 1265, 1256, 816 $cm^{-1}$.

Elemental Analysis. Calcd. for $C_{28}H_{27}N_3O_2 \cdot 0.1\ H_2O$: C, 73.82; H, 6.42; N, 9.22. Found: C, 73.85; H, 6.31; N, 9.08.

Example 94 (Production of Compound 95)

Into a solution of N-[4-(imidazolin-2-yl)methyl]phenyl]-7-(4-methylphenyl)-2,3-dihydro-1-benzooxepine-4-carboxamide (200 mg) in THF (10 ml)/DMF (1 ml) were added triethylamine (0.095 ml) and acetyl chloride (0.036 ml), and the resulting mixture was stirred at room temperature for one hour. The reaction mixture was mixed with an aqueous solution of sodium bicarbonate under ice cooling and was extracted with ethyl acetate. The extract was washed with an aqueous solution of sodium chloride, was dried (magnesium sulfate) and was then concentrated. The residue was subjected to purification using silica gel column chromatography (ethyl acetate) and further to recrystallization from ethyl acetate/diethyl ether to obtain N-[4-(1-acetyl-2-imidazolin-2-yl)methyl]phenyl]-7-(4-methylphenyl)-2,3-dihydro-1-benzooxepine-4-carboxamide (compound 95) (77 mg) as colorless crystals.

M. p. 174–176° C.

$^1$H-NMR (200 MHz, CDCl$_3$) δ: 2.13 (3H, s), 2.39 (3H, s), 3.0–3.15 (2H, m), 3.8–3.9 (4H, m), 4.15 (2H, s), 4.36 (2H, t, J=4.8), 7.05 (1H, d, J=8.0), 7.2–7.35 (4H, m), 7.4–7.6 (7H, m).

IR (KBr): 1655, 1532, 1516, 1493, 1395, 1319, 1244, 814 cm$^{-1}$.

Elemental Analysis. Calcd. for C$_{30}$H$_{29}$N$_3$O$_3$·0.8 H$_2$O: C, 72.94; H, 6.24; N, 8.51. Found: C, 72.99; H, 6.00; N, 8.53.

Example 95 (Production of Compound 96)

Into a suspension of N-[4-(2-imidazolin-2-yl)methyl] phenyl]-7-(4-methylphenyl)-2,3-dihydro-1-benzooxepine-4-carboxamide (150 mg) in THF (5 ml) were added triethylamine (0.06 ml) and methyl chlorocarbonate (0.03 ml). After being stirred at 0° C. for one hour, the reaction mixture was mixed with an aqueous solution of sodium bicarbonate under ice cooling and was extracted with ethyl acetate. The extract was washed with an aqueous solution of sodium chloride, was dried (magnesium sulfate), and was then concentrated under reduced pressure. The residue was subjected to purification using silica gel column chromatography (ethyl acetate/hexane=4/1) and further to recrystallization from ethyl acetate/hexane to obtain N-[4-[(1-methoxycarbonyl-2-imidazolin-2-yl)methyl]phenyl]-7-(4-methylphenyl)-2,3-dihydro-1-benzooxepine-4-carboxamide (compound 96) (71 mg) as colorless crystals.

M. p. 170–171° C.

$^1$H-NMR (200 MHz, CDCl$_3$) δ: 2.39 (3H, s), 3.07 (2H, t, J=5.0), 3.73 (3H, s), 3.81 (4H, s), 4.08 (2H, s), 4.36 (2H, t, J=5.0), 7.06 (1H, d, J=8.6), 7.2–7.35 (4H, m), 7.4–7.6 (7H, m).

IR (KBr): 1730, 1663, 1514, 1491, 1381, 1318, 1265, 1020, 810 cm$^{-1}$.

Elemental Analysis. Calcd. for C$_{30}$H$_{29}$N$_3$O$_4$: C, 72.71; H, 5.90; N, 8.48. Found: C, 72.43; H, 5.94; N, 8.33.

Reference Example 114

To 3-hydroxybenzaldehyde (5.00 g) dissolved in acetone (70 ml) were added 4-methylbenzyl chloride (6.51 ml), potassium carbonate (8.49 g) and sodium iodide (7.36 g), and the resulting mixture was heated at reflux for 24 hours and was then evaporated under reduced pressure to remove the solvent. The residue was mixed with water (200 ml) and was extracted with ethyl acetate. The organic layer was washed with an aqueous saturated solution of sodium chloride was dried with anhydrous sodium sulfate, and was then evaporated under reduced pressure to remove the solvent. The thus-obtained residue was subjected to purification using column chromatography (ethyl acetate/hexane=1/10) to obtain 3-(4-methylbenzyloxy)benzaldehyde (7.86 g) as a colorless oily substance.

IR (KBr) cm$^{-1}$: 2922, 1697, 1599, 1483, 1450, 1383, 1261, 1147, 1020, 789, 683.

$^1$H-NMR (200 MHz, CDCl$_3$) δ: 2.37 (3H, s), 5.09 (2H, s), 7.17–7.37 (5H, m), 7.52–7.60 (3H, m), 9.98 (1H, s).

Reference Example 115

To α,α'-Dibromo-p-xylene (12.5 g) dissolved in THF (100 ml) was added piperidine (4.68 ml), and the resulting mixture was stirred at room temperature for 4 hours. The reaction mixture was mixed with 1N hydrochloric acid (100 ml) and was stirred at room temperature for 5 minutes. After two layers were separated, the aqueous layer was washed with diethyl ether, was made alkaline by adding a 1N aqueous solution of sodium hydroxide and was then extracted with ethyl acetate. The organic layer was washed with an aqueous saturated solution of sodium chloride and was subjected directly to purification using column chromatography (ethyl acetate/hexane=2/1), and the objective fractions were concentrated to a solvent volume of approximately 200 ml. To this solution were added triphenylphosphine (7.46 g) and toluene (100 ml), and the resulting mixture was heated at reflux for 40 hours. The resulting precipitate was collected by filtration to obtain triphenyl[4-(piperidinomethyl)benzyl]phosphonium bromide (8.14) as colorless crystals.

M. p. 234–236° C.

Elemental Analysis. Calcd. for C$_{31}$H$_{33}$NBrP: C, 70.19; H, 6.27; N, 2.64. Found: C, 70.03; H, 6.37; N, 2.65.

IR (KBr) cm$^{-1}$: 2845, 1441, 1113, 995, 752, 719, 689.

$^1$H-NMR (200 MHz, DMSO-d$_6$) δ: 1.30–1.55 (6H, m), 2.12–2.32 (4H, m), 3.28–3.40 (2H, m), 5.14 (2H, d, J=15.4 Hz), 6.91 (2H, dd, J=2.2, 8.0 Hz), 7.12 (2H, d, J=8.0 Hz), 7.60–7.78 (12H, m), 7.85–7.95 (3H, m).

Example 96 (Production of Compound 97)

To a mixture comprising triphenyl[4-(piperidinomethyl)benzyl]phosphonium bromide (1.06 g) and THF (10 ml) was added dropwise under a nitrogen atmosphere a 1.6 M solution of butyllithium in hexane (1.28 ml), and the resulting mixture was stirred for 30 minutes. To this reaction mixture was added 3-(4-methylbenzyloxy)benzaldehyde (453 mg), and the resulting mixture was stirred at room temperature for one hour, was then mixed with water (100 ml) and was extracted with ethyl acetate. The organic layer was washed with an aqueous saturated solution of sodium chloride, was dried with anhydrous sodium sulfate and was then evaporated under reduced pressure to remove the solvent. The resulting residue was subjected to purification using column chromatography (ethyl acetate/triethylamine= 20/1) and to recrystallization to obtain (E)-1-[4-[3-(4-methylbenzyloxy)styryl]benzyl]piperidine (compound 97) (330 mg) as colorless crystals.

M. p. 87–88° C.

Elemental Analysis. Calcd. for C$_{28}$H$_{31}$NO: C, 84.59; H, 7.86; N, 3.52. Found: C, 84.30; H, 7.78; N, 3.60.

IR (KBr) cm$^{-1}$: 2924, 1601, 1578, 1443, 1281, 1157, 1036, 968, 797, 781, 685.

$^1$H-NMR (200 MHz, CDCl$_3$) δ: 1.38–1.65 (6H, m), 2.33–2.46 (7H, m), 3.48 (2H, s), 5.07 (2H, s), 6.83–6.90 (1H, m), 7.05–7.38 (11H, m), 7.46 (2H, d, J=8.2 Hz).

Example 97 (Production of Compound 98)

To (E)-1-[4-[3-(4-methylbenzyloxy)styryl]benzyl] piperidine (150 mg) dissolved in DMF (3 ml) was added methyl iodide (70 μl), and the resulting mixture was stirred at room temperature for 66 hours. The reaction mixture was mixed with ethyl acetate (100 ml) and the resulting precipitate was collected by filtration and recrystallized from ethyl acetate/methanol to obtain (E)-1-methyl-1-[4-[3-(4- methylbenzyloxy)styryl]benzyl]piperidinium iodide (compound 100) (183 mg) as colorless crystals.

M. p. 189–192° C.

Elemental Analysis. Calcd. for $C_{29}H_{34}NOI$: C, 64.56; H, 6.35; N, 2.60. Found: C, 64.29; H, 6.27; N, 2.88.

IR (KBr) cm$^{-1}$: 3442, 2956, 1593, 1466, 1443, 1267, 1211, 1189, 1014, 878, 806.

$^1$H-NMR (200 MHz, CDCl$_3$) δ: 1.75–2.05 (6H, m), 2.37 (3H, s), 3.21 (3H, s), 3.52–3.66 (2H, m), 3.75–3.90 (2H, m), 5.04 (2H, s), 5.16 (2H, s), 6.86–6.95 (1H, m), 7.03–7.15 (4H, m), 7.18–7.37 (5H, m), 7.49 (2H, d, J=8.4 Hz), 7.66 (2H, J=8.4 Hz).

Reference Example 116

A mixture of 2-hydroxybenzyl alcohol (3.00 g), 2-chloroethyl propyl ether (4.0 ml), sodium iodide (4.75 g), potassium carbonate (6.68 g) and DMF (30 ml) was stirred at 90° C. for 24 hours. The reaction mixture was mixed with water and was extracted with ethyl acetate. The organic layer was washed with water and an aqueous saturated solution of sodium chloride, and was dried with magnesium sulfate. After concentration under reduced pressure, the residue was subjected to purification using column chromatography (ethyl acetate:hexane 1:2) to obtain 2-(2-propoxyethoxy)benzyl alcohol (2.35 g) as a yellow oily substance.

$^1$H-NMR (200 MHz, CDCl$_3$) δ0.92 (3H, t, J=7.4 Hz), 1.54–1.68 (2H, m), 3.31 (1H, t, J=7.0 Hz), 3.48 (2H, t, J=6.8 Hz), 3.76–3.81 (2H, m), 4.19–4.24 (2H, m), 4.67 (2H, d, J=7.0 Hz), 6.89–6.99 (2H, m), 7.22–7.30 (2H, m).

IR (neat) 3427, 1603, 1601, 1495, 1454, 1288, 1244, 1120, 1051, 754 cm$^{-1}$.

Reference Example 117

Into a solution of methyl 7-hydroxy-1,1-dioxo-2,3-dihydro-1-benzothiepine-4-carboxylate (400 mg), 2-(2-propoxyethoxy)benzyl alcohol (0.63 g) and triphenylphosphine (782 mg) in THF (10 ml) was added at 0° C. diethyl azodicarboxylate (a 40% solution in toluene, 1.36 ml), and the resulting mixture was stirred at room temperature for 20 hours. After concentration under reduced pressure, the residue was subjected to separation and purification using column chromatography (ethyl acetate/hexane 1:2) to obtain crude methyl 7-[[2-(2-propoxyethoxy)benzyl]oxy]-1,1-dioxo-2,3-dihydro-1-benzothiepine-4-carboxylate (1.04 g).

Into a solution of crude methyl 7-[[2-(2-propoxyethoxy)benzyl]oxy]-1,1-dioxo-2,3-dihydro-1-benzothiepine-4-carboxylate in THF-methanol (10–5 ml) was added at room temperature an aqueous solution (2.1 ml) of potassium carbonate (622 mg), and the resulting mixture was stirred at 60° C. for 24 hours. After cooling to room temperature, the reaction mixture was extracted with ethyl acetate. To the aqueous layer was added 1 N hydrochloric acid (10 ml), and the resulting mixture was extracted with ethyl acetate. The organic layer was washed with an aqueous saturated solution of sodium chloride, and was dried with magnesium sulfate. The resulting organic layer was concentrated under reduced pressure to obtain 7-[[2-(2-propoxyethoxy)benzyl]oxy]-1,1-dioxo-2,3-dihydro-1-benzothiepine-4-carboxylic acid (136 mg) as a yellow amorphous substance.

$^1$H-NMR (200 MHz, CDCl$_3$) δ0.91 (3H, t, J=7.5 Hz), 1.55–1.65 (2H, m), 3.05–3.12 (2H, m), 3.48 (2H, t, J=6.6 Hz), 3.59–3.66 (2H, m), 3.78–3.83 (2H, m), 4.17–4.24 (2H, m), 5.24 (2H, s), 6.92–7.03 (2H, m), 7.09–7.12 (2H, m), 7.28–7.41 (2H, m), 7.87 (1H, s), 8.09 (1H, d, J=9.4 Hz).

Reference Example 118

A mixture (50 ml) of 4-hydroxybenzyl alcohol (1.5 g), 1-bromopropane (1.3 ml), potassium carbonate (2.5 g) and acetone (50 ml) was stirred at 60° C. for 8 hours. After concentration under reduced pressure, the residue was mixed with water and was extracted with ethyl acetate. The organic layer was washed with a 1N aqueous solution of sodium hydroxide and an aqueous saturated solution of sodium chloride, and was dried with magnesium sulfate. The resulting organic layer was concentrated under reduced pressure to obtain 4-propoxybenzyl alcohol (1.37 g) as a yellow oily substance.

$^1$H-NMR (200 MHz, CDCl$_3$) δ1.04 (3H, t, J=7.3 Hz), 1.52 (1H, t, J=5.4 Hz), 1.72–1.90 (2H, m), 3.93 (2H, t, J=6.6 Hz), 4.62 (2H, d, J=5.4 Hz), 6.89 (2H, d, J=8.8 Hz), 7.29 (2H, d, J=8.8 Hz).

Reference Example 119

Into a solution of methyl 7-hydroxy-1,1-dioxo-2,3-dihydro-1-benzothiepine-4-carboxylate (400 mg), 4-propoxybenzyl alcohol (495 mg) and triphenylphosphine (782 mg) in THF (10 ml) was added at 0° C. diethyl azodicarboxylate (a 40% solution in toluene, 1.36 ml), and the resulting mixture was stirred at room temperature for 64 hours. After concentration under reduced pressure, the residue was subjected to separation and purification using column chromatography (ethyl acetate/hexane 1:2) to obtain methyl 7-[[4-(propoxybenzyl)oxy]-1,1-dioxo-2,3-dihydro-1-benzothiepine-4-carboxylate (500 mg).

Into a solution of methyl 7-[[4-(propoxybenzyl)oxy]-1,1-dioxo-2,3-dihydro-1-benzothiepine-4-carboxylate (500 mg) in THF-methanol (10–5 ml) was added at room temperature an aqueous solution (1.7 ml) of potassium carbonate (498 mg), and the resulting mixture was stirred at 60° C. for 24 hours. After cooling to room temperature, the reaction mixture was extracted with ethyl acetate. To the aqueous layer was added 1 N hydrochloric acid (10 ml), and the resulting mixture was extracted with ethyl acetate. The organic layer was washed with an aqueous saturated solution of sodium chloride and was dried with magnesium sulfate. After concentration under reduced pressure, the precipitated crystals were collected by filtration. The crystals were washed with diisopropyl ether to obtain 7-[(4-(propoxybenzyl)oxy)-1,1-dioxo-2,3-dihydro-1-benzothiepine-4-carboxylic acid (255 mg) as light yellow crystals.

M. p. 250–254° C.

$^1$H-NMR (200 MHz, DMSO-d$_6$) δ0.97 (3H, t, J=7.3 Hz), 1.63–1.81 (2H, m), 2.90 (2H, t, J=6.6 Hz), 3.78 (2H, t, J=6.6 Hz), 3.93 (2H, t, J=6.6 Hz), 5.15 (2H, s), 6.95 (2H, d, J=8.8 Hz), 7.20 (1H, dd, J=8.8, 2.6 Hz), 7.36–7.40 (3H, m), 7.71 (1H, s), 7.93 (1H, d, J=8.8 Hz).

IR (KBr) 3075, 1674, 1597, 1566, 1512, 1416, 1294, 1277, 1163, 1128, 1069 cm$^{-1}$.

Elemental Analysis. Calcd. for $C_{21}H_{22}O_6S$: C, 62.67; H, 5.51. Found: C, 62.36; H, 5.60.

Reference Example 120

Into a solution of 2-ethoxybenzyl alcohol (0.46 g) in THF (10 ml) were added at room temperature thionyl chloride (0.44 ml) and pyridine (one drop), and the resulting mixture was stirred for 2 hours. After concentration under reduced pressure, into a solution of the residue in DMF (10 ml) were added methyl 7-hydroxy-1,1-dioxo-2,3-dihydro-1-benzothiepine-4-carboxylate (400 mg) and potassium carbonate (615 mg), and the resulting mixture was stirred at 60° C. for 20 hours. The reaction mixture was mixed with water and was extracted with ethyl acetate. The organic layer was washed with water and an aqueous saturated solution of sodium chloride, and was dried with magnesium sulfate. After concentration under reduced pressure, the residue was subjected to separation and purification using column chromatography (ethyl acetate:hexane 1:2) to obtain methyl 7-[[2-(ethoxybenzyl)oxy]-1,1-dioxo-2,3-dihydro-1-benzothiepine-4-carboxylate (249 mg) as orange crystals.

Into a solution of methyl 7-[(2-ethoxybenzyl)oxy]-1,1-dioxo-2,3-dihydro-1-benzothiepine-4-carboxylate (220 mg) in THF-methanol (5–2.5 ml) was added at room temperature an aqueous solution (1.0 ml) of potassium carbonate (151 mg), and the resulting mixture was stirred at 60° C. for 20 hours. After cooling to room temperature, the reaction mixture was mixed with 1 N hydrochloric acid (10 ml) and was extracted with ethyl acetate. The organic layer was washed with an aqueous saturated solution of sodium chloride and was dried with magnesium sulfate. After concentration under reduced pressure, the precipitated crystals were collected by filtration. The crystals were washed with diisopropyl ether to obtain 7-[(2-ethoxybenzyl)oxy]-1,1-dioxo-2,3-dihydro-1-benzothiepine-4-carboxylic acid (156 mg) as colorless crystals.

M. p. 158–160° C.

$^1$H-NMR (200 MHz, DMSO-$d_6$) δ1.32 (3H, t, J=6.9 Hz), 2.87–2.93 (2H, m), 3.65–3.71 (2H, m), 4.10 (2H, q, J=6.9 Hz), 5.19 (2H, s), 6.92–7.07 (2H, m), 7.20 (1H, dd, J=8.6, 2.6 Hz), 7.30–7.41 (3H, m), 7.72 (1H, s), 7.94 (1H, d, J=8.6 Hz).

IR (KBr) 3076, 1690, 1591, 1564, 1494, 1292, 1281, 1246, 1165, 1128, 1069 cm$^{-1}$.

Elemental Analysis. Calcd. for $C_{22}H_{20}O_6S.0.2 H_2O$: C, 61.27; H, 5.24. Found: C, 61.18; H, 5.17.

Reference Example 121

Into a solution of 2-methoxybenzyl alcohol (0.42 g) in THF (10 ml) were added at room temperature thionyl chloride (0.44 ml) and pyridine (one drop), and the resulting mixture was stirred for one hour. After concentration under reduced pressure, into a solution of the residue in DMF (10 ml) was added methyl 7-hydroxy-1,1-dioxo-2,3-dihydro-1-benzothiepine-4-carboxylate (400 mg) and potassium carbonate (830 mg), and the resulting mixture was stirred at 60° C. for 16 hours. The reaction mixture was mixed with water and was extracted with ethyl acetate. The organic layer was washed with water and an aqueous saturated solution of sodium chloride, and was dried with magnesium sulfate. After concentration under reduced pressure, the residue was subjected to separation and purification using column chromatography (ethyl acetate:hexane 1:2) to obtain methyl 7-[[2-(ethoxybenzyl)oxy]-1,1-dioxo-2,3-dihydro-1-benzothiepine-4-carboxylate (250 mg) as orange crystals.

Into a solution of methyl 7-[(2-methoxybenzyl)oxy]-1,1-dioxo-2,3-dihydro-1-benzothiepine-4-carboxylate (230 mg) in THF-methanol (5–2.5 ml) was added at room temperature an aqueous solution (1.0 ml) of potassium carbonate (164 mg), and the resulting mixture was stirred at 60° C. for 20 hours. After cooling to room temperature, the reaction mixture was mixed with 1 N hydrochloric acid (10 ml) and was extracted with ethyl acetate. The organic layer was washed with an aqueous saturated solution of sodium chloride and was dried with magnesium sulfate. After concentration under reduced pressure, the precipitated crystals were collected by filtration. The crystals were washed with diisopropyl ether to obtain 7-[(2-methoxybenzyl)oxy]-1,1-dioxo-2,3-dihydro-1-benzothiepine-4-carboxylic acid (172 mg) as colorless crystals.

M. p. 168–171° C.

$^1$H-NMR (200 MHz, DMSO-$d_6$) δ2.90 (2H, t, J=6.4 Hz), 3.68 (2H, t, J=6.4 Hz), 3.83 (3H, s), 5.19 (2H, s), 6.98 (1H, t, J=7.3 Hz), 7.07 (1H, d, J=7.8 Hz), 7.21 (1H, dd, J=8.8, 2.4 Hz), 7.32–7.44 (3H, m), 7.73 (1H, S), 7.94 (1H, d, J=8.8 Hz).

IR (KBr) 3185, 1676, 1588, 1497, 1325, 1296, 1283, 1252, 1165, 1128 cm$^{-1}$.

Elemental Analysis. Calcd. for $C_{19}H_{18}O_6S.0.25 H_2O$: C, 60.23; H, 4.92. Found: C, 60.02; H, 5.20.

Reference Example 122

A mixture of methyl 7-hydroxy-1,1-dioxo-2,3-dihydro-1-benzothiepine-4-carboxylate (400 mg), 2-chlorobenzyl chloride (0.25 ml), potassium carbonate (309 mg) and DMF (10 ml) was stirred at 60° C. for 5 hours. The reaction mixture was mixed with water and was extracted with ethyl acetate. The organic layer was washed with an aqueous saturated solution of sodium chloride and was dried with magnesium sulfate. After concentration under reduced pressure, the residue was subjected to separation and purification using column chromatography (ethyl acetate/hexane 1:2) to obtain methyl 7-[(2-chlorobenzyl)oxy]-1,1-dioxo-2,3-dihydro-1-benzothiepine-4-carboxylate (413 mg) as colorless crystals.

M. p. 182–184° C.

$^1$H-NMR (200 MHz, CDCl$_3$) δ3.04–3.11 (2H, m), 3.59–3.66 (2H, m), 3.86 (3H, s), 5.25 (2H, s), 7.04–7.09 (2H, m), 7.29–7.36 (2H, m), 7.40–7.53 (2H, m), 7.79 (1H, s), 8.12 (1H, d, J=8.4 Hz).

IR (KBr) 1701, 1588, 1433, 1329, 1312, 1285, 1260, 1167, 1128 cm$^{-1}$.

Elemental Analysis. Calcd. for $C_{19}H_{17}O_5SCl$: C, 58.09; H, 4.36. Found: C, 57.84; H, 4.42.

Reference Example 123

Into a solution of methyl 7-[(2-chlorobenzyl)oxy]-1,1-dioxo-2,3-dihydro-1-benzothiepine-4-carboxylate (350 mg) in THF-methanol (7–3.5 ml) was added at room temperature a 2 M aqueous solution of potassium carbonate (0.9 mg), and the resulting mixture was stirred at 65° C. for 20 hours. After cooling to room temperature, the reaction mixture was mixed with 1 N hydrochloric acid (10 ml) and was extracted with ethyl acetate. The organic layer was washed with an aqueous saturated solution of sodium chloride and was dried with magnesium sulfate. After concentration under reduced pressure, the precipitated crystals were collected by filtration. The crystals were washed with diisopropyl ether to obtain 7-[(2-chlorobenzyl)oxy]-1,1-dioxo-2,3-dihydro-1-benzothiepine-4-carboxylic acid (303 mg) as colorless crystals.

M. p. 238–241° C.

$^1$H-NMR (200 MHz, DMSO-$d_6$) δ2.88 (2H, m), 3.66–3.73 (2H, m), 5.30 (2H, s), 7.25 (1H, dd, J=8.8, 2.6 Hz), 7.40–7.66 (5H, m), 7.74 (1H, s), 7.97 (1H, d, J=8.8 Hz).

IR (KBr) 3086, 1672, 1590, 1318, 1296, 1260, 1167, 1127 cm$^{-1}$.

Elemental Analysis. Calcd. for $C_{18}H_{15}O_5SCl$: C, 57.07; H, 3.99. Found: C, 56.81; H, 4.12.

Reference Example 124

A mixture of 2-hydroxybenzyl alcohol (2.00 g), 2-bromoethyl ethyl ether (2.7 ml), potassium carbonate (4.45 g) and DMF (20 ml) was stirred at 90° C. for 3 days.

The reaction mixture was mixed with water and was extracted with ethyl acetate. The organic layer was washed with a 1 N aqueous solution of sodium hydroxide and an aqueous saturated solution of sodium chloride, and was dried with magnesium sulfate. After concentration under reduced pressure, the residue was subjected to purification using column chromatography (ethyl acetate:hexane 1:2) to obtain 2-(2-ethoxyethoxy)benzyl alcohol (2.30 g) as a light yellow oily substance.

$^1$H-NMR (200 MHz, CDCl$_3$) δ1.23 (3H, t, J=7.0 Hz), 3.58 (2H, q, J=7.0 Hz), 3.76–3.81 (2H, m), 4.19–4.24 (2H, m), 4.67 (2H, s), 6.89–6.99 (2H, m), 7.22–7.31 (2H, m)

IR (neat): 3441, 1603, 1590, 1493, 1453, 1244, 1119, 1049 cm$^{-1}$.

Reference Example 125

Into a solution of 2-(2-ethoxyethoxy)benzyl alcohol (0.60 g) in toluene (5 ml) were added at room temperature thionyl chloride (0.33 ml) and pyridine (one drop), and the resulting mixture was stirred for one hour. The reaction mixture was mixed with water and was extracted with ethyl acetate. The organic layer was washed with an aqueous saturated solution of sodium chloride and was dried with magnesium sulfate. After concentration under reduced pressure, into a solution of the residue in DMF (10 ml) were added methyl 7-hydroxy-1,1-dioxo-2,3-dihydro-1-benzothiepine-4-carboxylate (400 mg) and potassium carbonate (415 mg), and the resulting mixture was stirred at 65° C. for 3 hours. The reaction mixture was mixed with water and was extracted with ethyl acetate. The organic layer was washed with water and an aqueous saturated solution of sodium chloride, and was dried with magnesium sulfate. After concentration under reduced pressure, the residue was subjected to separation and purification using column chromatography (ethyl acetate:hexane 1:2→1:1) to obtain methyl 7-[[2-(2-ethoxyethoxy)benzyl]oxy]-1,1-dioxo-2,3-dihydro-1-benzothiepine-4-carboxylate (0.64 g) as a light yellow, oily substance.

Into a solution of methyl 7-[[2-(2-ethoxyethoxy)benzyl]oxy]-1,1-dioxo-2,3-dihydro-1-benzothiepine-4-carboxylate (0.64 g) in THF-methanol (6–3 ml) was added at room temperature a 1 M aqueous solution of potassium carbonate (2.9 ml), and the resulting mixture was stirred at 60° C. for 20 hours. After cooling to room temperature, the reaction mixture was extracted with ethyl acetate. To the aqueous layer was added 1 N hydrochloric acid (10 ml), and the resulting mixture was extracted with ethyl acetate. The organic layer was washed with an aqueous saturated solution of sodium chloride and was dried with magnesium sulfate. After concentration under reduced pressure, the precipitated crystals were collected by filtration. The crystals were washed with diisopropyl ether to obtain 7-[[2-(2-ethoxyethoxy)benzyl]oxy]-1,1-dioxo-2,3-dihydro-1-benzothiepine-4-carboxylic acid (385 mg) as light yellow crystals.

M. p. 134–136° C.

$^1$H-NMR (200 MHz, DMSO-d$_6$) δ1.04 (3H, t, J=7.0 Hz), 2.90 (2H, t, J=6.4 Hz), 3.46 (2H, q, J=7.0 Hz), 3.65–3.71 (4H, m), 4.14–4.18 (2H, m), 5.20 (2H, s), 6.95–7.10 (2H, m), 7.21 (1H, dd, J=8.8, 2.6 Hz), 7.30–7.44 (3H, m), 7.72 (1H, s), 7.94 (1H, d, J=8.8 Hz).

IR (KBr) 3447, 1686, 1622, 1586, 1281, 1250, 1163, 1127 cm$^{-1}$.

Elemental Analysis. Calcd. for C$_{22}$H$_{24}$O$_7$S: C, 61.10; H, 5.59. Found: C, 60.90; H, 5.72.

Reference Example 126

A mixture of 2-hydroxyphenethyl alcohol (1.50 g), bromopropane (1.3 ml, 14.9 mmol), potassium carbonate (2.25 g) and acetone (50 ml) was heated at reflux for 3 days. After concentration under reduced pressure, the residue was mixed with water and was extracted with ethyl acetate. The organic layer was washed with a 1 N aqueous solution of sodium hydroxide and an aqueous saturated solution of sodium chloride, and was dried with magnesium sulfate. The resulting organic layer was concentrated under reduced pressure to obtain 3-propoxyphenethyl alcohol (1.70 g) as a light yellow, oily substance.

$^1$H-NMR (200 MHz, CDCl$_3$) δ1.04 (3H, t, J=7.3 Hz), 1.40 (1H, t, J=5.8 Hz), 1.72–1.80 (2H, m), 2.84 (2H, t, J=6.4 Hz), 3.82–3.95 (4H, m), 6.74–6.82 (3H, m), 7.18–7.26 (1H, m).

IR (neat) 3289, 1601, 1583, 1487, 1449, 1392, 1259, 1157, 1047, 779, 696 cm$^{-1}$.

Reference Example 127

Into a solution of 3-propoxyphenethyl alcohol (0.54 g) and triethylamine (0.84 ml) in THF (10 ml) was added at 0° C. methanesulfonyl chloride (0.35 ml), and the resulting mixture was stirred for one hour. The reaction mixture was mixed with water and was extracted with ethyl acetate. The organic layer was washed with an aqueous saturated solution of sodium chloride and was dried with magnesium sulfate. After concentration under reduced pressure, into a solution of the residue in DMF (10 ml) were added methyl 7-hydroxy-1,1-dioxo-2,3-dihydro-1-benzothiepine-4-carboxylate (400 mg) and potassium carbonate (0.48 g), and the resulting mixture was stirred at 70° C. for 5 hours. The reaction mixture was mixed with water and was extracted with ethyl acetate. The organic layer was washed with an aqueous saturated solution of sodium chloride and was dried with magnesium sulfate. After concentration under reduced pressure, the residue was subjected to separation and purification using column chromatography (ethyl acetate/hexane 1:2) to obtain methyl 7-[(3-(propoxyphenethyl)oxy)-1,1-dioxo-2,3-dihydro-1-benzothiepine-4-carboxylate (0.42 g) as a light yellow, oily substance.

Into a solution of methyl 7-[(3-(propoxyphenethyl)oxy)-1,1-dioxo-2,3-dihydro-1-benzothiepine-4-carboxylate (0.42 g) in THF-methanol (10–5 ml) was added at room temperature a 1 M aqueous solution of potassium carbonate (2 ml), and the resulting mixture was stirred at 65° C. for 24 hours. After cooling to room temperature, 1 N hydrochloric acid was added to the reaction mixture, which was extracted with ethyl acetate. The organic layer was washed with an aqueous saturated solution of sodium chloride and was dried with magnesium sulfate. After concentration under reduced pressure, the precipitated crystals were collected by filtration. The crystals were washed with hexane to obtain the objective substance (291 mg) as brown crystals.

M. p. 86–88° C.

$^1$H-NMR (200 MHz, DMSO-d$_6$) δ0.97 (3H, t, J=7.3 Hz), 1.63–1.81 (2H, m), 2.89 (2H, t, J=7.0 Hz), 3.03 (2H, t, J=6.8 Hz), 3.67 (2H, t, J=6.8 Hz), 3.91 (2H, t, J=6.4 Hz), 4.33 (2H, t, J=7.0 Hz), 6.76–6.81 (1H, m), 6.86–6.90 (2H, m), 7.12–7.25 (2H, m), 7.34 (1H, d, J=2.6 Hz), 7.92 (1H, d, J=8.8 Hz).

IR (KBr) 3466, 1682, 1588, 1291, 1260, 1161, 1127, 1067 cm$^{-1}$.

Elemental Analysis. Calcd. for C$_{22}$H$_{24}$O$_6$S.0.25 H$_2$O: C, 62.77; H, 5.87. Found: C, 62.66; H, 5.83.

Reference Example 128

A mixture of 2-hydroxyphenethyl alcohol (1.5 g), 1-bromopropane (1.3 ml), potassium carbonate (2.25 g) and acetone (50 ml) was stirred at 60° C. for 64 hours. After concentration under reduced pressure, the residue was mixed with water and was extracted with ethyl acetate. The organic layer was washed with a 1 N aqueous solution of sodium hydroxide and an aqueous saturated solution of sodium chloride, and was dried with magnesium sulfate. The resulting organic layer was concentrated under reduced pressure to obtain 2-propoxyphenethyl alcohol (2.02 g) as a yellow oily substance.

$^1$H-NMR (200 MHz, CDCl$_3$) δ1.06 (3H, t, J=7.5 Hz), 1.68–1.92 (3H, m), 2.93 (2H, t, J=6.4 Hz), 3.81–3.87 (2H, m), 3.95 (2H, t, J=6.4 Hz), 6.84–6.94 (2H, m), 7.15–7.25 (2H, m).

IR (neat) 3343, 1601, 1494, 1474, 1454, 1242, 1119, 1049, 1019, 982, 752 cm$^{-1}$.

Reference Example 129

Into a solution of 2-propoxyphenethyl alcohol (0.54 g) and triethylamine (0.84 ml) in THF (10 ml) was added at 0° C. methanesulfonyl chloride (0.35 ml), and the resulting mixture was stirred for 1.5 hour. The reaction mixture was mixed with water and was extracted with ethyl acetate. The organic layer was washed with an aqueous saturated solution of sodium chloride and was dried with magnesium sulfate. After concentration under reduced pressure, into a solution of the residue in DMF (10 ml) were added methyl 7-hydroxy-1,1-dioxo-2,3-dihydro-1-benzothiepine-4-carboxylate (400 mg) and potassium carbonate (414 mg), and the resulting mixture was stirred at 60° C. for 22 hours. The reaction mixture was mixed with water and was extracted with ethyl acetate. The organic layer was washed with an aqueous saturated solution of sodium chloride and was dried with magnesium sulfate. After concentration under reduced pressure, the residue was subjected to separation and purification using column chromatography (ethyl acetate/hexane 1:2) to obtain methyl 7-[(2-(propoxyphenethyl)oxy)-1,1-dioxo-2,3-dihydro-1-benzothiepine-4-carboxylate (0.31 g) as a light yellow, oily substance.

Into a solution of methyl 7-[(2-(propoxyphenethyl)oxy)-1,1-dioxo-2,3-dihydro-1-benzothiepine-4-carboxylate (0.31 g) in THF-methanol (10–5 ml) was added at room temperature a 1 M aqueous solution of potassium carbonate (1.5 ml), and the resulting mixture was stirred at 65° C. for 24 hours. After cooling to room temperature, the reaction mixture was extracted with ethyl acetate. To the aqueous layer was added 1 N hydrochloric acid (10 ml), and the resulting mixture was extracted with ethyl acetate. The organic layer was washed with an aqueous saturated solution of sodium chloride and was dried with magnesium sulfate. After concentration under reduced pressure, the precipitated crystals were collected by filtration. The crystals were washed with diisopropyl ether to obtain 7-[(2-(propoxyphenethyl)oxy)-1,1-dioxo-2,3-dihydro-1-benzothiepine-4-carboxylic acid (136 mg) as colorless crystals.

M. p. 184–186° C.

$^1$H-NMR (200 MHz, DMSO-d$_6$) δ0.99 (3H, t, J=7.5 Hz), 1.65–1.81 (2H, m), 2.85–2.94 (2H, m), 3.01–3.09 (2H, m), 3.62–3.70 (2H, m), 3.96 (2H, t, J=6.4 Hz), 4.25–4.32 (2H, m), 6.83–6.98 (2H, m), 7.12–7.32 (4H, m), 7.72 (1H, s), 7.92 (1H, d, J=8.8 Hz).

IR (KBr) 1674, 1588, 1291, 1252, 1167, 1127 cm$^{-1}$.

Elemental Analysis. Calcd. for $C_{22}H_{24}O_6S$: C, 63.44; H, 5.81. Found: C, 63.06; H, 5.97.

Reference Example 130

A mixture of 4-hydroxybenzyl alcohol (3.00 g), 2-bromoethyl ethyl ether (4.1 ml), potassium carbonate (6.68 g) and DMF (30 ml) was stirred at 90° C. for 3 days. The reaction mixture was mixed with water and was extracted with ethyl acetate. The organic layer was washed with a 1 N aqueous solution of sodium hydroxide and an aqueous saturated solution of sodium chloride, and was dried with magnesium sulfate. After concentration under reduced pressure, the residue was subjected to separation and purification using column chromatography (ethyl acetate/hexane 1:2→1:1) to obtain 4-(2-ethoxyethoxy) benzyl alcohol (2.45 g) as a light yellow, oily substance.

$^1$H-NMR (200 MHz, CDCl$_3$) δ1.25 (3H, t, J=7.0 Hz), 1.56 (1H, t, J=5.4 Hz), 3.61 (2H, q, J=7.0 Hz), 3.77–3.82 (2H, m), 4.10–4.15 (2H, m), 4.62 (2H, d, J=5.4 Hz), 6.92 (2H, d, J=8.6 Hz), 7.29 (2H, d, J=8.6 Hz).

IR (neat) 3385, 1613, 1514, 1248, 1175, 1117, 1065 cm$^{-1}$.

Reference Example 131

Into a solution of 4-(2-ethoxyethoxy)benzyl alcohol (0.60 g) in toluene (5 ml) were added at room temperature thionyl chloride (0.33 ml) and pyridine (one drop), and the resulting mixture was stirred for 2 hours. The reaction mixture was mixed with water and was extracted with ethyl acetate. The organic layer was washed with an aqueous solution of sodium bicarbonate and an aqueous saturated solution of sodium chloride, and was dried with magnesium sulfate. After concentration under reduced pressure, into a solution of the residue in DMF (10 ml) were added methyl 7-hydroxy-1,1-dioxo-2,3-dihydro-1-benzothiepine-4-carboxylate (400 mg) and potassium carbonate (414 mg), and the resulting mixture was stirred at 70° C. for 3 hours. The reaction mixture was mixed with water and was extracted with ethyl acetate. The organic layer was washed with an aqueous saturated solution of sodium chloride and was dried with magnesium sulfate. After concentration under reduced pressure, the residue was subjected to separation and purification using column chromatography (ethyl acetate:hexane 1:2) to obtain methyl 7-[[4-(2-ethoxyethoxy) benzyl]oxy]-1,1-dioxo-2,3-dihydro-1-benzothiepine-4-carboxylate (0.59 g) as a light yellow, oily substance.

Into a solution of methyl 7-[[4-(2-ethoxyethoxy)benzyl] oxy]-1,1-dioxo-2,3-dihydro-1-benzothiepine-4-carboxylate (0.59 g) in THF-methanol (10–5 ml) was added at room temperature a 1 M aqueous solution of potassium carbonate (2.6 ml), and the resulting mixture was stirred at 65° C. for 24 hours. Into this reaction mixture was added further a 1 M aqueous solution of potassium carbonate (1.3 ml), and the resulting mixture was stirred at 65° C. for 16 hours. After cooling to room temperature, the reaction mixture was extracted with ethyl acetate. To the aqueous layer was added 1 N hydrochloric acid (10 ml), and the resulting mixture was extracted with ethyl acetate. The organic layer was washed with an aqueous saturated solution of sodium chloride and was dried with magnesium sulfate. After concentration under reduced pressure, the precipitated crystals were collected by filtration. The crystals were washed with diisopropyl ether to obtain 7-[[4-(2-ethoxyethoxy)benzyl]oxy]-1,1-dioxo-2,3-dihydro-1-benzothiepine-4-carboxylic acid (215 mg) as light yellow crystals.

M. p. 256–258° C.

$^1$H-NMR (200 MHz, DMSO-d$_6$) δ1.14 (3H, t, J=7.0 Hz), 2.90 (2H, t, J=6.2 Hz), 3.50 (2H, q, J=7.0 Hz), 3.65–3.71 (4H, m), 4.07–4.11 (2H, m), 5.16 (2H, s), 6.97 (2H, d, J=8.4 Hz), 7.21 (1H, dd, J=8.8, 2.6 Hz), 7.37–7.41 (3H, m), 7.72 (1H, s), 7.93 (1H, d, J=8.8 Hz)

IR (KBr) 3073, 1672, 1620, 1595, 1566, 1512, 1415, 1292, 1269, 1223, 1161, 1128, 1067 cm$^{-1}$.

Reference Example 132

A mixture of 4-hydroxybenzyl alcohol (3.00 g), 2-bromoethyl propyl ether (4.0 ml), sodium iodide (4.75 g), potassium carbonate (6.68 g) and DMF (30 ml) was stirred at 90° C. for 3 days. The reaction mixture was mixed with water, and was extracted with ethyl acetate. The organic layer was washed with water and an aqueous saturated solution of sodium chloride, and was dried with magnesium sulfate. After concentration under reduced pressure, the residue was subjected to separation and purification using column chromatography (ethyl acetate:hexane 1:2→1:1) to obtain 4-(2-propoxyethoxy)benzyl alcohol (2.27 g) as a light yellow, oily substance.

$^1$H-NMR (200 MHz, CDCl$_3$) δ0.93 (3H, t, J=7.5 Hz), 1.52–1.69 (3H, m), 3.50 (2H, t, J=6.8 Hz), 3.79 (2H, t, J=4.9 Hz), 4.13 (2H, t, J=4.9 Hz), 4.62 (2H, d, J=6.0 Hz), 6.92 (2H, d, J=8.6 Hz), 7.28 (2H, d, J=8.6 Hz).

IR (neat) 3382, 1613, 1586, 1514, 1456, 1302, 1246, 1175, 1125, 1065, 1022, 1069, 993, 824 cm$^{-1}$.

Reference Example 133

Into a solution of 4-(2-propoxyethoxy)benzyl alcohol (0.63 g) in toluene (5 ml) were added at room temperature thionyl chloride (0.33 ml) and pyridine (one drop), and the resulting mixture was stirred for 1.5 hours. The reaction mixture was mixed with water and was extracted with ethyl acetate. The organic layer was washed with an aqueous solution of sodium bicarbonate and an aqueous saturated solution of sodium chloride, and was dried with magnesium sulfate. After concentration under reduced pressure, into a solution of the residue in DMF (10 ml) were added methyl 7-hydroxy-1,1-dioxo-2,3-dihydro-1-benzothiepine-4-carboxylate (400 mg) and potassium carbonate (414 mg), and the resulting mixture was stirred at 65° C. for 2 hours. The reaction mixture was mixed with water and was extracted with ethyl acetate. The organic layer was washed with an aqueous saturated solution of sodium chloride and was dried with magnesium sulfate. After concentration under reduced pressure, the residue was subjected to separation and purification using column chromatography (ethyl acetate:hexane=1:2) to obtain methyl 7-[[4-(2-propoxyethoxy)benzyl]oxy]-1,1-dioxo-2,3-dihydro-1-benzothiepine-4-carboxylate (0.54 g) as a light yellow, oily substance.

Into a solution of methyl 7-[[4-(2-propoxyethoxy)benzyl]oxy]-1,1-dioxo-2,3-dihydro-1-benzothiepine-4-carboxylate (0.54 g) in THF-methanol (10–5 ml) was added at room temperature 2.4 ml of a 1 M aqueous solution of potassium carbonate (2.6 mmol), and the resulting mixture was stirred at 65° C. for 20 hours. After cooling to room temperature, the reaction mixture was extracted with ethyl acetate. To the aqueous layer was added 1 N hydrochloric acid (10 ml), and the resulting mixture was extracted with ethyl acetate. The organic layer was washed with an aqueous saturated solution of sodium chloride and was dried with magnesium sulfate. After concentration under reduced pressure, the precipitated crystals were collected by filtration. The crystals were washed with diisopropyl ether to obtain 7-[[4-(2-propoxyethoxy)benzyl]oxy]-1,1-dioxo-2,3-dihydro-1-benzothiepine-4-carboxylic acid (321 mg) as light yellow crystals.

M. p. 244–250° C.

$^1$H-NMR (200 MHz, DMSO-d$_6$) δ0.87 (3H, t, J=7.5 Hz), 1.44–1.61 (2H, m), 2.90 (2H, t, J=6.7 Hz), 3.41 (2H, t, J=6.6 Hz), 3.64–3.72 (4H, m), 4.07–4.12 (2H, m), 5.16 (2H, s), 6.97 (2H, d, J=8.4 Hz), 7.20 (1H, dd, J=8.4, 2.4 Hz), 7.37–7.41 (3H, m), 7.72 (1H, s), 7.93 (1H, d, J=8.4 Hz).

IR (KBr) 3418, 1688, 1615, 1588, 1566, 1514, 1417, 1292, 1250, 1163, 1128 cm$^{-1}$.

Elemental Analysis. Calcd. for C$_{23}$H$_{26}$O$_7$S.0.5 H$_2$O: C, 60.65; H, 5.97. Found: C, 60.61; H, 5.75.

Reference Example 134

To protocatechualdehyde (4.45 g) dissolved in dimethylformamide (65 ml) were added 1-propylbromide (9.91 g) and potassium carbonate (13.4 g), and the resulting mixture was stirred at room temperature for 19 hours. The reaction mixture was diluted with ethyl acetate, washed respectively with water, a 1 N aqueous solution of sodium hydroxide, water and an aqueous saturated solution of sodium chloride, and the organic layer was dried with anhydrous magnesium sulfate. After concentration under reduced pressure to remove the solvent, the residue was subjected to purification using silica gel column chromatography (hexane:ethyl acetate=4:1) to obtain 3,4-dipropoxybenzaldehyde (6.72 g) as a yellow oil.

$^1$H-NMR (200 MHz, CDCl$_3$) δ1.06 (3H, t, J=7.5 Hz), 1.07 (3H, t, J=7.4 Hz), 1.88 (2H, sextet, J=7.1 Hz), 1.89 (2H, sextet, J=7.1 Hz), 4.03 (2H, t, J=6.6 Hz), 4.05 (2H, t, J=6.6 Hz), 6.96 (1H, d, J=8.4 Hz), 7.40 (1H, s), 7.42 (1H, dd, J=8.4, 2.0 Hz), 9.83 (1H, s).

Reference Example 135

To a mixture of 3,4-dipropoxybenzaldehyde (6.65 g) and methanol (90 ml) was added sodium borohydride (1.13 g) at 0° C. The resulting mixture was stirred at 0° C. for 30 minutes. The reaction mixture was mixed with water and was extracted with ethyl acetate. The organic layer was washed with an aqueous saturated solution of sodium chloride and was dried with anhydrous magnesium sulfate. The solvent was evaporated under reduced pressure to obtain 3,4-dipropoxybenzyl alcohol (6.22 g) as a yellow oily substance.

$^1$H-NMR (200 MHz, CDCl$_3$) δ1.040 (3H, t, J=7.5 Hz), 1.044 (3H, t, J=7.4 Hz), 1.60 (1H, br s), 1.84 (2H, sextet, J=7.2 Hz), 1.85 (2H, sextet, J=7.1 Hz), 3.96 (2H, t, J=6.5 Hz), 3.98 (2H, t, J=6.6 Hz), 4.60 (2H, s), 6.86–6.93 (3H, m).

Reference Example 136

Into a solution of 3,4-dipropoxybenzyl alcohol (673 mg) in toluene (5 ml) were added at room temperature thionyl chloride (0.33 ml) and pyridine (one drop), and the resulting mixture was stirred for 2 hours. The reaction mixture was mixed with water and was extracted with ethyl acetate. The organic layer was washed with an aqueous solution of sodium bicarbonate and an aqueous saturated solution of sodium chloride, and was dried with magnesium sulfate. After concentration under reduced pressure, into a solution of the residue in DMF (10 ml) were added methyl 7-hydroxy-1,1-dioxo-2,3-dihydro-1-benzothiepine-4-carboxylate (400 mg) and potassium carbonate (414 mg), and the resulting mixture was stirred at 70° C. for 5 hours. The reaction mixture was mixed with water and was extracted with ethyl acetate. The organic layer was washed with an aqueous saturated solution of sodium chloride and was dried with magnesium sulfate. After concentration under reduced pressure, the residue was subjected to separation and purification using column chromatography (ethyl acetate:hexane 1:2) to obtain methyl 7-[3,4-dipropoxy]

benzyl]oxy]-1,1-dioxo-2,3-dihydro-1-benzothiepine-4-carboxylate (0.45 g) as a light yellow, oily substance.

Into a solution of methyl 7-[3,4-dipropoxy]benzyl]oxy]-1,1-dioxo-2,3-dihydro-1-benzothiepine-4-carboxylate (0.45 g) in THF-methanol (5–2.5 ml) was added at room temperature a 1 M aqueous solution of potassium carbonate (2.0 ml), and the resulting mixture was stirred at 65° C. for 24 hours. After cooling to room temperature, 1 N hydrochloric acid (10 ml) was added to the reaction mixture, which was extracted with ethyl acetate. The organic layer was washed with an aqueous saturated solution of sodium chloride and was dried with magnesium sulfate. After concentration under reduced pressure, the precipitated crystals were collected by filtration. The crystals were washed with diisopropyl ether to obtain 7-[(3,4-dipropoxy)benzyl]oxy]-1,1-dioxo-2,3-dihydro-1-benzothiepine-4-carboxylic acid (306 mg) as colorless crystals.

M. p. 147–150° C.

$^1$H-NMR (200 MHz, DMSO-d$_6$) δ0.98 (6H, t, J=7.6 Hz), 1.63–1.81 (4H, m), 2.69–2.93 (2H, m), 3.64–3.71 (2H, m), 3.92 (2H, t, J=6.6 Hz), 3.93 (2H, t, J=6.4 Hz), 5.14 (2H, s), 6.90–7.02 (2H, m), 7.07 (1H, s), 7.20 (1H, dd, J=8.8, 2.6 Hz), 7.41 (1H, d, J=2.6 Hz), 7.72 (1H, s), 7.94 (1H, d, J=8.8 Hz).

IR (KBr) 3076, 1674, 1593, 1566, 1512, 1294, 1275, 1256, 1163, 1128, 1067 cm$^{-1}$.

Elemental Analysis. Calcd. for $C_{24}H_{28}O_7S$: C, 62.59; H, 6.13. Found: C, 62.36; H, 6.14.

Reference Example 137

A mixture of ethyl vanillin (5.0 g), 2-chloroethyl propyl ether (4.6 ml), sodium iodide (5.46 g), potassium carbonate (6.23 g) and DMF (50 ml) was stirred at 90° C. for 3 days. The reaction mixture was mixed with water and was extracted with ethyl acetate. The organic layer was washed with water and an aqueous saturated solution of sodium chloride, and was dried with magnesium sulfate. After concentration under reduced pressure, the residue was subjected to separation and purification using column chromatography (ethyl acetate:hexane 1:2) to obtain 3-ethoxy-4-(2-propoxyethoxy)benzaldehyde (7.34 g) as a light yellow, oily substance.

$^1$H-NMR (200 MHz, CDCl$_3$) δ0.93 (3H, t, J=7.4 Hz), 1.47 (3H, t, J=7.0 Hz), 1.53–1.70 (2H, m), 3.53 (2H, t, J=6.7 Hz), 3.86 (2H, t, J=5.0 Hz), 4.14 (2H, q, J=7.0 Hz), 4.26 (2H, t, J=5.0 Hz), 7.02 (1H, d, J=8.0 Hz), 7.40–7.45 (2H, m), 9.84 (1H, s).

IR (neat) 1686, 1586, 1508, 1435, 1395, 1265, 1132, 1042 cm$^{-1}$.

Reference Example 138

Into a solution of 3-ethoxy-4-(2-propoxyethoxy)benzaldehyde (7.34 g) in methanol (30 ml) was added at 0° C. sodium borohydride (1.10 g), and the resulting mixture was stirred for one hour. After concentration under reduced pressure, 1 N hydrochloric acid was added to the reaction mixture, which was extracted with ethyl acetate. The organic layer was washed with an aqueous saturated solution of sodium chloride and was dried with magnesium sulfate. The resulting organic layer was concentrated under reduced pressure to obtain 3-ethoxy-4-(2-propoxyethoxy)benzyl alcohol (7.35 g) as a colorless oily substance.

$^1$H-NMR (200 MHz, CDCl$_3$) δ0.93 (3H, t, J=7.3 Hz), 1.44 (3H, t, J=6.9 Hz), 1.62–1.71 (3H, m), 3.51 (2H, t, J=6.6 Hz), 3.81 (2H, t, J=5.1 Hz), 4.04–4.19 (4H, m), 4.61 (2H, d, J=5.8 Hz), 6.83–6.94 (3H, m).

IR (neat) 3418, 1514, 1427, 1262, 1233, 1136, 1044 cm$^{-1}$.

Reference Example 139

Into a solution of 3-ethoxy-4-(2-propoxyethoxy)benzyl alcohol (0.76 g) in toluene (5 ml) were added at room temperature thionyl chloride (0.33 ml) and pyridine (one drop), and the resulting mixture was stirred for 2 hours. The reaction mixture was mixed with water and was extracted with ethyl acetate. The organic layer was washed with an aqueous solution of sodium bicarbonate and an aqueous saturated solution of sodium chloride, and was dried with magnesium sulfate. After concentration under reduced pressure, into a solution of the residue in DMF (10 ml) were added methyl 7-hydroxy-1,1-dioxo-2,3-dihydro-1-benzothiepine-4-carboxylate (400 mg) and potassium carbonate (414 mg), and the resulting mixture was stirred at 70° C. for 2 hours. The reaction mixture was mixed with water and was extracted with ethyl acetate. The organic layer was washed with an aqueous saturated solution of sodium chloride and was dried with magnesium sulfate. After concentration under reduced pressure, the residue was subjected to separation and purification using column chromatography (ethyl acetate:hexane 1:2→1:1) to obtain methyl 7-[[3-ethoxy-4-(propoxyethoxy)benzyl]oxy]-1,1-dioxo-2,3-dihydro-1-benzothiepine-4-carboxylate (0.76 g) as a light yellow, oily substance.

Into a solution of methyl 7-[[3-ethoxy-4-(propoxyethoxy)benzyl]oxy]-1,1-dioxo-2,3-dihydro-1-benzothiepine-4-carboxylate (0.76 g) in THF-methanol (10–5 ml) was added at room temperature a 1 M aqueous solution of potassium carbonate (3.0 ml), and the resulting mixture was stirred at 65° C. for 20 hours. After cooling to room temperature, the reaction mixture was extracted with ethyl acetate. To the aqueous layer was added 1 N hydrochloric acid (10 ml), and the resulting mixture was extracted with ethyl acetate. The organic layer was washed with an aqueous saturated solution of sodium chloride and was dried with magnesium sulfate. After concentration under reduced pressure, the precipitated crystals were collected by filtration. The crystals were washed with diisopropyl ether to obtain 7-[[3-ethoxy-4-(2-propoxyethoxy)benzyl]oxy]-1,1-dioxo-2,3-dihydro-1-benzothiepine-4-carboxylic acid (178 mg) as yellow crystals.

$^1$H-NMR (200 MHz, DMSO-d$_6$) δ0.87 (3H, t, J=7.3 Hz), 1.32 (3H, t, J=7.0 Hz), 1.44–1.62 (2H, m), 2.90 (2H, t, J=6.2 Hz), 3.43 (2H, t, J=6.6 Hz), 3.64–3.71 (4H, m), 3.98–4.10 (4H, m), 5.14 (2H, s), 6.94–7.01 (2H, m), 7.08 (1H, s), 7.20 (1H, dd, J=8.8, 2.6 Hz), 7.41 (1H, d, J=2.6 Hz), 7.72 (1H, s), 7.94 (1H, d, J=8.8 Hz).

IR (KBr) 3422, 1674, 1593, 1568, 1514, 1294, 1258, 1163, 1128, 1065 cm$^{-1}$.

Reference Example 140

To a mixture of methyl 7-hydroxy-1,1-dioxo-2,3-dihydro-1-benzothiepine-4-carboxylate (400 mg), 4-propoxyphenylboric acid (536 mg), cupric acetate (271 mg), MS (molecular sieves) 4A (1.0 g) and dichloromethane (15 ml) was added at room temperature triethylamine (1.04 ml), and the resulting mixture was stirred for 20 hours. The reaction mixture was filtered to remove an insoluble material and the filtrate was concentrated under reduced pressure. The residue was subjected to separation and purification using column chromatography (ethyl acetate:hexane 1:2) to obtain methyl 7-(4-propoxyphenoxy)-1,1-dioxo-2,3- dihydro-1-benzothiepine-4-carboxylate (0.31 g) as a light yellow, oily substance.

$^1$H-NMR (200 MHz, CDCl$_3$) δ1.06 (3H, t, J=7.5 Hz), 1.74–1.90 (2H, m), 3.04–3.10 (2H, m), 3.59–3.65 (2H, m), 3.84 (3H, s), 3.94 (2H, t, J=6.4 Hz), 6.91–7.03 (6H, m), 7.70 (1H, s), 8.07 (1H, d, J=8.8 Hz).

IR (neat) 1715, 1590, 1566, 1505, 1472, 1435, 1323, 1294, 1279, 1240, 1202, 1125, 912, 839, 747 cm$^{-1}$.

Reference Example 141

Into a solution of methyl 7-(4-propoxyphenoxy)-1,1-dioxo-2,3-dihydro-1-benzothiepine-4-carboxylate (0.31 g) in THF-methanol (5–2.5 ml) was added at room temperature a 1 M aqueous solution of potassium carbonate (1.5 ml), and the resulting mixture was stirred at 65° C. for 40 hours. After cooling to room temperature, 1 N hydrochloric acid (10 ml) was added to the reaction mixture, which was extracted with ethyl acetate. The organic layer was washed with an aqueous saturated solution of sodium chloride and was dried with magnesium sulfate. After concentration under reduced pressure, the precipitated crystals were collected by filtration. The crystals were washed with diisopropyl ether to obtain 7-(4-propoxyphenoxy)-1,1-dioxo-2,3-dihydro-1-benzothiepine-4-carboxylic acid (226 mg) as light yellow crystals.

M. p. 192–194° C.

$^1$H-NMR (200 MHz, DMSO-d$_6$) δ1.00 (3H, t, J=7.3 Hz), 1.65–1.83 (2H, m), 2.91 (2H, t, J=6.7 Hz), 3.71 (2H, t, J=6.7 Hz), 3.94 (2H, t, J=6.4 Hz), 6.99–7.13 (5H, m), 7.27 (1H, d, J=2.2 Hz), 7.66 (1H, s), 7.98 (1H, d, J=8.8 Hz).

IR (KBr) 1696, 1508, 1472, 1296, 1242, 1202, 1127 cm$^{-1}$.

Elemental Analysis. Calcd. for $C_{22}H_{20}O_6S \cdot 0.5\ H_2O$: C, 60.44; H, 5.33. Found: C, 60.43; H, 5.25.

Reference Example 142

To a mixture of methyl 7-hydroxy-1,1-dioxo-2,3-dihydro-1-benzothiepine-4-carboxylate (400 mg), 3-propoxyphenylboric acid (536 mg), cupric acetate (271 mg), MS 4A (0.8 g) and dichloromethane (15 ml) was added at room temperature triethylamine (1.04 ml), and the resulting mixture was stirred for 17 hours. The reaction mixture was filtered to remove an insoluble material and the filtrate was concentrated under reduced pressure. The residue was subjected to separation and purification using column chromatography (ethyl acetate:hexane 1:2) to obtain methyl 7-(3-propoxyphenoxy)-1,1-dioxo-2,3-dihydro-1-benzothiepine-4-carboxylate (0.39 g) as a light yellow, oily substance.

$^1$H-NMR (200 MHz, CDCl$_3$) δ1.04 (3H, t, J=7.3 Hz), 1.72–1.90 (2H, m), 3.05–3.12 (2H, m), 3.59–3.66 (2H, m), 3.84 (3H, s), 3.91 (2H, t, J=6.6 Hz), 6.60–6.66 (2H, m), 6.76–6.82 (1H, m), 7.04–7.09 (2H, m), 7.26–7.35 (1H, m), 7.12 (1H, s), 8.11 (1H, d, J=9.0 Hz).

IR (neat) 1715, 1609, 1586, 1566, 1487, 1472, 1435, 1321, 1277, 1242, 1215, 1163, 1128, 748 cm$^{-1}$.

Reference Example 143

Into a solution of methyl 7-(3-propoxyphenoxy)-1,1-dioxo-2,3-dihydro-1-benzothiepine-4-carboxylate (0.53 g) in THF-methanol (10–5 ml) was added at room temperature a 1 M aqueous solution of potassium carbonate (2.6 ml), and the resulting mixture was stirred at 65° C. for 40 hours. After cooling to room temperature, 1 N hydrochloric acid (10 ml) was added to the reaction mixture, which was extracted with ethyl acetate. The organic layer was washed with an aqueous saturated solution of sodium chloride and was dried with magnesium sulfate. After concentration under reduced pressure, the precipitated crystals were collected by filtration. The crystals were washed with diisopropyl ether to obtain 7-(3-propoxyphenoxy)-1,1-dioxo-2,3-dihydro-1-benzothiepine-4-carboxylic acid (412 mg) as light yellow crystals.

M. p. 180–181° C.

$^1$H-NMR (200 MHz, DMSO-d$_6$) δ0.97 (3H, t, J=7.3 Hz), 1.63–1.82 (2H, m), 2.88–2.95 (2H, m), 3.69–3.75 (2H, m), 3.93 (2H, t, J=6.4 Hz), 6.65–6.76 (2H, m), 6.81–6.85 (1H, m), 7.11 (1H, dd, J=8.8, 2.6 Hz), 7.31–7.40 (2H, m), 7.68 (1H, s), 8.00 (d, J=8.8 Hz).

IR (KBr) 3068, 1678, 1609, 1586, 1568, 1487, 1283, 1242, 1159, 1128, 1036 cm$^{-1}$.

Elemental Analysis. Calcd. for $C_{20}H_{20}O_6S$: C, 61.84; H, 5.19. Found: C, 61.63; H, 5.16.

Reference Example 144

To a mixture of methyl 7-hydroxy-1,1-dioxo-2,3-dihydro-1-benzothiepine-4-carboxylate (0.40 g), 4-propylphenylboric acid (0.49 g), cupric acetate (0.27 g), MS 4A (0.8 g) and dichloromethane (15 ml) was added at room temperature triethylamine (1.04 ml), and the resulting mixture was stirred for 20 hours. The reaction mixture was filtered to remove an insoluble material and the filtrate was concentrated under reduced pressure. The residue was subjected to separation and purification using column chromatography (ethyl acetate:hexane 1:2) to obtain methyl 7-(4-propylphenoxy)-1,1-dioxo-2,3-dihydro-1-benzothiepine-4-carboxylate (0.40 g) as a light yellow, oily substance.

$^1$H-NMR (200 MHz, CDCl$_3$) δ0.97 (3H, t, J=7.1 Hz), 1.57–1.77 (6H, m), 2.62 (2H, t, J=7.7 Hz), 3.04–3.11 (2H, m), 3.59–3.66 (2H, m), 3.84 (3H, s), 6.96–7.05 (4H, m), 7.23 (2H, d, J=8.4 Hz), 7.71 (1H, s), 8.09 (1H, d, J=9.2 Hz).

IR (neat) 1714, 1586, 1564, 1505, 1323, 1294, 1279, 1252, 1215, 1167, 1127, 748 cm$^{-1}$.

Reference Example 145

Into a solution of methyl 7-(4-propylphenoxy)-1,1-dioxo-2,3-dihydro-1-benzothiepine-4-carboxylate (0.40 g) in THF-methanol (10–5 ml) was added at room temperature a 1 M aqueous solution of potassium carbonate (3.0 ml), and the resulting mixture was stirred at 65° C. for 20 hours. After cooling to room temperature, 1 N hydrochloric acid (10 ml) was added to the reaction mixture, which was extracted with ethyl acetate. The organic layer was washed with an aqueous saturated solution of sodium chloride and was dried with magnesium sulfate. After concentration under reduced pressure, the precipitated crystals were collected by filtration. The crystals were washed with hexane to obtain 7-(4-propylphenoxy)-1,1-dioxo-2,3-dihydro-1-benzothiepine-4-carboxylic acid (254 mg) as light yellow crystals.

M. p. 147–149° C.

$^1$H-NMR (200 MHz, DMSO-d$_6$) δ0.93 (3H, t, J=7.4 Hz), 1.52–1.71 (2H, m), 2.54–2.62 (2H, m), 2.88–2.94 (2H, m), 3.68–3.75 (2H, m), 7.03–7.09 (3H, m), 7.29 (2H, d, J=8.8 Hz), 7.33 (1H, d, J=2.6 Hz), 7.66 (1H, s), 7.99 (1H, d, J=8.4 Hz).

IR (KBr) 1692, 1588, 1566, 1505, 1294, 1254, 1211, 1167, 1127 cm$^{-1}$.

Elemental Analysis. Calcd. for $C_{20}H_{20}O_5S$: C, 64.50; H, 5.41. Found: C, 64.32; H, 5.21.

Reference Example 146

To a mixture of methyl 7-hydroxy-1,1-dioxo-2,3-dihydro-1-benzothiepine-4-carboxylate (0.40 g), 3-ethoxy-4-(2-propoxyethoxy)phenylboric acid (0.80 g), cupric acetate (0.27 g), MS4A (0.8 g) and dichloromethane (15 ml) was added at room temperature triethylamine (1.04 ml), and the resulting mixture was stirred for 16 hours. The reaction mixture was filtered to remove an insoluble material and the filtrate was concentrated under reduced pressure. The residue was subjected to separation and purification using column chromatography (ethyl acetate:hexane 1:2→2:3) to obtain methyl 7-[3-ethoxy-4-(2-propoxyethoxy)phenoxy]-1,1-dioxo-2,3-dihydro-1-benzothiepine-4-carboxylate (0.45 g) as a light yellow, oily substance. $^1$H-NMR (200 MHz, CDCl$_3$) δ0.95 (3H, t, J=7.4 Hz), 1.44 (3H, t, J=7.0 Hz), 1.56–1.70 (2H, m), 3.04–3.11 (2H, m), 3.53 (2H, t, J=6.8 Hz), 3.58–3.65 (2H, m), 3.80–3.85 (5H, m), 4.03 (2H, q, j=7.0 Hz), 4.17–4.22 (2H, m), 6.56–6.63 (2H, m), 6.94–7.04 (3H, m), 7.70 (1H, s), 8.08 (1H, d, J=8.4 Hz).

IR (neat) 1715, 1588, 1566, 1507, 1480, 1321, 1277, 1244, 1219, 1165, 1127 cm$^{-1}$.

Reference Example 147

Into a solution of methyl 7-[3-ethoxy-4-(2-propoxyethoxy)phenoxy]-1,1-dioxo-2,3-dihydro-1-benzothiepine-4-carboxylate (0.45 g) in THF-methanol (10–5 ml) was added at room temperature a 1 M aqueous solution of potassium carbonate (1.8 ml), and the resulting mixture was stirred at 65° C. for 20 hours. After cooling to room temperature, 1 N hydrochloric acid (10 ml) was added to the reaction mixture, which was extracted with ethyl acetate. The organic layer was washed with an aqueous saturated solution of sodium chloride and was dried with magnesium sulfate. After concentration under reduced pressure, the precipitated crystals were collected by filtration. The crystals were washed with hexane to obtain 7-[3-ethoxy-4-(2-propoxyethoxy)phenoxy]-1,1-dioxo-2,3-dihydro-1-benzothiepine-4-carboxylic acid (283 mg) as light yellow crystals.

M. p. 116–118° C.

$^1$H-NMR (200 MHz, DMSO-d$_6$) δ0.88 (3H, t, J=7.5 Hz), 1.31 (3H, t, J=7.0 Hz), 1.44–1.62 (2H, m), 2.85–2.96 (2H, m), 3.44 (2H, t, J=6.6 Hz), 3.68–3.73 (4H, m), 4.01 (2H, q, J=7.0 Hz), 4.08–4.12 (2H, m), 6.66 (1H, dd, J=8.8, 2.4 Hz), 6.82 (1H, d, J=2.4 Hz), 7.01–7.07 (2H, m), 7.28 (1H, d, J=2.6 Hz), 7.66 (1H, s), 7.98 (1H, d, J=8.6 Hz).

IR (KBr) 3397, 1694, 1593, 1562, 1507, 1291, 1248, 1223, 1128 cm$^{-1}$.

Elemental Analysis. Calcd. for $C_{24}H_{28}O_8S \cdot 0.5\ H_2O$: C, 59.37; H, 6.02. Found: C, 59.23; H, 6.03.

Reference Example 148

Into a solution of 2-bromobenzyl alcohol (10.0 g) in THF (100 ml) was added at 0° C. sodium hydride (60%, 2.35 g), and the resulting mixture was stirred at room temperature for 2 hours. 1-Bromopropane (5.8 ml) was added to the reaction mixture, which was stirred at 60° C. for 20 hours. The reaction mixture was mixed with water and was extracted with ethyl acetate. The organic layer was washed with an aqueous saturated solution of sodium chloride and was dried with magnesium sulfate. After concentration under reduced pressure, the residue was subjected to separation and purification using column chromatography (ethyl acetate:hexane 1:9) to obtain 2-bromobenzyl propyl ether (7.88 g) as a colorless oily substance.

$^1$H-NMR (200 MHz, CDCl3) δ0.97 (3H, t, J=7.3 Hz), 1.59–1.77 (2H, m), 3.52 (2H, t, J=6.6 Hz), 4.57 (2H, s), 7.09–7.18 (1H, m), 7.28–7.35 (1H, m), 7.45–7.56 (2H, m).

Reference Example 149

To a mixture of magnesium (0.83 g) and THF (30 ml) was added 1,2-dibromoethane (0.1 ml) at room temperature and subsequently was added dropwise a solution of 2-bromobenzyl propyl ether (7.88 g) in THF (40 ml) at 60° C. over a period of 30 minutes, under an argon atmosphere. After the dropwise addition, the resulting mixture was stirred further at 60° C. for 2 hours and was then cooled to −78° C., and a solution of trimethylboric acid (12 ml) in THF (24 ml) was added dropwise. The resulting mixture was stirred at 78° C. for one hour and then at room temperature for 10 hours. To the reaction mixture was added 1 N hydrochloric acid (100 ml), and the resulting mixture was stirred for 30 minutes and was then extracted with ethyl acetate. The organic layer was washed with an aqueous saturated solution of sodium chloride and was dried with magnesium sulfate. After concentration under reduced pressure, the precipitated crystals were collected by filtration. The crystals were washed with hexane to obtain 2-propoxymethylphenylboric acid (2.95 g) as colorless crystals.

$^1$H-NMR (200 MHz, DMSO-d$_6$) δ0.88 (3H, t, J=7.3 Hz), 1.44–1.63 (2H, m), 3.38 (2H, t, J=6.6 Hz), 4.57 (2H, s), 7.19–7.33 (3H, m), 7.51 (1H, d, J=6.6 Hz).

Reference Example 150

To a mixture of methyl 7-hydroxy-1,1-dioxo-2,3-dihydro-1-benzothiepine-4-carboxylate (0.40 g), 2-propoxymethylphenylboric acid (0.80 g), cupric acetate (0.27 g), MS 4A (0.8 g) and dichloromethane (15 ml) was added at room temperature triethylamine (1.04 ml), and the resulting mixture was stirred for 20 hours. The reaction mixture was filtered to remove an insoluble material and the filtrate was concentrated under reduced pressure. The residue was subjected to separation and purification using column chromatography (ethyl acetate:hexane 1:2) to obtain methyl 7-(2-propoxymethylphenoxy)-1,1-dioxo-2,3-dihydro-1-benzothiepine-4-carboxylate (0.13 g) as a light yellow, oily substance.

$^1$H-NMR (200 MHz, CDCl$_3$) δ0.86 (3H, t, J=7.6 Hz), 1.44–1.62 (2H, m), 3.05–3.11 (2H, m), 3.39 (2H, t, J=6.8 Hz), 3.59–3.65 (2H, m), 3.84 (3H, s), 4.46 (2H, s), 6.97–7.02 (3H, m), 7.35–7.40 (2H, m), 7.58 (1H, dd, J=7.1, 2.1 Hz), 7.70 (1H, s), 8.09 (1H, d, J=9.6 Hz).

Reference Example 151

Into a solution of methyl 7-(2-propoxymethylphenoxy)-1,1-dioxo-2,3-dihydro-1-benzothiepine-4-carboxylate (0.37 g) in THF-methanol (10–5 ml) was added at room temperature a 1 M aqueous solution of potassium carbonate (1.8 ml), and the resulting mixture was stirred at 65° C. for 20 hours. After cooling to room temperature, 1 N hydrochloric acid (10 ml) was added to the reaction mixture, which was extracted with ethyl acetate. The organic layer was washed with an aqueous saturated solution of sodium chloride and was dried with magnesium sulfate. After concentration under reduced pressure, the precipitated crystals were collected by filtration. The crystals were washed with diisopropyl ether to obtain 7-(2-propoxymethylphenoxy)-1,1-dioxo-2,3-dihydro-1-benzothiepine-4-carboxylic acid (229 mg) as light yellow crystals.

M. p. 139–141° C.

¹H-NMR (200 MHz, DMSO-d₆) δ0.78 (3H t, J=7.5 Hz), 1.32–1.50 (2H, m), 2.91 (2H, t, J=6.3 Hz), 3.16–3.46 (2H, m), 3.71 (2H, t, J=6.3 Hz), 4.42 (2H, s), 7.00 (1H, dd, J=8.4, 2.6 Hz), 7.09–7.14 (1H, m), 7.27 (1H, d, J=2.6 Hz), 7.31–7.48 (2H, m), 7.55 (1H, dd, J=7.4, 1.8 Hz), 7.65 (1H, s), 7.98 (1H, d, J=8.4 Hz).

IR (KBr) 1676, 1563, 1296, 1264, 1219, 1123 cm⁻¹.

Elemental Analysis. Calcd. for $C_{21}H_{22}O_6S$: C, 62.67; H, 5.51. Found: C, 62.28; H, 5.79.

Example 98 (Production of Compound 99)

Into a solution of 7-[[2-(2-propoxyethoxy)benzyl]oxy]-1,1-dioxo-2,3-dihydro-1-benzothiepine-4-carboxylic acid (136 mg) in THF (10 ml) were added at room temperature thionyl chloride (0.095 ml) and DMF (one drop), and the resulting mixture was stirred for one hour. After concentration under reduced pressure to remove the solvent, the residue dissolved in THF (10 ml) was added dropwise at 0° C. to a solution of 4-[N-methyl-N-(tetrahydropyran-4-yl)amino]methyl]aniline (79 mg) and triethylamine (0.2 ml) in THF (2 ml). After being stirred at room temperature for 40 hours, the reaction mixture was mixed with water and was extracted with ethyl acetate. The organic layer was washed with an aqueous saturated solution of sodium chloride and was dried with magnesium sulfate. After concentration under reduced pressure, the residue was purified by column chromatography (ethanol:ethyl acetate 1:3), and further the resulting crystals were purified by recrystallization (ethanol) to obtain N-[4-[[N-methyl-N-(tetrahydropyran-4-yl)amino]methyl]phenyl]-7-[[2-(2-propoxyethoxy)benzyl]oxy]-1,1-dioxo-2,3-dihydro-1-benzothiepine-4-carboxamide (compound 99) (65 mg) as colorless crystals.

M. p. 136–138° C.

¹H-NMR (200 MHz, CDCl₃) δ0.89 (3H, t, J=7.5 Hz), 1.53–1.77 (6H, m), 2.21 (3H, s), 2.54–2.74 (1H, m), 3.09 (2H, t, J=6.7 Hz), 3.31–3.45 (2H, m), 3.48 (2H, t, J=6.7 Hz), 3.57 (2H, s), 3.69 (2H, t, J=6.7 Hz), 3.78–3.83 (2H, m), 3.99–4.09 (2H, m), 4.17–4.22 (2H, m), 5.24 (2H, s), 6.91–7.09 (4H, m), 7.22 (1H, s), 7.30–7.41 (4H, m), 7.52 (2H, d, J=8.4 Hz), 7.89 (1H, s), 8.07 (1H, d, J=8.4 Hz).

IR (KBr) 3235, 1653, 1636, 1591, 1532, 1514, 1495, 1412, 1316, 1292, 1258, 1121 cm⁻¹.

Elemental Analysis. Calcd. for $C_{36}H_{44}N_2O_7S$: C, 66.64; H, 6.84; N, 4.32. Found: C, 66.45; H, 6.96; N, 4.22.

Example 99 (Production of Compound 100)

Into a solution of 7-[(4-propoxybenzyl)oxy]-1,1-dioxo-2,3-dihydro-1-benzothiepine-4-carboxylic acid (180 mg) in THF (10 ml) were added at room temperature thionyl chloride (0.065 ml) and DMF (one drop), and the resulting mixture was stirred for one hour. After concentration under reduced pressure to remove the solvent, the residue dissolved in THF (10 ml) was added dropwise at 0° C. to a solution of 4-[[N-methyl-N-(tetrahydropyran-4-yl)amino]methyl]aniline (108 mg) and triethylamine (0.25 ml) in THF (2 ml). After being stirred at room temperature for 40 hours, the reaction mixture was mixed with water and was extracted with ethyl acetate. The organic layer was washed with an aqueous saturated solution of sodium chloride and was dried with magnesium sulfate. After concentration under reduced pressure, the residue was purified by column chromatography (ethanol:ethyl acetate 1:3), and further the resulting crystals were purified by recrystallization (ethanol) to obtain N-[4-[[N-methyl-N-(tetrahydropyran-4-yl)amino]methyl]phenyl]-7-[[(4-propoxybenzyl)oxy]-1,1-dioxo-2,3-dihydro-1-benzothiepine-4-carboxamide (compound 100) (139 mg) as colorless crystals.

M. p. 205–207° C.

¹H-NMR (200 MHz, CDCl₃) δ1.04 (3H, t, J=7.5 Hz), 1.64–1.87 (6H, m), 2.21 (3H, s), 2.56–2.73 (1H, m), 3.09 (2H, t, J=7.0 Hz), 3.30–3.44 (2H, m), 3.57 (2H, s), 3.69 (2H, t, J=7.0 Hz), 3.94 (2H, t, J=7.0 Hz), 4.00–4.10 (2H, m), 5.07 (2H, s), 6.93 (2H, d, J=8.8 Hz), 6.98–7.07 (2H, m), 7.20 (1H, s), 7.31–7.35 (4H, m), 7.53 (2H, d, J=8.4 Hz), 7.83 (1H, s), 8.09 (1H, d, J=8.4 Hz).

IR (KBr) 3244, 1653, 1634, 1599, 1514, 1410, 1319, 1292, 1254, 1123 cm⁻¹.

Elemental Analysis. Calcd. for $C_{34}H_{40}N_2O_6S$: C, 67.53; H, 6.67; N, 4.63. Found: C, 67.31; H, 6.72; N, 4.62.

Example 100 (Production of Compound 101)

Into a solution of 7-[(2-ethoxybenzyl)oxy]-1,1-dioxo-2,3-dihydro-1-benzothiepine-4-carboxylic acid (130 mg) in THF (10 ml) were added at room temperature thionyl chloride (0.045 ml) and DMF (one drop), and the resulting mixture was stirred for one hour. After concentration under reduced pressure to remove the solvent, the residue dissolved in THF (10 ml) was added dropwise at 0° C. to a solution of 4-[[N-methyl-N-(tetrahydropyran-4-yl)amino]methyl]aniline (80 mg) and triethylamine (0.18 ml) in THF (2 ml). After being stirred at room temperature for 16 hours, the reaction mixture was mixed with water and was extracted with ethyl acetate. The organic layer was washed with an aqueous saturated solution of sodium chloride and was dried with magnesium sulfate. After concentration under reduced pressure, the residue was purified by column chromatography (ethanol:ethyl acetate 1:3), and further the resulting crystals were purified by recrystallization (ethanol) to obtain 7-[(2-ethoxybenzyl)oxy]-N-[4-[[N-methyl-N-(tetrahydropyran-4-yl)amino]methyl]phenyl]-1,1-dioxo-2,3-dihydro-1-benzothiepine-4-carboxamide (compound 101) (103 mg) as colorless crystals.

M. p. 211–214° C.

¹H-NMR (200 MHz, CDCl₃) δ1.42 (3H, t, J=7.0 Hz), 1.66–1.83 (4H, m), 2.21 (3H, s), 2.55–2.74 (1H, m), 3.09 (2H, t, J=6.6 Hz), 3.31–3.42 (2H, m), 3.57 (2H, s), 3.69 (2H, t, J=6.6 Hz), 3.99–4.09 (2H, m), 4.11 (2H, q, J=7.0 Hz), 5.21 (2H, s), 6.89–7.02 (3H, m), 7.08 (1H, dd, J=8.8, 2.2 Hz), 7.22 (1H, s), 7.30–7.40 (4H, m), 7.53 (2H, d, J=8.4 Hz), 7.84 (1H, s), 8.08 (1H, d, J=8.8 Hz).

IR (KBr) 3252, 1655, 1636, 1605, 1590, 1530, 1497, 1412, 1318, 1292, 1250, 1167, 1121, 1044 cm⁻¹.

Elemental Analysis. Calcd. for $C_{33}H_{38}N_2O_6S$: C, 67.10; H, 6.48; N, 4.74. Found: C, 66.93; H, 6.34; N, 4.70.

Example 101 (Production of Compound 102)

Into a solution of 7-[(2-methoxybenzyl)oxy]-1,1-dioxo-2,3-dihydro-1-benzothiepine-4-carboxylic acid (140 mg) in THF (10 ml) were added at room temperature thionyl chloride (0.055 ml) and DMF (one drop), and the resulting mixture was stirred for one hour. After concentration under reduced pressure to remove the solvent, the residue dissolved in THF (10 ml) was added dropwise at 0° C. to a solution of 4-[[N-methyl-N-(tetrahydropyran-4-yl)amino]methyl]aniline (91 mg) and triethylamine (0.21 ml) in THF (2 ml). After being stirred at room temperature for 16 hours, the reaction mixture was mixed with water and was extracted with ethyl acetate. The organic layer was washed with an aqueous saturated solution of sodium chloride and was dried with magnesium sulfate. After concentration under reduced pressure, the residue was purified by column chromatography (ethanol:ethyl acetate 1:3), and further the resulting crystals were purified by recrystallization (ethanol) to obtain 7-[(2-methoxybenzyl)oxy]-N-[4-[[N-methyl-N-(tetrahydropyran-4-yl)amino]methyl]phenyl]-1,1-dioxo-2,3-dihydro-1-benzothiepine-4-carboxamide (compound 102) (101 mg) as colorless crystals.

M. p. 223–225° C.

$^1$H-NMR (200 MHz, CDCl$_3$) δ1.62–1.82 (4H, m), 2.21 (3H, s), 2.55–2.73 (1H, m), 3.09 (2H, t, J=6.8 Hz), 3.31–3.43 (2H, m), 3.57 (2H, s), 3.69 (2H, t, J=6.8 Hz), 3.88 (3H, s), 3.98–4.10 (2H, m), 5.19 (2H, s), 6.92–7.02 (3H, m), 7.07 (1H, dd, J=8.8, 2.6 Hz), 7.21 (1H, s), 7.30–7.41 (4H, m), 7.53 (2H, d, J=8.4 Hz), 7.84 (1H, s), 8.08 (1H, d, J=8.8 Hz).

IR (KBr) 3256, 1655, 1603, 1590, 1528, 1497, 1412, 1318, 1292, 1254, 1167, 1121 cm$^{-1}$.

Elemental Analysis. Calcd. for C$_{32}$H$_{36}$N$_2$O$_6$S: C, 66.64; H, 6.29; N, 4.86. Found: C, 66.41; H, 6.30; N, 4.80.

Example 102 (Production of Compound 103)

Into a solution of 7-[(2-chlorobenzyl)oxy]-1,1-dioxo-2,3-dihydro-1-benzothiepine-4-carboxylic acid (180 mg) in THF (10 ml) were added at room temperature thionyl chloride (0.070 ml) and DMF (one drop), and the resulting mixture was stirred for one hour. After concentration under reduced pressure to remove the solvent, the residue dissolved in THF (15 ml) was added dropwise at 0° C. to a solution of 4-[[N-methyl-N-(tetrahydropyran-4-yl)amino]methyl]aniline (115 mg) and triethylamine (0.26 ml) in THF (2 ml). After being stirred at room temperature for 20 hours, the reaction mixture was mixed with water and was extracted with ethyl acetate. The organic layer was washed with an aqueous saturated solution of sodium chloride and was dried with magnesium sulfate. After concentration under reduced pressure, the residue was purified by column chromatography (ethanol:ethyl acetate 1:3), and further the resulting crystals were purified by recrystallization (ethanol) to obtain 7-[(2-chlorobenzyl)oxy]-N-[4-[[N-methyl-N-(tetrahydropyran-4-yl)amino]methyl]phenyl]-1,1-dioxo-2,3-dihydro-1-benzothiepine-4-carboxamide (compound 103) (131 mg) as colorless crystals.

M. p. 205–207° C.

$^1$H-NMR (200 MHz, CDCl$_3$) δ1.68–1.83 (4H, m), 2.21 (3H, s), 2.55–2.72 (1H, m), 3.10 (2H, t, J=6.8 Hz), 3.31–3.43 (2H, m), 3.57 (2H, s), 3.70 (2H, t, J=6.8 Hz), 3.98–4.09 (2H, m), 5.25 (2H, s), 7.01–7.10 (2H, m), 7.23 (1H, s), 7.29–7.36 (4H, m), 7.40–7.56 (4H, m), 7.90 (1H, s), 8.11 (1H, d, J=8.8 Hz).

IR (KBr) 3282, 1657, 1637, 1591, 1530, 1410, 1318, 1292, 1254, 1167, 1142, 1123 cm$^{-1}$.

Elemental Analysis. Calcd. for C$_{31}$H$_{33}$N$_2$O$_5$SCl·0.3 H$_2$O: C, 63.48; H, 5.77; N, 4.78. Found: C, 63.29; H, 5.73; N, 4.55.

Example 103 (Production of Compound 104)

Into a solution of 7-[[2-(2-ethoxyethoxy)benzyl]oxy]-1,1-dioxo-2,3-dihydro-1-benzothiepine-4-carboxylic acid (180 mg) in THF (10 ml) were added at room temperature thionyl chloride (0.061 ml) and DMF (one drop), and the resulting mixture was stirred for one hour. After concentration under reduced pressure to remove the solvent, the residue dissolved in THF (10 ml) was added dropwise at 0° C. to a solution of 4-[N-methyl-N-(tetrahydropyran-4-yl)amino]methyl]aniline (102 mg) and triethylamine (0.23 ml) in THF (2 ml). After being stirred at room temperature for 16 hours, the reaction mixture was mixed with water and was extracted with ethyl acetate. The organic layer was washed with an aqueous saturated solution of sodium chloride and was dried with magnesium sulfate. After concentration under reduced pressure, the residue was purified by column chromatography (ethanol:ethyl acetate 1:3), and further the resulting crystals were purified by recrystallization (ethanol) to obtain 7-[[2-(2-ethoxyethoxy)benzyl]oxy]-N-[4-[[N-methyl-N-(tetrahydropyran-4-yl)amino]methyl]phenyl]-1,1-dioxo-2,3-dihydro-1-benzothiepine-4-carboxamide (compound 104) (109 mg) as colorless crystals.

M. p. 132–136° C.

$^1$H-NMR (200 MHz, CDCl$_3$) δ1.20 (3H, t, J=7.0 Hz), 1.68–1.83 (4H, m), 2.21 (3H, s), 2.56–2.75 (1H, m), 3.05–3.11 (2H, m), 3.31–3.45 (2H, m), 3.57 (2H, s), 3.59 (2H, q, J=7.0 Hz), 3.65–3.72 (2H, m), 3.79–3.84 (2H, m), 3.99–4.10 (2H, m), 4.17–4.22 (2H, m), 5.25 (2H, s), 6.90–7.10 (4H, m), 7.23 (1H, s), 7.30–7.41 (4H, m), 7.53 (2H, d, J=8.4 Hz), 8.02 (1H, s), 8.07 (1H, d, J=8.4 Hz).

IR (KBr) 3254, 1655, 1636, 1591, 1530, 1410, 1314, 1292, 1258, 1121 cm$^{-1}$.

Elemental Analysis. Calcd. for C$_{35}$H$_{42}$N$_2$O$_7$S: C, 66.22; H, 6.67; N, 4.41. Found: C, 65.88; H, 6.56; N, 4.43.

Example 104 (Production of Compound 105)

Into a solution of 7-[(3-propoxyphenethyl)oxyl-1,1-dioxo-2,3-dihydro-1-benzothiepine-4-carboxylic acid (140 mg) in THF (10 ml) were added at room temperature thionyl chloride (0.049 ml) and DMF (one drop), and the resulting mixture was stirred for 1.5 hours. After concentration under reduced pressure to remove the solvent, the residue dissolved in THF (10 ml) was added dropwise at 0° C. to a solution of 4-[[N-methyl-N-(tetrahydropyran-4-yl)amino]methyl]aniline (82 mg) and triethylamine (0.19 ml) in THF (2 ml). After being stirred at room temperature for 16 hours, the reaction mixture was mixed with water and was extracted with ethyl acetate. The organic layer was washed with an aqueous saturated solution of sodium chloride and was dried with magnesium sulfate. After concentration under reduced pressure, the residue was purified by column chromatography (ethanol:ethyl acetate 1:3), and further the resulting crystals were purified by recrystallization (ethanol) to obtain N-[4-[[N-methyl-N-(tetrahydropyran-4-yl)amino]methyl]phenyl]-7-[(3-propoxyphenethyl)oxy]-1,1-dioxo-2,3-dihydro-1-benzothiepine-4-carboxamide (compound 105) (95 mg) as light yellow crystals.

M. p. 153–154° C.

$^1$H-NMR (200 MHz, CDCl$_3$) δ1.04 (3H, t, J=7.3 Hz), 1.67–1.90 (6H, m), 2.21 (3H, s), 2.54–2.73 (1H, m), 3.02–3.14 (4H, m), 3.29–3.45 (2H, m), 3.57 (2H, s), 3.65–3.71 (2H, m), 3.92 (2H, t, J=6.5 Hz), 3.99–4.09 (2H, m), 4.24 (2H, t, J=7.0 Hz), 6.77–6.97 (5H, m), 7.19 (1H, s), 7.23–7.34 (3H, m), 7.53 (2H, d, J=8.4 Hz), 7.92 (1H, s), 8.06 (1H, d, J=8.8 Hz).

IR (KBr) 3254, 1655, 1634, 1599, 1530, 1410, 1318, 1292, 1260, 1159, 1123 cm$^{-1}$.

Elemental Analysis. Calcd. for C$_{35}$H$_{42}$N$_2$O$_6$S: C, 67.94; H, 6.84; N, 4.53. Found: C, 67.78; H, 6.56; N, 4.39.

Example 105 (Production of Compound 106)

Into a solution of 7-[(2-propoxyphenethyl)oxy]-1,1-dioxo-2,3-dihydro-1-benzothiepine-4-carboxylic acid (100 mg) in THF (10 ml) were added at room temperature thionyl chloride (0.035 ml) and DMF (one drop), and the resulting mixture was stirred for 1.5 hours. After concentration under reduced pressure to remove the solvent, the residue dissolved in THF (10 ml) was added dropwise at 0° C. to a solution of 4-[[N-methyl-N-(tetrahydropyran-4-yl)amino]methyl]aniline (59 mg) and triethylamine (0.13 ml) in THF (2 ml). After being stirred at room temperature for 20 hours, the reaction mixture was mixed with water and was extracted with ethyl acetate. The organic layer was washed with an aqueous saturated solution of sodium chloride and was dried with magnesium sulfate. After concentration under reduced pressure, the residue was purified by column chromatography (ethanol:ethyl acetate 1:3), and further the resulting crystals were purified by recrystallization (ethanol) to obtain N-[4-[[N-methyl-N-(tetrahydropyran-4-yl)amino]methyl]phenyl]-7-[(2-propoxyphenethyl)oxy]-1,1-dioxo-2,3-dihydro-1-benzothiepine-4-carboxamide (compound 106) (89 mg) as colorless crystals.

M. p. 161–162° C.

$^1$H-NMR (200 MHz, CDCl$_3$) δ1.06 (3H, t, J=7.5 Hz), 1.63–1.94 (6H, m), 2.21 (3H, s), 2.55–2.73 (1H, m), 3.05–3.18 (4H, m), 3.29–3.45 (2H, m), 3.57 (2H, s), 3.68 (2H, t, J=6.7 Hz), 3.97 (2H, t, J=6.4 Hz), 3.99–4.09 (2H, m), 4.25 (2H, t, J=7.5 Hz), 6.83–7.03 (4H, m), 7.19–7.23 (3H, m), 7.32 (2H, d, J=8.4 Hz), 7.53 (2H, d, J=8.4 Hz), 7.80 (1H, s), 8.06 (1H, d, J=8.6 Hz).

IR (KBr) 3268, 1651, 1634, 1599, 1530, 1495, 1410, 1316, 1291, 1256, 1240, 1121 cm$^{-1}$.

Elemental Analysis. Calcd. for C$_{35}$H$_{42}$N$_2$O$_6$S: C, 67.94; H, 6.84; N, 4.53. Found: C, 67.72; H, 6.56; N, 4.36.

Example 106 (Production of Compound 107)

Into a solution of 7-[[4-(2-ethoxyethoxy)benzyl]oxy]-1,1-dioxo-2,3-dihydro-1-benzothiepine-4-carboxylic acid (160 mg) in THF (10 ml) were added at room temperature thionyl chloride (0.054 ml) and DMF (one drop), and the resulting mixture was stirred for 1.5 hours. After concentration under reduced pressure to remove the solvent, the residue dissolved in THF (10 ml) was added dropwise at 0° C. to a solution of 4-[[N-methyl-N-(tetrahydropyran-4-yl)amino]methyl]aniline (90 mg) and triethylamine (0.21 ml) in THF (2 ml). After being stirred at room temperature for 3 days, the reaction mixture was mixed with water and was extracted with ethyl acetate. The organic layer was washed with an aqueous saturated solution of sodium chloride and was dried with magnesium sulfate. After concentration under reduced pressure, the residue was purified by column chromatography (ethanol:ethyl acetate 1:3), and further the resulting crystals were purified by recrystallization (ethanol) to obtain N-[4-[[N-methyl-N-(tetrahydropyran-4-yl)amino]methyl]phenyl]-7-[[4-(2-ethoxyethoxy)benzyl]oxy]-1,1-dioxo-2,3-dihydro-1-benzothiepine-4-carboxamide (compound 107) (135 mg) as colorless crystals.

M. p. 185–187° C.

$^1$H-NMR (200 MHz, CDCl$_3$) δ1.25 (3H, t, J=7.0 Hz), 1.66–1.82 (4H, m), 2.20 (3H, s), 2.56–2.73 (1H, m), 3.04–3.11 (2H, m), 3.29–3.44 (2H, m), 3.57 (2H, s), 3.61 (2H, q, J=7.0 Hz), 3.66–3.72 (2H, m), 3.78–3.83 (2H, m), 3.98–4.09 (2H, m), 4.11–4.16 (2H, m), 5.07 (2H, s), 6.94–7.06 (4H, m), 7.20 (1H, s), 7.29–7.35 (4H, m), 7.53 (2H, d, J=8.0 Hz), 7.96 (1H, s), 8.08 (1H, d, J=8.8 Hz).

IR (KBr) 3227, 1655, 1638, 1597, 1518, 1410, 1314, 1292, 1254, 1123 cm$^{-1}$.

Elemental Analysis. Calcd. for C$_{35}$H$_{42}$N$_2$O$_7$S: C, 66.22; H, 6.67; N, 4.41. Found: C, 65.95; H, 6.57; N, 4.30.

Example 107 (Production of Compound 108)

Into a solution of 7-[[4-(2-propoxyethoxy)benzyl]oxy]-1,1-dioxo-2,3-dihydro-1-benzothiepine-4-carboxylic acid (180 mg) in THF (10 ml) were added at room temperature thionyl chloride (0.059 ml) and DMF (one drop), and the resulting mixture was stirred for 1.5 hours. After concentration under reduced pressure to remove the solvent, the residue dissolved in THF (10 ml) was added dropwise at 0° C. to a solution of 4-[[N-methyl-N-(tetrahydropyran-4-yl)amino]methyl]aniline (97 mg) and triethylamine (0.22 ml) in THF (2 ml). After being stirred at room temperature for 18 hours, the reaction mixture was mixed with water and was extracted with ethyl acetate. The organic layer was washed with an aqueous saturated solution of sodium chloride and was dried with magnesium sulfate. After concentration under reduced pressure, the residue was purified by column chromatography (ethanol:ethyl acetate 1:3), and further the resulting crystals were purified by recrystallization (ethanol) to obtain N-[4-[[N-methyl-N-(tetrahydropyran-4-yl)amino]methyl]phenyl]-7-[[4-(2-propoxyethoxy)benzyl]oxy]-1,1-dioxo-2,3-dihydro-1-benzothiepine-4-carboxamide (compound 108) (141 mg) as colorless crystals.

M. p. 175–176° C.

$^1$H-NMR (200 MHz, CDCl$_3$) δ0.93 (3H, t, J=7.3 Hz), 1.56–1.78 (6H, m), 2.20 (3H, s), 2.55–2.71 (1H, m), 3.05–3.11 (2H, m), 3.30–3.45 (2H, m), 3.50 (2H, t, J=6.7 Hz), 3.57 (2H, s), 3.66–3.73 (2H, m), 3.77–3.82 (2H, m), 3.98–4.09 (2H, m), 4.11–4.16 (2H, m), 5.07 (2H, s), 6.94–7.07 (4H, m), 7.20 (1H, s), 7.30–7.51 (4H, m), 7.54 (2H, d, J=8.4 Hz), 7.94 (1H, s), 8.08 (1H, d, J=8.4 Hz).

IR (KBr) 3258, 1655, 1636, 1595, 1516, 1410, 1316, 1292, 1251, 1165, 1123 cm$^{-1}$.

Elemental Analysis. Calcd. for C$_{36}$H$_{44}$N$_2$O$_7$S: C, 66.64; H, 6.84; N, 4.32. Found: C, 66.78; H, 6.67; N, 4.08.

Example 108 (Production of Compound 109)

Into a solution of 7-[(3,4-dipropoxy)benzyl]oxy]-1,1-dioxo-2,3-dihydro-1-benzothiepine-4-carboxylic acid (180 mg) in THF (10 ml) were added at room temperature thionyl chloride (0.057 ml) and DMF (one drop), and the resulting mixture was stirred for 1.5 hours. After concentration under reduced pressure to remove the solvent, the residue dissolved in THF (15 ml) was added dropwise at 0° C. to a solution of 4-[[N-methyl-N-(tetrahydropyran-4-yl)amino]methyl]aniline (95 mg) and triethylamine (0.22 ml) in THF (2 ml). After being stirred at room temperature for 20 hours, the reaction mixture was mixed with water and was extracted with ethyl acetate. The organic layer was washed with an aqueous saturated solution of sodium chloride and was dried with magnesium sulfate. After concentration under reduced pressure, the residue was purified by column chromatography (ethanol:ethyl acetate 1:3), and further the resulting crystals were purified by recrystallization (ethanol) to obtain 7-[(3,4-dipropoxy)benzyl]oxy]-N-[4-[[N-methyl-N-(tetrahydropyran-4-yl)amino]methyl]phenyl]-1,1-dioxo-2,3-dihydro-1-benzothiepine-4-carboxamide (compound 109) (161 mg) as colorless crystals.

M. p. 186–187° C.

$^1$H-NMR (200 MHz, CDCl$_3$) δ1.04 (6H, t, J=7.4 Hz), 1.65–1.93 (8H, m), 2.20 (3H, s), 2.53–2.71 (1H, m), 3.05–3.12 (2H, m), 3.31–3.44 (2H, m), 3.57 (2H, s), 3.65–3.72 (2H, m), 3.97 (4H, t, J=6.5 Hz), 3.99–4.10 (2H, m), 5.05 (2H, s), 6.90–6.99 (4H, m), 7.04 (1H, dd, J=8.8, 2.6 Hz), 7.20 (1H, s), 7.32 (2H, d, J=8.6 Hz), 7.53 (2H, d, J=8.6 Hz), 7.84 (1H, s), 8.09 (1H, d, J=8.8 Hz).

IR (KBr) 3238, 1653, 1634, 1593, 1514, 1410, 1316, 1292, 1258, 1167, 1140, 1121 cm$^{-1}$.

Elemental Analysis. Calcd. for C$_{37}$H$_{46}$N$_2$O$_7$S: C, 67.04; H, 6.99; N, 4.23. Found: C, 66.83; H, 6.86; N, 4.31.

Example 109 (Production of Compound 110)

Into a solution of 7-[[3-ethoxy-4-(2-propoxyethoxy) benzyl]oxy]-1,1-dioxo-2,3-dihydro-1-benzothiepine-4-carboxylic acid (120 mg) in THF (10 ml) were added at room temperature thionyl chloride (0.036 ml) and DMF (one drop), and the resulting mixture was stirred for 1.5 hours. After concentration under reduced pressure to remove the solvent, the residue dissolved in THF (10 ml) was added dropwise at 0° C. to a solution of 4-[[N-methyl-N-(tetrahydropyran-4-yl)amino]methyl]aniline (58 mg) and triethylamine (0.13 ml) in THF (2 ml). After being stirred at room temperature for 20 hours, the reaction mixture was mixed with water and was extracted with ethyl acetate. The organic layer was washed with an aqueous saturated solution of sodium chloride and was dried with magnesium sulfate. After concentration under reduced pressure, the residue was purified by column chromatography (ethanol:ethyl acetate 1:3), and further the resulting crystals were purified by recrystallization (ethanol) to obtain 7-[[3-ethoxy-4-(2-propoxyethoxy)benzyl]oxy]-N-[4-[[N-methyl-N-(tetrahydropyran-4-yl)amino]methyl]phenyl]-1,1-dioxo-2,3-dihydro-1-benzothiepine-4-carboxamide (compound 110) (47 mg) as light yellow crystals.

M. p. 146–147° C.

$^1$H-NMR (200 MHz, CDCl$_3$) δ0.93 (3H, t, J=7.3 Hz), 1.44 (3H, t, J=7.0 Hz), 1.54–1.81 (6H, m), 2.22 (3H, s), 2.56–2.76 (1H, m), 3.05–3.12 (2H, m), 3.30–3.44 (2H, m), 3.52 (2H, t, J=6.8 Hz), 3.59 (2H, s), 3.65–3.72 (2H, m), 3.82 (2H, t, J=5.2 Hz), 3.98–4.12 (4H, m), 4.18 (2H, t, J=5.2 Hz), 5.06 (2H, s), 6.94–7.07 (5H, m), 7.21 (1H, s), 7.33 (2H, d, J=8.2 Hz), 7.53 (2H, d, J=8.2 Hz), 7.81 (1H, s), 8.09 (1H, d, J=8.4 Hz).

IR (KBr) 3115, 1653, 1595, 1514, 1410, 1316, 1291, 1260, 1123 cm$^{-1}$.

Elemental Analysis. Calcd. for C$_{38}$H$_{48}$N$_2$O$_8$S.1.0 H$_2$O: C, 64.20; H, 7.09; N, 3.94. Found: C, 64.47; H, 6.86; N, 3.99.

Example 110 (Production of Compound 111)

Into a solution of 7-(4-propoxyphenoxy)-1,1-dioxo-2,3-dihydro-1-benzothiepine-4-carboxylic acid (110 mg) in THF (10 ml) were added at room temperature thionyl chloride (0.041 ml) and DMF (one drop), and the resulting mixture was stirred for one hour. After concentration under reduced pressure to remove the solvent, the residue dissolved in THF (10 ml) was added dropwise at 0° C. to a solution of 4-[[N-methyl-N-(tetrahydropyran-4-yl)amino]methyl] aniline (69 mg) and triethylamine (0.16 ml) in THF (2 ml). After being stirred at room temperature for 20 hours, the reaction mixture was mixed with water and was extracted with ethyl acetate. The organic layer was washed with an aqueous saturated solution of sodium chloride and was dried with magnesium sulfate. After concentration under reduced pressure, the residue was purified by column chromatography (ethanol:ethyl acetate 1:3), and further the resulting crystals were purified by recrystallization (ethanol) to obtain N-[4-[[N-methyl-N-(tetrahydropyran-4-yl)amino]methyl] phenyl]-7-(4-propoxyphenoxy)-1,1-dioxo-2,3-dihydro-1-benzothiepine-4-carboxamide (compound 111) (68 mg) as colorless crystals.

M. p. 139–141° C.

$^1$H-NMR (200 MHz, CDCl$_3$) δ1.05 (3H, t, J=7.3 Hz), 1.61–1.88 (6H, m), 2.20 (3H, s), 2.53–2.72 (1H, m), 3.10 (2H, t, J=6.8 Hz), 3.30–3.46 (2H, m), 3.57 (2H, s), 3.70 (2H, t, J=6.8 Hz), 3.93 (2H, t, J=6.6 Hz), 3.99–4.10 (2H, m), 6.91–7.04 (6H, m), 7.15 (1H, s), 7.31 (2H, d, J=8.6 Hz), 7.52 (2H, d, J=8.6 Hz), 7.86 (1H, s), 8.08 (1H, d, J=8.8 Hz).

IR (KBr) 3262, 1649, 1601, 1534, 1503, 1410, 1318, 1308, 1294, 1236, 1204, 1125 cm$^{-1}$.

Elemental Analysis. Calcd. for C$_{33}$H$_{38}$N$_2$O$_6$S: C, 67.10; H, 6.48; N, 4.74. Found: C, 66.99; H, 6.38; N, 4.71.

Example 111 (Production of Compound 112)

Into a solution of 7-(3-propoxyphenoxy)-1,1-dioxo-2,3-dihydro-1-benzothiepine-4-carboxylic acid (200 mg) in THF (10 ml) were added at room temperature thionyl chloride (0.075 ml) and DMF (one drop), and the resulting mixture was stirred for 1.5 hours. After concentration under reduced pressure to remove the solvent, the residue dissolved in THF (10 ml) was added dropwise at 0° C. to a solution of 4-[[N-methyl-N-(tetrahydropyran-4-yl)amino] methyl]aniline (124 mg) and triethylamine (0.28 ml) in THF (2 ml). After being stirred at room temperature for 67 hours, the reaction mixture was mixed with water and was extracted with ethyl acetate. The organic layer was washed with an aqueous saturated solution of sodium chloride and was dried with magnesium sulfate. After concentration under reduced pressure, the residue was purified by column chromatography (ethanol:ethyl acetate 1:3), and further the resulting crystals were purified by recrystallization (ethanol) to obtain N-[4-[[N-methyl-N-(tetrahydropyran-4-yl)amino] methyl]phenyl]-7-(3-propoxyphenoxy)-1,1-dioxo-2,3-dihydro-1-benzothiepine-4-carboxamide (compound 112) (146 mg) as colorless crystals.

M. p. 143–144° C.

$^1$H-NMR (200 MHz, CDCl$_3$) δ1.04 (3H, t, J=7.3 Hz), 1.67–1.89 (6H, m), 2.20 (3H, s), 2.54–2.70 (1H, m), 3.08–3.14 (2H, m), 3.30–3.43 (2H, m), 3.56 (2H, s), 3.67–3.74 (2H, m), 3.91 (2H, t, J=6.6 Hz), 3.98–4.08 (2H, m), 6.62–6.66 (2H, m), 6.78 (1H, dd, J=9.0, 2.2 Hz), 6.97 (1H, d, J=2.2 Hz), 7.06 (1H, dd, J=8.8, 2.2 Hz), 7.16 (1H, s), 77.29–7.50 (3H, m), 7.51 (2H, d, J=8.4 Hz), 7.88 (1H, s), 8.10 (1H, d, J=8.8 Hz).

IR (KBr) 3241, 1651, 1630, 1599, 1563, 1530, 1473, 1410, 1319, 1294, 1267, 1165, 1138, 1125 cm$^{-1}$.

Elemental Analysis. Calcd. for C$_{33}$H$_{38}$N$_2$O$_6$S: C, 67.10; H, 6.48; N, 4.74. Found: C, 67.34; H, 6.50; N, 4.88.

Example 112 (Production of Compound 113)

Into a solution of 7-(4-propylphenoxy)-1,1-dioxo-2,3-dihydro-1-benzothiepine-4-carboxylic acid (150 mg) in THF (10 ml) were added at room temperature thionyl chloride (0.059 ml) and DMF (one drop), and the resulting mixture was stirred for 1.5 hours. After concentration under reduced pressure to remove the solvent, the residue dissolved in THF (10 ml) was added dropwise at 0° C. to a solution of 4-[[N-methyl-N-(tetrahydropyran-4-yl)amino] methyl]aniline (97 mg) and triethylamine (0.22 ml) in THF (2 ml). After being stirred at room temperature for 13 hours, the reaction mixture was mixed with water and was extracted with ethyl acetate. The organic layer was washed with an aqueous saturated solution of sodium chloride and was dried with magnesium sulfate. After concentration under reduced pressure, the residue was purified by column chromatography (ethanol:ethyl acetate 1:3), and further the resulting crystals were purified by recrystallization (ethanol) to obtain N-[4-[[N-methyl-N-(tetrahydropyran-4-yl)amino] methyl]phenyl]-7-(4-propylphenoxy)-1,1-dioxo-2,3-dihydro-1-benzothiepine-4-carboxamide (compound 113) (124 mg) as colorless crystals.

M. p. 147–149° C.

$^1$H-NMR (200 MHz, CDCl$_3$) δ0.97 (3H, t, J=6.8 Hz), 1.57–1.81 (6H, m), 2.20 (3H, s), 2.55–2.73 (3H, m), 3.07–3.14 (2H, m), 3.29–3.44 (2H, m), 3.57 (2H, s), 3.67–3.74 (2H, m), 3.98–4.10 (2H, m), 6.95–7.06 (4H, m), 7.15 (1H, s), 7.23 (2H, d, J=8.8 Hz), 7.31 (2H, d, J=8.4 Hz), 7.51 (2H, d, J=8.4 Hz), 7.88 (1H, s), 8.09 (1H, d, J=8.4 Hz).

IR (KBr) 3289, 1651, 1597, 1566, 1507, 1410, 1318, 1294, 1254, 1206, 1140, 1121 cm$^{-1}$.

Elemental Analysis. Calcd. for $C_{33}H_{38}N_2O_5S$: C, 68.96; H, 6.66; N, 4.87. Found: C, 69.22; H, 6.48; N, 4.93.

Example 113 (Production of Compound 114)

Into a solution of 7-[3-ethoxy-4-(2-propoxyethoxy)phenoxy]-1,1-dioxo-2,3-dihydro-1-benzothiepine-4-carboxylic acid (180 mg) in THF (10 ml) were added at room temperature thionyl chloride (0.055 ml) and DMF (one drop), and the resulting mixture was stirred for 1.5 hours. After concentration under reduced pressure to remove the solvent, the residue dissolved in THF (10 ml) was added dropwise at 0° C. to a solution of 4-[[N-methyl-N-(tetrahydropyran-4-yl)amino]methyl]aniline (92 mg) and triethylamine (0.21 ml) in THF (2 ml). After being stirred at room temperature for 4 hours, the reaction mixture was mixed with water and was extracted with ethyl acetate. The organic layer was washed with an aqueous saturated solution of sodium chloride and was dried with magnesium sulfate. After concentration under reduced pressure, the residue was purified by column chromatography (ethanol:ethyl acetate 1:3), and further the resulting crystals were purified by recrystallization (ethanol) to obtain 7-[3-ethoxy-4-(2-propoxyethoxy)phenoxy]-N-[4-[[N-methyl-N-(tetrahydropyran-4-yl)amino]methyl]phenyl]-1,1-dioxo-2,3-dihydro-1-benzothiepine-4-carboxamide (compound 114) (140 mg) as colorless crystals.

M. p. 159–60° C.

$^1$H-NMR (200 MHz, CDCl$_3$) δ0.94 (3H, t, J=7.4 Hz), 1.44 (3H, t, J=7.0 Hz), 1.50–1.83 (6H, m), 2.20 (3H, s), 2.54–2.75 (1H, m), 3.07–3.14 (2H, m), 3.30–3.43 (2H, m), 3.52 (2H, t, J=6.7 Hz), 3.57 (2H, s), 3.66–3.73 (2H, m), 3.82 (2H, t, J=5.0 Hz), 3.98–4.08 (4H, m), 4.18 (2H, t, J=5.0 Hz), 6.57–6.63 (2H, m), 6.91–7.04 (3H, m), 7.15 (1H, s), 7.31 (2H, d, J=8.3 Hz), 7.52 (2H, d, J=8.3 Hz), 7.91 (1H, s), 8.09 (1H, d, J=8.8 Hz).

IR (KBr) 3310, 1655, 1601, 1534, 1508, 1408, 1312, 1250, 1219, 1169, 1140, 1125 cm$^{-1}$.

Elemental Analysis. Calcd. for $C_{37}H_{46}N_2O_8S \cdot 0.25\ H_2O$: C, 65.03; H, 6.86; N, 4.10. Found: C, 65.05; H, 6.94; N, 4.03.

Example 114 (Production of Compound 115)

Into a solution of 7-(2-propoxymethylphenoxy)-1,1-dioxo-2,3-dihydro-1-benzothiepine-4-carboxylic acid (150 mg) in THF (10 ml) were added at room temperature thionyl chloride (0.054 ml) and DMF (one drop), and the resulting mixture was stirred for 1.5 hours. After concentration under reduced pressure to remove the solvent, the residue dissolved in THF (10 ml) was added dropwise at 0° C. to a solution of 4-[[N-methyl-N-(tetrahydropyran-4-yl)amino]methyl]aniline (90 mg) and triethylamine (0.21 ml) in THF (2 ml). After being stirred at room temperature for 20 hours, the reaction mixture was mixed with water and was extracted with ethyl acetate. The organic layer was washed with an aqueous saturated solution of sodium chloride and was dried with magnesium sulfate. After concentration under reduced pressure, the residue was purified by column chromatography (ethanol:ethyl acetate 1:3), and further the resulting crystals were purified by recrystallization (ethanol) to obtain N-[4-[[N-methyl-N-(tetrahydropyran-4-yl)amino]methyl]phenyl]-7-(2-propoxymethylphenoxy)-1,1-dioxo-2,3-dihydro-1-benzothiepine-4-carboxamide (compound 115) (130 mg) as colorless crystals.

M. p. 162–164° C.

$^1$H-NMR (200 MHz, CDCl$_3$) δ0.86 (3H, t, J=7.5 Hz), 1.45–1.80 (6H, m), 2.20 (3H, s), 2.55–2.72 (1H, m), 3.08–3.15 (2H, m), 3.30–3.42 (4H, m), 3.57 (2H, s), 3.67–3.74 (2H, m), 3.99–4.11 (2H, m), 4.47 (2H, s), 6.92 (1H, d, J=2.6 Hz), 6.99–7.03 (2H, m), 7.14 (1H, s), 7.24–7.40 (4H, m), 7.48–7.61 (3H, m), 7.74 (1H, s), 8.10 (1H, d, J=8.8 Hz).

IR (KBr) 3329, 1646, 1626, 1599, 1562, 1531, 1512, 1411, 1314, 1259, 1159, 1125 cm$^{-1}$.

Elemental Analysis. Calcd. for $C_{34}H_{40}N_2O_6S$: C, 67.53; H, 6.67; N, 4.63. Found: C, 67.25; H, 6.81; N, 4.51.

Reference Example 152

To 3-methyl-4-propoxyethoxyphenylboric acid (710 mg), methyl 7-hydroxy-1,1-dioxo-2,3-dihydro-1-benzothiepine-4-carboxylate (400 mg) and cupric acetate (270 mg) suspended in dichloromethane (15 ml) was added triethylamine (1.04 ml). The resulting mixture was stirred for one day with a calcium chloride tube attached to the reaction vessel, was then mixed with celite and was filtered to remove an insoluble material. The filtrate was concentrated and the residue was subjected to purification using silica gel column chromatography to obtain methyl 7-[3-methyl-4-(2-propoxyethoxy)phenoxy]-1,1-dioxo-2,3-dihydro-1-benzothiepine-4-carboxylate (475 mg) as a brown oily substance.

$^1$H-NMR (200 MHz, CDCl$_3$) δ0.95 (t, 3H, J=7.4 Hz), 1.55–1.70 (m, 2H), 2.25 (s, 3H), 3.07 (t, 2H, J=7.2 Hz), 3.53 (t, 2H, J=6.6 Hz), 3.62 (t, 2H, J=5.8 Hz), 3.80–3.85 (m, 5H), 4.15 (t, 2H, J=4.8 Hz), 6.85–6.86 (m, 3H), 6.95–7.02 (m, 2H), 7.70 (s, 1H), 8.07 (d, 1H, J=8.2 Hz).

Reference Example 153

Into a mixed solution of methyl 7-[3-methyl-4-(2-propoxyethoxy)phenoxy]-1,1-dioxo-2,3-dihydro-1-benzothiepine-4-carboxylate (470 mg) in tetrahydrofuran (10 ml) and methanol (5 ml) was added a 1 N aqueous solution of potassium carbonate (2.9 ml), and the resulting mixture was heated at 65° C. for one day. After cooling, the reaction mixture was mixed with water, was acidified (pH=4) with 1N hydrochloric acid and was extracted with ethyl acetate. The organic layer was washed with an aqueous saturated solution of sodium chloride and was dried with magnesium sulfate. The solvent was evaporated under reduced pressure to obtain 7-[3-methyl-4-(2-propoxyethoxy)phenoxy]-1,1-dioxo-2,3-dihydro-1-benzothiepine-4-carboxylic acid (375 mg) as a brown oily substance.

$^1$H-NMR (200 MHz, CDCl$_3$) δ0.95 (t, 3H, J=7.4 Hz), 1.60–1.70 (m, 2H), 2.25 (s, 3H), 3.09 (t, 2H, J=6.6 Hz), 3.54 (t, 2H, J=6.6 Hz), 3.63 (t, 2H, J=6.2 Hz), 3.83 (t, 2H, J=5.2 Hz), 4.15 (t, 2H, J=4.8 Hz), 6.85–6.86 (m, 3H), 6.98–7.02 (m, 2H), 7.79 (s, 1H), 8.09 (d, 1H, J=8.8 Hz).

Example 115 (Production of Compound 116)

To 7-[3-methyl-4-(2-propoxyethoxy)phenoxy]-1,1-dioxo-2,3-dihydro-1-benzothiepine-4-carboxylic acid (370 mg) dissolved in tetrahydrofuran (10 ml) was added DMF (0.1 ml). Thionyl chloride (196 mg) was then added at 0° C. to the resulting mixture, which was stirred for 1.5 hr at room temperature under a nitrogen atmosphere. After concentration under reduced pressure to remove the solvent and excess thionyl chloride, the residue dissolved in tetrahydrofuran (10 ml) was added at 0° C. to a solution of 4-[[N-methyl-N-(tetrahydropyran-4-yl)amino]methyl]aniline (201 mg) and triethylamine (185 mg) in tetrahydrofuran (10 ml). The temperature of the resulting mixture was brought back to the room temperature, and after being stirred overnight, the reaction mixture was mixed with water and was extracted with ethyl acetate. The organic layer was washed with an aqueous saturated solution of sodium chloride and was dried with magnesium sulfate. After concentration under reduced pressure to remove the solvent, the residue was subjected to separation and purification using silica gel column chromatography and to recrystallization from hexane/ethyl acetate to obtain (compound 116) (94 mg) as colorless crystals.

$^1$H-NMR (200 MHz, CDCl$_3$) δ0.94 (t, 3H, J=6.2 Hz), 1.60–1.80 (m, 6H), 2.20 (s, 3H), 2.25 (s, 3H), 2.64 (br, 1H), 3.10 (t, 2H, J=7.2 Hz), 3.36 (dt, 2H, J=11.0, 2.2 Hz), 3.52 (t, 2H, J=6.6 Hz), 3.57 (s, 2H), 3.70 (t, 2H, J=7.4 Hz), 3.81 (t, 2H, J=5.6 Hz), 4.04 (d, 2H, J=11.8 Hz), 4.14 (t, 2H, J=5.2 Hz), 6.86–6.90 (m, 4H), 6.99 (dd, 2H, J=9.2, 2.2 Hz), 7.14 (s, 1H), 7.31 (d, 2H, J=8.2 Hz), 7.51 (d, 2H, J=8.4 Hz), 7.87 (s, 1H), 8.08 (d, 1H, J=8.8 Hz).

Elemental Analysis. Calcd. for C$_{36}$H$_{44}$N$_2$O$_7$S: C, 66.64; H, 6.84; N, 4.32. Found: C, 66.59; H, 6.76; N, 4.27.

Reference Example 154

Methyl 7-hydroxy-1,1-dioxo-2,3-dihydro-1-benzothiepine-4-carboxylate (400 mg), 3-methoxybenzyl chloride (350 mg) and potassium carbonate (412 mg) were suspended in DMF (15 ml), and the resulting suspension was stirred at 60° C. for 13 hours. The reaction mixture was diluted with ethyl acetate and washed respectively with water and an aqueous saturated solution of sodium chloride, and the organic layer was dried with anhydrous magnesium sulfate. After concentration under reduced pressure to remove the solvent, the residue was subjected to purification using silica gel column chromatography (hexane:ethyl acetate=4:1-hexane:ethyl acetate=3:1) to obtain methyl 7-(3-methoxybenzyloxy)-1,1-dioxo-2,3-dihydro-1-benzothiepine-4-carboxylate (459 mg) as a light yellow, amorphous substance.

$^1$H-NMR (200 MHz, CDCl$_3$) δ3.06 (2H, t, J=6.6 Hz), 3.61 (2H, t, J=7.0 Hz), 3.83 (3H, s), 3.85 (3H, s), 5.13 (2H, s), 6.87–7.02 (4H, m), 7.06 (1H, s), 7.32 (1H, t, J=7.7 Hz), 7.77 (1H, s), 8.08 (1H, d, J=8.4 Hz).

IR (KBr) 1713, 1590, 1493, 1321, 1292, 1269, 1246, 1217, 1163, 1128 cm$^{-1}$.

Reference Example 155

To methyl 7-(3-methoxybenzyloxy)-1,1-dioxo-2,3-dihydro-1-benzothiepine-4-carboxylate (436 mg) dissolved in THF-methanol (10–5 ml) was added a 2 M aqueous solution of potassium carbonate (1.2 ml), and the resulting mixture was stirred at 60° C. for 14.5 hours. The reaction mixture was treated with 1 N hydrochloric acid to bring the pH to 2. The resulting mixture was diluted with ethyl acetate and was washed respectively with water and an aqueous saturated solution of sodium chloride, and the organic layer was dried with anhydrous magnesium sulfate. After concentration under reduced pressure to remove the solvent, the precipitated crystals were washed with hexane-ethyl acetate to obtain 7-(3-methoxybenzyloxy)-1,1-dioxo-2,3-dihydro-1-benzothiepine-4-carboxylic acid (271 mg) as white crystals.

M. p. 220–222° C.

$^1$H-NMR (200 MHz, DMSO-d$_6$) δ2.91 (2H, t-like), 3.69 (2H, t, J=6.2 Hz), 3.77 (3H, s), 5.23 (2H, s), 6.90–6.94 (1H, m), 7.05 (2H, s, d-like), 7.20–7.43 (3H, m), 7.72 (1H, s), 7.95 (1H, d, J=8.8 Hz).

IR (KBr) 1684, 1597, 1564, 1493, 1454, 1285, 1256, 1173, 1130, 1130, 1073, 1032, 772 cm$^{-1}$.

Anal. Calcd. for C$_{19}$H$_{18}$O$_6$S: C, 60.95; H, 4.85. Found: C, 60.70; H, 4.94.

Example 116 (Production of Compound 117)

To 7-(3-methoxybenzyloxy)-1,1-dioxo-2,3-dihydro-1-benzothiepine-4-carboxylic acid (204 mg) suspended in THF (10 ml) were added DMF (one drop) and thionyl chloride (0.079 ml), and the resulting mixture was stirred at room temperature for one hour. After concentration under reduced pressure, the residue was dissolved in THF (10 ml). To 4-[[N-methyl-N-(tetrahydropyran-4-yl)amino]methyl] aniline dihydrochloride (192 mg) suspended in THF (10 ml) was added dropwise triethylamine (0.57 ml), and then thereto was added dropwise at 0° C. the above-prepared solution of the acid chloride in THF. The resulting mixture was stirred at room temperature for 3 hours. The reaction mixture was concentrated, ethyl acetate was added to the residue and the resulting mixture was washed successively with water and an aqueous saturated solution of sodium chloride, and was then dried with anhydrous magnesium sulfate. After concentration under reduced pressure to remove the solvent, the residue was subjected to purification using silica gel column chromatography (ethyl acetate→ethyl acetate:ethanol=10:1), and further to recrystallization from ethanol to obtain 7-(3-methoxybenzyloxy)-N-[4-[[N-methyl-N-(tetrahydropyran-4-yl)amino]methyl]phenyl]-1,1-dioxo-2,3-dihydro-1-benzothiepine-4-carboxamide (compound 117) (217 mg) as light yellow crystals.

M. p. 181–185° C.

$^1$H-NMR (200 MHz, CDCl$_3$) δ1.69–1.77 (4H, m), 2.21 (3H, s), 2.57–2.69 (1H, m), 3.09 (2H, t, J=6.6 Hz), 3.37 (2H, td, J=11.1, 3.3 Hz), 3.57 (2H, s), 3.69 (2H, t, J=6.8 Hz), 3.83 (3H, s), 4.01–4.07 (2H, m), 5.13 (2H, s), 6.87–7.07 (5H, m), 7.20 (1H, s), 7.29–7.37 (3H, m), 7.53 (2H, d, J=8.8 Hz), 7.81 (1H, s), 8.09 (1H, d, J=8.4 Hz)

IR (KBr) 1667, 1597, 1566, 1522, 1491, 1410, 1314, 1287, 1267, 1163, 1142, 1127, 1065, 737 cm$^{-1}$.

Anal. Calcd. for C$_{32}$H$_{36}$N$_2$O$_6$S (0.4 H$_2$O): C, 65.82; H, 6.35; N, 4.80. Found: C, 65.76; H, 6.33; N, 4.50.

Reference Example 156

To a mixture of 3-hydroxybenzyl alcohol (3.56 g) and acetone (100 ml) were added iodoethane (6.7 g) and potassium carbonate (7.9 g), and the resulting mixture was heated at reflux for 61 hours. The reaction mixture was concentrated, ethyl acetate was added to the residue and the resulting mixture was washed successively with water and an aqueous saturated solution of sodium chloride, and was then dried with anhydrous magnesium sulfate. The solvent was evaporated under reduced pressure to obtain 3-ethoxybenzyl alcohol (4.15 g) as an oil.

$^1$H-NMR (200 MHz, CDCl$_3$) δ1.42 (3H, t, J=7.0 Hz), 1.69–1.73 (1H, m), 4.05 (2H, q, J=6.9 Hz), 4.67 (2H, d, J=5.8 Hz), 6.83 (1H, dd, J=8.2, 2.6 Hz), 6.91–6.95 (2H, m), 7.27 (1H, t, J=8.1 Hz).

Reference Example 157

To a mixture of 3-ethoxybenzyl alcohol (4.15 g) and toluene (50 ml) were added one drop of pyridine and thionyl chloride (3.0 ml), and the resulting mixture was stirred at room temperature for one hour. The reaction mixture was diluted with ethyl acetate, washed successively with water, an aqueous saturated solution of sodium bicarbonate, water and an aqueous saturated solution of sodium chloride, and was then dried with anhydrous magnesium sulfate. The resulting organic layer was evaporated under reduced pressure to remove the solvent to obtain 3-ethoxybenzyl chloride (5.34 g) as an oil.

Methyl 7-hydroxy-1,1-dioxo-2,3-dihydro-1-benzothiepine-4-carboxylate (400 mg), the above-mentioned 3-ethoxybenzyl chloride (636 mg) and potassium carbonate (515 mg) were suspended in DMF (15 ml), and the resulting suspension was stirred at 60° C. for 14 hours. The reaction mixture was diluted with ethyl acetate and was washed respectively with water and an aqueous saturated solution of sodium chloride, and the organic layer was dried with anhydrous magnesium sulfate. The resulting organic layer was concentrated under reduced pressure to remove the solvent, and the residue was subjected to purification using silica gel column chromatography (hexane:ethyl acetate=3:1) to obtain methyl 7-(3-ethoxybenzyloxy)-1,1-dioxo-2,3-dihydro-1-benzothiepine-4-carboxylate (308 mg) as a yellow amorphous substance.

$^1$H-NMR (200 MHz, CDCl$_3$) δ1.43 (3H, t, J=7.2 Hz), 3.07 (2H, t, J=6.6 Hz), 3.61 (2H, t, J=6.7 Hz), 3.86 (3H, s), 4.05 (2H, q, J=7.2 Hz), 5.13 (2H, s), 6.91–7.06 (4H, m), 7.24–7.31 (2H, m), 7.77 (1H, s), 8.08 (1H, d, J=8.4 Hz)

IR (KBr) 1713, 1590, 1289, 1267, 1215, 1163, 1128 cm$^{-1}$.

Reference Example 158

To methyl 7-(3-ethoxybenzyloxy)-1,1-dioxo-2,3-dihydro-1-benzothiepine-4-carboxylate (298 mg) dissolved in THF-methanol (10–5 ml) was added a 2 M aqueous solution of potassium carbonate (0.75 ml), and the resulting mixture was stirred at 60° C. for 16.5 hours. The reaction mixture was treated with 1 N hydrochloric acid to bring the pH to 2. The resulting mixture was extracted with ethyl acetate, and the organic layer was dried with anhydrous magnesium sulfate. After concentration under reduced pressure to remove the solvent, the precipitated crystals were washed with hexane-ethyl acetate to obtain 7-(3-ethoxybenzyloxy)-1,1-dioxo-2,3-dihydro-1-benzothiepine-4-carboxylic acid (45 mg) as white crystals. The mother liquor was concentrated under reduced pressure to obtain 7-(3-ethoxybenzyloxy)-1,1-dioxo-2,3-dihydro-1-benzothiepine-4-carboxylic acid (340 mg) as a brown oil. This compound was used in the next reaction without further purification.

M. p. 150–154° C.

$^1$H-NMR (200 MHz, DMSO-d$_6$) δ1.33 (3H, t, J=7.0 Hz), 2.90 (2H, t, J=6.2 Hz), 3.67 (2H, t, J=6.7 Hz), 4.03 (2H, q, J=7.1 Hz), 5.21 (2H, s), 6.86–6.91 (1H, m), 6.99–7.02 (2H, m), 7.21 (1H, d, J=8.8 Hz), 7.30 (1H, t, J=8.0 Hz), 7.41 (1H, d-like), 7.72 (1H, s), 7.94 (1H, d, J=8.8 Hz).

IR (KBr) 1692, 1588, 1292, 1277, 1258, 1159, 1127 cm$^{-1}$.

Anal. Calcd. for $C_{22}H_{20}O_6S$ (0.2 H$_2$O): C, 61.27; H, 5.19. Found: C, 61.06; H, 5.26.

Example 117 (Production of Compound 118)

To 7-(3-ethoxybenzyloxy)-1,1-dioxo-2,3-dihydro-1-benzothiepine-4-carboxylic acid (250 mg) suspended in THF (10 ml) were added DMF (one drop) and thionyl chloride (0.090 ml), and the resulting mixture was stirred at room temperature for one hour. After concentration under reduced pressure, the residue was dissolved in THF (10 ml).

To 4-[N-methyl-N-(tetrahydropyran-4-yl)amino]methyl]aniline dihydrochloride (226 mg) suspended in THF (5 ml) was added dropwise triethylamine (0.67 ml), and then thereto was added dropwise at 0° C. the above-prepared solution of the acid chloride in THF. The resulting mixture was stirred at 0° C. for 20 minutes and at room temperature for 16 hours. The reaction mixture was concentrated, ethyl acetate was added to the residue and the resulting mixture was washed successively with water and an aqueous saturated solution of sodium chloride, and was then dried with anhydrous magnesium sulfate. After concentration under reduced pressure to remove the solvent, the residue was subjected to purification using silica gel column chromatography (ethyl acetate→ethyl acetate:ethanol=10:1), and further to recrystallization from ethanol to obtain 7-(3-ethoxybenzyloxy)-N-[4-[[N-methyl-N-(tetrahydropyran-4-yl)amino]methyl]phenyl]-1,1-dioxo-2,3-dihydro-1-benzothiepine-4-carboxamide (compound 118) (71 mg) as white crystals.

M. p. 189–192° C.

$^1$H-NMR (200 MHz, CDCl$_3$) δ1.42 (3H, t, J=6.9 Hz), 1.60–1.75 (4H, m), 2.21 (3H, s), 2.60–2.69 (1H, m), 3.08 (2H, t, J=6.8 Hz), 3.37 (2H, td, J=11.2, 3.1 Hz), 3.57 (2H, s), 3.68 (2H, t, J=6.8 Hz), 4.04 (2H, q, J=7.0 Hz), 3.99–4.10 (2H, m), 5.12 (2H, s), 6.86–7.06 (5H, m), 7.20 (1H, s), 7.29–7.34 (3H, m), 7.53 (2H, d, J=8.4 Hz), 7.85 (1H, s), 8.08 (1H, d, J=8.4 Hz).

IR (KBr) 1663, 1597, 1566, 1410, 1291, 1264, 1163, 1142, 1125, 1065, 735 cm$^{-1}$.

Anal. Calcd. for $C_{33}H_{38}N_2O_6S$ (0.3 H$_2$O): C, 66.49; H, 6.53; N, 4.70. Found: C, 66.29; H, 6.42; N, 4.47.

Reference Example 159

To salicylaldehyde (12.2 g) dissolved in DMF (100 ml) were added 1-bromopropane (14.7 g) and potassium carbonate (20.7 g), and the resulting mixture was stirred at room temperature for 21.5 hours. The reaction mixture was diluted with ethyl acetate and washed with water and an aqueous saturated solution of sodium chloride, and the organic layer was dried with anhydrous magnesium sulfate. The resulting organic layer was evaporated under reduced pressure to remove the solvent to obtain 2-propoxybenzaldehyde (15.47 g) as an oil.

$^1$H-NMR (200 MHz, CDCl$_3$) δ1.08 (3H, t, J=7.3 Hz), 1.89 (2H, sextet, J=7.0 Hz), 4.05 (2H, t, J=6.4 Hz), 6.96–7.05 (2H, m), 7.54 (1H, td, J=7.9, 1.9 Hz), 7.84 (1H, dd, J=7.6, 1.8 Hz), 10.53 (1H, s).

Reference Example 160

3-Propoxybenzaldehyde (15.47 g) and methyl (triphenylphosphoranylidene)acetate was suspended in toluene (150 ml), and the resulting suspension was heated at reflux for 2 hours. The reaction mixture was diluted with ethyl acetate and was washed respectively with water and an aqueous saturated solution of sodium chloride, and the organic layer was dried with anhydrous magnesium sulfate. After concentration under reduced pressure to remove the solvent, the precipitated triphenylphosphine oxide was removed and was washed with ether. The filtrate was concentrated under reduced pressure, and the residue was purified by silica gel column chromatography (hexane:ethyl acetate=6:1) to obtain ethyl 2-propoxycinnamate (21.24 g) as a yellow oil.

$^1$H-NMR (200 MHz, CDCl$_3$, ratio: ca. 5:1) δ1.03 (0.5H, t, J=7.5 Hz), 1.08 (2.5H, t, J=7.5 Hz), 1.21 (0.5H, t, J=7.1

Hz), 1.34 (2.5H, t, J=7.1 Hz), 1.85 and 1.89 (2H, each sextet, J=7.1 Hz), 3.94 (0.33H, t, J=6.4 Hz), 4.00 (1.67H, t, J=6.6 Hz), 4.14 (0.33H, q, J=7.4 Hz), 4.26 (1.67H, q, J=7.2 Hz), 5.95 (0.17H, d, J=12.4 Hz), 6.54 (0.83H, d, J=16.2 Hz), 6.85 (0.17H, d, J=8.4 Hz), 6.90 (0.83H, d, J=9.2 Hz), 6.94 (1H, t, J=7.1 Hz), 7.00 (0.17H, d, J=12.8 Hz), 7.32 (1H, td, J=7.8, 1.6 Hz), 7.51 (0.83H, dd, J=7.5, 1.7 Hz), 7.58 (0.17H, dd, J=7.5, 1.7 Hz), 8.02 (0.83H, d, J=16.6 Hz).

Reference Example 161

To lithium aluminum hydride (6.87 g) suspended in diethyl ether (300 ml) was added dropwise at 0° C. a solution of ethyl 2-propoxycinnamate (21.2 g) in diethyl ether (100 ml) over a period of 40 minutes. After the dropwise addition, the resulting mixture was stirred at room temperature for one hour. Water (7 ml), a 15% aqueous solution of sodium hydroxide (7 ml) and water (21 ml) were added to the reaction mixture, and the resulting mixture was further stirred at room temperature for one hour. The reaction mixture was diluted with diethyl ether and was dried by addition of anhydrous magnesium sulfate. After the resulting mixture was filtered, the filtrate was concentrated under reduced pressure to obtain 3-(2-propoxyphenyl)-1-propanol (17.01 g) as a colorless oil.

$^1$H-NMR (200 MHz, CDCl$_3$) δ1.06 (3H, t, J=7.3 Hz), 1.75–1.93 (4H, m), 2.75 (2H, t, J=7.1 Hz), 3.60 (2H, q, J=5.7 Hz), 3.95 (2H, t, J=6.4 Hz), 6.83–6.92 (2H, m), 7.13–7.24 (2H, m).

Reference Example 162

To 3-(2-propoxyphenyl)-1-propanol (729 mg) dissolved in THF (35 ml) were added at 0° C. triethylamine (1.57 ml) and methanesulfonyl chloride (0.44 ml). The resulting mixture was stirred at 0° C. for 20 minutes and at room temperature for 2 hours. The reaction mixture was diluted with ethyl acetate and was washed respectively with water and an aqueous saturated solution of sodium chloride, and the organic layer was dried with magnesium sulfate. The resulting organic layer was evaporated under reduced pressure to remove the solvent to obtain 3-(2-propoxyphenyl)propyl methanesulfonate (1.06 g) as a colorless oil.

$^1$H-NMR (200 MHz, CDCl$_3$) δ1.06 (3H, t, J=7.5 Hz), 1.83 (2H, sextet, J=7.0 Hz), 2.07 (2H, quint, J=6.9 Hz), 2.76 (2H, t, J=7.3 Hz), 2.98 (3H, s), 3.93 (2H, t, J=6.4 Hz), 4.24 (2H, t, J=6.6 Hz), 6.82–6.91 (2H, m), 7.11–7.22 (2H, m).

Reference Example 163

Methyl 7-hydroxy-1,1-dioxo-2,3-dihydro-1-benzothiepine-4-carboxylate (400 mg), 3-(2-propoxyphenyl)propyl methanesulfonate (1.06 g) and potassium carbonate (309 mg) were suspended in DMF (15 ml), and the resulting suspension was stirred at 60° C. for 3 hours. The reaction mixture was diluted with ethyl acetate and was washed respectively with water and an aqueous saturated solution of sodium chloride, and the organic layer was dried with anhydrous magnesium sulfate. After concentration under reduced pressure to remove the solvent, the residue was purified by silica gel column chromatography (hexane:ethyl acetate=3:1) to obtain methyl 7-[3-(2-propoxyphenyl)propoxy]-1,1-dioxo-2,3-dihydro-1-benzothiepine-4-carboxylate (832 mg) as a yellow oil.

To methyl 7-[3-(2-propoxyphenyl)propoxy]-1,1-dioxo-2,3-dihydro-1-benzothiepine-4-carboxylate (832 mg) dissolved in THF-methanol (15–7.5 ml) was added a 2 M aqueous solution of potassium carbonate (1.5 ml), and the resulting mixture was stirred at 60° C. for 20 hours. The reaction mixture was treated with 1 N hydrochloric acid to bring the pH to 2. The resulting mixture was extracted with ethyl acetate, and the organic layer was washed with an aqueous saturated solution of sodium chloride and was dried with anhydrous magnesium sulfate. After concentration under reduced pressure to remove the solvent, the precipitated crystals were washed with ethyl acetate to obtain 7-[3-(2-propoxyphenyl)propoxy]-1,1-dioxo-2,3-dihydro-1-benzothiepine-4-carboxylic acid (474 mg) as white crystals.

M. p. 153–157° C.

$^1$H-NMR (200 MHz, DMSO-d$_6$) δ0.98 (3H, t, J=7.3 Hz), 1.70 (2H, sextet, J=6.9 Hz), 2.00 (2H, quint-like), 2.72 (2H, t, J=7.6 Hz), 2.90 (2H, t, J=6.4 Hz), 3.67 (2H, t, J=6.6 Hz), 3.90 (2H, t, J=6.3 Hz), 4.11 (2H, t, J=6.3 Hz), 6.84 (1H, t, J=7.3 Hz), 6.92 (1H, d, J=7.2 Hz), 7.09–7.19 (3H, m), 7.30 (1H, d, J=2.2 Hz), 7.72 (1H, s), 7.92 (1H, d, J=8.8 Hz).

IR (KBr) 1674, 1597, 1566, 1493, 1454, 1319, 1296, 1279, 1251, 1167, 1130, 1071, 747, 527 cm$^{-1}$.

Anal. Calcd. for $C_{23}H_{26}O_6S$ (0.4 H$_2$O): C, 63.11; H, 6.17. Found: C, 62.92; H, 6.37

Example 118 (Production of Compound 119)

To 7-[3-(2-propoxyphenyl)propoxy]-1,1-dioxo-2,3-dihydro-1-benzothiepine-4-carboxylic acid (504 mg) suspended in THF (20 ml) were added DMF (one drop) and thionyl chloride (0.17 ml), and the resulting mixture was stirred at room temperature for one hour. After concentration under reduced pressure, the residue was dissolved in THF (25 ml). To 4-[[N-methyl-N-(tetrahydropyran-4-yl)amino]methyl]aniline dihydrochloride (412 mg) suspended in THF (12 ml) was added dropwise triethylamine (1.22 ml), and then thereto was added dropwise at 0° C. the above-prepared solution of the acid chloride in THF. The resulting mixture was stirred at room temperature for 4 hours. The reaction mixture was concentrated, ethyl acetate was added to the residue, and the resulting mixture was washed successively with water and an aqueous saturated solution of sodium chloride, and was then dried with anhydrous magnesium sulfate. After concentration under reduced pressure to remove the solvent, the solid residue was recrystallized from ethanol to obtain N-[4-[[N-methyl-N-(tetrahydropyran-4-yl)amino]methyl]phenyl]-7-[3-(2-propoxyphenyl)propoxy]-1,1-dioxo-2,3-dihydro-1-benzothiepine-4-carboxamide (compound 119) (469 mg) as white crystals.

M. p. 184–186° C.

$^1$H-NMR (200 MHz, CDCl$_3$) δ1.05 (3H, t, J=7.5 Hz), 1.64–1.82 (4H, m), 1.80 (2H, sextet, J=7.1 Hz), 2.12 (2H, quint, J=7.3 Hz), 2.21 (3H, s), 2.57–2.72 (1H, m), 2.82 (2H, t, J=7.3 Hz), 3.08 (2H, t, J=6.6 Hz), 3.37 (2H, td, J=11.2, 3.0 Hz), 3.58 (2H, s), 3.68 (2H, t, J=6.8 Hz), 3.92 (2H, t, J=6.4 Hz), 4.00–4.07 (2H, m), 4.03 (2H, t, J=6.4 Hz), 6.82–6.96 (4H, m), 7.11–7.22 (3H, m), 7.32 (2H, d, J=8.4 Hz), 7.54 (2H, d, J=8.4 Hz), 7.84 (1H, s), 8.06 (1H, d, J=8.8 Hz).

IR (KBr) 2940, 1667, 1595, 1522, 1493, 1454, 1410, 1291, 1260, 1242, 1163, 1125, 1065, 754, 735 cm$^{-1}$.

Anal. Calcd. for $C_{36}H_{44}N_2O_6S$ (0.1 H$_2$O): C, 68.13; H, 7.02, N. 4.41. Found: C, 67.93; H, 7.02; N, 4.24.

Reference Example 164

To 3-hydroxybenzaldehyde (12.2 g) dissolved in DMF (100 ml) were added 1-bromopropane (14.7 g) and potassium carbonate (20.7 g), and the resulting mixture was stirred at room temperature for 17 hours. The reaction mixture was diluted with ethyl acetate and washed respectively with water and an aqueous saturated solution of sodium chloride, and the organic layer was dried with anhydrous magnesium sulfate. The resulting organic layer was evaporated under reduced pressure to remove the solvent to obtain 2-propoxybenzaldehyde (16.18 g) as an oil.

$^1$H-NMR (200 MHz, CDCl$_3$) δ1.05 (3H, t, J=7.5 Hz), 1.84 (2H, sextet, J=7.0 Hz), 3.98 (2H, t, J=6.6 Hz), 7.15–7.22 (1H,; m), 7.38–7.46 (3H, m), 9.97 (1H, s).

Reference Example 165

To ethyl diethylphosphonoacetate (24.7 g) was added THF (200 ml), and sodium hydride (60%, 4.4 g) was added at 0° C. to the resulting mixture, to which was then added dropwise a solution of 3-propoxybenzaldehyde (16.1 g) in THF (100 ml). The resulting mixture was stirred at room temperature for 1.5 hours. The reaction mixture was poured into water, was neutralized with hydrochloric acid and was extracted with ethyl acetate. The organic layer was washed with an aqueous saturated solution of sodium chloride and was dried with anhydrous magnesium sulfate. After concentration under reduced pressure to remove the solvent, the residue was purified by silica gel column chromatography (hexane:ethyl acetate=6:1) to obtain ethyl 3-propoxycinnamate (24.0 g) as a yellow oil.

$^1$H-NMR (200 MHz, CDCl$_3$) δ1.05 (3H, t, J=7.5 Hz), 1.34 (3H, t, J=7.1 Hz), 1.82 (2H, sextet, J=7.0 Hz), 3.94 (2H, t, J=6.4 Hz), 4.27 (2H, q, J=7.2 Hz), 6.42 (1H, d, J=16.2 Hz), 6.90–6.95 (1H, m), 7.05–7.12 (2H, m), 7.29 (1H, t, J=7.7 Hz), 7.65 (1H, d, J=16.2 Hz).

Reference Example 166

To lithium aluminum hydride (7.58 g) suspended in diethyl ether (300 ml) was added dropwise at 0° C. a solution of ethyl 3-propoxycinnamate (24.0 g) in diethyl ether (100 ml) over a period of one hour. After the dropwise addition, the resulting mixture was stirred at room temperature for one hour. Water (7.6 ml), a 15% aqueous solution of sodium hydroxide (7.6 ml) and water (22 ml) were added to the reaction mixture, which was further stirred at room temperature for 0.5 hour. The reaction mixture was diluted with diethyl ether and was dried with anhydrous magnesium sulfate. After the resulting mixture was filtered, the filtrate was concentrated under reduced pressure, and the residue was purified by silica gel column chromatography (hexane:ethyl acetate 4:1) to obtain 3-(3-propoxyphenyl)-1-propanol (15.23 g) as a colorless oil.

$^1$H-NMR (200 MHz, CDCl$_3$) δ1.04 (3H, t, J=7.5 Hz), 1.27 (1H, t, J=3.7 Hz), 1.83 (2H, sextet, J=7.1 Hz), 1.81–1.96 (2H, m), 2.68 (2H, t, J=7.7 Hz), 3.68 (2H, q, J=5.9 Hz), 3.91 (2H, t, J=6.6 Hz), 6.70–6.80 (3H, m), 7.19 (1H, t, J=8.1 Hz).

Reference Example 167

To a mixture of 3-(3-propoxyphenyl)-1-propanol (731 mg) and THF (20 ml) were added at 0° C. triethylamine (1.57 ml) and methanesulfonyl chloride (0.44 ml). The resulting mixture was stirred at 0° C. for 20 minutes and at room temperature for 0.5 hour. The reaction mixture was diluted with ethyl acetate and was washed respectively with water and an aqueous saturated solution of sodium chloride, and the organic layer was dried with anhydrous magnesium sulfate. The resulting organic layer was evaporated under reduced pressure to remove the solvent to obtain 3-(3-propoxyphenyl)propyl methanesulfonate (1.10 g) as a colorless oil.

$^1$H-NMR (200 MHz, CDCl$_3$) δ1.04 (3H, t, J=7.3 Hz), 1.80 (2H, sextet, J=7.1 Hz), 2.01–2.14 (2H, m), 2.72 (2H, t, J=7.5 Hz) 3.00 (3H, s), 3.91 (2H, t, J=6.6 Hz), 4.23 (2H, t, J=6.2 Hz), 6.74–6.78 (3H, m), 7.16–7.24 (1H, m).

Reference Example 168

Methyl 7-hydroxy-1,1-dioxo-2,3-dihydro-1-benzothiepine-4-carboxylate (394 mg), propoxyphenyl)propyl methanesulfonate (1099 mg) and potassium carbonate (304 mg) were suspended in DMF (15 ml), and the resulting suspension was stirred at 70° C. for 5 hours. The reaction mixture was diluted with ethyl acetate and was washed respectively with water and an aqueous saturated solution of sodium chloride, and the organic layer was dried with anhydrous magnesium sulfate. After concentration under reduced pressure to remove the solvent, is the residue was purified by silica gel column chromatography (hexane:ethyl acetate=3:1) to obtain methyl 7-[3-(3-propoxyphenyl)propoxy]-1,1-dioxo-2,3-dihydro-1-benzothiepine-4-carboxylate (765 mg) as a yellow oil.

To methyl 7-[3-(3-propoxyphenyl)propoxy]-1,1-dioxo-2,3-dihydro-1-benzothiepine-4-carboxylate (765 mg) dissolved in THF-methanol (15–7.5 ml) was added a 2 M aqueous solution of potassium carbonate (1.5 ml), and the resulting mixture was stirred at 60° C. for 18 hours. The reaction mixture was treated with 1 N hydrochloric acid to bring the pH to 2. The resulting mixture was extracted with ethyl acetate and the organic layer was washed with an aqueous saturated solution of sodium chloride and was dried with anhydrous magnesium sulfate. After concentration under reduced pressure to remove the solvent, the precipitated crystals were washed with hexane-ethyl acetate to obtain 7-[3-(3-propoxyphenyl)propoxy]-1,1-dioxo-2,3-dihydro-1-benzothiepine-4-carboxylic acid (470 mg) as white crystals.

M. p. 128–131° C.

$^1$H-NMR (200 MHz, DMSO-d$_6$) δ0.95 (3H, t, J=7.3 Hz), 1.69 (2H, sextet, J=7.0 Hz), 2.04 (2H, quint, J=7.1 Hz), 2.71 (2H, t, J=7.4 Hz), 2.90 (2H, t, J=6.6 Hz), 3.67 (2H, t, J=6.6 Hz), 3.87 (2H, t, J=6.6 Hz), 4.09 (2H, t, J=6.2 Hz), 6.72–6.80 (3H, m), 7.14 (1H, dd, J=8.4, 2.2 Hz), 7.18 (1H, t, J=7.9 Hz), 7.32 (1H, d-like), 7.72 (1H, s), 7.93 (1H, d, J=8.4 Hz).

IR (KBr) 1698, 1595, 1564, 1319, 1291, 1277, 1258, 1163, 1130, 1071, 748 cm$^{-1}$.

Anal. Calcd. for $C_{23}H_{26}O_6S$ (0.4 $H_2O$): C, 63.11; H, 6.17. Found: C, 62.95; H, 5.95.

Example 119 (Production of Compound 120)

To 7-[3-(3-propoxyphenyl)propoxy]-1,1-dioxo-2,3-dihydro-1-benzothiepine-4-carboxylic acid (395 mg) suspended in THF (12 ml) were added DMF (one drop) and thionyl chloride (0.13 ml), and the resulting mixture was stirred at room temperature for one hour. After concentration under reduced pressure, the residue was dissolved in THF (10 ml). To 4-[[N-methyl-N-(tetrahydropyran-4-yl)amino]methyl]aniline dihydrochloride (323 mg) suspended in THF (12 ml) was added dropwise triethylamine (0.96 ml), and then thereto was added dropwise at 0° C. the above-prepared solution of the acid chloride in THF. The resulting mixture was stirred at room temperature for 15 hours. The reaction mixture was concentrated and was diluted with ethyl acetate, ant and the resulting mixture was washed successively with water and an aqueous saturated solution of sodium chloride, and was then dried with anhydrous magnesium sulfate. After concentration under reduced pressure to remove the solvent, the residue was subjected to purification using, silica gel column chromatography (ethyl acetate→ethyl acetate:ethanol=10:1) and further to recrystallization from ethanol to obtain N-[4-[[N-methyl-N-(tetrahydropyran-4-yl) amino]methyl]phenyl]-7-[3-(3-propoxyphenyl)propoxy]-1, 1-dioxo-dihydro-1-benzothiepine-4-carboxamide (compound 120) (302 mg) as white crystals.

M. p. 145–146° C.

$^1$H-NMR (200 MHz, CDCl$_3$) δ1.02 (3H, t, J=7.5 Hz), 1.66–1.81 (4H, m), 1.79 (2H, sextet, J=7.2 Hz), 2.14 (2H, quint, J=7.1 Hz), 2.21 (3H, s), 2.57–2.70 (1H, m), 2.78 (2H, t, J=7.5 Hz), 3.09 (2H, t, J=6.8 Hz), 3.37 (2H, td, J=11.2, 2.9 Hz), 3.57 (2H, s), 3.68 (2H, t, J=6.7 Hz), 3.89 (2H, t, J=6.6 Hz), 4.00–4.06 (2H, m), 4.03 (2H, t, J=6.3 Hz), 6.73–6.79 (3H, m), 6.88 (1H, d, J=2.2 Hz), 6.94 (1H, dd, J=8.8, 2.6 Hz), 7.20 (1H, s and 1H, t, J=8.1 Hz), 7.32 (2H, d, J=8.4 Hz), 7.54 (2H, d, J=8.4 Hz), 7.84 (1H, s), 8.07 (1H, d, J=8.8 Hz).

IR (KBr) 2948, 1667, 1595, 1564, 1526, 1518, 1408, 1316, 1289, 1262, 1161, 1142, 1125, 1065 cm$^{-1}$.

Anal. Calcd. for C$_{36}$H$_{44}$N$_2$O$_6$S (0.4 H$_2$O): C, 67.56; H, 7.06; N, 4.38. Found: C, 67.32; H, 6.82; N, 4.30.

Reference Example 169

A mixture of 3-(4-hydroxyphenyl)-1-propanol (1.33 g), 1-bromopropane (1.2 ml) and potassium carbonate (2.25 g) and acetone (100 ml) was heated at reflux for 2 days. After concentration under reduced pressure, the residue was mixed with water and was extracted with ethyl acetate. The organic layer was washed with a 1 N aqueous solution of sodium hydroxide and an aqueous saturated solution of sodium chloride, and was dried with magnesium sulfate. The resulting organic layer was evaporated under reduced pressure to remove the solvent to obtain 3-(4-propoxyphenyl)-1-propanol (1.61 g) as a colorless oily substance.

$^1$H-NMR (200 MHz, CDCl$_3$) δ1.03 (3H, t, J=7.5 Hz), 1.70–1.91 (4H, m), 2.61–2.69 (3H, m), 3.67 (2H, t, J=6.5 Hz), 3.90 (2H, t, J=6.6 Hz), 6.83 (2H, d, J=8.4 Hz), 7.10 (2H, d, J=8.4 Hz).

Reference Example 170

To a mixture of 3-(4-propoxyphenyl)-1-propanol (735 mg) and THF (20 ml) were added at 0° C. triethylamine (1.58 ml) and methanesulfonyl chloride (0.44 ml). The resulting mixture was stirred at 0° C. for 20 minutes and at room temperature for 20 minutes. The reaction mixture was diluted with ethyl acetate and was washed respectively with water and an aqueous saturated solution of sodium chloride, and the organic layer was dried with anhydrous magnesium sulfate. The resulting organic layer was evaporated under reduced pressure to remove the solvent to obtain 3-(4-propoxyphenyl)propyl methanesulfonate (1.02 g) as a colorless oil.

$^1$H-NMR (200 MHz, CDCl$_3$) δ1.03 (3H, t, J=7.5 Hz), 1.80 (2H, sextet, J=7.0 Hz), 2.04 (2H, quint, J=7.0 Hz), 2.69 (2H, t, J=7.5 Hz), 2.99 (3H, s), 3.90 (2H, t, J=6.6 Hz), 4.22 (2H, t, J=6.4 Hz), 6.81–6.87 (2H, m), 7.07–7.11 (2H, m).

Reference Example 171

Methyl 7-hydroxy-1,1-dioxo-2,3-dihydro-1-benzothiepine-4-carboxylate (401 mg), 3-(4-propoxyphenyl)propyl methanesulfonate (1017 mg) and potassium carbonate (310 mg) were suspended in DMF (15 ml), and the resulting suspension was stirred at 70° C. for 5 hours. The reaction mixture was diluted with ethyl acetate and was washed respectively with water and an aqueous saturated solution of sodium chloride, and the organic layer was dried with anhydrous magnesium sulfate. After concentration under reduced pressure to remove the solvent, the residue was purified by silica gel column chromatography (hexane:ethyl acetate=3:1) to obtain methyl 7-[3-(4-propoxyphenyl)propoxy]-1,1-dioxo-2,3-dihydro-1-benzothiepine-4-carboxylate (937 mg) as a yellow oil.

To methyl 7-[3-(4-propoxyphenyl)propoxy]-1,1-dioxo-2, 3-dihydro-1-benzothiepine-4-carboxylate (937 mg) dissolved in THF-methanol (15–7.5 ml) was added a 2 M aqueous solution (1.5 ml) of potassium carbonate, and the resulting mixture was stirred at 60° C. for 18.5 hours. The reaction mixture was treated with 1 N hydrochloric acid to bring the pH to 2. The resulting mixture was extracted with ethyl acetate, and the organic layer was washed with an aqueous saturated solution of sodium chloride and was dried with anhydrous magnesium sulfate. After evaporation under reduced pressure to remove the solvent, the precipitated crystals were washed with hexane-ethyl acetate to obtain 7-[3-(4-propoxyphenyl)propoxy]-1,1-dioxo-2,3-dihydro-1-benzothiepine-4-carboxylic acid (333 mg) as white crystals.

M. p. 168–170° C.

$^1$H-NMR (200 MHz, DMSO-d$_6$) δ0.97 (3H, t, J=7.3 Hz), 1.71 (2H, sextet, J=7.1 Hz), 2.00 (2H, quint-like), 2.67 (2H, t, J=7.3 Hz), 2.90 (2H, t-like), 3.67 (2H, t, J=6.6 Hz), 3.87 (2H, t, J=6.6 Hz), 4.08 (2H, t-like), 6.83 (2H, d, J=8.4 Hz), 7.10–7.14 (1H, m), 7.12 (2H, d, J=8.4 Hz), 7.30 (1H, d-like), 7.72 (1H, s), 7.93 (1H, d, J=9.0 Hz).

IR (KBr) 1686, 1593, 1564, 1510, 1294, 1279, 1240, 1163, 1130, 1073 cm$^{-1}$.

Anal. Calcd. for C$_{23}$H$_{26}$O$_6$S (0.3 H$_2$O): C, 63.37; H, 6.15. Found: C, 63.07; H, 6.21.

Example 120 (Production of Compound 121)

To 7-[3-(4-propoxyphenyl)propoxy]-1,1-dioxo-2,3-dihydro-1-benzothiepine-4-carboxylic acid (260 mg) suspended in THF (12 ml) were added DMF (one drop) and thionyl chloride (0.088 ml), and the resulting mixture was stirred at room temperature for one hour. After concentration under reduced pressure, the residue was dissolved in THF (10 ml). To 4-[[N-methyl-N-(tetrahydropyran-4-yl)amino] methyl]aniline dihydrochloride (213 mg) suspended in THF (12 ml) was added dropwise triethylamine (0.63 ml), and then thereto was added dropwise at 0° C. the above-prepared solution of the acid chloride in THE. The resulting mixture was stirred at room temperature for 15 hours. The reaction mixture was concentrated and was diluted with ethyl acetate, and the resulting mixture was washed successively with water and an aqueous saturated solution of sodium chloride, and was then dried with anhydrous magnesium sulfate. After concentration under reduced pressure to remove the solvent, the residue was subjected to purification using silica gel column chromatography (ethyl acetate→ethyl acetate:ethanol=10:1) and further to recrystallization from ethanol to obtain N-[4-[[N-methyl-N-(tetrahydropyran-4-yl) amino]methyl]phenyl]-7-[3-(4-propoxyphenyl)propoxy]-1, 1-dioxo-2,3-dihydro-1-benzothiepine-4-carboxamide (compound 121) (281 mg) as white crystals.

M. p. 178–181° C.

$^1$H-NMR (200 MHz, CDCl$_3$) δ1.02 (3H, t, J=7.4 Hz), 1.69–1.81 (4H, m), 1.79 (2H, sextet, J=7.1 Hz), 2.10 (2H, quint, J=7.3 Hz), 2.20 (3H, s), 2.57 –2.67 (1H, m), 2.75 (2H, t, J=7.4 Hz), 3.08 (2H, t, J=6.6 Hz), 3.37 (2H, td, J=11.1, 3.1 Hz), 3.57 (2H, s), 3.68 (2H, t, J=6.7 Hz), 3.89 (2H, t, J=6.6 Hz), 4.01 (2H, t, J=6.2 Hz), 4.01–4.06 (2H, m), 6.83 (2H, d, J=8.4 Hz), 6.89 (1H, d, J=2.2 H z), 6.94 (1H, dd, J=8.6, 2.4 Hz), 7.09 (2H, d, J=8.8 Hz), 7.20 (1H, s), 7.32 (2H, d, J=8.8 Hz), 7.53 (2H, d, J=8.4 Hz), 7.84 (1H, s), 8.07 (1H, d, J=8.8 Hz)

IR (KBr) 2942, 1665, 1595, 1512, 1408, 1314, 1289, 1244, 1163, 1125, 1065 cm$^{-1}$.

Anal. Calcd. for $C_{36}H_{44}N_2O_6S$ (0.6 $H_2O$): C, 67.18; H, 7.08; N, 4.35. Found: C, 66.93; H, 6.93; N, 4.43.

Reference Example 172

To protocatechualdehyde (5.15 g) dissolved in DMF (70 ml) were added iodoethane (14.5 g) and potassium carbonate (15.5 g), and the resulting mixture was stirred at room temperature for 17.5 hours. The reaction mixture was diluted with ethyl acetate and washed respectively with water, a 1 N aqueous solution of sodium hydroxide, water and an aqueous saturated solution of sodium chloride, and the organic layer was dried with anhydrous magnesium sulfate. After evaporation under reduced pressure to remove the solvent, the residue was purified by silica gel column chromatography (hexane:ethyl acetate=4:1) to obtain 3,4-diethoxybenzaldehyde (6.73 g) as a yellow oil.

$^1$H-NMR (200 MHz, CDCl$_3$) δ1.48 (3H, t, J=6.9 Hz), 1.51 (3H, t, J=6.9 Hz), 4.16 (2H, q, J=7.0 Hz), 4.19 (2H, q, J=6.9 Hz), 6.96 (1H, d, J=8.0 Hz), 7.40 (1H, s), 7.43 (1H, dd, J=8.0, 1.8 Hz), 9.84 (1H, s).

Reference Example 173

To a mixture of 3,4-diethoxybenzaldehyde (6.68 g) and methanol (100 ml) was added sodium borohydride (1.30 g) at 0° C. The resulting mixture was stirred at 0° C. for 45 minutes. The reaction mixture was mixed with water and was extracted with ethyl acetate. The organic layer was washed with an aqueous saturated solution of sodium chloride and was dried with anhydrous magnesium sulfate. The resulting organic layer was evaporated under reduced pressure to remove the solvent to obtain 3,4-diethoxybenzyl alcohol (6.64 g) as a yellow oil.

$^1$H-NMR (200 MHz, CDCl$_3$) δ1.445 (3H, t, J=7.0 Hz), 1.452 (3H, t, J=7.1 Hz), 1.62 (1H, br s), 4.09 (2H, q, J=6.9 Hz), 4.11 (2H, q, J=7.0 Hz), 4.60 (2H, s), 6.86–6.93 (3H, m).

Reference Example 174

To 3,4-diethoxybenzyl alcohol (736 mg) dissolved in toluene (10 ml) were added pyridine (one drop) and thionyl chloride (0.41 ml), and the resulting mixture was stirred at room temperature for 20 minutes. The reaction mixture was diluted with ethyl acetate and the resulting mixture was washed with water, an aqueous saturated solution of sodium hydrogen carbonate and an aqueous saturated solution of sodium chloride, and was dried with anhydrous magnesium sulfate. The resulting organic layer was evaporated under reduced pressure to remove the solvent to obtain 3,4-diethoxybenzyl chloride (802 mg) as an oil.

Methyl 7-hydroxy-1,1-dioxo-2,3-dihydro-1-benzothiepine-4-carboxylate (403 mg), 3,4-diethoxybenzyl chloride (802 mg) and potassium carbonate (311 mg) were suspended in DMF (15 ml), and the resulting suspension was stirred at 70° C. for 3 hours. The reaction mixture was diluted with ethyl acetate and was washed respectively with water and an aqueous saturated solution of sodium chloride, and the organic layer was dried with anhydrous magnesium sulfate. After evaporation under reduced pressure to remove the solvent, the residue was purified by silica gel column chromatography (hexane:ethyl acetate=3:1) to obtain methyl 7-(3,4-diethoxybenzyloxy)-1,1-dioxo-2,3-dihydro-1-benzothiepine-4-carboxylate (818 mg) as a yellow amorphous substance.

To methyl 7-(3,4-diethoxybenzyloxy)-1,1-dioxo-2,3-dihydro-1-benzothiepine-4-carboxylate (818 mg) dissolved in THF-methanol (15–7.5 ml) was added a 2 M aqueous solution of potassium carbonate (1.5 ml), and the resulting mixture was stirred at 60° C. for 14 hours. The reaction mixture was treated with 1 N hydrochloric acid to bring the pH to 2. The resulting mixture was extracted with ethyl acetate, and the organic layer was washed with an aqueous saturated solution of sodium chloride and was dried with anhydrous magnesium sulfate. After evaporation under reduced pressure to remove the solvent, the precipitated crystals were washed with hexane-ethyl acetate to obtain 7-(3,4-diethoxybenzyloxy)-1,1-dioxo-2,3-dihydro-1-benzothiepine-4-carboxylic acid (3.02 g) as white crystals.

M. p. 145–146° C. (dec.).

$^1$H-NMR (200 MHz, DMSO-d$_6$) δ1.32 (6H, t, J=6.9 Hz), 2.90 (2H, t, J=6.6 Hz), 3.68 (2H, t, J=6.4 Hz), 4.02 (2H, q, J=7.2 Hz), 4.03 (2H, q, J=7.0 Hz), 5.14 (2H, s), 6.94 (1H, d, J=8.0 Hz), 6.99 (1H, d, J=9.8 Hz), 7.07 (1H, s), 7.21 (1H, dd, J=8.9, 2.3 Hz), 7.41 (1H, d, J=2.2 Hz), 7.72 (1H, s), 7.94 (1H, d, J=8.8 Hz).

IR (KBr) 1674, 1593, 1566, 1514, 1292, 1258, 1225, 1165, 1128, 1069, 1038 cm$^{-1}$.

Anal. Calcd. for $C_{22}H_{24}O_7S$ (0.3 $H_2O$): C, 60.34; H, 5.66. Found: C, 60.15; H, 5.58.

Example 121 (Production of Compound 122)

To 7-(3,4-diethoxybenzyloxy)-1,1-dioxo-2,3-dihydro-1-benzothiepine-4-carboxylic acid (293 mg) suspended in THF (13 ml) were added DMF (one drop) and thionyl chloride (0.15 ml), and the resulting mixture was stirred at room temperature for one hour. After concentration under reduced pressure, the residue was dissolved in THF (10 ml). To 4-[[N-methyl-N-(tetrahydropyran-4-yl)amino]methyl] aniline dihydrochloride (298 mg) suspended in THF (12 ml) was added dropwise triethylamine (0.91 ml), and then thereto was added dropwise at 0° C. the above-prepared solution of the acid chloride in THF. The resulting mixture was stirred at room temperature for 60.5 hours. The reaction mixture was concentrated and was diluted with ethyl acetate, and the resulting mixture was washed successively with water and an aqueous saturated solution of sodium chloride, and was then dried with anhydrous magnesium sulfate. After evaporation under reduced pressure to remove the solvent, the residue was subjected to purification using silica gel column chromatography (ethyl acetate→ethyl acetate:ethanol=10:1) and further to recrystallization from ethanol to obtain N-[4-[[N-methyl-N-(tetrahydropyran-4-yl)amino]methyl]phenyl]-7-(3,4-diethoxybenzyloxy)-1,1-dioxo-2,3-dihydro-1-benzothiepine-4-carboxamide (compound 122) (212 mg) as white crystals.

M. p. 186–188° C.

$^1$H-NMR (200 MHz, CDCl$_3$) δ1.46 (6H, t, J=7.0 Hz), 1.69–1.77 (4H, m), 2.21 (3H, s), 2.57–2.70 (1H, m), 3.09 (2H, t, J=6.8 Hz), 3.37 (2H, td, J=11.2, 2.9 Hz), 3.57 (2H, s), 3.69 (2H, t, J=6.8 Hz), 4.01–4.05 (2H, m), 4.11 (4H, q, J=7.1 Hz), 5.05 (2H, s), 6.86–6.98 (4H, m), 7.04 (1H, dd, J=8.6, 2.4 Hz), 7.21 (1H, s), 7.32 (2H, d, J=8.6 Hz), 7.54 (2H, d, J=8.4 Hz), 7.87 (1H, s), 8.09 (1H, d, J=8.8 Hz)

IR (KBr) 1669, 1595, 1514, 1410, 1312, 1289, 1260, 1236, 1163, 1140, 1125, 1063, 1042, 737 cm$^{-1}$.

Anal. Calcd. for $C_{35}H_{42}N_2O_7S$ (0.3 $H_2O$): C, 65.66; H, 6.71; N, 4.38. Found: C, 65.56; H, 6.56; N, 4.35.

Reference Example 175

To methyl 7-hydroxy-1,1-dioxo-2,3-dihydro-1-benzothiepine-4-carboxylate (0.40 g) dissolved in methylene chloride (15 ml) was added 4-(2-propoxyethoxy) phenylboric acid (0.67 g) and molecular sieves 4A (0.8 g), and the resulting mixture was stirred for 5 minutes. To the reaction mixture were added cupric acetate (0.27 g) and triethylamine (1.04 ml), and the resulting mixture was stirred at room temperature for 5 hours. The reaction mixture was filtered through celite, and the filtrate was washed with ethyl acetate. The resulting solution was evaporated under reduced pressure to remove the solvent, and the residue was purified by silica gel column chromatography (hexane/ethyl acetate=3/2) to obtain methyl 7-[4-(2-propoxyethoxy) phenoxy]-1,1-dioxo-2,3-dihydro-1-benzothiepine-4-carboxylate (0.23 g).

$^1$H-NMR (200 MHz, CDCl$_3$) δ0.95 (3H, t, J=7.4 Hz), 1.57–1.71 (2H, m), 3.07 (2H, t, J=6.6 Hz), 3.55 (2H, t, J=6.6 Hz), 3.65 (2H, t, 6.6 Hz), 3.78–3.85 (2H, m), 3.84 (3H, s), 4.10–4.17 (2H, m), 6.95–7.02 (6H, m), 7.69 (1H, s), 8.08 (1H, d, J=8.8 Hz).

Reference Example 176

To methyl 7-[4-(2-propoxyethoxy)phenoxy]-1,1-dioxo-2,3-dihydro-1-benzothiepine-4-carboxylate (0.40 g) dissolved in THF (12 ml)/methanol (6.0 ml) was added a 1 N aqueous solution (2.7 ml) of sodium hydroxide, and the resulting mixture was stirred at 65° C. for 16 hours. After cooling to the room temperature, the reaction mixture was concentrated under reduced pressure to remove a half of the solvent. A 1 N aqueous solution of sodium hydroxide (3.0 ml) was added to the resulting mixture, which was washed with ethyl acetate. After being adjusted to pH=about 5, the resulting aqueous layer was extracted with ethyl acetate and the extract was washed with an aqueous saturated solution of sodium chloride and was then dried with magnesium sulfate. After evaporation to remove the solvent, the resulting residue was washed with hexane/ethyl acetate (=8/1) to obtain 7-[4-(2-propoxyethoxy)phenoxy]-1,1-dioxo-2,3-dihydro-1-benzothiepine-4-carboxylic acid (0.25 g).

$^1$H-NMR (200 MHz, CDCl$_3$) δ0.95 (3H, t, J=7.4 Hz), 1.56–1.74 (2H, m), 3.08 (2H, t, J=6.2 Hz), 3.52 (2H, t, J=6.6 Hz), 3.59–3.67 (2H, m), 3.79–3.84 (2H, m), 4.10–4.17 (2H, m), 6.97–7.03 (6H, m), 7.29 (1H, m), 8.09 (1H, d, J=8.6 Hz).

Example 122 (Production of Compound 123)

To 7-[4-(2-propoxyethoxy)phenoxy]-1,1-dioxo-2,3-dihydro-1-benzothiepine-4-carboxylic acid (0.25 g) dissolved in THF (7.5 ml) were added DMF (2 drops) and thionyl chloride (50 μl), and the resulting solution, which was stirred at room temperature for one hour, was added dropwise under ice cooling to a solution of 4-[N-methyl-N-(tetrahydropyranyl-4-yl)aminomethyl]aniline (140 mg) and triethylamine (0.40 ml) in THF (7.5 ml), and the resulting mixture was stirred at room temperature for 2 hours. The reaction mixture was added into water, and the resulting mixture was extracted with ethyl acetate. The organic layer was washed with an aqueous saturated solution of sodium chloride and was then dried with magnesium sulfate. After evaporation under reduced pressure to remove the solvent, the resulting residue was subjected to purification using silica gel column chromatography (ethyl acetate/ethanol=3/1) and to recrystallization from hexane/ethyl acetate to obtain N-[4-[N-methyl-N-(tetrahydropyranyl-4-yl) aminomethyl]phenyl]-7-[4-(2-propoxyethoxy)phenoxy]-1, 1-dioxo-2,3-dihydro-1-benzothiepine-4-carboxamide (compound 123) (115 mg).

M. p. 106–109° C.

$^1$H-NMR (200 MHz, CDCl$_3$) δ0.94 (3H, t, J=7.4 Hz), 1.55–1.75 (6H, m), 2.20 (3H, s), 2.64 (1H, m), 3.10 (2H, t, J=6.6 Hz), 3.37 (2H, td, J=11.0, 3.0 Hz), 3.50 (2H, t, J=6.6 Hz), 3.57 (2H, s), 3.70 (2H, t, J=6.6 Hz), 3.77–3.83 (2H, m), 4.00–4.16 (4H, m), 6.89–7.02 (5H, m), 7.04 (1H, s), 7.31 (2H, d, J=8.4 Hz), 7.51 (2H, d, J=8.6 Hz), 7.89 (1H, s), 8.08 (1H, d, J=8.4 Hz)

IR (KBr) 3281, 2955, 1649, 1599, 1501, 1410, 1238, 1204, 1125, 988, 829 cm$^{-1}$.

Reference Example 177

To methyl 7-hydroxy-1,1-dioxo-2,3-dihydro-1-benzothiepine-4-carboxylate (0.40 g) dissolved in methylene chloride (15 ml) were added 3-(2-propoxyethoxy) phenylboric acid (0.67 g) and molecular sieves 4A (0.8 g), and the resulting mixture was stirred for 5 minutes. Thereto were added cupric acetate (0.27 g) and triethylamine (1.04 ml), and the resulting mixture was stirred at room temperature for 5 hours. The reaction mixture was filtered through celite, and the filtrate was washed with ethyl acetate. The resulting solution was evaporated under reduced pressure to remove the solvent, and the residue was purified by silica gel column chromatography (hexane/ethyl acetate=3/2) to obtain methyl 7-[3-(2-propoxyethoxy)phenoxy]-1,1-dioxo-2,3-dihydro-1-benzothiepine-4-carboxylate (0.36 g).

$^1$H-NMR (200 MHz, CDCl$_3$) δ0.93 (3H, t, J=7.4 Hz), 1.56–1.69 (2H, m), 3.09 (2H, t, J=6.4 Hz), 3.49 (2H, t, J=6.6 Hz), 3.59–3.66 (2H, m), 3.76–3.81 (2H, m), 3.84 (3H, s), 4.09–4.14 (2H, m), 6.63–6.69 (2H, m), 6.79–6.85 (1H, m), 7.03–7.09 (2H, m), 7.31–7.35 (1H, m), 7.71 (1H, s), 8.10 (1H, d, J=8.4 Hz).

Reference Example 178

To methyl 7-[3-(2-propoxyethoxy)phenoxy]-1,1-dioxo-2, 3-dihydro-1-benzothiepine-4-carboxylate (0.36 g) dissolved in THF (10.8 ml)/methanol (5.4 ml) was added a 1 N aqueous solution (2.4 ml) of sodium hydroxide, and the resulting mixture was stirred at 65° C. for 16 hours. After cooling to the room temperature, the reaction mixture was concentrated under reduced pressure to remove a half of the solvent. A 1 N aqueous solution (3.0 ml) of sodium hydroxide was added to the resulting mixture, which was washed with ethyl acetate. After being adjusted to pH=about 5 with a 1 N aqueous solution of hydrochloric acid, the resulting aqueous layer was extracted with ethyl acetate, and the extract was washed with an aqueous saturated solution of sodium chloride and was then dried with magnesium sulfate. After evaporation to remove the solvent, the resulting residue was washed with hexane/ethyl acetate (=8/1) to obtain 7-[3-(2-propoxyethoxy)phenoxy]-1,1-dioxo-2,3-dihydro-1-benzothiepine-4-carboxylic acid (0.27 g).

$^1$H-NMR (200 MHz, CDCl$_3$) δ0.93 (3H, t, J=7.4 Hz), 1.54–1.71 (2H, m), 3.06–3.13 (2H, m), 3.50 (2H, t, J=6.6 Hz), 3.60–3.67 (2H, m), 3.76–3.82 (2H, m), 4.07–4.13 (2H, m), 6.64–6.69 (2H, m), 6.79–6.85 (1H, m), 7.04–7.10 (2H, m), 7.26–7.36 (1H, m), 7.81 (1H, s), 8.12 (1H, d, J=9.4 Hz).

Example 123 (Production of Compound 124)

To 7-[3-(2-propoxyethoxy)phenoxy]-1,1-dioxo-2,3-dihydro-1-benzothiepine-4-carboxylic acid (0.26 g) dissolved in THF (7.8 ml) were added DMF (2 drops) and thionyl chloride (53 μl), and the resulting mixture, which was stirred at room temperature for one hour, was added dropwise under ice cooling to a solution of 4-[N-methyl-N-(tetrahydropyranyl-4-yl)aminomethyl]aniline (146 mg) and triethylamine (0.42 ml) in THF (7.8 ml), and the resulting mixture was stirred at room temperature for 2 hours. The reaction mixture was mixed with water and was extracted with ethyl acetate. The organic layer was washed with an aqueous saturated solution of sodium chloride and was then dried with magnesium sulfate. After evaporation under reduced pressure to remove the solvent, the resulting residue was subjected to purification using silica gel column chromatography (ethyl acetate/ethanol=4/1) and to recrystallization from hexane/ethyl acetate to obtain N-[4-[N-methyl-N-(tetrahydropyranyl-4-yl)aminomethyl]phenyl]-7-[3-(2-propoxyethoxy)phenoxy]-1,1-dioxo-2,3-dihydro-1-benzothiepine-4-carboxamide (compound 124) (108 mg)

M. p. 98–102° C.

$^1$H-NMR (200 MHz, CDCl$_3$) δ0.92 (3H, t, J=7.2 Hz), 1.56–1.82 (6H, m), 2.20 (3H, s), 2.65 (1H, m), 3.10 (2H, t, J=6.6 Hz), 3.36 (2H, td, J=11.0, 2.6 Hz), 3.48 (2H, t, J=6.6 Hz), 3.57 (2H, s), 3.64–3.72 (2H, m), 3.75–3.81 (2H, m), 4.10–4.13 (4H, m), 6.63–6.68 (2H, m), 6.77–6.83 (1H, m), 6.95 (1H, d, J=2.2 Hz), 7.05 (1H, dd, J=8.8, 2.4 Hz), 7.17 (1H, s), 7.26–7.35 (3H, m), 7.52 (2H, d, J=8.4 Hz), 8.05 (1H, s), 8.09 (1H, d, J=8.4 Hz).

IR (KBr) 3289, 2942, 1647, 1599, 1530, 1410, 1304, 1138, 1055 cm$^{-1}$.

Example 124 (Production of Compound 125)

To 7-[4-(3-ethoxypropyl)phenoxy]-1,1-dioxo-2,3-dihydro-1-benzothiepine-4-carboxylic acid (0.12 g) dissolved in THF (5 ml) were added under ice cooling thionyl chloride (0.05 ml) and DMF (a catalytic amount), and the resulting mixture was stirred at room temperature for 1.5 hours. After evaporation under reduced pressure to remove the solvent, the residue dissolved in THF (10 ml) was added dropwise to a solution of 4-[N-methyl-N-(tetrahydro-2H-pyran-4-yl)aminomethyl]aniline (0.08 g) and triethylamine (0.21 ml) in THF (5 ml) under ice cooling. After being stirred under a nitrogen atmosphere at room temperature for 4 hours, the reaction mixture was evaporated under reduced pressure to remove the solvent, was mixed with water and was extracted with ethyl acetate. The organic layer was washed with water and an aqueous saturated solution of sodium chloride, and was dried with anhydrous magnesium sulfate. After resulting organic layer was evaporated under reduced pressure to remove the solvent, the residue was subjected to purification using silica gel column chromatography (ethyl acetate/methanol/triethylamine) to obtain crude crystals. The crude crystals were recrystallized from ethyl acetate/hexane to obtain 7-[4-(3-ethoxypropyl)phenoxy]-N-[4-[[N-methyl-N-(tetrahydro-2H-pyran-4-yl)amino]methyl]phenyl]-1,1-dioxo-2,3-dihydro-1-benzothiepine-4-carboxamide (compound 125) (0.15 g) as colorless crystals.

M. p. 156–157° C.

$^1$H-NMR (δ ppm, CDCl$_3$) 1.22 (3H, t, J=6.9 Hz), 1.57–1.76 (4H, m), 1.84–1.98 (2H, m), 2.20 (3H, s), 2.59–2.69 (1H, m), 2.72 (2H, t, J=6.2 Hz), 3.11 (2H, t, J=6.6 Hz), 3.30–3.54 (6H, m), 3.56 (2H, s), 3.69 (2H, t, J=6.8 Hz), 4.01–4.07 (2H, m), 6.95–7.05 (4H, m), 7.16 (1H, s), 7.23–7.33 (4H, m), 7.51 (2H, d, J=8.4 Hz), 7.75 (1H, s), 8.09 (1H, d, J=8.4 Hz).

IR (KBr) ν: 2946, 2853, 1667, 1595, 1507 cm$^{-1}$.

Anal. Calcd. for C$_{35}$H$_{42}$N$_2$O$_6$S: C, 67.94; H, 6.84; N, 4.53. Found: C, 67.64; H, 6.82; N, 4.41.

Example 125 (Production of Compound 126)

To 7-[4-(2-ethoxyethoxy)-3,5-dimethylphenoxy]-1,1-dioxo-2,3-dihydro-1-benzothiepine-4-carboxylic acid (0.25 g) dissolved in THF (5 ml) were added under ice cooling thionyl chloride (0.08 ml) and DMF (a catalytic amount), and the resulting mixture was stirred at room temperature for 1.5 hours. After evaporation under reduced pressure to remove the solvent, the residue dissolved in THF (10 ml) was added dropwise to a solution of 4-[N-methyl-N-(tetrahydro-2H-pyran-4-yl)aminomethyl]aniline (0.14 g) and triethylamine (0.4 ml) in THF (5 ml) under ice cooling. The resulting mixture was stirred overnight under a nitrogen atmosphere at room temperature. The reaction mixture was evaporated under reduced pressure to remove the solvent, was mixed with water and was extracted with ethyl acetate. The organic layer was washed with water and an aqueous saturated solution of sodium chloride, and was dried with anhydrous magnesium sulfate. The resulting organic layer was evaporated under reduced pressure to remove the solvent, and the residue was subjected to purification using silica gel column chromatography (ethyl acetate/methanol/triethylamine) to obtain crude crystals. The crude crystals were recrystallized from ethyl acetate/hexane to obtain 7-[4-(2-ethoxyethoxy)-3,5-dimethylphenoxy]-N-[4-[[N-methyl-N-(tetrahydro-2H-pyran-4-yl)amino]methyl]phenyl]-1,1-dioxo-2,3-dihydro-1-benzothiepine-4-carboxamide (compound 126) (0.28 g) as colorless crystals.

M. p. 111–113° C.

$^1$H-NMR (δ ppm, CDCl$_3$) 1.26 (3H, t, J=6.9 Hz), 1.63–1.74 (4H, m), 2.20 (3H, s), 2.30 (6H, s), 2.50–2.71 (1H, m), 3.11 (2H, t, J=6.8 Hz), 3.37 (2H, dt, J=3.0, 11.0 Hz), 3.57 (2H, s), 3.60–3.80 (6H, m), 3.94–4.06 (4H, m), 6.72 (2H, s), 6.93 (1H, d, J=2.4 Hz), 7.02 (1H, dd, J=2.4, 8.4 Hz), 7.16 (1H, s), 7.31 (2H, d, J=8.6 Hz), 7.51 (2H, d, J=8.6 Hz), 7.72 (1H, s), 8.09 (1H, d, J=8.8 Hz).

IR (KBr) ν: 2934, 2849, 1669, 1597, 1564, 1520 cm$^{-1}$.

Anal. Calcd. for C$_{36}$H$_{44}$N$_2$O$_7$S: C, 66.64; H, 6.84; N, 4.32. Found: C, 66.52; H, 6.87; N, 4.10.

Reference Example 179

A suspension of magnesium (0.37 g) in THF (5 ml) was stirred under a nitrogen atmosphere, and thereto was then added dibromoethane (a catalytic amount) and was subsequently added dropwise a solution of 1-bromo-4-(3-ethoxypropyl)benzene (3.4 g) in anhydrous THF (30 ml). The resulting mixture was heated at 50° C. for 1.5 hours and was then cooled to −78° C., and thereto was added dropwise trimethyl borate (3.1 ml). The reaction mixture was brought back to the room temperature and was stirred overnight. The reaction mixture was mixed with 1 N hydrochloric acid, was concentrated and was extracted with ethyl acetate. The organic layer was washed with water and an aqueous saturated solution of sodium chloride, and was dried with anhydrous magnesium sulfate. The resulting organic layer was evaporated under reduced pressure to remove the solvent, and the residue was purified by silica gel chromatography (ethyl acetate/triethylamine) to obtain 4-(3-ethoxypropyl)phenylboric acid (1.25 g) as a light yellow, oily substance.

$^1$H-NMR (δ ppm, CDCl$_3$) 1.23 (3H, t, J=7.0 Hz), 1.90–2.00 (2H, m), 2.79 (2H, t, J=7.7 Hz), 3.42–3.55 (4H, m), 7.34 (2H, d, J=7.6 Hz), 8.16 (2H, d, J=7.6 Hz).

Reference Example 180

To methyl 7-hydroxy-1,1-dioxo-2,3-dihydro-1-benzothiepine-4-carboxylate (0.4 g), 4-(3-ethoxypropyl)phenylboric acid (0.65 g), cupric acetate (0.27 g) and molecular sieves 4A (0.8 g) suspended in dichloromethane (15 ml) was added triethylamine (1.0 ml), and the resulting mixture was stirred overnight at room temperature. The reaction mixture was filtered through celite, and the filtrate was evaporated to remove the solvent. The residue was purified by silica gel column chromatography (ethyl acetate/hexane) to obtain methyl 7-[4-(3-ethoxypropyl)phenoxy]-1,1-dioxo-2,3-dihydro-1-benzothiepine-4-carboxylate (0.28 g) as colorless crystals.

M. p. 93–94° C.

$^1$H-NMR (δ ppm, CDCl$_3$) 1.23 (3H, t, J=6.9 Hz), 1.85–1.99 (2H, m), 2.73 (2H, t, J=7.7 Hz), 3.08 (2H, t, J=6.6 Hz), 3.43–3.66 (6H, m), 3.84 (3H, s), 6.97–7.05 (4H, m), 7.25 (2H, d, J=8.4 Hz), 7.71 (1H, s), 8.09 (1H, d, J=9.6 Hz).

IR (KBr) ν: 2975, 2949, 2865, 1713 cm$^{-1}$.

Reference Example 181

To methyl 7-[4-(3-ethoxypropyl)phenoxy]-1,1-dioxo-2,3-dihydro-1-benzothiepine-4-carboxylate (0.28 g) dissolved methanol (5 ml) and THF (10 ml) was added a 1 N aqueous solution of sodium hydroxide (0.6 ml), and the resulting mixture was stirred at 70° C. for 5 hours. The reaction mixture was concentrated, was then neutralized with 1 N hydrochloric acid and was extracted with ethyl acetate. The organic layer was washed with water and an aqueous saturated solution of sodium chloride, and was dried with anhydrous magnesium sulfate. The resulting organic layer was evaporated under reduced pressure to remove the solvent to obtain 7-[4-(3-ethoxypropyl)phenoxy]-1,1-dioxo-2,3-dihydro-1-benzothiepine-4-carboxylic acid (0.12 g) as colorless crystals.

$^1$H-NMR (δ ppm, CDCl$_3$) 1.23 (3H, t, J=7.2 Hz), 1.85–1.99 (2H, m), 2.73 (2H, t, J=7.9 Hz), 3.09 (2H, t, J=6.6 Hz), 3.43–3.56 (4H, m), 3.64 (2H, t, J=6.8 Hz), 6.96–7.05 (4H, m), 7.23–7.26 (2H, m), 7.81 (1H, s), 8.10 (1H, d, J=9.6 Hz).

IR (KBr) ν: 2975, 2934, 2870, 1713 cm$^{-1}$.

Reference Example 182

To 60% sodium hydride (4.4 g) suspended in DMF (50 ml) was added dropwise under ice cooling a solution of 4-bromo-2,6-dimethylphenol (20 g) in DMF (100 ml). After stirring at room temperature for 2 hours under a nitrogen atmosphere, bromoethyl ethyl ether (12.3 ml) and sodium iodide (16.4 g) were added thereto, and the resulting mixture was heated overnight at 75° C. The reaction mixture was poured into water and was extracted with ethyl acetate. The organic layer was washed with water and an aqueous saturated solution of sodium chloride, and was dried with anhydrous magnesium sulfate. The resulting organic layer was evaporated under reduced pressure to remove the solvent, and the residue was purified by silica gel chromatography (ethyl acetate/hexane) to obtain 5-bromo-2-(2-ethoxyethoxy)-1,3-dimethylbenzene (24.1 g) as a colorless oil.

$^1$H-NMR (δ ppm, CDCl$_3$) 1.25 (3H, t, J=7.0 Hz), 2.26 (6H, s), 3.60 (2H, q, J=7.0 Hz), 3.72–3.77 (2H, m), 3.88–3.93 (2H, m), 7.13 (2H, s).

IR (neat) ν: 2975, 2926, 2870, 1472 cm$^{-1}$.

Reference Example 183

A suspension of magnesium (2.36 g) in THF (100 ml) was stirred under a nitrogen atmosphere, and thereto was added dibromoethane (a catalytic amount) and was subsequently added dropwise a solution of 5-bromo-2-(2-ethoxyethoxy)-1,3-dimethylbenzene (24.1 g) in anhydrous THF (100 ml). The resulting mixture was heated at 55° C. for 2.5 hours and was then cooled to −78° C., and thereto was added dropwise trimethyl borate (19.8 ml). The reaction mixture was brought back to the room temperature and was stirred overnight. The reaction mixture was mixed with 1 N hydrochloric acid, was concentrated and was extracted with ethyl acetate. The organic layer was washed with water and an aqueous saturated solution of sodium chloride, and was dried with anhydrous magnesium sulfate. The resulting organic layer was evaporated under reduced pressure to remove the solvent to obtain 4-(2-ethoxyethoxy)-3,5-dimethylphenylboric acid (8.4 g) as colorless crystals.

$^1$H-NMR (δ ppm, CDCl$_3$) 1.16 (3H, t, J=7.2 Hz), 2.21 (3H, s), 2.26 (3H, s), 3.46 (2H, q, J=7.2 Hz), 3.65–3.69 (2H, m), 3.85–3.90 (2H, m), 7.48 (2H, s).

Reference Example 184

To methyl 7-hydroxy-1,1-dioxo-2,3-dihydro-1-benzothiepine-4-carboxylate (0.4 g), 4-(2-ethoxyethoxy)-3,5-dimethylphenylboric acid (0.71 g), cupric acetate (0.27 g) and molecular sieves 4A (0.8 g) suspended in dichloromethane (15 ml) was added triethylamine (1.0 ml), and the resulting mixture was stirred overnight at room temperature. The reaction mixture was filtered through celite, and the filtrate was evaporated to remove the solvent. The residue was purified by silica gel column chromatography (ethyl acetate/hexane) to obtain methyl 7-[4-(2-ethoxyethoxy)-3,5-dimethylphenoxy]-1,1-dioxo-2,3-dihydro-1-benzothiepine-4-carboxylate (0.39 g) as a light yellow oil.

$^1$H-NMR (δ ppm, CDCl$_3$) 1.27 (3H, t, J=7.0 Hz), 2.31 (6H, s), 3.08 (2H, t, J=6.4 Hz), 3.58–3.68 (4H, m), 3.76–3.81 (2H, m), 3.84 (3H, s), 3.95–4.00 (2H, m), 6.71 (2H, s), 6.99–7.04 (2H, m), 7.71 (1H, s), 8.08 (1H, d, J=8.4 Hz).

IR (neat) ν: 2975, 2951, 2926, 2868, 1713 cm$^{-1}$.

Reference Example 185

To methyl 7-[4-(2-ethoxyethoxy)-3,5-dimethylphenoxy]-1,1-dioxo-2,3-dihydro-1-benzothiepine-4-carboxylate (0.39 g) dissolved in methanol (5 ml) and THF (10 ml) was added a 1 M aqueous solution of potassium carbonate (2.5 ml), and the resulting mixture was stirred overnight at 70° C. The reaction mixture was concentrated, was then neutralized with 1 N hydrochloric acid and was extracted with ethyl acetate. The organic layer was washed with water and an aqueous saturated solution of sodium chloride, and was dried with anhydrous magnesium sulfate. The resulting organic layer was evaporated under reduced pressure to remove the solvent to obtain 7-[4-(2-ethoxyethoxy)-3,5-dimethylphenoxy]-1,1-dioxo-2,3-dihydro-1-benzothiepine-4-carboxylic acid (0.33 g) as colorless crystals.

M. p. 149–153° C.

$^1$H-NMR (δ ppm, CDCl$_3$) 1.27 (3H, t, J=7.0 Hz), 2.31 (6H, s), 3.10 (2H, t, J=6.4 Hz), 3.58–3.69 (4H, m), 3.77–3.81 (2H, m), 3.96–4.00 (2H, m), 6.72 (2H, s), 7.02–7.06 (2H, m), 7.83 (1H, s), 8.10 (1H, d, J=9.0 Hz).

IR (KBr) ν: 2976, 2865, 1709, 1694 cm$^{-1}$.

Anal. Calcd. for $C_{23}H_{26}O_7S$: C, 61.87; H, 5.87. Found: C, 61.59; H, 5.71.

INDUSTRIAL APPLICABILITY

Since compounds represented by formula (1) or salts thereof of the present invention have a potent antagonistic activity against CCR5, they may be used advantageously for the treatment of a variety of HIV infectious diseases in humans, for example, for the prophylaxis and the therapeutics of AIDS.

What is claimed is:
1. A compound presented by formula

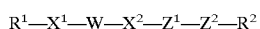

wherein $R^1$ indicates a 5- to 6-membered cyclic ring group that may be substituted, $X^1$ indicates a bond or a bivalent group, in which the number of atoms constituting the straight-chain portion is 1 to 4, W indicates a bivalent group that is represented by formula

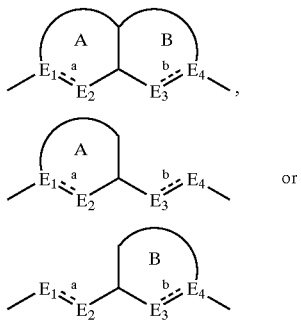

—(wherein each of ring A and ring B indicates a 5- to 7-membered cyclic ring group that may be substituted,
each of $E_1$ and $E_4$ indicates the carbon atom that may be substituted or the nitrogen atom that may be substituted,
each of $E_2$ and $E_3$ indicates the carbon atom that may be substituted and each of a and b indicates to be a single bond or a double bond)-, $X^2$ indicates a bivalent group, in which the number of atoms constituting the straight-chain portion is 1 to 4, $Z^1$ indicates a bond or a bivalent cyclic ring group, $Z^2$ indicates a bond or a bivalent cyclic ring group, in which the number of atoms constituting the straight-chain portion is 1 to 4, and $R^2$ indicates
(1) an amino group that may be substituted, where the nitrogen atom may be converted into a quaternary ammonium or the N-oxide,
(2) a nitrogen-containing, heterocyclic ring group that may be substituted and may contain the sulfur atom or the oxygen atom as a ring-constituting atom, where the nitrogen atom may be converted into a quaternary ammonium or the N-oxide,
(3) a group that is bonded via the sulfur atom,
(4) a group represented by formula

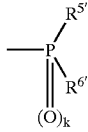

—(wherein k indicates 0 or 1,
the phosphorus atom may form a phosphonium salt when k is 0,
and each of $R^{5'}$ and $R^{6'}$ indicates the hydrocarbon atom that may be substituted, the hydroxyl group that may be substituted or an amino group that may be substituted, and $R^{5'}$ and $R^{6'}$ may bind each other to form a cyclic ring group together with the adjacent phosphorus atom)-,
(5) an amidino group that may be substituted or
(6) a guanidino group that may be substituted;

provided that, when a group represented by formula $R^1$—$X^1$—W—$X^2$—$Z^1$—$Z^2$— indicates a group represented by formula

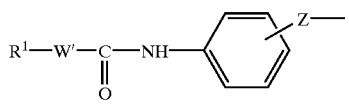

—(wherein $R^1$ indicates the same meaning as described above,

W' indicates a bivalent group represented by formula

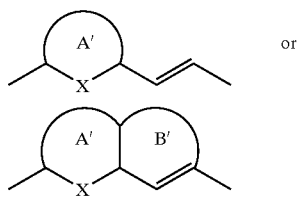

—(wherein ring A' indicates a 5- to 6-membered aromatic ring that may be substituted,
X indicates the carbon atom that may be substituted,
and ring B' indicates a 5- to 7-membered ring that may be substituted)-and Z indicates a bivalent group, in which the number of atoms constituting the straight-chain portion is 1 to 4, $R^2$ indicates an amidino group that may be substituted or a guanidino group that may be substituted;

when a group represented by formula $R^1$—$X^1$—W—$X^2$—$Z^1$—$Z^2$— indicates a group represented by formula

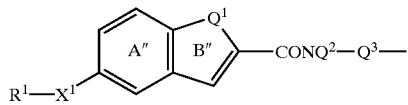

—(wherein $R^1$ and $X^1$ indicate the same meanings as described above, ring A'' indicates a benzene ring that may be substituted, $Q^1$ indicates a bivalent group, in which ring B'' forms a 5- to 7-membered ring, $Q^2$ indicates the hydrogen atom, a hydrocarbon group that may be substituted, a heterocyclic ring group that may be substituted and $Q^3$ indicates a bond or a bivalent group)-, $R^2$ does not indicate a group represented by formula

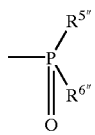

—(wherein each of $R^{5''}$ and $R^{6''}$ indicates the hydroxyl group that may be substituted, and R$^{5"}$ and R$^{6"}$ may bind each other to form a cyclic ring group together with the adjacent phosphorus atom), or salts thereof.

2. A prodrug of the compound or salt thereof as claimed in claim 1.

3. The compound as claimed in claim 1, wherein R$^1$ is a group that is formed by removing one hydrogen atom from benzene, furan, thiophene, pyridine, cyclopentane, cyclohexane, pyrrolidine, piperidine, piperazine, morpholine, thiomorpholine or tetrahydrofuran, each of which may be substituted.

4. The compound as claimed in claim 1, wherein R$^1$ is a phenyl that may be substituted.

5. The compound as claimed in claim 1, wherein X$^1$ is a bond,
—(CH$_2$)$_{a'}$— (wherein a' indicates an integer of 1 to 4),
—(CH$_2$)$_{b'}$—X$^3$—
(wherein b' indicates an integer of 0 to 3 and
X$^3$ indicates an imino group that may be substituted, the carbonyl group, the oxygen atom or the sulfur atom that may be oxidized),
—CH=CH—,
—C≡C—,
—CO—NH— or
—SO$_2$—NH—.

6. The compound as claimed in claim 1, wherein X$^1$ is a bond.

7. The compound as claimed in claim 1,
wherein X$^1$ is —(CH$_2$)$_{b'}$—X$^3$—
(wherein b' indicates an integer of 0 to 3, and
X$^3$ indicates an imino group that may be substituted, the carbonyl group, the oxygen atom or the sulfur atom that may be oxidized).

8. The compound as claimed in claim 1, wherein ring A is furan, thiophene, pyrrole, pyridine, pyran or benzene, each of which may be substituted.

9. The compound as claimed in claim 1, wherein ring A is a benzene that may be substituted.

10. The compound as claimed in claim 1, wherein ring B is a 5- to 7-membered ring that may be substituted at a substitutable optional position, which is represented by formula

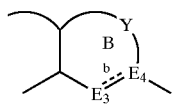

wherein E$_3$ indicates the carbon atom that may be substituted,
E$_4$ indicates the carbon atom that may be substituted or the nitrogen atom,
b indicates a single bond or a double bond and
Y indicates
—Y'—(CH$_2$)$_{m'}$—
(Y' indicates —S(O)$_m$—
(m indicates an integer of 0 to 2),
—O—,
—NH— or
—CH$_2$—, and
m' indicates an integer of 0 to 2),
—CH=,
—CH=CH— or
—N=CH—).

11. The compound as claimed in claim 10, wherein Y indicates —Y'—(CH$_2$)$_2$—
(Y' indicates
—S(O)$_m$—
(m indicates an integer of 0 to 2),
—O—,
—NH— or
—CH$_2$—).

12. The compound as claimed in claim 1, wherein, E$_4$ indicates the carbon atom that may be substituted and b indicates a double bond.

13. The compound as claimed in claim 1, wherein X$^2$ is
—(CH$_2$)$_{a'}$—
(a' indicates an integer of 1 to 4),
—(CH$_2$)$_{b'}$—X$^3$—
(b' indicates an integer of 0 to 3, and
X$^3$ indicates an imino group that may be substituted, the carbonyl group, the oxygen atom or the sulfur atom that may be oxidized),
—CH=CH—,
—C≡C—,
—CO—NH— or
—SO$_2$—NH—.

14. The compound as claimed in claim 1, wherein X$^2$ is —CO—NH—.

15. The compound as claimed in claim 1, wherein Z$^1$ is (1) a bond or (2) a bivalent cyclic ring group that is formed by removing two hydrogen atoms from benzene, furan, thiophene, pyridine, cyclopentane, cyclohexane, pyrrolidine, piperidine, piperazine, morpholine, thiomorpholine or tetrahydropyran, each of which may be substituted.

16. The compound as claimed in claim 1, wherein Z$^1$ is (1) a bond or (2) a bivalent cyclic ring group that is formed by removing two hydrogen atoms from benzene, cyclohexane or piperidine, each of which may be substituted.

17. The compound as claimed in claim 1, wherein Z$^1$ is a phenylene that may be substituted.

18. The compound as claimed in claim 1, wherein Z$^2$ is a bond or a C$_{1-3}$ alkylene that may be substituted.

19. The compound as claimed in claim 1, wherein Z$^2$ is a bivalent group that has a skeleton represented by —Z'—(CH$_2$)n—
(Z' indicates
—CH(OH)—,
—C(O)— or
—CH$_2$—, and
n indicates an integer of 0 to 2) and may have a substituent at an optional methylene group.

20. The compound as claimed in claim 1, wherein Z$^2$ is a bond or a methylene.

21. The compound as claimed in claim 1, wherein Z$^1$ is a 6-membered, bicyclic ring group, and Z$^2$ is substituted at the para position of X$^2$.

22. The compound as claimed in claim 1, wherein R$^2$ is (1) an amino group that may be substituted, where the nitrogen atom may be converted into a quaternary ammonium or the N-oxide, (2) a nitrogen-containing, heterocyclic ring group that may be substituted and may contain the sulfur atom or the oxygen atom as a ring-constituting atom, where the nitrogen atom may be converted into a quaternary ammonium or the N-oxide, (3) an amidino group that may be substituted or (4) a guanidino group that may be substituted.

23. The compound as claimed in claim 1, wherein R$^2$ is an amino group that may be substituted.

24. The compound as claimed in claim 1, wherein $R^2$ is an amidino group that may be substituted or a guanidino group that may be substituted.

25. N-[4-[N-Methyl-N-(tetrahydropyran-4-yl) aminomethyl]phenyl]-7-[2-(4-propoxyphenyl)ethoxy]-1,1-dioxo-2,3-dihydro-1-benzothiepine-4-carboxamide, N-[4-[N-methyl-N-(tetrahydropyran-4-yl)aminomethyl]phenyl]-7-[(3-propoxybenzyl)oxy]-1,1-dioxo-2,3-dihydro-1-benzothiepine-4-carboxamide, N-[4-[N-methyl-N-(tetrahydropyran-4-yl)aminomethyl]phenyl]-7-[(2-propoxybenzyl)oxy]-1,1-dioxo-2,3-dihydro-1-benzothiepine-4-carboxamide, N-[4-[N-methyl-N-(tetrahydropyran-4-yl)aminomethyl]phenyl]-7-[(4-propoxyphenyl)methoxy]-1,1-dioxo-2,3-dihydro-1-benzothiepine-4-carboxamide, N-[4-[N-methyl-N-(tetrahydropyran-4-yl)aminomethyl]phenyl]-7-[(4-propoxyethoxyphenyl)methoxy]-1,1-dioxo-2,3-dihydro-1-benzothiepine-4-carboxamide, N-[4-[N-methyl-N-(tetrahydropyran-4-yl)aminomethyl]phenyl]-7-[3-(4-propoxyphenyl)propoxy]-1,1-dioxo-2,3-dihydro-1-benzothiepine-4-carboxamide, or salts thereof.

26. Prodrug of the compound or salt thereof as claimed in claim 25.

27. A pharmaceutical composition comprising the compound or salt thereof as claimed in claim 1 and a pharmaceutically acceptable carrier.

28. A pharmaceutical composition for CCR antagonism comprising a compound represented by formula $$R^1-X^1-W-X^2-Z^1-Z^2-R^2$$

wherein $R^1$ indicates a 5- to 6-membered cyclic ring group that may be substituted, $X^1$ indicates a bond or a bivalent group, in which the number of atoms constituting the straight-chain portion is 1 to 4, W indicates a bivalent group that is represented by formula

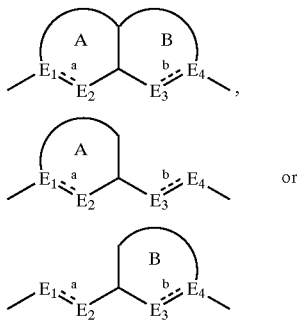

(wherein each ring A and ring B indicates a 5- to 7-membered cyclic ring group that may by substituted, each of $E_1$ and $E_4$ indicates the carbon atom that may be substituted or the nitrogen atom that may be substituted, each of $E_2$ and $E_3$ indicates the carbon atom that may be substituted and each of a and b indicates to be a single bond or a double bond), $X^2$ indicates a bivalent group, in which the number of atoms constituting the straight-chain portion is 1 to 4, $Z^1$ indicates a bond or a bivalent cyclic ring group, $Z^2$ indicates a bond or a bivalent cyclic ring group, in which the number of atoms constituting the straight-chain portion is 1 to 4, and $R^2$ indicates
(1) an amino group that may be substituted, where the nitrogen atom may be converted into a quaternary ammonium or the N-oxide,
(2) a nitrogen-containing, heterocyclic ring group that may be substituted and may contain the sulfur atom or the oxygen atom as a ring-constituting atom, where the nitrogen atom may be converted into a quaternary ammonium or the N-oxide,
(3) a group that bonded via the sulfur atom,
(4) a group represented by formula

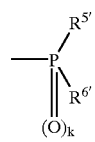

(wherein k indicates 0 or 1,
the phosphorus atom may form a phosphonium salt when k is 0, and
each of $R^{5'}$ and $R^{6'}$ indicates the hydrocarbon atom that may be substituted, the hydroxyl group that may be substituted or an amino group that may be substituted and $R^{5'}$ and $R^{6'}$ may bind each other to form a cyclic ring group together with the adjacent phosphorus atom),
(5) an amidino group that may be substituted or
(6) a guanidino group that may be substituted;
provided that, when a group represented by formula $R^1-X^1-W-X^2-Z^1-Z^2-$ indicates a group represented by formula

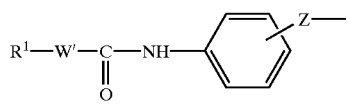

(wherein $R^1$ indicates the same meaning as described above,
W' indicates a bivalent group represented by formula

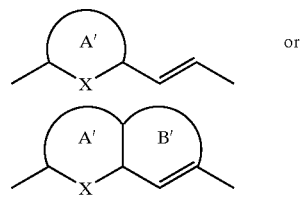

(wherein ring A' indicates a 5- to 6-membered aromatic ring that may be substituted,
X indicates the carbon atom that may be substituted, and
ring B' indicates a 5- to 7-membered ring that may be substituted) and
Z indicates a bivalent group, in which the number of atoms constituting the straight-chain portion is 1 to 4),
$R^2$ indicates an amidino group that may be substituted or a guanidino group that may be substituted;
or a salt thereof and a pharmaceutically acceptable carrier.

29. The composition as claimed in claim 28 which is a prophylactic/therapeutic agent of HIV infectious diseases.

30. The composition as claimed in claim 28 which is a prophylactic/therapeutic agent of AIDS.

31. The composition as claimed in claim 28 which is a depressant against the pathologic progress of AIDS.

32. The composition as claimed in claim 29 which is in combination with a protease inhibitor and/or a reverse transcriptase inhibitor.

33. The composition as claimed in claim 32, wherein the reverse transcriptase inhibitor is zidovudine, didanosine, zalcitabine, lamivudine, stavudine, nevirapine, delavirdine, efavirenz or abacavir.

34. The composition as claimed in claim 32, wherein the protease inhibitor is saquinavir, ritonavir, indinavir, amprenavir or nelfinavir.

35. A method for antagonizing CCR comprising administrating an effective amount of the compound or a salt thereof as claimed in claim 28 to a mammal in need thereof.

* * * * *